(12) United States Patent
Zhong et al.

(10) Patent No.: US 12,215,130 B2
(45) Date of Patent: *Feb. 4, 2025

(54) CYTOKINE-ALBUMIN BINDING MOIETY FUSION PROTEINS AND USES THEREOF

(71) Applicant: Anwita Biosciences, Inc., San Carlos, CA (US)

(72) Inventors: Ziyang Zhong, Belmont, CA (US); Fan Ye, Mountain View, CA (US); Matthew Siegel, Menlo Park, CA (US); Jianing Huang, San Mateo, CA (US); Eric Liao, San Francisco, CA (US); Ella Li, San Francisco, CA (US)

(73) Assignee: ANWITA BIOSCIENCES, INC., San Carlos, CA (US)

( * ) Notice: Subject to any disclaimer, the term of this patent is extended or adjusted under 35 U.S.C. 154(b) by 995 days.

This patent is subject to a terminal disclaimer.

(21) Appl. No.: 17/253,481

(22) PCT Filed: Jun. 17, 2019

(86) PCT No.: PCT/US2019/037558
§ 371 (c)(1),
(2) Date: Dec. 17, 2020

(87) PCT Pub. No.: WO2019/246004
PCT Pub. Date: Dec. 26, 2019

(65) Prior Publication Data

US 2021/0230242 A1 Jul. 29, 2021

Related U.S. Application Data

(60) Provisional application No. 62/809,496, filed on Feb. 22, 2019, provisional application No. 62/686,481, filed on Jun. 18, 2018.

(51) Int. Cl.
*C07K 16/46* (2006.01)
*A61K 45/06* (2006.01)
(Continued)

(52) U.S. Cl.
CPC .............. *C07K 14/54* (2013.01); *A61K 45/06* (2013.01); *A61P 35/00* (2018.01);
(Continued)

(58) Field of Classification Search
None
See application file for complete search history.

(56) References Cited

U.S. PATENT DOCUMENTS 4,485,045 A 11/1984 Regen
4,544,545 A 10/1985 Ryan et al.
(Continued)

FOREIGN PATENT DOCUMENTS

CN 105198999 A 12/2015
WO 1991001743 A1 2/1991
(Continued)

OTHER PUBLICATIONS

Dinarello, C.A., Historical Review of Cytokines, Eur. J. Immunol. 37:S34-45, 2007.*
(Continued)

*Primary Examiner* — Claire Kaufman
(74) *Attorney, Agent, or Firm* — Lin Yu; Juniv LLP

(57) ABSTRACT

The present application provides fusion proteins that comprise a cytokine fused to an albumin binding moiety. The fusion proteins may further comprise an antigen binding moiety such as a therapeutic antibody. The present application also provides methods of making and using the fusion proteins. The present application also provides methods of (Continued)

treatment comprises administering a fusion protein comprising a cytokine fused to a half-life extending domain and a second agent.

18 Claims, 34 Drawing Sheets

Specification includes a Sequence Listing.

(51) Int. Cl.

| | | |
|---|---|---|
| *A61P 35/00* | (2006.01) | |
| *C07K 14/54* | (2006.01) | |
| *C07K 14/765* | (2006.01) | |
| *C07K 16/30* | (2006.01) | |
| *C07K 16/44* | (2006.01) | |
| *A61K 38/00* | (2006.01) | |
| *A61K 39/00* | (2006.01) | |

(52) U.S. Cl.
CPC ........ *C07K 14/5443* (2013.01); *C07K 14/765* (2013.01); *C07K 16/30* (2013.01); *C07K 16/44* (2013.01); *A61K 38/00* (2013.01); *A61K 2039/505* (2013.01); *C07K 2317/31* (2013.01); *C07K 2317/565* (2013.01); *C07K 2317/569* (2013.01); *C07K 2319/00* (2013.01); *C07K 2319/30* (2013.01); *C07K 2319/31* (2013.01)

(56) References Cited

U.S. PATENT DOCUMENTS

| | | | |
|---|---|---|---|
| 4,816,567 A | 3/1989 | Cabilly et al. | |
| 5,013,556 A | 5/1991 | Woodle et al. | |
| 5,571,894 A | 11/1996 | Wels et al. | |
| 5,587,458 A | 12/1996 | King et al. | |
| 5,869,046 A | 2/1999 | Presta et al. | |
| 6,054,297 A | 4/2000 | Carter et al. | |
| 6,407,213 B1 | 6/2002 | Carter et al. | |
| 6,639,055 B1 | 10/2003 | Carter et al. | |
| 6,719,971 B1 | 4/2004 | Carter et al. | |
| 6,800,738 B1 | 10/2004 | Carter et al. | |
| 7,189,690 B2 | 3/2007 | Rosen et al. | |
| 8,969,289 B2 * | 3/2015 | Gosselin ................. | A61P 9/00 530/300 |
| 10,011,858 B2 | 7/2018 | Igawa et al. | |
| 11,028,166 B2 * | 6/2021 | Cini ................. | A61K 39/00114 |
| 11,426,468 B2 * | 8/2022 | Janssen ................. | C07K 16/18 |
| 2007/0048282 A1 | 3/2007 | Rosen et al. | |
| 2007/0071675 A1 | 3/2007 | Wu et al. | |
| 2007/0079271 A1 | 4/2007 | Ushiyama | |
| 2007/0269422 A1 | 11/2007 | Beirnaert et al. | |
| 2016/0152686 A1 | 6/2016 | Camphausen et al. | |

FOREIGN PATENT DOCUMENTS

| | | |
|---|---|---|
| WO | 1993016185 A2 | 8/1993 |
| WO | 1994004678 A1 | 3/1994 |
| WO | 1996027011 A1 | 9/1996 |
| WO | 2001045746 A2 | 6/2001 |
| WO | 2001079271 A1 | 10/2001 |
| WO | 2002076489 A1 | 10/2002 |
| WO | 2003059934 A2 | 7/2003 |
| WO | 2004041865 A2 | 5/2004 |
| WO | 2006106905 A1 | 10/2006 |
| WO | 2011124718 A1 | 10/2011 |
| WO | 2011140086 A2 | 11/2011 |
| WO | 2012059486 A1 | 5/2012 |
| WO | 2016009041 A1 | 1/2016 |
| WO | 2016196211 A1 | 12/2016 |
| WO | 2017158436 A1 | 9/2017 |
| WO | 2018151868 A2 | 8/2018 |
| WO | 2019246003 A1 | 12/2019 |

OTHER PUBLICATIONS

Chichili et al., Linkers in the structural biology of protein-potein interactions, Prot. Sci. 22:153-167, 2013.*
Adams et al., "Extending the half-life of a fab fragment through generation of a humanized anti-human serum albumin Fv domain: An investigation into the correlation between affinity and serum half-life," MAbs 2016, 8, 1336-46.
Morrison et al., "Chimeric human antibody molecules: mouse antigen-binding domains with human constant region domains," Proc. Natl. Acad. Sic. U.S.A. 1984, 81, 6851-5.
Liu et al., "An engineered IL-21 with half-life extension enhances anti-tumor immunity as a monotherapy or in combination with PD-1 or TIGIT blockade," Int. Immunopharmacol. 2021, 101, 108307.
Walker et al., "Anti-serum albumin domain antibodies in the development of highly potent, efficacious and long-acting interferon," Protein Eng. Des. Sel. 2010, 23, 271-8.
Atwell et al., "Stable heterodimers from remodeling the domain interface of a homodimer using a phage display library," J. Mol. Biol. 1997, 270, 26-35.
Carter et al., "High level *Escherichia coli* expression and production of a bivalent humanized antibody fragment," Biotechnology (NY) 1992, 10, 163-67.
Choe et al., "Fc-Binding ligands of immunoglobulin G: An overview of high affinity proteins and peptides," Materials (Basel) 2016, 9, 994.
Cohen et al., "Oxidation of the alarmin IL-33 regulates ST2-dependent inflammation," Nat. Commun. 2015, 6, 8327.
Dennis et al., "Albumin binding as a general strategy for improving the pharmacokinetics of proteins," J. Biol. Chem. 2002, 277, 35035-43.
Dudakov et al., "Interleukin-22: immunobiology and pathology," Annu. Rev. Immunol. 2015, 33, 747-85.
Epstein et al., "Biological activity of liposome-encapsulated murine interferon gamma is mediated by a cell membrane receptor," Proc. Natl. Acad. Sci. U.S.A. 1985, 82, 3688-92.
Firan et al., "The MHC class I-related receptor, FcRn, plays an essential role in the maternofetal transfer of gamma-globulin in humans," Int. Immunol. 2001, 13, 993-1002.
Greenberg et al., "A new antigen receptor gene family that undergoes rearrangement and extensive somatic diversification in sharks," Nature 1995, 374, 168-73.
Gunasekaran et al., "Enhancing antibody Fc heterodimer formation through electrostatic steering effects: applications to bispecific molecules and monovalent IgG," J. Biol. Chem. 2010, 285, 19637-46.
Hamers-Casterman et al., "Naturally occurring antibodies devoid of light chains," Nature 1993, 363, 446-8.
Han et al., "IL-15:IL-15 receptor alpha superagonist complex: high-level co-expression in recombinant mammalian cells, purification and characterization," Cytokine 2011, 56, 804-10.
Hassanzadeh-Ghassabeh et al., "Nanobodies and their potential applications," Nanomedicine (Lond) 2013, 8, 1013-26.
Huang et al., "A novel strategy to produce high level and high purity of bioactive IL 15 fusion proteins from mammalian cells," Protein Expr. Purif. 2018, 148, 30-9.
Hudson et al., "Engineered antibodies," Nat. Med. 2003, 9, 129-34.
Hwang et al., "Hepatic uptake and degradation of unilamellar sphingomyelin/cholesterol liposomes: a kinetic study," Proc. Natl. Acad. Sci. U.S.A. 1980, 77, 4030-4.
Kam et al., "Carbon nanotubes as multifunctional biological transporters and near-infrared agents for selective cancer cell destruction," Proc. Natl. Acad. Sci. U.S.A. 2005, 102, 11600-5.
Klein et al., "Progress in overcoming the chain association issue in bispecific heterodimeric IgG antibodies," MAbs 2012, 4, 653-63.
Leonard and Wan, "IL-21 signaling in immunity," F1000Res. 2016, 5(F1000 Faculty Rev), 224, 10 pages.
Liew et al., "Interleukin-33 in health and disease," Nat. Rev. Immunol. 2016, 16, 676-89.
Lin et al., "The role of IL-7 in immunity and cancer," Anticancer Res. 2017, 37, 963-7.
Mackall et al., "Harnessing the biology of IL-7 for therapeutic application," Nat. Rev. Immunol. 2011, 11, 330-42.

(56) References Cited

OTHER PUBLICATIONS

Merchant et al., "An efficient route to human bispecific IgG," Nat. Biotechnol. 1998, 16, 677-81.
Moore et al., "A novel bispecific antibody format enables simultaneous bivalent and monovalent co-engagement of distinct target antigens," MAbs 2011, 3, 546-57.
Nilvebrant and Hober, "The albumin-binding domain as a scaffold for protein engineering," Comput. Struct. Biotechnol. 2013, 6, e201303009.
Nygren et al., "Analysis and use of the serum albumin binding domains of streptococcal protein G," J. Mol. Recogn. 1988, 1, 69-74.
Pluckthun, Antibodies from *Escherichia coli*. In The Pharmacology of Monoclonal Antibodies; Rosenburg and Moore Eds.; Springer-Verlag: New York, 1994; vol. 113, pp. 269-315.
Ridgway et al., "'Knobs-into-holes' engineering of antibody CH3 domains for heavy chain heterodimerization," Protein Eng. 1996, 9, 617-21.
Robinson and Schluns, "The potential and promise of IL-15 in immuno-oncogenic therapies," Immunol. Lett. 2017, 159-68.
Schmidt et al., "Safety and clinical effect of subcutaneous human interleukin-21 in patients with metastatic melanoma or renal cell carcinoma: a phase I trial," Clin. Cancer Res. 2010, 16, 5312-9.
Sheriff and Constantine, "Redefining the minimal antigen-binding fragment," Nat. Struct. Biol. 1996, 3, 733-6.
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 2001, 276, 6591-604.
Sola and Griebenow, "Effects of glycosylation on the stability of protein pharmaceuticals," J. Pharm. Sci. 2009, 98, 1223-45.
Sola et al., "Modulation of protein biophysical properties by chemical glycosylation: biochemical insights and biomedical implications," Cell. Mol. Life Sci. 2007, 64, 2133-52.
Steel et al., "Interleukin-15 biology and its therapeutic implications in cancer," Trends Pharmacol. Sci 2012, 33, 35-41.
Streltsov et al., "Structural evidence for evolution of shark Ig new antigen receptor variable domain antibodies from a cell-surface receptor," Proc. Natl. Acad. Sci. U.S.A. 2004, 101, 12444-9.
Woolven et al., "The structure of the llama heavy chain constant genes reveals a mechanism for heavy-chain antibody formation," Immunogenetics 1999, 50, 98-101.
Yeung et al., "Engineering human IgG1 affinity to human neonatal Fc receptor: impact of affinity improvement on pharmacokinetics in primates," J. Immunol. 2009, 182, 7663-71.

\* cited by examiner

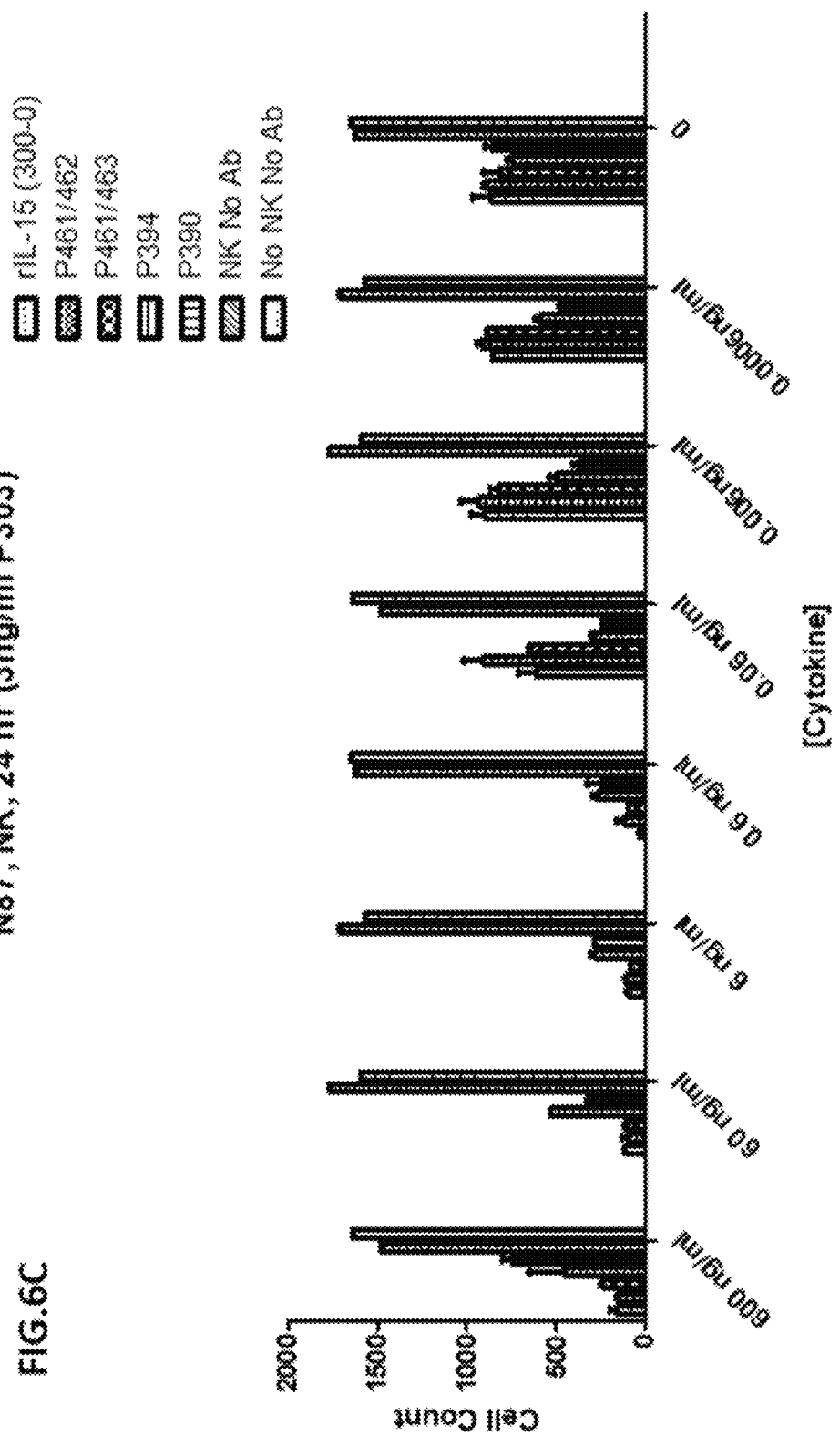

Lane 1: AWT-P394 from one-step purification
Lane 2: AWT-P394 from two-step purification
Lane 3: AWT-P593 from one-step purification
Lane 4: AWT-P593 from two-step purification

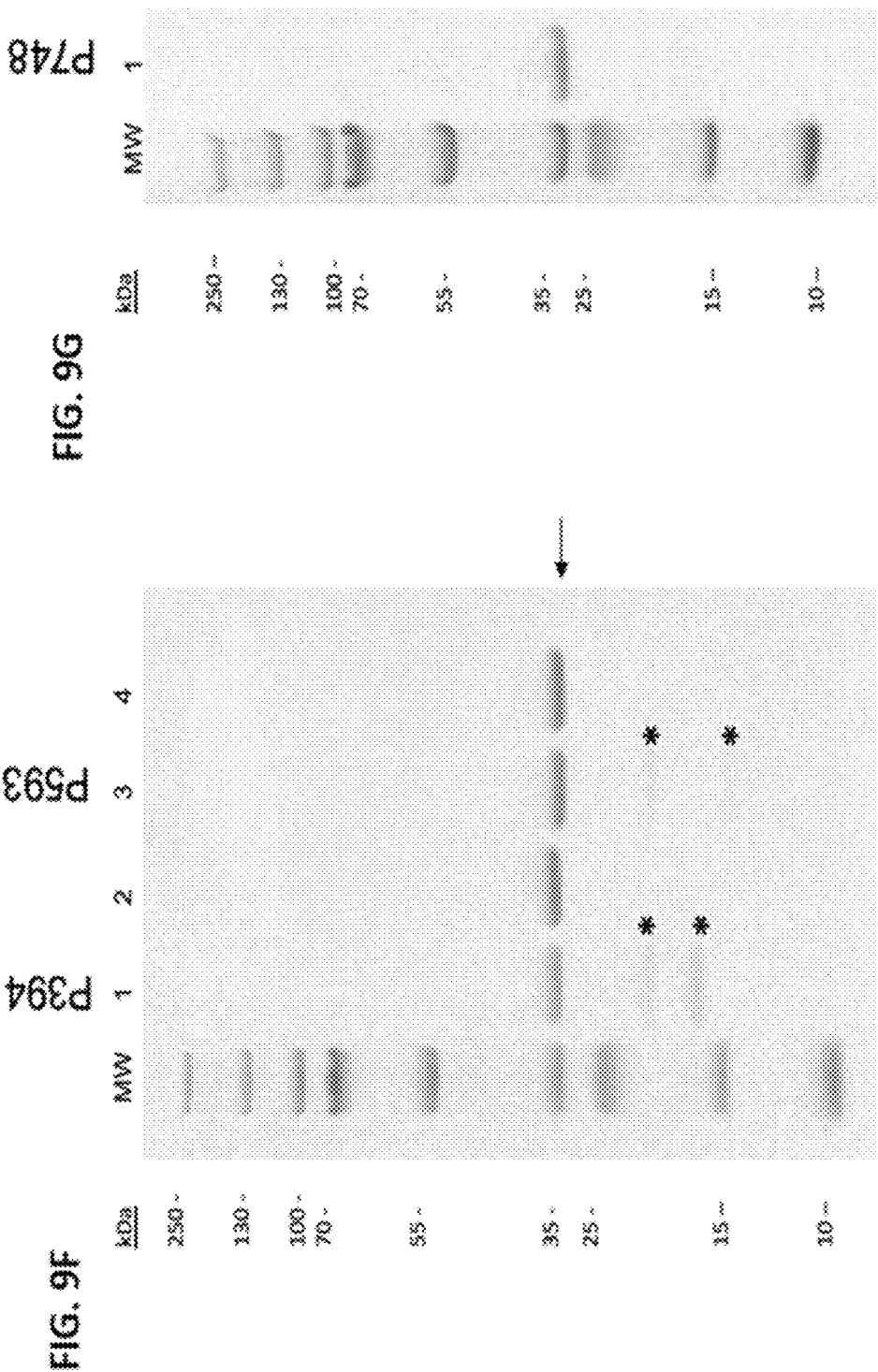

FIG. 10E

| Antibody | Antigen | $K_D$ |
|---|---|---|
| AWT-P367 | Human SA | 1.75E-08 |
| | Monkey SA | 2.79E-08 |
| | Mouse SA | 7.69E-08 |
| AWT-P494 | Human SA | 1.72E-08 |
| | Monkey SA | 1.74E-08 |
| | Mouse SA | 4.72E-08 |

IL21R+ in CD8+

IL21R+ in total CD4+

IL21R+ in NK cells

INFγ-Positive Cells in Splenocytes

SEQUENCE LISTING

```
<160> NUMBER OF SEQ ID NOS: 196

<210> SEQ ID NO 1
<211> LENGTH: 133
<212> TYPE: PRT
<213> ORGANISM: Homo sapiens

<400> SEQUENCE: 1

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130

<210> SEQ ID NO 2
<211> LENGTH: 123
<212> TYPE: PRT
<213> ORGANISM: Homo sapiens
```

<400> SEQUENCE: 2

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu
            115                 120

<210> SEQ ID NO 3
<211> LENGTH: 46
<212> TYPE: PRT
<213> ORGANISM: Artificial Sequence
<220> FEATURE:
<223> OTHER INFORMATION: Synthetic Construct

<400> SEQUENCE: 3

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 4
<211> LENGTH: 46
<212> TYPE: PRT
<213> ORGANISM: Artificial Sequence
<220> FEATURE:
<223> OTHER INFORMATION: Synthetic Construct

<400> SEQUENCE: 4

Leu Ala Glu Ala Lys Val Leu Ala Asn Arg Glu Leu Asp Lys Tyr Gly
1               5                   10                  15

Val Ser Asp Phe Ala Lys Arg Leu Ile Asn Lys Ala Lys Thr Val Glu
            20                  25                  30

Gly Val Glu Ala Leu Lys Asp Glu Ile Leu Ala Ala Leu Pro
        35                  40                  45

<210> SEQ ID NO 5
<211> LENGTH: 46
<212> TYPE: PRT
<213> ORGANISM: Artificial Sequence
<220> FEATURE:
<223> OTHER INFORMATION: Synthetic Construct

<400> SEQUENCE: 5

Leu Ala Glu Ala Lys Val Leu Ala Asn Arg Glu Leu Asp Lys Tyr Gly
1               5                   10                  15

Val Ser Asp Phe Ala Lys Arg Ala Ile Asn Lys Ala Lys Thr Val Glu

```
            20                  25                  30

Gly Val Glu Ala Leu Lys Asp Glu Ile Leu Ala Ala Leu Pro
        35                  40                  45

<210> SEQ ID NO 6
<211> LENGTH: 46
<212> TYPE: PRT
<213> ORGANISM: Artificial Sequence
<220> FEATURE:
<223> OTHER INFORMATION: Synthetic Construct

<400> SEQUENCE: 6

Leu Ala Glu Ala Lys Val Leu Ala Asn Arg Glu Leu Asp Lys Tyr Gly
1               5                   10                  15

Val Ser Asp Phe Ala Lys Arg Ala Ile Asn Lys Ala Lys Thr Val Glu
            20                  25                  30

Gly Ala Glu Ala Leu Lys Asp Glu Ile Leu Ala Ala Leu Pro
        35                  40                  45

<210> SEQ ID NO 7
<211> LENGTH: 46
<212> TYPE: PRT
<213> ORGANISM: Artificial Sequence
<220> FEATURE:
<223> OTHER INFORMATION: Synthetic Construct

<400> SEQUENCE: 7

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 8
<211> LENGTH: 46
<212> TYPE: PRT
<213> ORGANISM: Artificial Sequence
<220> FEATURE:
<223> OTHER INFORMATION: Synthetic Construct

<400> SEQUENCE: 8

Leu Ala Glu Ala Lys Val Leu Ala Asn Arg Glu Leu Asp Lys Tyr Gly
1               5                   10                  15

Val Ser Asp Tyr Ala Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 9
<211> LENGTH: 46
<212> TYPE: PRT
<213> ORGANISM: Artificial Sequence
<220> FEATURE:
<223> OTHER INFORMATION: Synthetic Construct

<400> SEQUENCE: 9

Leu Ala Glu Ala Lys Val Leu Ala Asn Arg Glu Leu Asp Lys Tyr Gly
1               5                   10                  15

Val Ala Asp Ala Tyr Ala Asn Leu Ile Asn Asn Ala Lys Thr Val Glu
            20                  25                  30

Gly Val Lys Ala Leu Ile Asp Glu Ile Leu Ala Ala Leu Pro
```

```
<210> SEQ ID NO 10
<211> LENGTH: 45
<212> TYPE: PRT
<213> ORGANISM: Artificial Sequence
<220> FEATURE:
<223> OTHER INFORMATION: Synthetic Construct

<400> SEQUENCE: 10

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Ala Leu Lys Asp Glu Ile Leu Lys Ala
        35                  40                  45

<210> SEQ ID NO 11
<211> LENGTH: 51
<212> TYPE: PRT
<213> ORGANISM: Artificial Sequence
<220> FEATURE:
<223> OTHER INFORMATION: Synthetic Construct

<400> SEQUENCE: 11

Thr Ile Asp Glu Trp Leu Leu Lys Glu Ala Lys Glu Lys Ala Ile Glu
1               5                   10                  15

Glu Leu Lys Lys Ala Gly Ile Thr Ser Asp Tyr Tyr Phe Asp Leu Ile
            20                  25                  30

Asn Lys Ala Lys Thr Val Glu Gly Val Asn Ala Leu Lys Asp Glu Ile
        35                  40                  45

Leu Lys Ala
    50

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(3)
<223> OTHER INFORMATION: Can be present in repeats of up to 6
<220> FEATURE:
<221> NAME/KEY: VARIANT
<222> LOCATION: (1)..(3)
<223> OTHER INFORMATION: Can be present in repeats of up to 5

<400> SEQUENCE: 12

Gly Ser Gly Gly Ser Gly
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 6

<400> SEQUENCE: 13

Gly Gly Gly Ser
```

```
<210> SEQ ID NO 14
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of up to 6

<400> SEQUENCE: 14

Gly Gly Gly Gly Ser
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of up to 6

<400> SEQUENCE: 15

Glu Ala Ala Ala Lys Ala
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeats of up to 6

<400> SEQUENCE: 16

Pro Ala Pro Ala Pro
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ile Lys Arg Thr Val Ala Ala Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Arg Ala Lys Pro Ser
1               5
```

```
<210> SEQ ID NO 19
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 4

<400> SEQUENCE: 19

Gly Ser Gly Ser
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 4

<400> SEQUENCE: 20

Gly Gly Ser Gly
1

<210> SEQ ID NO 21
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 3

<400> SEQUENCE: 21

Pro Ala Pro Ala
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(4)
<223> OTHER INFORMATION: Can be present in repeats of up to 3

<400> SEQUENCE: 22

Pro Gln Pro Gln
1

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Ile Lys Arg Ala Asp Ala Ala Pro
```

```
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic Construct

<400> SEQUENCE: 24

Ala Glu Ala Ala Ala Lys Glu Ala Ala Ala Lys Ala
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Construct

<400> SEQUENCE: 25

Gly Thr Asn Glu Val Cys Lys Cys Pro Lys Cys Pro
1               5                   10

<210> SEQ ID NO 26
<211> LENGTH: 35
<212> TYPE: PRT
<213> ORGANISM: Artificial Sequence
<220> FEATURE:
<223> OTHER INFORMATION: Synthetic Construct

<400> SEQUENCE: 26

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Cys Thr Cys Pro
            20                  25                  30

Lys Cys Pro
        35

<210> SEQ ID NO 27
<211> LENGTH: 28
<212> TYPE: PRT
<213> ORGANISM: Artificial Sequence
<220> FEATURE:
<223> OTHER INFORMATION: Synthetic Construct

<400> SEQUENCE: 27

Arg Arg Lys Arg Ala Pro Val Lys Gln Thr Leu Asn Phe Asp Leu Leu
1               5                   10                  15

Lys Leu Ala Gly Asp Val Glu Ser Asn Pro Gly Pro
            20                  25

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct

<400> SEQUENCE: 28

Ser Gly Arg Ser Ala
1               5

<210> SEQ ID NO 29
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 29

Pro Val Gly Leu Ile Gly
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Lys Gly Pro Gln Gly Ile Ala Gly Gln
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Phe Gly Pro Gln Gly Leu Ala Gly Gln
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Arg Gly Pro Gln Gly Ile Phe Gly Gln
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Ile Gly Pro Gln Gly Ile Trp Gly Gln
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Met Gly Pro Gln Gly Ile Leu Gly Gln
1               5

<210> SEQ ID NO 35
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 35

Lys Gly Pro Gln Ser Ile Ala Gly Gln
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Phe Gly Pro Gln Ser Leu Ala Gly Gln
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

Arg Gly Pro Gln Ser Ile Phe Gly Gln
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Ile Gly Pro Gln Ser Ile Trp Gly Gln
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Met Gly Pro Gln Ser Ile Leu Gly Gln
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

Lys Gly Pro Gln Thr Ile Ala Gly Gln
1               5

<210> SEQ ID NO 41
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 41

Phe Gly Pro Gln Thr Leu Ala Gly Gln
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Arg Gly Pro Gln Thr Ile Phe Gly Gln
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Ile Gly Pro Gln Thr Ile Trp Gly Gln
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Phe Arg Pro Arg Ser Ile Thr Gly Gln
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Met Gly Pro Gln Thr Ile Leu Gly Gln
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Construct

<400> SEQUENCE: 46

Gly Ile Thr Phe Pro Val Asn Ala
1               5

<210> SEQ ID NO 47
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 47

Ile Ser Ala Gly Gly Thr Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Gln Arg Arg Ile Gly Met Leu Arg Asp Tyr
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Gly Arg Thr Leu Glu Ser Tyr Val
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Ile Asn Trp Ser Ser Gly Arg Leu
1               5

<210> SEQ ID NO 51
<211> LENGTH: 50
<212> TYPE: PRT
<213> ORGANISM: Artificial Sequence
<220> FEATURE:
<223> OTHER INFORMATION: Synthetic Construct

<400> SEQUENCE: 51

Val Gln Lys Leu Leu Gly Pro His Val Glu Gly Leu Lys Ala Glu Glu
1               5                   10                  15

Arg His Arg Pro Val Arg Asp Trp Ile Leu Arg Gln Arg Gln Asp Asp
                20                  25                  30

Leu Asp Thr Leu Gly Leu Gly Leu Gln Gly Gly Ile Pro Asn Gly Tyr
            35                  40                  45

Leu Val
    50

<210> SEQ ID NO 52
<211> LENGTH: 609
<212> TYPE: PRT
<213> ORGANISM: Homo sapiens

<400> SEQUENCE: 52

Met Lys Trp Val Thr Phe Ile Ser Leu Leu Phe Leu Phe Ser Ser Ala
1               5                   10                  15
```

-continued

```
Tyr Ser Arg Gly Val Phe Arg Arg Asp Ala His Lys Ser Glu Val Ala
             20                  25                  30

His Arg Phe Lys Asp Leu Gly Glu Glu Asn Phe Lys Ala Leu Val Leu
         35                  40                  45

Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
             85                  90                  95

Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
```

```
                435                 440                 445
Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 53
<211> LENGTH: 417
<212> TYPE: PRT
<213> ORGANISM: Homo sapiens

<400> SEQUENCE: 53

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Trp Ala Val
        35                  40                  45

Ala Arg Leu Ser Gln Arg Phe Pro Lys Ala Glu Phe Ala Glu Val Ser
    50                  55                  60

Lys Leu Val Thr Asp Leu Thr Lys Val His Thr Glu Cys Cys His Gly
65                  70                  75                  80

Asp Leu Leu Glu Cys Ala Asp Asp Arg Ala Asp Leu Ala Lys Tyr Ile
                85                  90                  95

Cys Glu Asn Gln Asp Ser Ile Ser Ser Lys Leu Lys Glu Cys Cys Glu
            100                 105                 110

Lys Pro Leu Leu Glu Lys Ser His Cys Ile Ala Glu Val Glu Asn Asp
        115                 120                 125

Glu Met Pro Ala Asp Leu Pro Ser Leu Ala Ala Asp Phe Val Glu Ser
    130                 135                 140

Lys Asp Val Cys Lys Asn Tyr Ala Glu Ala Lys Asp Val Phe Leu Gly
145                 150                 155                 160

Met Phe Leu Tyr Glu Tyr Ala Arg Arg His Pro Asp Tyr Ser Val Val
                165                 170                 175

Leu Leu Leu Arg Leu Ala Lys Thr Tyr Glu Thr Thr Leu Glu Lys Cys
            180                 185                 190

Cys Ala Ala Ala Asp Pro His Glu Cys Tyr Ala Lys Val Phe Asp Glu
```

```
            195                 200                 205
Phe Lys Pro Leu Val Glu Glu Pro Gln Asn Leu Ile Lys Gln Asn Cys
210                 215                 220

Glu Leu Phe Glu Gln Leu Gly Glu Tyr Lys Phe Gln Asn Ala Leu Leu
225                 230                 235                 240

Val Arg Tyr Thr Lys Lys Val Pro Gln Val Ser Thr Pro Thr Leu Val
                245                 250                 255

Glu Val Ser Arg Asn Leu Gly Lys Val Gly Ser Lys Cys Cys Lys His
                260                 265                 270

Pro Glu Ala Lys Arg Met Pro Cys Ala Glu Asp Tyr Leu Ser Val Val
                275                 280                 285

Leu Asn Gln Leu Cys Val Leu His Glu Lys Thr Pro Val Ser Asp Arg
290                 295                 300

Val Thr Lys Cys Cys Thr Glu Ser Leu Val Asn Arg Arg Pro Cys Phe
305                 310                 315                 320

Ser Ala Leu Glu Val Asp Glu Thr Tyr Val Pro Lys Glu Phe Asn Ala
                325                 330                 335

Glu Thr Phe Thr Phe His Ala Asp Ile Cys Thr Leu Ser Glu Lys Glu
                340                 345                 350

Arg Gln Ile Lys Lys Gln Thr Ala Leu Val Glu Leu Val Lys His Lys
                355                 360                 365

Pro Lys Ala Thr Lys Glu Gln Leu Lys Ala Val Met Asp Asp Phe Ala
                370                 375                 380

Ala Phe Val Glu Lys Cys Cys Lys Ala Asp Asp Lys Glu Thr Cys Phe
385                 390                 395                 400

Ala Glu Glu Gly Lys Lys Leu Val Ala Ala Ser Gln Ala Ala Leu Gly
                405                 410                 415

Leu

<210> SEQ ID NO 54
<211> LENGTH: 396
<212> TYPE: PRT
<213> ORGANISM: Homo sapiens

<400> SEQUENCE: 54

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
                100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
```

```
            145                 150                 155                 160
    Lys Tyr Leu Tyr Glu Thr Thr Leu Glu Lys Cys Cys Ala Ala Ala Asp
                        165                 170                 175

Pro His Glu Cys Tyr Ala Lys Val Phe Asp Glu Phe Lys Pro Leu Val
                        180                 185                 190

Glu Glu Pro Gln Asn Leu Ile Lys Gln Asn Cys Glu Leu Phe Glu Gln
                        195                 200                 205

Leu Gly Glu Tyr Lys Phe Gln Asn Ala Leu Leu Val Arg Tyr Thr Lys
                210                 215                 220

Lys Val Pro Gln Val Ser Thr Pro Thr Leu Val Glu Val Ser Arg Asn
    225                 230                 235                 240

Leu Gly Lys Val Gly Ser Lys Cys Cys Lys His Pro Glu Ala Lys Arg
                        245                 250                 255

Met Pro Cys Ala Glu Asp Tyr Leu Ser Val Val Leu Asn Gln Leu Cys
                        260                 265                 270

Val Leu His Glu Lys Thr Pro Val Ser Asp Arg Val Thr Lys Cys Cys
                        275                 280                 285

Thr Glu Ser Leu Val Asn Arg Arg Pro Cys Phe Ser Ala Leu Glu Val
                        290                 295                 300

Asp Glu Thr Tyr Val Pro Lys Glu Phe Asn Ala Glu Thr Phe Thr Phe
    305                 310                 315                 320

His Ala Asp Ile Cys Thr Leu Ser Glu Lys Glu Arg Gln Ile Lys Lys
                        325                 330                 335

Gln Thr Ala Leu Val Glu Leu Val Lys His Lys Pro Lys Ala Thr Lys
                        340                 345                 350

Glu Gln Leu Lys Ala Val Met Asp Asp Phe Ala Ala Phe Val Glu Lys
                        355                 360                 365

Cys Cys Lys Ala Asp Asp Lys Glu Thr Cys Phe Ala Glu Glu Gly Lys
                        370                 375                 380

Lys Leu Val Ala Ala Ser Gln Ala Ala Leu Gly Leu
    385                 390                 395

<210> SEQ ID NO 55
<211> LENGTH: 585
<212> TYPE: PRT
<213> ORGANISM: Homo sapiens

<400> SEQUENCE: 55

Asp Ala His Lys Ser Glu Val Ala His Arg Phe Lys Asp Leu Gly Glu
    1               5                   10                  15

Glu Asn Phe Lys Ala Leu Val Leu Ile Ala Phe Ala Gln Tyr Leu Gln
                        20                  25                  30

Gln Cys Pro Phe Glu Asp His Val Lys Leu Val Asn Glu Val Thr Glu
                        35                  40                  45

Phe Ala Lys Thr Cys Val Ala Asp Glu Ser Ala Glu Asn Cys Asp Lys
                50                  55                  60

Ser Leu His Thr Leu Phe Gly Asp Lys Leu Cys Thr Val Ala Thr Leu
    65                  70                  75                  80

Arg Glu Thr Tyr Gly Glu Met Ala Asp Cys Cys Ala Lys Gln Glu Pro
                        85                  90                  95

Glu Arg Asn Glu Cys Phe Leu Gln His Lys Asp Asp Asn Pro Asn Leu
                        100                 105                 110

Pro Arg Leu Val Arg Pro Glu Val Asp Val Met Cys Thr Ala Phe His
                        115                 120                 125
```

-continued

```
Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Gly Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Gly Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Cys Leu Ser Val Phe Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Gly Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
```

```
                545                 550                 555                 560
Ala Asp Asp Lys Glu Thr Cys Phe Ala Glu Glu Gly Lys Lys Leu Val
                    565                 570                 575
Ala Ala Ser Gln Ala Ala Leu Gly Leu
            580                 585

<210> SEQ ID NO 56
<211> LENGTH: 630
<212> TYPE: PRT
<213> ORGANISM: Homo sapiens

<400> SEQUENCE: 56

Met Ala Leu Pro Thr Ala Arg Pro Leu Leu Gly Ser Cys Gly Thr Pro
1               5                   10                  15
Ala Leu Gly Ser Leu Leu Phe Leu Leu Phe Ser Leu Gly Trp Val Gln
            20                  25                  30
Pro Ser Arg Thr Leu Ala Gly Glu Thr Gly Gln Glu Ala Ala Pro Leu
        35                  40                  45
Asp Gly Val Leu Ala Asn Pro Pro Asn Ile Ser Ser Leu Ser Pro Arg
    50                  55                  60
Gln Leu Leu Gly Phe Pro Cys Ala Glu Val Ser Gly Leu Ser Thr Glu
65                  70                  75                  80
Arg Val Arg Glu Leu Ala Val Ala Leu Ala Gln Lys Asn Val Lys Leu
                85                  90                  95
Ser Thr Glu Gln Leu Arg Cys Leu Ala His Arg Leu Ser Glu Pro Pro
            100                 105                 110
Glu Asp Leu Asp Ala Leu Pro Leu Asp Leu Leu Leu Phe Leu Asn Pro
        115                 120                 125
Asp Ala Phe Ser Gly Pro Gln Ala Cys Thr Arg Phe Phe Ser Arg Ile
    130                 135                 140
Thr Lys Ala Asn Val Asp Leu Leu Pro Arg Gly Ala Pro Glu Arg Gln
145                 150                 155                 160
Arg Leu Leu Pro Ala Ala Leu Ala Cys Trp Gly Val Arg Gly Ser Leu
                165                 170                 175
Leu Ser Glu Ala Asp Val Arg Ala Leu Gly Gly Leu Ala Cys Asp Leu
            180                 185                 190
Pro Gly Arg Phe Val Ala Glu Ser Ala Glu Val Leu Leu Pro Arg Leu
        195                 200                 205
Val Ser Cys Pro Gly Pro Leu Asp Gln Asp Gln Gln Glu Ala Ala Arg
    210                 215                 220
Ala Ala Leu Gln Gly Gly Gly Pro Pro Tyr Gly Pro Pro Ser Thr Trp
225                 230                 235                 240
Ser Val Ser Thr Met Asp Ala Leu Arg Gly Leu Leu Pro Val Leu Gly
                245                 250                 255
Gln Pro Ile Ile Arg Ser Ile Pro Gln Gly Ile Val Ala Ala Trp Arg
            260                 265                 270
Gln Arg Ser Ser Arg Asp Pro Ser Trp Arg Gln Pro Glu Arg Thr Ile
        275                 280                 285
Leu Arg Pro Arg Phe Arg Arg Glu Val Glu Lys Thr Ala Cys Pro Ser
    290                 295                 300
Gly Lys Lys Ala Arg Glu Ile Asp Glu Ser Leu Ile Phe Tyr Lys Lys
305                 310                 315                 320
Trp Glu Leu Glu Ala Cys Val Asp Ala Ala Leu Leu Ala Thr Gln Met
                325                 330                 335
```

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
        370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630

<210> SEQ ID NO 57
<211> LENGTH: 630
<212> TYPE: PRT
<213> ORGANISM: Homo sapiens

<400> SEQUENCE: 57

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

```
Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495
```

-continued

```
Gly Ser Glu Tyr Phe Val Lys Ile Gln Ser Phe Leu Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630

<210> SEQ ID NO 58
<211> LENGTH: 656
<212> TYPE: PRT
<213> ORGANISM: Homo sapiens

<400> SEQUENCE: 58

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240
```

-continued

Ser Val Ser Thr Met Asp Ala Leu Arg Gly Leu Leu Pro Val Leu Gly
            245                 250                 255

Gln Pro Ile Ile Arg Ser Ile Pro Gln Gly Ile Val Ala Ala Trp Arg
        260                 265                 270

Gln Arg Ser Ser Arg Asp Pro Ser Trp Arg Gln Pro Glu Arg Thr Ile
    275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Gly Gly Arg Gly Gly Gln Ala Arg Ala Gly Arg Ala Gly
        595                 600                 605

Gly Val Glu Val Gly Ala Leu Ser His Pro Ser Leu Cys Arg Gly Pro
    610                 615                 620

Leu Gly Asp Ala Leu Pro Pro Arg Thr Trp Thr Cys Ser His Arg Pro
625                 630                 635                 640

Gly Thr Ala Pro Ser Leu His Pro Gly Leu Arg Ala Pro Leu Pro Cys
                645                 650                 655

-continued

```
<210> SEQ ID NO 59
<211> LENGTH: 621
<212> TYPE: PRT
<213> ORGANISM: Homo sapiens

<400> SEQUENCE: 59
```

| | | | | | | | | | | | | | | |
|---|---|---|---|---|---|---|---|---|---|---|---|---|---|---|
| Met | Ala | Leu | Pro | Thr | Ala | Arg | Pro | Leu | Leu | Gly | Ser | Cys | Gly | Thr | Pro |
| 1 | | | | 5 | | | | | 10 | | | | | 15 |

Ala Leu Gly Ser Leu Leu Phe Leu Phe Ser Leu Gly Trp Val Gln
                20                  25                  30

Pro Ser Arg Thr Leu Ala Gly Glu Thr Gly Gln Ala Ala Pro Leu Asp
            35                  40                  45

Gly Val Leu Ala Asn Pro Pro Asn Ile Ser Ser Leu Ser Pro Arg Gln
 50                  55                  60

Leu Leu Gly Phe Pro Cys Ala Glu Val Ser Gly Leu Ser Thr Glu Arg
 65                  70                  75                  80

Val Arg Glu Leu Ala Val Ala Leu Ala Gln Lys Asn Val Lys Leu Ser
                 85                  90                  95

Thr Glu Gln Leu Arg Cys Leu Ala His Arg Leu Ser Glu Pro Pro Glu
            100                 105                 110

Asp Leu Asp Ala Leu Pro Leu Asp Leu Leu Leu Phe Leu Asn Pro Asp
        115                 120                 125

Ala Phe Ser Gly Pro Gln Ala Cys Thr Arg Phe Phe Ser Arg Ile Thr
130                 135                 140

Lys Ala Asn Val Asp Leu Leu Pro Arg Gly Ala Pro Glu Arg Gln Arg
145                 150                 155                 160

Leu Leu Pro Ala Ala Leu Ala Cys Trp Gly Val Arg Gly Ser Leu Leu
                165                 170                 175

Ser Glu Ala Asp Val Arg Ala Leu Gly Gly Leu Ala Cys Asp Leu Pro
            180                 185                 190

Gly Arg Phe Val Ala Glu Ser Ala Glu Val Leu Leu Pro Arg Leu Val
        195                 200                 205

Ser Cys Pro Gly Pro Leu Asp Gln Asp Gln Gln Glu Ala Ala Arg Ala
210                 215                 220

Ala Leu Gln Gly Gly Gly Pro Pro Tyr Gly Pro Ser Thr Trp Ser
225                 230                 235                 240

Val Ser Thr Met Asp Ala Leu Arg Gly Leu Leu Pro Val Leu Gly Gln
                245                 250                 255

Pro Ile Ile Arg Ser Ile Pro Gln Gly Ile Val Ala Ala Trp Arg Gln
            260                 265                 270

Arg Ser Ser Arg Asp Pro Ser Trp Arg Gln Pro Glu Arg Thr Ile Leu
        275                 280                 285

Arg Pro Arg Phe Arg Arg Glu Val Glu Lys Thr Ala Cys Pro Ser Gly
290                 295                 300

Lys Lys Ala Arg Glu Ile Asp Glu Ser Leu Ile Phe Tyr Lys Lys Trp
305                 310                 315                 320

Glu Leu Glu Ala Cys Val Asp Ala Ala Leu Leu Ala Thr Gln Met Asp
                325                 330                 335

Arg Val Asn Ala Ile Pro Phe Thr Tyr Glu Gln Leu Asp Val Leu Lys
            340                 345                 350

His Lys Leu Asp Glu Leu Tyr Pro Gln Gly Tyr Pro Glu Ser Val Ile
        355                 360                 365

Gln His Leu Gly Tyr Leu Phe Leu Lys Met Ser Pro Glu Asp Ile Arg
370                 375                 380

```
Lys Trp Asn Val Thr Ser Leu Glu Thr Leu Lys Ala Leu Leu Glu Val
385                 390                 395                 400

Asn Lys Gly His Glu Met Ser Pro Gln Val Ala Thr Leu Ile Asp Arg
            405                 410                 415

Phe Val Lys Gly Arg Gly Gln Leu Asp Lys Asp Thr Leu Asp Thr Leu
        420                 425                 430

Thr Ala Phe Tyr Pro Gly Tyr Leu Cys Ser Leu Ser Pro Glu Glu Leu
        435                 440                 445

Ser Ser Val Pro Pro Ser Ser Ile Trp Ala Val Arg Pro Gln Asp Leu
    450                 455                 460

Asp Thr Cys Asp Pro Arg Gln Leu Asp Val Leu Tyr Pro Lys Ala Arg
465                 470                 475                 480

Leu Ala Phe Gln Asn Met Asn Gly Ser Glu Tyr Phe Val Lys Ile Gln
            485                 490                 495

Ser Phe Leu Gly Gly Ala Pro Thr Glu Asp Leu Lys Ala Leu Ser Gln
            500                 505                 510

Gln Asn Val Ser Met Asp Leu Ala Thr Phe Met Lys Leu Arg Thr Asp
        515                 520                 525

Ala Val Leu Pro Leu Thr Val Ala Glu Val Gln Lys Leu Leu Gly Pro
    530                 535                 540

His Val Glu Gly Leu Lys Ala Glu Glu Arg His Arg Pro Val Arg Asp
545                 550                 555                 560

Trp Ile Leu Arg Gln Arg Gln Asp Asp Leu Asp Thr Leu Gly Leu Gly
            565                 570                 575

Leu Gln Gly Gly Ile Pro Asn Gly Tyr Leu Val Leu Asp Leu Ser Met
            580                 585                 590

Gln Glu Ala Leu Ser Gly Thr Pro Cys Leu Leu Gly Pro Gly Pro Val
        595                 600                 605

Leu Thr Val Leu Ala Leu Leu Leu Ala Ser Thr Leu Ala
    610                 615                 620

<210> SEQ ID NO 60
<211> LENGTH: 124
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Thr Tyr
            20                  25                  30

Ala Met Gly Trp Phe Arg Gln Pro Pro Gly Lys Glu Arg Glu Phe Val
        35                  40                  45

Ala Ser Ile Asn Arg Ser Gly Asp Ser Thr Tyr Tyr Ala Asp Ser Val
    50                  55                  60

Lys Gly Arg Phe Thr Ile Ser Arg Asp Asn Ala Lys Asn Thr Gly Tyr
65                  70                  75                  80

Leu Gln Met Ser Ser Leu Lys Pro Glu Asp Thr Ala Val Tyr Tyr Cys
            85                  90                  95

Ala Ala Asp Ser Asp Gly Ile Gly Trp Phe Asn Ser Phe Glu Tyr Asp
            100                 105                 110

Tyr Trp Gly Arg Gly Thr Gln Val Thr Val Ser Ser
        115                 120
```

<210> SEQ ID NO 61
<211> LENGTH: 125
<212> TYPE: PRT
<213> ORGANISM: Artificial Sequence
<220> FEATURE:
<223> OTHER INFORMATION: Synthetic Construct

<400> SEQUENCE: 61

```
Gln Val Gln Leu Val Glu Ser Gly Gly Gly Leu Val Gln Ala Gly Gly
1               5                   10                  15
Ser Leu Arg Leu Ser Cys Ala Ala Ser Gly Arg Ser Val Ser Leu Tyr
            20                  25                  30
His Val Gly Trp Phe Arg His Thr Pro Gly Lys Glu Arg Glu Phe Val
        35                  40                  45
Ala Ala Thr Ala Trp His Asp Gly Ser Thr Ser Tyr Ala Asp Ser Val
    50                  55                  60
Lys Gly Arg Phe Thr Ile Ser Arg Asn Asn Ala Lys Asn Thr Val Tyr
65                  70                  75                  80
Leu Gln Met Asn Ser Leu Gln Pro Glu Asp Thr Ala Val Tyr Tyr Cys
                85                  90                  95
Ala Gly Glu Ala Lys Leu Gly Gly Ile Tyr Ser Arg Trp Arg Asp Tyr
            100                 105                 110
Glu Tyr Trp Gly Gln Gly Thr Gln Val Thr Val Ser Ser
        115                 120                 125
```

<210> SEQ ID NO 62
<211> LENGTH: 124
<212> TYPE: PRT
<213> ORGANISM: Artificial Sequence
<220> FEATURE:
<223> OTHER INFORMATION: Synthetic Construct

<400> SEQUENCE: 62

```
Gln Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Ser Ile Tyr
            20                  25                  30
Asp Met Gly Trp Phe Arg Gln Ala Pro Gly Lys Glu Arg Glu Phe Val
        35                  40                  45
Ala Ala Thr Asn Leu Arg Gly Val Ser Thr Arg Tyr Ala Asp Ser Val
    50                  55                  60
Lys Gly Arg Phe Thr Ile Ser Gly Asp Asn Ala Lys Asn Thr Val Ser
65                  70                  75                  80
Leu Gln Met Asn Ser Leu Ile Pro Glu Asp Thr Ala Val Tyr Tyr Cys
                85                  90                  95
Ala Ala Ala Val Ser Asn Trp Leu Ala Lys Asp Pro Ser Ala Tyr Ser
            100                 105                 110
Tyr Trp Gly Gln Gly Thr Gln Val Thr Val Ser Ser
        115                 120
```

<210> SEQ ID NO 63
<211> LENGTH: 124
<212> TYPE: PRT
<213> ORGANISM: Artificial Sequence
<220> FEATURE:
<223> OTHER INFORMATION: Synthetic Construct

<400> SEQUENCE: 63

-continued

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Thr Tyr
            20                  25                  30

Ala Met Gly Trp Phe Arg Gln Pro Pro Gly Lys Glu Arg Glu Phe Val
        35                  40                  45

Ala Ser Ile Asn Arg Ser Gly Asp Ser Thr Tyr Tyr Ala Asp Ser Val
    50                  55                  60

Lys Gly Arg Phe Thr Ile Ser Arg Asp Asp Ala Lys Asn Met Gly Tyr
65                  70                  75                  80

Leu Gln Met Ser Ser Leu Lys Pro Glu Asp Thr Ala Val Tyr Tyr Cys
                85                  90                  95

Ala Ala Asp Ser Asp Gly Ile Gly Trp Phe Asn Ser Phe Glu Tyr Asp
            100                 105                 110

Tyr Trp Gly Arg Gly Thr Gln Val Thr Val Ser Ser
        115                 120

<210> SEQ ID NO 64
<211> LENGTH: 124
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Pro Ile Phe Ser Thr Tyr
            20                  25                  30

Ala Met Gly Trp Phe Arg Gln Pro Pro Gly Lys Glu Arg Glu Phe Val
        35                  40                  45

Ala Ser Ile Asn Arg Ser Gly Asp Ser Thr Tyr Tyr Ala Asp Ser Val
    50                  55                  60

Lys Gly Arg Phe Thr Ile Ser Arg Asp Asn Ala Lys Asn Thr Gly Tyr
65                  70                  75                  80

Leu Gln Met Ser Ser Leu Lys Pro Glu Asp Thr Ala Val Tyr Tyr Cys
                85                  90                  95

Ala Ala Asp Ser Asp Gly Ile Gly Trp Phe Asn Ser Phe Glu Tyr Asp
            100                 105                 110

Tyr Trp Gly Arg Gly Thr Gln Val Thr Val Ser Ser
        115                 120

<210> SEQ ID NO 65
<211> LENGTH: 125
<212> TYPE: PRT
<213> ORGANISM: Artificial Sequence
<220> FEATURE:
<223> OTHER INFORMATION: Synthetic Construct

<400> SEQUENCE: 65

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Val Ser Leu Tyr
            20                  25                  30

His Val Gly Trp Phe Arg His Thr Pro Gly Lys Glu Arg Glu Phe Val
        35                  40                  45

Ala Ala Thr Ala Trp His Asp Gly Ser Thr Ser Tyr Ala Asp Ser Val
    50                  55                  60

```
Lys Gly Arg Phe Thr Ile Ser Arg Asn Asn Ala Lys Asn Thr Val Tyr
 65                  70                  75                  80

Leu Gln Met Asn Ser Leu Gln Pro Glu Asp Thr Ala Val Tyr Tyr Cys
                 85                  90                  95

Ala Gly Glu Ala Lys Leu Gly Gly Ile Tyr Ser Arg Trp Arg Asp Tyr
            100                 105                 110

Glu Tyr Trp Gly Gln Gly Thr Gln Val Thr Val Ser Ser
        115                 120                 125

<210> SEQ ID NO 66
<211> LENGTH: 123
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Ser Val Ser Leu Tyr
                 20                  25                  30

His Val Gly Trp Phe Arg His Thr Pro Gly Lys Glu Arg Glu Phe Val
            35                  40                  45

Ala Ala Thr Ala Trp His Asp Gly Ser Thr Ser Tyr Ala Asp Ser Val
 50                  55                  60

Lys Gly Arg Phe Thr Ile Ser Arg Asp Ser Ala Lys Asn Thr Val Phe
 65                  70                  75                  80

Leu Gln Met Ser Ser Leu Gln Pro Glu Asp Thr Ala Val Tyr Tyr Cys
                 85                  90                  95

Ala Ala Asp Pro Gly Gly Ser Ser Trp Ser Gln Pro Trp Tyr Asp Tyr
            100                 105                 110

Trp Gly Gln Gly Thr Gln Val Thr Val Ser Ser
        115                 120

<210> SEQ ID NO 67
<211> LENGTH: 116
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Val Glu Ser Gly Gly Gly Leu Val Gln Pro Gly Gly
 1               5                  10                  15

Ser Leu Arg Leu Ser Cys Ala Ala Ser Gly Ser Thr Trp Ser Ile Asn
                 20                  25                  30

Thr Leu Ala Trp Tyr Arg Gln Ala Pro Gly Lys Gln Arg Asp Leu Val
            35                  40                  45

Ala Arg Ile Ser Ser Gly Gly Ser Thr His Tyr Ala Asp Ser Val Lys
 50                  55                  60

Gly Arg Phe Thr Val Ser Arg Asp Asn Ala Glu Asn Thr Leu Val Leu
 65                  70                  75                  80

Gln Met Asn Ser Leu Lys Pro Glu Asp Thr Ala Val Tyr Tyr Cys Tyr
                 85                  90                  95

Ala Gln Ser Thr Trp Tyr Pro Pro Ser Trp Gly Gln Gly Thr Gln Val
            100                 105                 110

Thr Val Ser Ser
```

<210> SEQ ID NO 68
<211> LENGTH: 122
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Asp
            20                  25                  30

Ala Met Gly Trp Phe Arg Gln Ala Pro Gly Lys Glu Arg Val Phe Val
        35                  40                  45

Ala Thr Ile Ser Trp Lys Ser Ser Thr Tyr Tyr Ala Asp Ser Val Lys
    50                  55                  60

Gly Arg Phe Thr Ile Ser Arg Asp His Ala Lys Asn Thr Val Tyr Leu
65                  70                  75                  80

Gln Met Asn Asn Leu Lys Pro Glu Asp Thr Ala Val Tyr Tyr Cys Val
                85                  90                  95

Ala Asp Pro Tyr Gly Leu Gly Phe Asn Pro Ser Asp Tyr Asp Tyr Trp
            100                 105                 110

Gly Gln Gly Thr Gln Val Thr Val Ser Ser
        115                 120

<210> SEQ ID NO 69
<211> LENGTH: 8
<212> TYPE: PRT
<213> ORGANISM: Artificial Sequence
<220> FEATURE:
<223> OTHER INFORMATION: Synthetic Construct

<400> SEQUENCE: 69

Gly Arg Ile Phe Ser Thr Tyr Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Construct

<400> SEQUENCE: 70

Ile Asn Arg Ser Gly Asp Ser Thr
1               5

<210> SEQ ID NO 71
<211> LENGTH: 17
<212> TYPE: PRT
<213> ORGANISM: Artificial Sequence
<220> FEATURE:
<223> OTHER INFORMATION: Synthetic Construct

<400> SEQUENCE: 71

Ala Ala Asp Ser Asp Gly Ile Gly Trp Phe Asn Ser Phe Glu Tyr Asp
1               5                   10                  15

Tyr

<210> SEQ ID NO 72

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 72

Gly Arg Ser Val Ser Leu Tyr His
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Construct

<400> SEQUENCE: 73

Thr Ala Trp His Asp Gly Ser Thr
1               5

<210> SEQ ID NO 74
<211> LENGTH: 18
<212> TYPE: PRT
<213> ORGANISM: Artificial Sequence
<220> FEATURE:
<223> OTHER INFORMATION: Synthetic Construct

<400> SEQUENCE: 74

Ala Gly Glu Ala Lys Leu Gly Gly Ile Tyr Ser Arg Trp Arg Asp Tyr
1               5                   10                  15

Glu Tyr

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Gly Arg Thr Phe Ser Ile Tyr Asp
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

Thr Asn Leu Arg Gly Val Ser Thr
1               5

<210> SEQ ID NO 77
<211> LENGTH: 16
<212> TYPE: PRT
<213> ORGANISM: Artificial Sequence
<220> FEATURE:
<223> OTHER INFORMATION: Synthetic Construct

<400> SEQUENCE: 77

Ala Ala Ala Val Ser Asn Trp Leu Ala Lys Asp Pro Ser Ala Tyr Ser
1               5                   10                  15
```

<210> SEQ ID NO 78
<211> LENGTH: 8
<212> TYPE: PRT
<213> ORGANISM: Artificial Sequence
<220> FEATURE:
<223> OTHER INFORMATION: Synthetic Construct

<400> SEQUENCE: 78

Gly Arg Ile Phe Ser Thr Tyr Ala
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Construct

<400> SEQUENCE: 79

Ile Asn Arg Ser Gly Asp Ser Thr
1               5

<210> SEQ ID NO 80
<211> LENGTH: 17
<212> TYPE: PRT
<213> ORGANISM: Artificial Sequence
<220> FEATURE:
<223> OTHER INFORMATION: Synthetic Construct

<400> SEQUENCE: 80

Ala Ala Asp Ser Asp Gly Ile Gly Trp Phe Asn Ser Phe Glu Tyr Asp
1               5                   10                  15

Tyr

<210> SEQ ID NO 81
<211> LENGTH: 8
<212> TYPE: PRT
<213> ORGANISM: Artificial Sequence
<220> FEATURE:
<223> OTHER INFORMATION: Synthetic Construct

<400> SEQUENCE: 81

Gly Pro Ile Phe Ser Thr Tyr Ala
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct

<400> SEQUENCE: 82

Ile Asn Arg Ser Gly Asp Ser Thr
1               5

<210> SEQ ID NO 83
<211> LENGTH: 17
<212> TYPE: PRT
<213> ORGANISM: Artificial Sequence
<220> FEATURE:
<223> OTHER INFORMATION: Synthetic Construct

<400> SEQUENCE: 83

Ala Ala Asp Ser Asp Gly Ile Gly Trp Phe Asn Ser Phe Glu Tyr Asp
1               5                   10                  15

Tyr

<210> SEQ ID NO 84
<211> LENGTH: 8
<212> TYPE: PRT
<213> ORGANISM: Artificial Sequence
<220> FEATURE:
<223> OTHER INFORMATION: Synthetic Construct

<400> SEQUENCE: 84

Gly Arg Ser Val Ser Leu Tyr His
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic Construct

<400> SEQUENCE: 85

Thr Ala Trp His Asp Gly Ser Thr
1               5

<210> SEQ ID NO 86
<211> LENGTH: 17
<212> TYPE: PRT
<213> ORGANISM: Artificial Sequence
<220> FEATURE:
<223> OTHER INFORMATION: Synthetic Construct

<400> SEQUENCE: 86

Ala Gly Glu Ala Lys Leu Gly Gly Ile Tyr Ser Arg Trp Arg Asp Tyr
1               5                   10                  15

Glu

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct

<400> SEQUENCE: 87

Gly Arg Ser Val Ser Leu Tyr His
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Thr Ala Trp His Asp Gly Ser Thr
1               5

<210> SEQ ID NO 89
<211> LENGTH: 15
<212> TYPE: PRT
<213> ORGANISM: Artificial Sequence
<220> FEATURE:
<223> OTHER INFORMATION: Synthetic Construct

<400> SEQUENCE: 89

Ala Ala Asp Pro Gly Gly Ser Ser Trp Ser Gln Pro Trp Tyr Asp
1               5                   10                  15

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90

Gly Ser Thr Trp Ser Ile Asn Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct

<400> SEQUENCE: 91

Ile Ser Ser Gly Gly Ser Thr
1               5

<210> SEQ ID NO 92
<211> LENGTH: 10
<212> TYPE: PRT
<213> ORGANISM: Artificial Sequence
<220> FEATURE:
<223> OTHER INFORMATION: Synthetic Construct

<400> SEQUENCE: 92

Tyr Ala Gln Ser Thr Trp Tyr Pro Pro Ser
1               5                   10

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct

<400> SEQUENCE: 93

Gly Arg Thr Phe Ser Asn Asp Ala
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic Construct

<400> SEQUENCE: 94

Ile Ser Trp Lys Ser Ser Thr
1               5

<210> SEQ ID NO 95
<211> LENGTH: 15
<212> TYPE: PRT
<213> ORGANISM: Artificial Sequence
<220> FEATURE:
<223> OTHER INFORMATION: Synthetic Construct

<400> SEQUENCE: 95

Val Ala Asp Pro Tyr Gly Leu Gly Phe Asn Pro Ser Asp Tyr Asp

<210> SEQ ID NO 96
<211> LENGTH: 152
<212> TYPE: PRT
<213> ORGANISM: Homo sapiens

<400> SEQUENCE: 96

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 97
<211> LENGTH: 177
<212> TYPE: PRT
<213> ORGANISM: Homo sapiens

<400> SEQUENCE: 97

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu

His

<210> SEQ ID NO 98
<211> LENGTH: 152
<212> TYPE: PRT
<213> ORGANISM: Homo sapiens

<400> SEQUENCE: 98

```
Asp Cys Asp Ile Glu Gly Lys Asp Gly Lys Gln Tyr Glu Ser Val Leu
1               5                   10                  15
Met Val Ser Ile Asp Gln Leu Leu Asp Ser Met Lys Glu Ile Gly Ser
            20                  25                  30
Asn Cys Leu Asn Asn Glu Phe Asn Phe Phe Lys Arg His Ile Cys Asp
        35                  40                  45
Ala Asn Lys Glu Gly Met Phe Leu Phe Arg Ala Ala Arg Lys Leu Arg
    50                  55                  60
Gln Phe Leu Lys Met Asn Ser Thr Gly Asp Phe Asp Leu His Leu Leu
65                  70                  75                  80
Lys Val Ser Glu Gly Thr Thr Ile Leu Leu Asn Cys Thr Gly Gln Val
                85                  90                  95
Lys Gly Arg Lys Pro Ala Ala Leu Gly Glu Ala Gln Pro Thr Lys Ser
            100                 105                 110
Leu Glu Glu Asn Lys Ser Leu Lys Glu Gln Lys Lys Leu Asn Asp Leu
        115                 120                 125
Cys Phe Leu Lys Arg Leu Leu Gln Glu Ile Lys Thr Cys Trp Asn Lys
    130                 135                 140
Ile Leu Met Gly Thr Lys Glu His
145                 150
```

<210> SEQ ID NO 99
<211> LENGTH: 114
<212> TYPE: PRT
<213> ORGANISM: Homo sapiens

<400> SEQUENCE: 99

```
Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
        35                  40                  45
Val Ile Ser His Glu Ser Gly Asp Thr Asp Ile His Asp Thr Val Glu
    50                  55                  60
Asn Leu Ile Ile Leu Ala Asn Asn Ile Leu Ser Ser Asn Gly Asn Ile
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser
```

<210> SEQ ID NO 100
<211> LENGTH: 162
<212> TYPE: PRT
<213> ORGANISM: Homo sapiens -continued

<400> SEQUENCE: 100

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65              70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 101
<211> LENGTH: 267
<212> TYPE: PRT
<213> ORGANISM: Homo sapiens

<400> SEQUENCE: 101

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65              70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
        130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile

```
              195                 200                 205
Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
        260                 265
```

<210> SEQ ID NO 102
<211> LENGTH: 237
<212> TYPE: PRT
<213> ORGANISM: Homo sapiens

<400> SEQUENCE: 102

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
            180                 185                 190

Leu Leu Ala Cys Tyr Leu Lys Ser Arg Gln Thr Pro Pro Leu Ala Ser
        195                 200                 205

Val Glu Met Glu Ala Met Glu Ala Leu Pro Val Thr Trp Gly Thr Ser
    210                 215                 220

Ser Arg Asp Glu Asp Leu Glu Asn Cys Ser His His Leu
225                 230                 235
```

<210> SEQ ID NO 103
<211> LENGTH: 65
<212> TYPE: PRT
<213> ORGANISM: Homo sapiens

<400> SEQUENCE: 103

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
```

```
                20                  25                  30
Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg
65

<210> SEQ ID NO 104
<211> LENGTH: 77
<212> TYPE: PRT
<213> ORGANISM: Homo sapiens

<400> SEQUENCE: 104

Ile Thr Cys Pro Pro Met Ser Val Glu His Ala Asp Ile Trp Val
1               5                  10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro
65                  70                  75

<210> SEQ ID NO 105
<211> LENGTH: 234
<212> TYPE: PRT
<213> ORGANISM: Homo sapiens

<400> SEQUENCE: 105

Met Ala Pro Arg Arg Ala Arg Gly Cys Arg Thr Leu Gly Leu Pro Ala
1               5                  10                  15

Leu Leu Leu Leu Leu Leu Leu Arg Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Lys Pro
                85                  90                  95

Ala Ala Ser Ser Pro Ser Ser Asn Asn Thr Ala Ala Thr Thr Ala Ala
            100                 105                 110

Ile Val Pro Gly Ser Gln Leu Met Pro Ser Lys Ser Pro Ser Thr Gly
        115                 120                 125

Thr Thr Glu Ile Ser Ser His Glu Ser Ser His Gly Thr Pro Ser Gln
    130                 135                 140

Thr Thr Ala Lys Asn Trp Glu Leu Thr Ala Ser Ala Ser His Gln Pro
145                 150                 155                 160

Pro Gly Val Tyr Pro Gln Gly His Ser Asp Thr Thr Val Ala Ile Ser
                165                 170                 175

Thr Ser Thr Val Leu Leu Cys Gly Leu Ser Ala Val Ser Leu Leu Ala
            180                 185                 190

Cys Tyr Leu Lys Ser Arg Gln Thr Pro Pro Leu Ala Ser Val Glu Met
```

```
                195                 200                 205
Glu Ala Met Glu Ala Leu Pro Val Thr Trp Gly Thr Ser Ser Arg Asp
            210                 215                 220

Glu Asp Leu Glu Asn Cys Ser His His Leu
225                 230
```

<210> SEQ ID NO 106
<211> LENGTH: 252
<212> TYPE: PRT
<213> ORGANISM: Homo sapiens

<400> SEQUENCE: 106

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Ala Ser Val Cys Ser Cys His Pro Arg
225                 230                 235                 240

Ser Ala Gly His Thr Cys Ser Val Gly Ser Val Cys
                245                 250
```

<210> SEQ ID NO 107
<211> LENGTH: 219
<212> TYPE: PRT
<213> ORGANISM: Homo sapiens

<400> SEQUENCE: 107

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
```

```
                35                  40                  45
Tyr Ser Leu Tyr Ser Arg Glu Arg Tyr Ile Cys Asn Ser Gly Phe Lys
 50                  55                  60

Arg Lys Ala Gly Thr Ser Ser Leu Thr Glu Cys Val Leu Asn Lys Ala
 65                  70                  75                  80

Thr Asn Val Ala His Trp Thr Thr Pro Ser Leu Lys Cys Ile Lys Pro
                 85                  90                  95

Ala Ala Ser Ser Pro Ser Ser Asn Asn Thr Ala Ala Thr Thr Ala Ala
                100                 105                 110

Ile Val Pro Gly Ser Gln Leu Met Pro Ser Lys Ser Pro Ser Thr Gly
                115                 120                 125

Thr Thr Glu Ile Ser Ser His Glu Ser Ser His Gly Thr Pro Ser Gln
130                 135                 140

Thr Thr Ala Lys Asn Trp Glu Leu Thr Ala Ser Ala Ser His Gln Pro
145                 150                 155                 160

Pro Gly Val Tyr Pro Gln Gly His Ser Asp Thr Thr Val Ala Ile Ser
                165                 170                 175

Thr Ser Thr Val Leu Leu Cys Gly Leu Ser Ala Val Ser Leu Leu Ala
                180                 185                 190

Cys Tyr Leu Lys Ser Arg Ala Ser Val Cys Ser Cys His Pro Arg Ser
                195                 200                 205

Ala Gly His Thr Cys Ser Val Gly Ser Val Cys
                210                 215

<210> SEQ ID NO 108
<211> LENGTH: 231
<212> TYPE: PRT
<213> ORGANISM: Homo sapiens

<400> SEQUENCE: 108

Met Ser Val Glu His Ala Asp Ile Trp Val Lys Ser Tyr Ser Leu Tyr
  1               5                  10                  15

Ser Arg Glu Arg Tyr Ile Cys Asn Ser Gly Phe Lys Arg Lys Ala Gly
                 20                  25                  30

Thr Ser Ser Leu Thr Glu Cys Val Leu Asn Lys Ala Thr Asn Val Ala
                 35                  40                  45

His Trp Thr Thr Pro Ser Leu Lys Cys Ile Arg Asp Pro Ala Leu Val
 50                  55                  60

His Gln Arg Pro Ala Pro Pro Ser Thr Val Thr Thr Ala Gly Val Thr
 65                  70                  75                  80

Pro Gln Pro Glu Ser Leu Ser Pro Ser Gly Lys Glu Pro Ala Ala Ser
                 85                  90                  95

Ser Pro Ser Ser Asn Asn Thr Ala Ala Thr Thr Ala Ala Ile Val Pro
                100                 105                 110

Gly Ser Gln Leu Met Pro Ser Lys Ser Pro Ser Thr Gly Thr Thr Glu
                115                 120                 125

Ile Ser Ser His Glu Ser Ser His Gly Thr Pro Ser Gln Thr Thr Ala
                130                 135                 140

Lys Asn Trp Glu Leu Thr Ala Ser Ala Ser His Gln Pro Pro Gly Val
145                 150                 155                 160

Tyr Pro Gln Gly His Ser Asp Thr Thr Val Ala Ile Ser Thr Ser Thr
                165                 170                 175

Val Leu Leu Cys Gly Leu Ser Ala Val Ser Leu Leu Ala Cys Tyr Leu
                180                 185                 190
```

```
Lys Ser Arg Gln Thr Pro Pro Leu Ala Ser Val Glu Met Glu Ala Met
            195                 200                 205

Glu Ala Leu Pro Val Thr Trp Gly Thr Ser Ser Arg Asp Glu Asp Leu
    210                 215                 220

Glu Asn Cys Ser His His Leu
225                 230

<210> SEQ ID NO 109
<211> LENGTH: 270
<212> TYPE: PRT
<213> ORGANISM: Homo sapiens

<400> SEQUENCE: 109

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 110
<211> LENGTH: 179
<212> TYPE: PRT
<213> ORGANISM: Homo sapiens

<400> SEQUENCE: 110

Met Ala Ala Leu Gln Lys Ser Val Ser Ser Phe Leu Met Gly Thr Leu
1               5                   10                  15
```

Ala Thr Ser Cys Leu Leu Leu Ala Leu Val Gln Gly Gly Ala
         20                  25                  30

Ala Ala Pro Ile Ser Ser His Cys Arg Leu Asp Lys Ser Asn Phe Gln
         35                  40                  45

Gln Pro Tyr Ile Thr Asn Arg Thr Phe Met Leu Ala Lys Glu Ala Ser
     50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                 85                  90                  95

Asn Phe Thr Leu Glu Glu Val Leu Phe Pro Gln Ser Asp Arg Phe Gln
             100                 105                 110

Pro Tyr Met Gln Glu Val Val Pro Phe Leu Ala Arg Leu Ser Asn Arg
         115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 111
<211> LENGTH: 146
<212> TYPE: PRT
<213> ORGANISM: Homo sapiens

<400> SEQUENCE: 111

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 112
<211> LENGTH: 26
<212> TYPE: PRT
<213> ORGANISM: Homo sapiens

<400> SEQUENCE: 112

Glu Val Gln Leu Val Glu Ser Gly Gly Gly Leu Val Gln Pro Gly Gly

```
                1               5                   10                  15
Ser Leu Arg Leu Ser Cys Ala Ala Ser Gly
            20                  25

<210> SEQ ID NO 113
<211> LENGTH: 25
<212> TYPE: PRT
<213> ORGANISM: Homo sapiens

<400> SEQUENCE: 113

Gln Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 114
<211> LENGTH: 25
<212> TYPE: PRT
<213> ORGANISM: Homo sapiens

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 115
<211> LENGTH: 17
<212> TYPE: PRT
<213> ORGANISM: Homo sapiens

<400> SEQUENCE: 115

Met Ser Trp Val Arg Gln Ala Pro Gly Lys Gly Leu Glu Trp Val Ser
1               5                   10                  15

Ala

<210> SEQ ID NO 116
<211> LENGTH: 17
<212> TYPE: PRT
<213> ORGANISM: Homo sapiens

<400> SEQUENCE: 116

Met His Trp Val Arg Gln Ala Pro Gly Lys Gly Leu Glu Tyr Val Ser
1               5                   10                  15

Ala

<210> SEQ ID NO 117
<211> LENGTH: 17
<212> TYPE: PRT
<213> ORGANISM: Homo sapiens

<400> SEQUENCE: 117

Met Ser Trp Val Arg Gln Ala Pro Gly Lys Gly Leu Glu Trp Val Ser
1               5                   10                  15

Val

<210> SEQ ID NO 118
<211> LENGTH: 39
<212> TYPE: PRT
<213> ORGANISM: Homo sapiens

<400> SEQUENCE: 118
```

```
Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala
            35

<210> SEQ ID NO 119
<211> LENGTH: 33
<212> TYPE: PRT
<213> ORGANISM: Homo sapiens

<400> SEQUENCE: 119

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr

<210> SEQ ID NO 120
<211> LENGTH: 252
<212> TYPE: PRT
<213> ORGANISM: Artificial Sequence
<220> FEATURE:
<223> OTHER INFORMATION: Synthetic Construct

<400> SEQUENCE: 120

Gln Gly Pro Asp Arg Leu Leu Ile Arg Leu Arg His Leu Ile Asp Ile
1               5                   10                  15

Val Glu Gln Leu Lys Ile Tyr Glu Asn Asp Leu Asp Pro Glu Leu Leu
            20                  25                  30

Ser Ala Pro Gln Asp Val Lys Gly His Cys Glu His Ala Ala Phe Ala
        35                  40                  45

Cys Phe Gln Lys Ala Lys Leu Lys Pro Ser Asn Pro Gly Asn Asn Lys
    50                  55                  60

Thr Phe Ile Ile Asp Leu Val Ala Gln Leu Arg Arg Arg Leu Pro Ala
65                  70                  75                  80

Arg Arg Gly Gly Lys Lys Gln Lys His Ile Ala Lys Cys Pro Ser Cys
                85                  90                  95

Asp Ser Tyr Glu Lys Arg Thr Pro Lys Glu Phe Leu Glu Arg Leu Lys
            100                 105                 110

Trp Leu Leu Gln Lys Met Ile His Gln His Leu Ser Gly Ser Gly Gly
        115                 120                 125

Ser Gly Gly Ser Gly Gly Ser Gly Gln Val Gln Leu Val Glu Ser Gly
    130                 135                 140

Gly Gly Leu Val Gln Pro Gly Gly Ser Leu Arg Leu Ser Cys Ala Ala
145                 150                 155                 160

Ser Gly Ser Thr Trp Ser Ile Asn Thr Leu Ala Trp Tyr Arg Gln Ala
                165                 170                 175

Pro Gly Lys Gln Arg Asp Leu Val Ala Arg Ile Ser Ser Gly Gly Ser
            180                 185                 190

Thr His Tyr Ala Asp Ser Val Lys Gly Arg Phe Thr Val Ser Arg Asp
        195                 200                 205

Asn Ala Glu Asn Thr Leu Val Leu Gln Met Asn Ser Leu Lys Pro Glu
    210                 215                 220

Asp Thr Ala Val Tyr Tyr Cys Tyr Ala Gln Ser Thr Trp Tyr Pro Pro
```

```
                    225                 230                 235                 240
Ser Trp Gly Gln Gly Thr Gln Val Thr Val Ser Ser
                245                 250

<210> SEQ ID NO 121
<211> LENGTH: 261
<212> TYPE: PRT
<213> ORGANISM: Artificial Sequence
<220> FEATURE:
<223> OTHER INFORMATION: Synthetic Construct

<400> SEQUENCE: 121

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Ser Gly Ser Gly Ser Gly Ser Gly Ser Ser
    130                 135                 140

Gly Gln Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr His Tyr Ala Asp Ser Val
        195                 200                 205

Lys Gly Arg Phe Thr Val Ser Arg Asp Asn Ala Glu Asn Thr Leu Val
    210                 215                 220

Leu Gln Met Asn Ser Leu Lys Pro Glu Asp Thr Ala Val Tyr Tyr Cys
225                 230                 235                 240

Tyr Ala Gln Ser Thr Trp Tyr Pro Pro Ser Trp Gly Gln Gly Thr Gln
                245                 250                 255

Val Thr Val Ser Ser
            260

<210> SEQ ID NO 122
<211> LENGTH: 355
<212> TYPE: PRT
<213> ORGANISM: Artificial Sequence
<220> FEATURE:
<223> OTHER INFORMATION: Synthetic Construct

<400> SEQUENCE: 122

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
            35                  40                  45

Ala Arg Ile Ser Ser Gly Gly Ser Thr His Tyr Ala Asp Ser Val Lys
 50                  55                  60

Gly Arg Phe Thr Val Ser Arg Asp Asn Ala Glu Asn Thr Leu Val Leu
 65                  70                  75                  80

Gln Met Asn Ser Leu Lys Pro Glu Asp Thr Ala Val Tyr Tyr Cys Tyr
            85                  90                  95

Ala Gln Ser Thr Trp Tyr Pro Pro Ser Trp Gly Gln Gly Thr Gln Val
            100                 105                 110

Thr Val Ser Ser Gly Gly Gly Ser Gly Gly Gly Ser Gly Gly
            115                 120                 125

Gly Gly Ser Gly Gly Gly Ser Ile Thr Cys Pro Pro Met Ser
 130                 135                 140

Val Glu His Ala Asp Ile Trp Val Lys Ser Tyr Ser Leu Tyr Ser Arg
145                 150                 155                 160

Glu Arg Tyr Ile Cys Asn Ser Gly Phe Lys Arg Lys Ala Gly Thr Ser
            165                 170                 175

Ser Leu Thr Glu Cys Val Leu Asn Lys Ala Thr Asn Val Ala His Trp
            180                 185                 190

Thr Thr Pro Ser Leu Lys Cys Ile Arg Asp Pro Ala Leu Val His Gln
            195                 200                 205

Arg Pro Ala Pro Pro Arg Lys Arg Ala Pro Val Lys Gln Thr Leu
 210                 215                 220

Asn Phe Asp Leu Leu Lys Leu Ala Gly Asp Val Glu Ser Asn Pro Gly
225                 230                 235                 240

Pro Asn Trp Val Asn Val Ile Ser Asp Leu Lys Lys Ile Glu Asp Leu
            245                 250                 255

Ile Gln Ser Met His Ile Asp Ala Thr Leu Tyr Thr Glu Ser Asp Val
            260                 265                 270

His Pro Ser Cys Lys Val Thr Ala Met Lys Cys Phe Leu Leu Glu Leu
            275                 280                 285

Gln Val Ile Ser Leu Glu Ser Gly Asp Ala Ser Ile His Asp Thr Val
            290                 295                 300

Glu Asn Leu Ile Ile Leu Ala Asn Asn Ser Leu Ser Ser Asn Gly Asn
305                 310                 315                 320

Val Thr Glu Ser Gly Cys Lys Glu Cys Glu Glu Leu Glu Glu Lys Asn
            325                 330                 335

Ile Lys Glu Phe Leu Gln Ser Phe Val His Ile Val Gln Met Phe Ile
            340                 345                 350

Asn Thr Ser
    355

<210> SEQ ID NO 123
<211> LENGTH: 114
<212> TYPE: PRT
<213> ORGANISM: Homo sapiens

<400> SEQUENCE: 123

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30
```

```
Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
 50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 124
<211> LENGTH: 201
<212> TYPE: PRT
<213> ORGANISM: Artificial Sequence
<220> FEATURE:
<223> OTHER INFORMATION: Synthetic Construct

<400> SEQUENCE: 124

Gln Val Gln Leu Val Glu Ser Gly Gly Gly Leu Val Gln Pro Gly Gly
 1               5                  10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr His Tyr Ala Asp Ser Val Lys
 50                  55                  60

Gly Arg Phe Thr Val Ser Arg Asp Asn Ala Glu Asn Thr Leu Val Leu
 65                  70                  75                  80

Gln Met Asn Ser Leu Lys Pro Glu Asp Thr Ala Val Tyr Tyr Cys Tyr
                85                  90                  95

Ala Gln Ser Thr Trp Tyr Pro Pro Ser Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Ile Thr Cys Pro Pro Pro Met Ser
    130                 135                 140

Val Glu His Ala Asp Ile Trp Val Lys Ser Tyr Ser Leu Tyr Ser Arg
145                 150                 155                 160

Glu Arg Tyr Ile Cys Asn Ser Gly Phe Lys Arg Lys Ala Gly Thr Ser
                165                 170                 175

Ser Leu Thr Glu Cys Val Leu Asn Lys Ala Thr Asn Val Ala His Trp
            180                 185                 190

Thr Thr Pro Ser Leu Lys Cys Ile Arg
        195                 200

<210> SEQ ID NO 125
<211> LENGTH: 213
<212> TYPE: PRT
<213> ORGANISM: Artificial Sequence
<220> FEATURE:
<223> OTHER INFORMATION: Synthetic Construct

<400> SEQUENCE: 125

Gln Val Gln Leu Val Glu Ser Gly Gly Gly Leu Val Gln Pro Gly Gly
 1               5                  10                  15
```

```
Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr His Tyr Ala Asp Ser Val Lys
 50                  55                  60

Gly Arg Phe Thr Val Ser Arg Asp Asn Ala Glu Asn Thr Leu Val Leu
 65                  70                  75                  80

Gln Met Asn Ser Leu Lys Pro Glu Asp Thr Ala Val Tyr Tyr Cys Tyr
                85                  90                  95

Ala Gln Ser Thr Trp Tyr Pro Pro Ser Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Ile Thr Cys Pro Pro Pro Met Ser
130                 135                 140

Val Glu His Ala Asp Ile Trp Val Lys Ser Tyr Ser Leu Tyr Ser Arg
145                 150                 155                 160

Glu Arg Tyr Ile Cys Asn Ser Gly Phe Lys Arg Lys Ala Gly Thr Ser
                165                 170                 175

Ser Leu Thr Glu Cys Val Leu Asn Lys Ala Thr Asn Val Ala His Trp
            180                 185                 190

Thr Thr Pro Ser Leu Lys Cys Ile Arg Asp Pro Ala Leu Val His Gln
        195                 200                 205

Arg Pro Ala Pro Pro
        210

<210> SEQ ID NO 126
<211> LENGTH: 122
<212> TYPE: PRT
<213> ORGANISM: Homo sapiens

<400> SEQUENCE: 126

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His
        115                 120

<210> SEQ ID NO 127
<211> LENGTH: 65
<212> TYPE: PRT
<213> ORGANISM: Homo sapiens

<400> SEQUENCE: 127
```

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg
65

<210> SEQ ID NO 128
<211> LENGTH: 77
<212> TYPE: PRT
<213> ORGANISM: Homo sapiens

<400> SEQUENCE: 128

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro
65                  70                  75

<210> SEQ ID NO 129
<211> LENGTH: 260
<212> TYPE: PRT
<213> ORGANISM: Artificial Sequence
<220> FEATURE:
<223> OTHER INFORMATION: Synthetic Construct

<400> SEQUENCE: 129

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
            85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Ala Glu Ala Ala Lys
            115                 120                 125

Glu Ala Ala Ala Lys Glu Ala Ala Ala Lys Glu Ala Ala Ala Lys Ala
        130                 135                 140

Gln Val Gln Leu Val Glu Ser Gly Gly Gly Leu Val Gln Pro Gly Gly
145                 150                 155                 160
```

```
Ser Leu Arg Leu Ser Cys Ala Ala Ser Gly Ser Thr Trp Ser Ile Asn
                165                 170                 175

Thr Leu Ala Trp Tyr Arg Gln Ala Pro Gly Lys Gln Arg Asp Leu Val
            180                 185                 190

Ala Arg Ile Ser Ser Gly Gly Ser Thr His Tyr Ala Asp Ser Val Lys
            195                 200                 205

Gly Arg Phe Thr Val Ser Arg Asp Asn Ala Glu Asn Thr Leu Val Leu
            210                 215                 220

Gln Met Asn Ser Leu Lys Pro Glu Asp Thr Ala Val Tyr Tyr Cys Tyr
225                 230                 235                 240

Ala Gln Ser Thr Trp Tyr Pro Pro Ser Trp Gly Gln Gly Thr Gln Val
                245                 250                 255

Thr Val Ser Ser
            260

<210> SEQ ID NO 130
<211> LENGTH: 247
<212> TYPE: PRT
<213> ORGANISM: Artificial Sequence
<220> FEATURE:
<223> OTHER INFORMATION: Synthetic Construct

<400> SEQUENCE: 130

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile Gly Ser Gly Ser Gly Gly Ser Gly Gly
        115                 120                 125

Gly Ser Gly Gln Val Gln Leu Val Glu Ser Gly Gly Gly Leu Val Gln
    130                 135                 140

Pro Gly Gly Ser Leu Arg Leu Ser Cys Ala Ala Ser Gly Ser Thr Trp
145                 150                 155                 160

Ser Ile Asn Thr Leu Ala Trp Tyr Arg Gln Ala Pro Gly Lys Gln Arg
                165                 170                 175

Asp Leu Val Ala Arg Ile Ser Ser Gly Gly Ser Thr His Tyr Ala Asp
            180                 185                 190

Ser Val Lys Gly Arg Phe Thr Val Ser Arg Asp Asn Ala Glu Asn Thr
        195                 200                 205

Leu Val Leu Gln Met Asn Ser Leu Lys Pro Glu Asp Thr Ala Val Tyr
    210                 215                 220

Tyr Cys Tyr Ala Gln Ser Thr Trp Tyr Pro Pro Ser Trp Gly Gln Gly
225                 230                 235                 240

Thr Gln Val Thr Val Ser Ser
                245
```

<210> SEQ ID NO 131
<211> LENGTH: 248
<212> TYPE: PRT
<213> ORGANISM: Artificial Sequence
<220> FEATURE:
<223> OTHER INFORMATION: Synthetic Construct

<400> SEQUENCE: 131

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gly Ser Gly Gly Ser Gly Gly Ser
        115                 120                 125

Gly Gly Ser Gly Gln Val Gln Leu Val Glu Ser Gly Gly Gly Leu Val
    130                 135                 140

Gln Pro Gly Gly Ser Leu Arg Leu Ser Cys Ala Ala Ser Gly Ser Thr
145                 150                 155                 160

Trp Ser Ile Asn Thr Leu Ala Trp Tyr Arg Gln Ala Pro Gly Lys Gln
                165                 170                 175

Arg Asp Leu Val Ala Arg Ile Ser Ser Gly Gly Ser Thr His Tyr Ala
            180                 185                 190

Asp Ser Val Lys Gly Arg Phe Thr Val Ser Arg Asp Asn Ala Glu Asn
        195                 200                 205

Thr Leu Val Leu Gln Met Asn Ser Leu Lys Pro Glu Asp Thr Ala Val
    210                 215                 220

Tyr Tyr Cys Tyr Ala Gln Ser Thr Trp Tyr Pro Pro Ser Trp Gly Gln
225                 230                 235                 240

Gly Thr Gln Val Thr Val Ser Ser
                245
```

<210> SEQ ID NO 132
<211> LENGTH: 260
<212> TYPE: PRT
<213> ORGANISM: Artificial Sequence
<220> FEATURE:
<223> OTHER INFORMATION: Synthetic Construct

<400> SEQUENCE: 132

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60
```

```
Arg Ile Ile Asn Val Ser Ile Lys Lys Leu Lys Arg Lys Pro Pro Ser
 65                  70                  75                  80

Thr Asn Ala Gly Arg Gln Lys His Arg Leu Thr Cys Pro Ser Cys
                 85                  90                  95

Asp Ser Tyr Glu Lys Lys Pro Pro Lys Glu Phe Leu Gly Arg Phe Lys
            100                 105                 110

Ser Leu Leu Gln Lys Met Ile His Gln His Ala Glu Ala Ala Lys
        115                 120                 125

Glu Ala Ala Ala Lys Glu Ala Ala Lys Glu Ala Ala Lys Ala
130                 135                 140

Glu Val Gln Leu Val Glu Ser Gly Gly Leu Val Gln Pro Gly Gly
145                 150                 155                 160

Ser Leu Arg Leu Ser Cys Ala Ala Ser Gly Ser Thr Trp Ser Ile Asn
                165                 170                 175

Thr Leu Ala Trp Tyr Arg Gln Ala Pro Gly Lys Gln Arg Asp Leu Val
            180                 185                 190

Ala Arg Ile Ser Ser Gly Gly Ser Thr Tyr Tyr Ala Asp Ser Val Lys
        195                 200                 205

Gly Arg Phe Thr Ile Ser Arg Asp Asn Ser Lys Asn Thr Leu Tyr Leu
    210                 215                 220

Gln Met Asn Ser Leu Arg Ala Glu Asp Thr Ala Val Tyr Tyr Cys Tyr
225                 230                 235                 240

Ala Gln Ser Thr Trp Tyr Pro Pro Ser Trp Gly Gln Gly Thr Leu Val
                245                 250                 255

Thr Val Ser Ser
            260

<210> SEQ ID NO 133
<211> LENGTH: 260
<212> TYPE: PRT
<213> ORGANISM: Artificial Sequence
<220> FEATURE:
<223> OTHER INFORMATION: Synthetic Construct

<400> SEQUENCE: 133

Gln Val Gln Leu Val Glu Ser Gly Gly Gly Val Val Gln Pro Gly Gly
 1               5                  10                  15

Ser Leu Arg Leu Ser Cys Ala Ala Ser Gly Phe Ala Phe Arg Gly Phe
                20                  25                  30

Gly Met Ser Trp Val Arg Gln Ala Pro Gly Lys Gly Leu Glu Trp Val
            35                  40                  45

Ser Ser Ile Asn Asn Gly Gly Ser Asp Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser Ala Glu Ala Ala Ala Lys Glu Ala Ala Ala Lys Glu
        115                 120                 125

Ala Ala Ala Lys Glu Ala Ala Ala Lys Ala Gln Gly Gln Asp Arg His
    130                 135                 140

Met Ile Arg Met Arg Gln Leu Ile Asp Ile Val Asp Gln Leu Lys Asn
145                 150                 155                 160
```

```
Tyr Val Asn Asp Leu Val Pro Glu Phe Leu Pro Ala Pro Glu Asp Val
            165                 170                 175

Glu Thr Asn Cys Glu Trp Ser Ala Phe Ser Cys Phe Gln Lys Ala Gln
            180                 185                 190

Leu Lys Ser Ala Asn Thr Gly Asn Asn Glu Arg Ile Ile Asn Val Ser
        195                 200                 205

Ile Lys Lys Leu Lys Arg Lys Pro Pro Ser Thr Asn Ala Gly Arg Arg
    210                 215                 220

Gln Lys His Arg Leu Thr Cys Pro Ser Cys Asp Ser Tyr Glu Lys Lys
225                 230                 235                 240

Pro Pro Lys Glu Phe Leu Glu Arg Phe Lys Ser Leu Leu Gln Lys Met
                245                 250                 255

Ile His Gln His
            260

<210> SEQ ID NO 134
<211> LENGTH: 261
<212> TYPE: PRT
<213> ORGANISM: Artificial Sequence
<220> FEATURE:
<223> OTHER INFORMATION: Synthetic Construct

<400> SEQUENCE: 134

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Ser Gly Ser Gly Ser Gly Gly Ser Gly Ser
    130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255
```

```
<210> SEQ ID NO 135
<211> LENGTH: 271
<212> TYPE: PRT
<213> ORGANISM: Artificial Sequence
<220> FEATURE:
<223> OTHER INFORMATION: Synthetic Construct

<400> SEQUENCE: 135

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Ala Glu Ala Ala Lys Glu Ala Ala Lys
    130                 135                 140

Glu Ala Ala Ala Lys Glu Ala Ala Ala Lys Ala Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Ser Thr Trp Ser Ile Asn Thr Leu Ala Trp Tyr
            180                 185                 190

Arg Gln Ala Pro Gly Lys Gln Arg Asp Leu Val Ala Arg Ile Ser Ser
        195                 200                 205

Gly Gly Ser Thr Tyr Tyr Ala Asp Ser Val Lys Gly Arg Phe Thr Ile
    210                 215                 220

Ser Arg Asp Asn Ser Lys Asn Thr Leu Tyr Leu Gln Met Asn Ser Leu
225                 230                 235                 240

Arg Ala Glu Asp Thr Ala Val Tyr Tyr Cys Tyr Ala Gln Ser Thr Trp
                245                 250                 255

Tyr Pro Pro Ser Trp Gly Gln Gly Thr Leu Val Thr Val Ser Ser
            260                 265                 270

<210> SEQ ID NO 136
<211> LENGTH: 260
<212> TYPE: PRT
<213> ORGANISM: Artificial Sequence
<220> FEATURE:
<223> OTHER INFORMATION: Synthetic Construct

<400> SEQUENCE: 136

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
```

(continuing at top: Val Thr Val Ser Ser / 260)

```
            20                  25                  30
Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Ala Glu Ala Ala Ala Lys
        115                 120                 125

Glu Ala Ala Ala Lys Glu Ala Ala Ala Lys Glu Ala Ala Ala Lys Ala
    130                 135                 140

Gln Val Gln Leu Val Glu Ser Gly Gly Gly Val Val Gln Pro Gly Gly
145                 150                 155                 160

Ser Leu Arg Leu Ser Cys Ala Ala Ser Gly Phe Ala Phe Arg Gly Phe
                165                 170                 175

Gly Met Ser Trp Val Arg Gln Ala Pro Gly Lys Gly Phe Glu Trp Val
            180                 185                 190

Ser Ser Ile Asn Asn Gly Gly Ser Asp Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Ala Ile Gly Gly Pro Gly Ala Ser Pro Ser Gly Gln Gly Thr Gln Val
                245                 250                 255

Thr Val Ser Ser
            260

<210> SEQ ID NO 137
<211> LENGTH: 250
<212> TYPE: PRT
<213> ORGANISM: Artificial Sequence
<220> FEATURE:
<223> OTHER INFORMATION: Synthetic Construct

<400> SEQUENCE: 137

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Gly Ser Gly Gly Ser Gly
```

```
                    115                 120                 125
Gly Ser Gly Gly Ser Gly Glu Val Gln Leu Val Glu Ser Gly Gly
            130                 135                 140

Leu Val Gln Pro Gly Gly Ser Leu Arg Leu Ser Cys Ala Ala Ser Gly
145                 150                 155                 160

Ser Thr Trp Ser Ile Asn Thr Leu Ala Trp Tyr Arg Gln Ala Pro Gly
                        165                 170                 175

Lys Gln Arg Asp Leu Val Ala Arg Ile Ser Ser Gly Gly Ser Thr Tyr
                    180                 185                 190

Tyr Ala Asp Ser Val Lys Gly Arg Phe Thr Ile Ser Arg Asp Asn Ser
                195                 200                 205

Lys Asn Thr Leu Tyr Leu Gln Met Asn Ser Leu Arg Ala Glu Asp Thr
            210                 215                 220

Ala Val Tyr Tyr Cys Tyr Ala Gln Ser Thr Trp Tyr Pro Pro Ser Trp
225                 230                 235                 240

Gly Gln Gly Thr Leu Val Thr Val Ser Ser
                        245                 250

<210> SEQ ID NO 138
<211> LENGTH: 253
<212> TYPE: PRT
<213> ORGANISM: Artificial Sequence
<220> FEATURE:
<223> OTHER INFORMATION: Synthetic Construct

<400> SEQUENCE: 138

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Gly Gly Gly Gly Ser Gly
        115                 120                 125

Gly Gly Gly Ser Gly Gly Gly Ser Glu Val Gln Leu Val Glu Ser
            130                 135                 140

Gly Gly Gly Leu Val Gln Pro Gly Gly Ser Leu Arg Leu Ser Cys Ala
145                 150                 155                 160

Ala Ser Gly Ser Thr Trp Ser Ile Asn Thr Leu Ala Trp Tyr Arg Gln
                        165                 170                 175

Ala Pro Gly Lys Gln Arg Asp Leu Val Ala Arg Ile Ser Ser Gly Gly
                    180                 185                 190

Ser Thr Tyr Tyr Ala Asp Ser Val Lys Gly Arg Phe Thr Ile Ser Arg
                195                 200                 205

Asp Asn Ser Lys Asn Thr Leu Tyr Leu Gln Met Asn Ser Leu Arg Ala
            210                 215                 220

Glu Asp Thr Ala Val Tyr Tyr Cys Tyr Ala Gln Ser Thr Trp Tyr Pro
```

```
                225                 230                 235                 240

Pro Ser Trp Gly Gln Gly Thr Leu Val Thr Val Ser Ser
                245                 250

<210> SEQ ID NO 139
<211> LENGTH: 238
<212> TYPE: PRT
<213> ORGANISM: Artificial Sequence
<220> FEATURE:
<223> OTHER INFORMATION: Synthetic Construct

<400> SEQUENCE: 139

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Ser Thr Trp Ser Ile Asn Thr Leu Ala Trp Tyr Arg
145                 150                 155                 160

Gln Ala Pro Gly Lys Gln Arg Asp Leu Val Ala Arg Ile Ser Ser Gly
                165                 170                 175

Gly Ser Thr Tyr Tyr Ala Asp Ser Val Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Tyr Cys Tyr Ala Gln Ser Thr Trp Tyr
    210                 215                 220

Pro Pro Ser Trp Gly Gln Gly Thr Leu Val Thr Val Ser Ser
225                 230                 235

<210> SEQ ID NO 140
<211> LENGTH: 249
<212> TYPE: PRT
<213> ORGANISM: Artificial Sequence
<220> FEATURE:
<223> OTHER INFORMATION: Synthetic Construct

<400> SEQUENCE: 140

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45
```

```
Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Glu Val Gln Leu Val Glu Ser Gly Gly Gly Leu
130                 135                 140

Val Gln Pro Gly Gly Ser Leu Arg Leu Ser Cys Ala Ala Ser Gly Ser
145                 150                 155                 160

Thr Trp Ser Ile Asn Thr Leu Ala Trp Tyr Arg Gln Ala Pro Gly Lys
                165                 170                 175

Gln Arg Asp Leu Val Ala Arg Ile Ser Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
210                 215                 220

Val Tyr Tyr Cys Tyr Ala Gln Ser Thr Trp Tyr Pro Pro Ser Trp Gly
225                 230                 235                 240

Gln Gly Thr Leu Val Thr Val Ser Ser
                245

<210> SEQ ID NO 141
<211> LENGTH: 246
<212> TYPE: PRT
<213> ORGANISM: Artificial Sequence
<220> FEATURE:
<223> OTHER INFORMATION: Synthetic Construct

<400> SEQUENCE: 141

Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
                 20                  25                  30

Pro Ala Pro Glu Asp Val Glu Thr Asn Cys Glu Trp Ser Ala Phe Ser
             35                  40                  45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Ile Lys Arg Thr Val Ala
        115                 120                 125

Ala Pro Glu Val Gln Leu Val Glu Ser Gly Gly Gly Leu Val Gln Pro
130                 135                 140

Gly Gly Ser Leu Arg Leu Ser Cys Ala Ala Ser Gly Ser Thr Trp Ser
145                 150                 155                 160
```

```
Ile Asn Thr Leu Ala Trp Tyr Arg Gln Ala Pro Gly Lys Gln Arg Asp
                165                 170                 175

Leu Val Ala Arg Ile Ser Ser Gly Gly Ser Thr Tyr Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Tyr Ala Gln Ser Thr Trp Tyr Pro Pro Ser Trp Gly Gln Gly Thr
225                 230                 235                 240

Leu Val Thr Val Ser Ser
                245
```

<210> SEQ ID NO 142
<211> LENGTH: 246
<212> TYPE: PRT
<213> ORGANISM: Artificial Sequence
<220> FEATURE:
<223> OTHER INFORMATION: Synthetic Construct

<400> SEQUENCE: 142

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Ala Ser Thr Lys Gly Pro
        115                 120                 125

Ser Val Glu Val Gln Leu Val Glu Ser Gly Gly Gly Leu Val Gln Pro
    130                 135                 140

Gly Gly Ser Leu Arg Leu Ser Cys Ala Ala Ser Gly Ser Thr Trp Ser
145                 150                 155                 160

Ile Asn Thr Leu Ala Trp Tyr Arg Gln Ala Pro Gly Lys Gln Arg Asp
                165                 170                 175

Leu Val Ala Arg Ile Ser Ser Gly Gly Ser Thr Tyr Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Tyr Ala Gln Ser Thr Trp Tyr Pro Pro Ser Trp Gly Gln Gly Thr
225                 230                 235                 240

Leu Val Thr Val Ser Ser
                245
```

<210> SEQ ID NO 143
<211> LENGTH: 271

```
<212> TYPE: PRT
<213> ORGANISM: Artificial Sequence
<220> FEATURE:
<223> OTHER INFORMATION: Synthetic Construct

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser Ala Glu Ala Ala Ala Lys Glu Ala Ala Ala Lys Glu
        115                 120                 125

Ala Ala Ala Lys Glu Ala Ala Ala Lys Ala Gln Gly Gln Asp Arg His
    130                 135                 140

Met Ile Arg Met Arg Gln Leu Ile Asp Ile Val Asp Gln Leu Lys Asn
145                 150                 155                 160

Tyr Val Asn Asp Leu Val Pro Glu Phe Leu Pro Ala Pro Glu Asp Val
                165                 170                 175

Glu Thr Asn Cys Glu Trp Ser Ala Phe Ser Cys Phe Gln Lys Ala Gln
            180                 185                 190

Leu Lys Ser Ala Asn Thr Gly Asn Asn Glu Arg Ile Ile Asn Val Ser
        195                 200                 205

Ile Lys Lys Leu Lys Arg Lys Pro Pro Ser Thr Asn Ala Gly Arg Arg
    210                 215                 220

Gln Lys His Arg Leu Thr Cys Pro Ser Cys Asp Ser Tyr Glu Lys Lys
225                 230                 235                 240

Pro Pro Lys Glu Phe Leu Glu Arg Phe Lys Ser Leu Leu Gln Lys Met
                245                 250                 255

Ile His Gln His Leu Ser Ser Arg Thr His Gly Ser Glu Asp Ser
            260                 265                 270

<210> SEQ ID NO 144
<211> LENGTH: 264
<212> TYPE: PRT
<213> ORGANISM: Artificial Sequence
<220> FEATURE:
<223> OTHER INFORMATION: Synthetic Construct

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Tyr
                 85                  90                  95

Ala Gln Ser Thr Trp Tyr Pro Pro Ser Trp Gly Gln Gly Thr Leu Val
            100                 105                 110

Thr Val Ser Ser Gly Gly Gly Ser Gly Gly Gly Ser Gly Gly
            115                 120                 125

Gly Gly Ser Gln Gly Gln Asp Arg His Met Ile Arg Met Arg Gln Leu
130                 135                 140

Ile Asp Ile Val Asp Gln Leu Lys Asn Tyr Val Asn Asp Leu Val Pro
145                 150                 155                 160

Glu Phe Leu Pro Ala Pro Glu Asp Val Glu Thr Asn Cys Glu Trp Ser
                165                 170                 175

Ala Phe Ser Cys Phe Gln Lys Ala Gln Leu Lys Ser Ala Asn Thr Gly
            180                 185                 190

Asn Asn Glu Arg Ile Ile Asn Val Ser Ile Lys Lys Leu Lys Arg Lys
                195                 200                 205

Pro Pro Ser Thr Asn Ala Gly Arg Arg Gln Lys His Arg Leu Thr Cys
210                 215                 220

Pro Ser Cys Asp Ser Tyr Glu Lys Lys Pro Pro Lys Glu Phe Leu Glu
225                 230                 235                 240

Arg Phe Lys Ser Leu Leu Gln Lys Met Ile His Gln His Leu Ser Ser
                245                 250                 255

Arg Thr His Gly Ser Glu Asp Ser
            260

<210> SEQ ID NO 145
<211> LENGTH: 249
<212> TYPE: PRT
<213> ORGANISM: Artificial Sequence
<220> FEATURE:
<223> OTHER INFORMATION: Synthetic Construct

<400> SEQUENCE: 145

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ser Thr Trp Ser Ile Asn
                 20                  25                  30

Thr Leu Ala Trp Tyr Arg Gln Ala Pro Gly Lys Gln Arg Asp Leu Val
             35                  40                  45

Ala Arg Ile Ser Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Tyr
                 85                  90                  95

Ala Gln Ser Thr Trp Tyr Pro Pro Ser Trp Gly Gln Gly Thr Leu Val
            100                 105                 110

Thr Val Ser Ser Gln Gly Gln Asp Arg His Met Ile Arg Met Arg Gln
            115                 120                 125

Leu Ile Asp Ile Val Asp Gln Leu Lys Asn Tyr Val Asn Asp Leu Val
        130                 135                 140

Pro Glu Phe Leu Pro Ala Pro Glu Asp Val Glu Thr Asn Cys Glu Trp
145                 150                 155                 160
```

```
Ser Ala Phe Ser Cys Phe Gln Lys Ala Gln Leu Lys Ser Ala Asn Thr
            165                 170                 175

Gly Asn Asn Glu Arg Ile Ile Asn Val Ser Ile Lys Lys Leu Lys Arg
        180                 185                 190

Lys Pro Pro Ser Thr Asn Ala Gly Arg Arg Gln Lys His Arg Leu Thr
        195                 200                 205

Cys Pro Ser Cys Asp Ser Tyr Glu Lys Pro Pro Lys Glu Phe Leu
210                 215                 220

Glu Arg Phe Lys Ser Leu Leu Gln Lys Met Ile His Gln His Leu Ser
225                 230                 235                 240

Ser Arg Thr His Gly Ser Glu Asp Ser
                245
```

<210> SEQ ID NO 146
<211> LENGTH: 260
<212> TYPE: PRT
<213> ORGANISM: Artificial Sequence
<220> FEATURE:
<223> OTHER INFORMATION: Synthetic Construct

<400> SEQUENCE: 146

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
            85                  90                  95

Ala Gln Ser Thr Trp Tyr Pro Pro Ser Trp Gly Gln Gly Thr Leu Val
        100                 105                 110

Thr Val Ser Ser Ala Glu Ala Ala Ala Lys Glu Ala Ala Ala Lys Glu
        115                 120                 125

Ala Ala Ala Lys Glu Ala Ala Ala Lys Ala Gln Gly Gln Asp Arg His
    130                 135                 140

Met Ile Arg Met Arg Gln Leu Ile Asp Ile Val Asp Gln Leu Lys Asn
145                 150                 155                 160

Tyr Val Asn Asp Leu Val Pro Glu Phe Leu Pro Ala Pro Glu Asp Val
            165                 170                 175

Glu Thr Asn Cys Glu Trp Ser Ala Phe Ser Cys Phe Gln Lys Ala Gln
        180                 185                 190

Leu Lys Ser Ala Asn Thr Gly Asn Asn Glu Arg Ile Ile Asn Val Ser
    195                 200                 205

Ile Lys Lys Leu Lys Arg Lys Pro Pro Ser Thr Asn Ala Gly Arg Arg
210                 215                 220

Gln Lys His Arg Leu Thr Cys Pro Ser Cys Asp Ser Tyr Glu Lys Lys
225                 230                 235                 240

Pro Pro Lys Glu Phe Leu Glu Arg Phe Lys Ser Leu Leu Gln Lys Met
            245                 250                 255

Ile His Gln His
        260
```

```
<210> SEQ ID NO 147
<211> LENGTH: 253
<212> TYPE: PRT
<213> ORGANISM: Artificial Sequence
<220> FEATURE:
<223> OTHER INFORMATION: Synthetic Construct

<400> SEQUENCE: 147
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Ser | Thr | Trp | Ser | Ile | Asn |
| | | | 20 | | | | | 25 | | | | | 30 | | |
| Thr | Leu | Ala | Trp | Tyr | Arg | Gln | Ala | Pro | Gly | Lys | Gln | Arg | Asp | Leu | Val |
| | | | | 35 | | | | | 40 | | | | 45 | | |
| Ala | Arg | Ile | Ser | Ser | Gly | Gly | Ser | Thr | Tyr | Tyr | Ala | Asp | Ser | Val | Lys |
| | 50 | | | | | 55 | | | | | 60 | | | | |
| Gly | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Tyr |
| | | | | 85 | | | | | 90 | | | | | 95 | |
| Ala | Gln | Ser | Thr | Trp | Tyr | Pro | Pro | Ser | Trp | Gly | Gln | Gly | Thr | Leu | Val |
| | | | 100 | | | | | 105 | | | | | 110 | | |
| Thr | Val | Ser | Ser | Gly | Gly | Gly | Gly | Ser | Gly | Gly | Gly | Ser | Gly | Gly | |
| | | | 115 | | | | | 120 | | | | | 125 | | |
| Gly | Gly | Ser | Gln | Gly | Gln | Asp | Arg | His | Met | Ile | Arg | Met | Arg | Gln | Leu |
| | 130 | | | | | 135 | | | | | 140 | | | | |
| Ile | Asp | Ile | Val | Asp | Gln | Leu | Lys | Asn | Tyr | Val | Asn | Asp | Leu | Val | Pro |
| 145 | | | | | 150 | | | | | 155 | | | | | 160 |
| Glu | Phe | Leu | Pro | Ala | Pro | Glu | Asp | Val | Glu | Thr | Asn | Cys | Glu | Trp | Ser |
| | | | | 165 | | | | | 170 | | | | | 175 | |
| Ala | Phe | Ser | Cys | Phe | Gln | Lys | Ala | Gln | Leu | Lys | Ser | Ala | Asn | Thr | Gly |
| | | | 180 | | | | | 185 | | | | | 190 | | |
| Asn | Asn | Glu | Arg | Ile | Ile | Asn | Val | Ser | Ile | Lys | Lys | Leu | Lys | Arg | Lys |
| | | | 195 | | | | | 200 | | | | | 205 | | |
| Pro | Pro | Ser | Thr | Asn | Ala | Gly | Arg | Arg | Gln | Lys | His | Arg | Leu | Thr | Cys |
| | | 210 | | | | | 215 | | | | | 220 | | | |
| Pro | Ser | Cys | Asp | Ser | Tyr | Glu | Lys | Lys | Pro | Pro | Lys | Glu | Phe | Leu | Glu |
| 225 | | | | | 230 | | | | | 235 | | | | | 240 |
| Arg | Phe | Lys | Ser | Leu | Leu | Gln | Lys | Met | Ile | His | Gln | His | | | |
| | | | | 245 | | | | | 250 | | | | | | |

```
<210> SEQ ID NO 148
<211> LENGTH: 238
<212> TYPE: PRT
<213> ORGANISM: Artificial Sequence
<220> FEATURE:
<223> OTHER INFORMATION: Synthetic Construct

<400> SEQUENCE: 148
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Ser | Thr | Trp | Ser | Ile | Asn |
| | | | 20 | | | | | 25 | | | | | 30 | | |
| Thr | Leu | Ala | Trp | Tyr | Arg | Gln | Ala | Pro | Gly | Lys | Gln | Arg | Asp | Leu | Val |
| | | | | 35 | | | | | 40 | | | | 45 | | |
| Ala | Arg | Ile | Ser | Ser | Gly | Gly | Ser | Thr | Tyr | Tyr | Ala | Asp | Ser | Val | Lys |

```
Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser Gln Gly Gln Asp Arg His Met Ile Arg Met Arg Gln
        115                 120                 125

Leu Ile Asp Ile Val Asp Gln Leu Lys Asn Tyr Val Asn Asp Leu Val
    130                 135                 140

Pro Glu Phe Leu Pro Ala Pro Glu Asp Val Glu Thr Asn Cys Glu Trp
145                 150                 155                 160

Ser Ala Phe Ser Cys Phe Gln Lys Ala Gln Leu Lys Ser Ala Asn Thr
                165                 170                 175

Gly Asn Asn Glu Arg Ile Ile Asn Val Ser Ile Lys Lys Leu Lys Arg
            180                 185                 190

Lys Pro Pro Ser Thr Asn Ala Gly Arg Arg Gln Lys His Arg Leu Thr
        195                 200                 205

Cys Pro Ser Cys Asp Ser Tyr Glu Lys Lys Pro Lys Glu Phe Leu
    210                 215                 220

Glu Arg Phe Lys Ser Leu Leu Gln Lys Met Ile His Gln His
225                 230                 235

<210> SEQ ID NO 149
<211> LENGTH: 255
<212> TYPE: PRT
<213> ORGANISM: Artificial Sequence
<220> FEATURE:
<223> OTHER INFORMATION: Synthetic Construct

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser Ala Ser Thr Lys Gly Pro Gln Gly Gln Asp Arg His
        115                 120                 125

Met Ile Arg Met Arg Gln Leu Ile Asp Ile Val Asp Gln Leu Lys Asn
    130                 135                 140

Tyr Val Asn Asp Leu Val Pro Glu Phe Leu Pro Ala Pro Glu Asp Val
145                 150                 155                 160

Glu Thr Asn Cys Glu Trp Ser Ala Phe Ser Cys Phe Gln Lys Ala Gln
                165                 170                 175

Leu Lys Ser Ala Asn Thr Gly Asn Asn Glu Arg Ile Ile Asn Val Ser
```

```
                 180                 185                 190

Ile Lys Lys Leu Lys Arg Lys Pro Pro Ser Thr Asn Ala Gly Arg Arg
            195                 200                 205

Gln Lys His Arg Leu Thr Cys Pro Ser Cys Asp Ser Tyr Glu Lys Lys
            210                 215                 220

Pro Pro Lys Glu Phe Leu Glu Arg Phe Lys Ser Leu Leu Gln Lys Met
225                 230                 235                 240

Ile His Gln His Leu Ser Ser Arg Thr His Gly Ser Glu Asp Ser
                245                 250                 255

<210> SEQ ID NO 150
<211> LENGTH: 244
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser Ala Ser Thr Lys Gly Pro Gly Gln Asp Arg His
        115                 120                 125

Met Ile Arg Met Arg Gln Leu Ile Asp Ile Val Asp Gln Leu Lys Asn
    130                 135                 140

Tyr Val Asn Asp Leu Val Pro Glu Phe Leu Pro Ala Pro Glu Asp Val
145                 150                 155                 160

Glu Thr Asn Cys Glu Trp Ser Ala Phe Ser Cys Phe Gln Lys Ala Gln
                165                 170                 175

Leu Lys Ser Ala Asn Thr Gly Asn Asn Glu Arg Ile Ile Asn Val Ser
            180                 185                 190

Ile Lys Lys Leu Lys Arg Lys Pro Pro Ser Thr Asn Ala Gly Arg Arg
        195                 200                 205

Gln Lys His Arg Leu Thr Cys Pro Ser Cys Asp Ser Tyr Glu Lys Lys
    210                 215                 220

Pro Pro Lys Glu Phe Leu Glu Arg Phe Lys Ser Leu Leu Gln Lys Met
225                 230                 235                 240

Ile His Gln His

<210> SEQ ID NO 151
<211> LENGTH: 308
<212> TYPE: PRT
<213> ORGANISM: Artificial Sequence
<220> FEATURE:
<223> OTHER INFORMATION: Synthetic Construct
```

<400> SEQUENCE: 151

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr His Tyr Ala Asp Ser Val Lys
    50                  55                  60

Gly Arg Phe Thr Val Ser Arg Asp Asn Ala Glu Asn Thr Leu Val Leu
65                  70                  75                  80

Gln Met Asn Ser Leu Lys Pro Glu Asp Thr Ala Val Tyr Tyr Cys Tyr
                85                  90                  95

Ala Gln Ser Thr Trp Tyr Pro Pro Ser Trp Gly Gln Gly Thr Gln Val
            100                 105                 110

Thr Val Ser Ser Gly Gly Gly Ser Gly Gly Gly Ser Gly Gly Gly Ser
        115                 120                 125

Gly Gly Gly Ser Ala Phe Gly Ile Ser Gly Val Gln Lys Tyr Thr Arg
    130                 135                 140

Ala Leu His Asp Ser Ser Ile Thr Gly Ile Ser Pro Ile Thr Glu Tyr
145                 150                 155                 160

Leu Ala Ser Leu Ser Thr Tyr Asn Asp Gln Ser Ile Thr Phe Ala Leu
                165                 170                 175

Glu Asp Glu Ser Tyr Glu Ile Tyr Val Glu Asp Leu Lys Lys Asp Glu
            180                 185                 190

Lys Lys Asp Lys Val Leu Leu Ser Tyr Tyr Glu Ser Gln His Pro Ser
        195                 200                 205

Asn Glu Ser Gly Asp Gly Val Asp Gly Lys Met Leu Met Val Thr Leu
    210                 215                 220

Ser Pro Thr Lys Asp Phe Trp Leu His Ala Asn Asn Lys Glu His Ser
225                 230                 235                 240

Val Glu Leu His Lys Ser Glu Lys Pro Leu Pro Asp Gln Ala Phe Phe
                245                 250                 255

Val Leu His Asn Met His Ser Asn Ser Val Ser Phe Glu Ser Lys Thr
            260                 265                 270

Asp Pro Gly Val Phe Ile Gly Val Lys Asp Asn His Leu Ala Leu Ile
        275                 280                 285

Lys Val Asp Ser Ser Glu Asn Leu Ser Thr Glu Asn Ile Leu Phe Lys
    290                 295                 300

Leu Ser Glu Thr
305

<210> SEQ ID NO 152
<211> LENGTH: 291
<212> TYPE: PRT
<213> ORGANISM: Artificial Sequence
<220> FEATURE:
<223> OTHER INFORMATION: Synthetic Construct

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val

```
                35                  40                  45
Ala Arg Ile Ser Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Tyr
                 85                  90                  95

Ala Gln Ser Thr Trp Tyr Pro Pro Ser Trp Gly Gln Gly Thr Leu Val
                100                 105                 110

Thr Val Ser Ser Gly Gly Gly Ser Gly Gly Ser Gly Gly Gly Gly Ser
                115                 120                 125

Gly Gly Gly Ser Ser Ile Thr Gly Ile Ser Pro Ile Thr Glu Tyr Leu
130                 135                 140

Ala Ser Leu Ser Thr Tyr Asn Asp Gln Ser Ile Thr Phe Ala Leu Glu
145                 150                 155                 160

Asp Glu Ser Tyr Glu Ile Tyr Val Glu Asp Leu Lys Lys Asp Glu Lys
                165                 170                 175

Lys Asp Lys Val Leu Leu Ser Tyr Tyr Glu Ser Gln His Pro Ser Asn
                180                 185                 190

Glu Ser Gly Asp Gly Val Asp Gly Lys Met Leu Met Val Thr Leu Ser
                195                 200                 205

Pro Thr Lys Asp Phe Trp Leu His Ala Asn Asn Lys Glu His Ser Val
210                 215                 220

Glu Leu His Lys Ser Glu Lys Pro Leu Pro Asp Gln Ala Phe Phe Val
225                 230                 235                 240

Leu His Asn Met His Ser Asn Ser Val Ser Phe Glu Ser Lys Thr Asp
                245                 250                 255

Pro Gly Val Phe Ile Gly Val Lys Asp Asn His Leu Ala Leu Ile Lys
                260                 265                 270

Val Asp Ser Ser Glu Asn Leu Ser Thr Glu Asn Ile Leu Phe Lys Leu
                275                 280                 285

Ser Glu Thr
    290

<210> SEQ ID NO 153
<211> LENGTH: 292
<212> TYPE: PRT
<213> ORGANISM: Artificial Sequence
<220> FEATURE:
<223> OTHER INFORMATION: Synthetic Construct

<400> SEQUENCE: 153

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
                20                  25                  30

Thr Leu Ala Trp Tyr Arg Gln Ala Pro Gly Lys Gln Arg Asp Leu Val
                35                  40                  45

Ala Arg Ile Ser Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Tyr
                 85                  90                  95

Ala Gln Ser Thr Trp Tyr Pro Pro Ser Trp Gly Gln Gly Thr Leu Val
```

```
                100             105             110
Thr Val Ser Ser Ala Phe Gly Ile Ser Gly Val Gln Lys Tyr Thr Arg
            115                 120                 125
Ala Leu His Asp Ser Ser Ile Thr Gly Ile Ser Pro Ile Thr Glu Tyr
        130                 135                 140
Leu Ala Ser Leu Ser Thr Tyr Asn Asp Gln Ser Ile Thr Phe Ala Leu
145                 150                 155                 160
Glu Asp Glu Ser Tyr Glu Ile Tyr Val Glu Asp Leu Lys Lys Asp Glu
                165                 170                 175
Lys Lys Asp Lys Val Leu Leu Ser Tyr Tyr Glu Ser Gln His Pro Ser
            180                 185                 190
Asn Glu Ser Gly Asp Gly Val Asp Gly Lys Met Leu Met Val Thr Leu
        195                 200                 205
Ser Pro Thr Lys Asp Phe Trp Leu His Ala Asn Asn Lys Glu His Ser
210                 215                 220
Val Glu Leu His Lys Ser Glu Lys Pro Leu Pro Asp Gln Ala Phe Phe
225                 230                 235                 240
Val Leu His Asn Met His Ser Asn Ser Val Ser Phe Glu Ser Lys Thr
                245                 250                 255
Asp Pro Gly Val Phe Ile Gly Val Lys Asp Asn His Leu Ala Leu Ile
            260                 265                 270
Lys Val Asp Ser Ser Glu Asn Leu Ser Thr Glu Asn Ile Leu Phe Lys
        275                 280                 285
Leu Ser Glu Thr
    290

<210> SEQ ID NO 154
<211> LENGTH: 286
<212> TYPE: PRT
<213> ORGANISM: Artificial Sequence
<220> FEATURE:
<223> OTHER INFORMATION: Synthetic Construct

<400> SEQUENCE: 154

Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Thr Trp Ser Ile Asn
            20                  25                  30
Thr Leu Ala Trp Tyr Arg Gln Ala Pro Gly Lys Gln Arg Asp Leu Val
        35                  40                  45
Ala Arg Ile Ser Ser Gly Gly Ser Thr Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Tyr
                85                  90                  95
Ala Gln Ser Thr Trp Tyr Pro Pro Ser Trp Gly Gln Gly Thr Leu Val
            100                 105                 110
Thr Val Ser Ser Gly Gly Gly Gly Ser Gly Gly Gly Ser Gly Gly Gly Ser
        115                 120                 125
Gly Gly Gly Ser Ser Pro Ile Thr Glu Tyr Leu Ala Ser Leu Ser Thr
    130                 135                 140
Tyr Asn Asp Gln Ser Ile Thr Phe Ala Leu Glu Asp Glu Ser Tyr Glu
145                 150                 155                 160
Ile Tyr Val Glu Asp Leu Lys Lys Asp Glu Lys Lys Asp Lys Val Leu
```

```
                165                 170                 175
Leu Ser Tyr Tyr Glu Ser Gln His Pro Ser Asn Glu Ser Gly Asp Gly
            180                 185                 190

Val Asp Gly Lys Met Leu Met Val Thr Leu Ser Pro Thr Lys Asp Phe
            195                 200                 205

Trp Leu His Ala Asn Asn Lys Glu His Ser Val Glu Leu His Lys Ser
    210                 215                 220

Glu Lys Pro Leu Pro Asp Gln Ala Phe Phe Val Leu His Asn Met His
225                 230                 235                 240

Ser Asn Ser Val Ser Phe Glu Ser Lys Thr Asp Pro Gly Val Phe Ile
                245                 250                 255

Gly Val Lys Asp Asn His Leu Ala Leu Ile Lys Val Asp Ser Ser Glu
                260                 265                 270

Asn Leu Ser Thr Glu Asn Ile Leu Phe Lys Leu Ser Glu Thr
                275                 280                 285
```

<210> SEQ ID NO 155
<211> LENGTH: 176
<212> TYPE: PRT
<213> ORGANISM: Homo sapiens

<400> SEQUENCE: 155

```
Ala Phe Gly Ile Ser Gly Val Gln Lys Tyr Thr Arg Ala Leu His Asp
1               5                   10                  15

Ser Ser Ile Thr Gly Ile Ser Pro Ile Thr Glu Tyr Leu Ala Ser Leu
                20                  25                  30

Ser Thr Tyr Asn Asp Gln Ser Ile Thr Phe Ala Leu Glu Asp Glu Ser
            35                  40                  45

Tyr Glu Ile Tyr Val Glu Asp Leu Lys Lys Asp Glu Lys Lys Asp Lys
        50                  55                  60

Val Leu Leu Ser Tyr Tyr Glu Ser Gln His Pro Ser Asn Glu Ser Gly
65                  70                  75                  80

Asp Gly Val Asp Gly Lys Met Leu Met Val Thr Leu Ser Pro Thr Lys
                85                  90                  95

Asp Phe Trp Leu His Ala Asn Asn Lys Glu His Ser Val Glu Leu His
            100                 105                 110

Lys Ser Glu Lys Pro Leu Pro Asp Gln Ala Phe Phe Val Leu His Asn
        115                 120                 125

Met His Ser Asn Ser Val Ser Phe Glu Ser Lys Thr Asp Pro Gly Val
    130                 135                 140

Phe Ile Gly Val Lys Asp Asn His Leu Ala Leu Ile Lys Val Asp Ser
145                 150                 155                 160

Ser Glu Asn Leu Ser Thr Glu Asn Ile Leu Phe Lys Leu Ser Glu Thr
                165                 170                 175
```

<210> SEQ ID NO 156
<211> LENGTH: 159
<212> TYPE: PRT
<213> ORGANISM: Homo sapiens

<400> SEQUENCE: 156

```
Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
                20                  25                  30

Glu Ile Tyr Val Glu Asp Leu Lys Lys Asp Glu Lys Lys Asp Lys Val
```

```
                35                  40                  45

Leu Leu Ser Tyr Tyr Glu Ser Gln His Pro Ser Asn Glu Ser Gly Asp
 50                      55                  60

Gly Val Asp Gly Lys Met Leu Met Val Thr Leu Ser Pro Thr Lys Asp
 65                  70                  75                  80

Phe Trp Leu His Ala Asn Asn Lys Glu His Ser Val Glu Leu His Lys
                 85                  90                  95

Ser Glu Lys Pro Leu Pro Asp Gln Ala Phe Phe Val Leu His Asn Met
            100                 105                 110

His Ser Asn Ser Val Ser Phe Glu Ser Lys Thr Asp Pro Gly Val Phe
        115                 120                 125

Ile Gly Val Lys Asp Asn His Leu Ala Leu Ile Lys Val Asp Ser Ser
130                 135                 140

Glu Asn Leu Ser Thr Glu Asn Ile Leu Phe Lys Leu Ser Glu Thr
145                 150                 155

<210> SEQ ID NO 157
<211> LENGTH: 154
<212> TYPE: PRT
<213> ORGANISM: Homo sapiens

<400> SEQUENCE: 157

Ser Pro Ile Thr Glu Tyr Leu Ala Ser Leu Ser Thr Tyr Asn Asp Gln
 1                5                  10                  15

Ser Ile Thr Phe Ala Leu Glu Asp Glu Ser Tyr Glu Ile Tyr Val Glu
             20                  25                  30

Asp Leu Lys Lys Asp Glu Lys Lys Asp Lys Val Leu Leu Ser Tyr Tyr
         35                  40                  45

Glu Ser Gln His Pro Ser Asn Glu Ser Gly Asp Gly Val Asp Gly Lys
 50                  55                  60

Met Leu Met Val Thr Leu Ser Pro Thr Lys Asp Phe Trp Leu His Ala
 65                  70                  75                  80

Asn Asn Lys Glu His Ser Val Glu Leu His Lys Ser Glu Lys Pro Leu
                 85                  90                  95

Pro Asp Gln Ala Phe Phe Val Leu His Asn Met His Ser Asn Ser Val
            100                 105                 110

Ser Phe Glu Ser Lys Thr Asp Pro Gly Val Phe Ile Gly Val Lys Asp
        115                 120                 125

Asn His Leu Ala Leu Ile Lys Val Asp Ser Ser Glu Asn Leu Ser Thr
130                 135                 140

Glu Asn Ile Leu Phe Lys Leu Ser Glu Thr
145                 150

<210> SEQ ID NO 158
<211> LENGTH: 8
<212> TYPE: PRT
<213> ORGANISM: Artificial Sequence
<220> FEATURE:
<223> OTHER INFORMATION: Synthetic Construct

<400> SEQUENCE: 158

Ala Ser Thr Lys Gly Pro Ser Val
 1                5

<210> SEQ ID NO 159
<211> LENGTH: 6
<212> TYPE: PRT
<213> ORGANISM: Artificial Sequence
```

<220> FEATURE:
<223> OTHER INFORMATION: Synthetic Construct

<400> SEQUENCE: 159

Ala Ser Thr Lys Gly Pro
1               5

<210> SEQ ID NO 160
<211> LENGTH: 343
<212> TYPE: PRT
<213> ORGANISM: Artificial Sequence
<220> FEATURE:
<223> OTHER INFORMATION: Synthetic Construct

<400> SEQUENCE: 160

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr His Tyr Ala Asp Ser Val Lys
    50                  55                  60

Gly Arg Phe Thr Val Ser Arg Asp Asn Ala Glu Asn Thr Leu Val Leu
65                  70                  75                  80

Gln Met Asn Ser Leu Lys Pro Glu Asp Thr Ala Val Tyr Tyr Cys Tyr
                85                  90                  95

Ala Gln Ser Thr Trp Tyr Pro Pro Ser Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Ile Thr Cys Pro Pro Pro Met Ser
    130                 135                 140

Val Glu His Ala Asp Ile Trp Val Lys Ser Tyr Ser Leu Tyr Ser Arg
145                 150                 155                 160

Glu Arg Tyr Ile Cys Asn Ser Gly Phe Lys Arg Lys Ala Gly Thr Ser
                165                 170                 175

Ser Leu Thr Glu Cys Val Leu Asn Lys Ala Thr Asn Val Ala His Trp
            180                 185                 190

Thr Thr Pro Ser Leu Lys Cys Ile Arg Arg Lys Arg Ala Pro Val
        195                 200                 205

Lys Gln Thr Leu Asn Phe Asp Leu Leu Lys Leu Ala Gly Asp Val Glu
    210                 215                 220

Ser Asn Pro Gly Pro Asn Trp Val Asn Val Ile Ser Asp Leu Lys Lys
225                 230                 235                 240

Ile Glu Asp Leu Ile Gln Ser Met His Ile Asp Ala Thr Leu Tyr Thr
                245                 250                 255

Glu Ser Asp Val His Pro Ser Cys Lys Val Thr Ala Met Lys Cys Phe
            260                 265                 270

Leu Leu Glu Leu Gln Val Ile Ser Leu Glu Ser Gly Asp Ala Ser Ile
        275                 280                 285

His Asp Thr Val Glu Asn Leu Ile Ile Leu Ala Asn Asn Ser Leu Ser
    290                 295                 300

Ser Asn Gly Asn Val Thr Glu Ser Gly Cys Lys Glu Cys Glu Glu Leu
305                 310                 315                 320

Glu Glu Lys Asn Ile Lys Glu Phe Leu Gln Ser Phe Val His Ile Val
```

325                 330                 335
Gln Met Phe Ile Asn Thr Ser
            340

<210> SEQ ID NO 161
<211> LENGTH: 346
<212> TYPE: PRT
<213> ORGANISM: Artificial Sequence
<220> FEATURE:
<223> OTHER INFORMATION: Synthetic Construct

<400> SEQUENCE: 161

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr His Tyr Ala Asp Ser Val Lys
    50                  55                  60

Gly Arg Phe Thr Val Ser Arg Asp Asn Ala Glu Asn Thr Leu Val Leu
65                  70                  75                  80

Gln Met Asn Ser Leu Lys Pro Glu Asp Thr Ala Val Tyr Tyr Cys Tyr
                85                  90                  95

Ala Gln Ser Thr Trp Tyr Pro Pro Ser Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Gly Gly Gly Gly Ser Ile Thr Cys Pro Pro Pro Met Ser
    130                 135                 140

Val Glu His Ala Asp Ile Trp Val Lys Ser Tyr Ser Leu Tyr Ser Arg
145                 150                 155                 160

Glu Arg Tyr Ile Cys Asn Ser Gly Phe Lys Arg Lys Ala Gly Thr Ser
                165                 170                 175

Ser Leu Thr Glu Cys Val Leu Asn Lys Ala Thr Asn Val Ala His Trp
            180                 185                 190

Thr Thr Pro Ser Leu Lys Cys Ile Arg Asp Pro Ala Leu Val His Gln
        195                 200                 205

Arg Pro Ala Pro Pro Gly Ser Gly Gly Gly Ser Gly Gly Gly
    210                 215                 220

Ser Gly Gly Gly Gly Ser Leu Gln Asn Trp Val Asn Val Ile Ser Asp
225                 230                 235                 240

Leu Lys Lys Ile Glu Asp Leu Ile Gln Ser Met His Ile Asp Ala Thr
                245                 250                 255

Leu Tyr Thr Glu Ser Asp Val His Pro Ser Cys Lys Val Thr Ala Met
            260                 265                 270

Lys Cys Phe Leu Leu Glu Leu Gln Val Ile Ser Leu Glu Ser Gly Asp
        275                 280                 285

Ala Ser Ile His Asp Thr Val Glu Asn Leu Ile Ile Leu Ala Asn Asn
    290                 295                 300

Ser Leu Ser Ser Asn Gly Asn Val Thr Glu Ser Gly Cys Lys Glu Cys
305                 310                 315                 320

Glu Glu Leu Glu Glu Lys Asn Ile Lys Glu Phe Leu Gln Ser Phe Val
                325                 330                 335

His Ile Val Gln Met Phe Ile Asn Thr Ser
            340

340             345

<210> SEQ ID NO 162
<211> LENGTH: 480
<212> TYPE: PRT
<213> ORGANISM: Artificial Sequence
<220> FEATURE:
<223> OTHER INFORMATION: Synthetic Construct

<400> SEQUENCE: 162

Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gln Arg Asp Leu Val
        35                  40                  45

Ala Ile Ile Ser Ala Gly Gly Thr Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Leu Gln Arg Arg Ile Gly Met Leu Arg Asp Tyr Trp Gly Gln Gly Thr
            100                 105                 110

Gln Val Thr Val Ser Ser Gly Gly Gly Ser Gly Gly Gly Ser Gly Gly
        115                 120                 125

Gly Ser Gly Gly Gly Ser Gln Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Ser Thr Trp Ser Ile Asn Thr Leu Ala Trp Tyr Arg Gln Ala Pro Gly
                165                 170                 175

Lys Gln Arg Asp Leu Val Ala Arg Ile Ser Ser Gly Ser Thr His
            180                 185                 190

Tyr Ala Asp Ser Val Lys Gly Arg Phe Thr Val Ser Arg Asp Asn Ala
        195                 200                 205

Glu Asn Thr Leu Val Leu Gln Met Asn Ser Leu Lys Pro Glu Asp Thr
    210                 215                 220

Ala Val Tyr Tyr Cys Tyr Ala Gln Ser Thr Trp Tyr Pro Pro Ser Trp
225                 230                 235                 240

Gly Gln Gly Thr Gln Val Thr Val Ser Ser Gly Gly Gly Gly Ser Gly
                245                 250                 255

Gly Gly Ser Gly Gly Gly Ser Gly Gly Gly Ser Ile Thr
            260                 265                 270

Cys Pro Pro Pro Met Ser Val Glu His Ala Asp Ile Trp Val Lys Ser
        275                 280                 285

Tyr Ser Leu Tyr Ser Arg Glu Arg Tyr Ile Cys Asn Ser Gly Phe Lys
    290                 295                 300

Arg Lys Ala Gly Thr Ser Ser Leu Thr Glu Cys Val Leu Asn Lys Ala
305                 310                 315                 320

Thr Asn Val Ala His Trp Thr Thr Pro Ser Leu Lys Cys Ile Arg Asp
                325                 330                 335

Pro Ala Leu Val His Gln Arg Pro Ala Pro Gly Gly Ser Gly Gly
            340                 345                 350

Gly Gly Ser Gly Gly Gly Ser Gly Gly Gly Gly Ser Leu Gln Asn Trp

-continued

```
                355                 360                 365
Val Asn Val Ile Ser Asp Leu Lys Lys Ile Glu Asp Leu Ile Gln Ser
    370                 375                 380

Met His Ile Asp Ala Thr Leu Tyr Thr Glu Ser Asp Val His Pro Ser
385                 390                 395                 400

Cys Lys Val Thr Ala Met Lys Cys Phe Leu Glu Leu Gln Val Ile
                405                 410                 415

Ser Leu Glu Ser Gly Asp Ala Ser Ile His Asp Thr Val Glu Asn Leu
                420                 425                 430

Ile Ile Leu Ala Asn Asn Ser Leu Ser Ser Asn Gly Asn Val Thr Glu
            435                 440                 445

Ser Gly Cys Lys Glu Cys Glu Glu Leu Glu Glu Lys Asn Ile Lys Glu
            450                 455                 460

Phe Leu Gln Ser Phe Val His Ile Val Gln Met Phe Ile Asn Thr Ser
465                 470                 475                 480

<210> SEQ ID NO 163
<211> LENGTH: 389
<212> TYPE: PRT
<213> ORGANISM: Artificial Sequence
<220> FEATURE:
<223> OTHER INFORMATION: Synthetic Construct

<400> SEQUENCE: 163

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser Gly Ser Gly Ser Gly Ser Gly Gly Ser
        130                 135                 140

Gly Gln Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr His Tyr Ala Asp Ser Val
        195                 200                 205

Lys Gly Arg Phe Thr Val Ser Arg Asp Asn Ala Glu Asn Thr Leu Val
    210                 215                 220

Leu Gln Met Asn Ser Leu Lys Pro Glu Asp Thr Ala Val Tyr Tyr Cys
225                 230                 235                 240

Tyr Ala Gln Ser Thr Trp Tyr Pro Pro Ser Trp Gly Gln Gly Thr Gln
```

```
            245                 250                 255
Val Thr Val Ser Ser Gly Gly Ser Gly Gly Gly Ser Gly Gly Gly
            260                 265                 270

Ser Gly Gly Gly Ser Gln Val Gln Leu Val Glu Ser Gly Gly Leu
            275                 280                 285

Val Gln Pro Gly Gly Ser Leu Arg Leu Ser Cys Ala Ala Ser Gly Arg
            290                 295                 300

Thr Leu Glu Ser Tyr Val Met Ala Trp Phe Arg Gln Ala Pro Gly Lys
305                 310                 315                 320

Glu Arg Glu Ala Val Ala Ser Ile Asn Trp Ser Ser Gly Arg Leu Ile
                325                 330                 335

Tyr Ala Asp Ser Val Lys Gly Arg Phe Thr Ile Ser Arg Asp Asn Ser
                340                 345                 350

Lys Asn Thr Leu Tyr Leu Gln Met Asn Ser Leu Arg Ala Glu Asp Thr
                355                 360                 365

Ala Val Tyr Tyr Cys Ala Ala Gly Arg Tyr Trp Gly Gln Gly Thr Gln
            370                 375                 380

Val Thr Val Ser Ser
385

<210> SEQ ID NO 164
<211> LENGTH: 630
<212> TYPE: PRT
<213> ORGANISM: Artificial Sequence
<220> FEATURE:
<223> OTHER INFORMATION: Synthetic Construct

<400> SEQUENCE: 164

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Ser Gly Gly Ser Gly Gly Ser Gly Gly Ser
    130                 135                 140

Gly Gln Val Gln Leu Val Glu Ser Gly Gly Leu Val Gln Pro Gly Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
                180                 185                 190

Val Ala Arg Ile Ser Ser Gly Gly Ser Thr His Tyr Ala Asp Ser Val
            195                 200                 205

Lys Gly Arg Phe Thr Val Ser Arg Asp Asn Ala Glu Asn Thr Leu Val
```

```
              210                 215                 220
Leu Gln Met Asn Ser Leu Lys Pro Glu Asp Thr Ala Val Tyr Tyr Cys
225                 230                 235                 240

Tyr Ala Gln Ser Thr Trp Tyr Pro Pro Ser Trp Gly Gln Gly Thr Gln
                245                 250                 255

Val Thr Val Ser Ser Gly Gly Gly Gly Gly Gly Ser Gly Gly Gly Gly
                260                 265                 270

Ser Gly Gly Gly Ser Gly Gly Gly Ser Gly Arg Ser Ala Gly Gly
        275                 280                 285

Gly Gly Ser Gln Val Gln Leu Val Glu Ser Gly Gly Leu Val Gln
        290                 295                 300

Pro Gly Gly Ser Leu Arg Leu Ser Cys Ala Ala Ser Gly Arg Thr Leu
305                 310                 315                 320

Glu Ser Tyr Val Met Ala Trp Phe Arg Gln Ala Pro Gly Lys Glu Arg
                325                 330                 335

Glu Ala Val Ala Ser Ile Asn Trp Ser Ser Gly Arg Leu Ile Tyr Ala
                340                 345                 350

Asp Ser Val Lys Gly Arg Phe Thr Ile Ser Arg Asp Asn Ser Lys Asn
        355                 360                 365

Thr Leu Tyr Leu Gln Met Asn Ser Leu Arg Ala Glu Asp Thr Ala Val
        370                 375                 380

Tyr Tyr Cys Ala Ala Gly Arg Tyr Trp Gly Gln Gly Thr Gln Val Thr
385                 390                 395                 400

Val Ser Ser Asp Lys Thr His Thr Cys Pro Pro Cys Pro Ala Pro Glu
                405                 410                 415

Leu Leu Gly Gly Pro Ser Val Phe Leu Phe Pro Pro Lys Pro Lys Asp
                420                 425                 430

Thr Leu Met Ile Ser Arg Thr Pro Glu Val Thr Cys Val Val Val Asp
        435                 440                 445

Val Ser His Glu Asp Pro Glu Val Lys Phe Asn Trp Tyr Val Asp Gly
        450                 455                 460

Val Glu Val His Asn Ala Lys Thr Lys Pro Arg Glu Glu Gln Tyr Asn
465                 470                 475                 480

Ser Thr Tyr Arg Val Val Ser Val Leu Thr Val Leu His Gln Asp Trp
                485                 490                 495

Leu Asn Gly Lys Glu Tyr Lys Cys Lys Val Ser Asn Lys Ala Leu Pro
                500                 505                 510

Ala Pro Ile Glu Lys Thr Ile Ser Lys Ala Lys Gly Gln Pro Arg Glu
        515                 520                 525

Pro Gln Val Tyr Thr Leu Pro Pro Cys Arg Glu Glu Met Thr Lys Asn
        530                 535                 540

Gln Val Ser Leu Trp Cys Leu Val Lys Gly Phe Tyr Pro Ser Asp Ile
545                 550                 555                 560

Ala Val Glu Trp Glu Ser Asn Gly Gln Pro Glu Asn Asn Tyr Lys Thr
                565                 570                 575

Thr Pro Pro Val Leu Asp Ser Asp Gly Ser Phe Phe Leu Tyr Ser Lys
                580                 585                 590

Leu Thr Val Asp Lys Ser Arg Trp Gln Gln Gly Asn Val Phe Ser Cys
        595                 600                 605

Ser Val Met His Glu Ala Leu His Asn His Tyr Thr Gln Lys Ser Leu
        610                 615                 620

Ser Leu Ser Pro Gly Lys
625                 630
```

```
<210> SEQ ID NO 165
<211> LENGTH: 339
<212> TYPE: PRT
<213> ORGANISM: Artificial Sequence
<220> FEATURE:
<223> OTHER INFORMATION: Synthetic Construct

<400> SEQUENCE: 165

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Glu Arg Glu Ala Val
        35                  40                  45

Ala Ser Ile Asn Trp Ser Gly Arg Leu Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

Asp Lys Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
    130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
    210                 215                 220

Glu Lys Thr Ile Ser Lys Ala Lys Gly Gln Pro Arg Glu Pro Gln Val
225                 230                 235                 240

Cys Thr Leu Pro Pro Ser Arg Glu Glu Met Thr Lys Asn Gln Val Ser
                245                 250                 255

Leu Ser Cys Ala Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Val Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys

<210> SEQ ID NO 166
<211> LENGTH: 484
```

```
<212> TYPE: PRT
<213> ORGANISM: Artificial Sequence
<220> FEATURE:
<223> OTHER INFORMATION: Synthetic Construct

<400> SEQUENCE: 166

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gly Ser Gly Ser Gly Ser Gly Gly Ser Gly Ser
    130                 135                 140

Gly Gln Val Gln Leu Val Glu Ser Gly Gly Gly Leu Val Glu Ala Gly
145                 150                 155                 160

Asp Ser Leu Arg Leu Ser Cys Val Val Ser Gly Arg Thr Leu Glu Ser
                165                 170                 175

Tyr Val Met Ala Trp Phe Arg Gln Ala Pro Gly Lys Glu Arg Glu Ala
            180                 185                 190

Val Ala Ser Ile Asn Trp Ser Ser Gly Arg Leu Ile Tyr Ala Asp Phe
        195                 200                 205

Val Lys Gly Arg Phe Thr Ile Ser Arg Asp Tyr Glu Lys Asn Thr Ile
    210                 215                 220

Tyr Leu Ser Met Asn Asn Leu Lys Pro Glu Asp Thr Ala Val Tyr Tyr
225                 230                 235                 240

Cys Ala Ala Gly Arg Tyr Trp Gly Gln Gly Thr Gln Val Thr Val Ser
                245                 250                 255

Ser Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380
```

```
Val Tyr Thr Leu Pro Pro Cys Arg Glu Glu Met Thr Lys Asn Gln Val
385                 390                 395                 400

Ser Leu Trp Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
        420                 425                 430

Pro Val Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
        450                 455                 460

Met His Glu Ala Leu His Asn His Tyr Thr Gln Lys Ser Leu Ser Leu
465                 470                 475                 480

Ser Pro Gly Lys

<210> SEQ ID NO 167
<211> LENGTH: 345
<212> TYPE: PRT
<213> ORGANISM: Artificial Sequence
<220> FEATURE:
<223> OTHER INFORMATION: Synthetic Construct

<400> SEQUENCE: 167

Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gln Arg Asp Leu Val
        35                  40                  45

Ala Ile Ile Ser Ala Gly Gly Thr Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Leu Gln Arg Arg Ile Gly Met Leu Arg Asp Tyr Trp Gly Gln Gly Thr
            100                 105                 110

Gln Val Thr Val Ser Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Cys Thr Leu Pro Pro Ser Arg Glu Glu Met
                245                 250                 255

Thr Lys Asn Gln Val Ser Leu Ser Cys Ala Val Lys Gly Phe Tyr Pro
```

```
                260                 265                 270
Ser Asp Ile Ala Val Glu Trp Glu Ser Asn Gly Gln Pro Glu Asn Asn
            275                 280                 285

Tyr Lys Thr Thr Pro Pro Val Leu Asp Ser Asp Gly Ser Phe Phe Leu
            290                 295                 300

Val Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 168
<211> LENGTH: 116
<212> TYPE: PRT
<213> ORGANISM: Artificial Sequence
<220> FEATURE:
<223> OTHER INFORMATION: Synthetic Construct

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser
        115

<210> SEQ ID NO 169
<211> LENGTH: 116
<212> TYPE: PRT
<213> ORGANISM: Artificial Sequence
<220> FEATURE:
<223> OTHER INFORMATION: Synthetic Construct

<400> SEQUENCE: 169

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Leu Glu Trp Val
        35                  40                  45

Ser Ser Ile Asn Asn Gly Gly Ser Asp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Ile Gly Gly Pro Gly Ala Ser Pro Ser Gly Gln Gly Thr Gln Val
            100                 105                 110

Thr Val Ser Ser
        115

<210> SEQ ID NO 170
<211> LENGTH: 116
<212> TYPE: PRT
<213> ORGANISM: Artificial Sequence
<220> FEATURE:
<223> OTHER INFORMATION: Synthetic Construct

<400> SEQUENCE: 170

Gln Val Gln Leu Val Glu Ser Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Phe Glu Trp Val
            35                  40                  45

Ser Ser Ile Asn Asn Gly Gly Ser Asp Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser
        115

<210> SEQ ID NO 171
<211> LENGTH: 119
<212> TYPE: PRT
<213> ORGANISM: Homo sapiens

<400> SEQUENCE: 171

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile
        115

<210> SEQ ID NO 172
<211> LENGTH: 120
<212> TYPE: PRT
<213> ORGANISM: Homo sapiens

<400> SEQUENCE: 172
```

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His
            115                 120

<210> SEQ ID NO 173
<211> LENGTH: 119
<212> TYPE: PRT
<213> ORGANISM: Artificial Sequence
<220> FEATURE:
<223> OTHER INFORMATION: Synthetic Construct

<400> SEQUENCE: 173

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Ile Arg
                20                  25                  30

His Met Arg Trp Tyr Arg Gln Ala Pro Gly Lys Gln Arg Glu Leu Val
            35                  40                  45

Ala Thr Val Ser Asn Asp Gly Ser Ala Tyr Tyr Leu Gly Ser Val Lys
        50                  55                  60

Gly Arg Phe Thr Ile Ser Arg Thr Asn Ala Lys Asn Thr Leu Leu Tyr
65                  70                  75                  80

Leu Gln Met Asn Ser Leu Lys Pro Glu Asp Ser Ala Leu Tyr Ile Cys
                85                  90                  95

Asn Ala Asp Thr Trp Gly Trp Pro Gly Ala Asp Tyr Trp Gly Gln Gly
            100                 105                 110

Thr Gln Val Thr Val Ser Ser
        115

<210> SEQ ID NO 174
<211> LENGTH: 112
<212> TYPE: PRT
<213> ORGANISM: Artificial Sequence
<220> FEATURE:
<223> OTHER INFORMATION: Synthetic Construct

<400> SEQUENCE: 174

Gln Val Gln Leu Val Glu Ser Gly Gly Gly Leu Val Glu Ala Gly Asp
1               5                   10                  15

Ser Leu Arg Leu Ser Cys Val Val Ser Gly Arg Thr Leu Glu Ser Tyr
                20                  25                  30

Val Met Ala Trp Phe Arg Gln Ala Pro Gly Lys Glu Arg Glu Ala Val
            35                  40                  45

Ala Ser Ile Asn Trp Ser Ser Gly Arg Leu Ile Tyr Ala Asp Phe Val
```

```
                  50                  55                  60
Lys Gly Arg Phe Thr Ile Ser Arg Asp Tyr Glu Lys Asn Thr Ile Tyr
 65                  70                  75                  80

Leu Ser Met Asn Asn Leu Lys Pro Glu Asp Thr Ala Val Tyr Tyr Cys
                     85                  90                  95

Ala Ala Gly Arg Tyr Trp Gly Gln Gly Thr Gln Val Thr Val Ser Ser
                100                 105                 110

<210> SEQ ID NO 175
<211> LENGTH: 118
<212> TYPE: PRT
<213> ORGANISM: Artificial Sequence
<220> FEATURE:
<223> OTHER INFORMATION: Synthetic Construct

<400> SEQUENCE: 175

Gln Val Gln Leu Val Glu Ser Gly Gly Gly Leu Val Gln Ala Gly Gly
 1               5                  10                  15

Ser Leu Arg Leu Ser Cys Ala Ala Ser Gly Ile Thr Phe Pro Val Asn
                20                  25                  30

Ala Tyr Gly Trp Tyr Arg Gln Ala Pro Gly Lys Gln Arg Asp Leu Val
            35                  40                  45

Ala Ile Ile Ser Ala Gly Gly Thr Thr Asn Tyr Ala Asp Ser Val Lys
 50                  55                  60

Gly Arg Phe Ala Ile Ser Lys Asp Asn Val Asn Thr Val Tyr Leu
 65                  70                  75                  80

Gln Met Asn Ser Leu Thr Ser Glu Asp Thr Gly Val Tyr Tyr Cys Tyr
                     85                  90                  95

Leu Gln Arg Arg Ile Gly Met Leu Arg Asp Tyr Trp Gly Gln Gly Thr
                100                 105                 110

Gln Val Thr Val Ser Ser
            115

<210> SEQ ID NO 176
<211> LENGTH: 118
<212> TYPE: PRT
<213> ORGANISM: Artificial Sequence
<220> FEATURE:
<223> OTHER INFORMATION: Synthetic Construct

<400> SEQUENCE: 176

Gln Val Gln Leu Val Glu Ser Gly Gly Gly Leu Val Gln Pro Gly Gly
 1               5                  10                  15

Ser Leu Arg Leu Ser Cys Ala Ala Ser Gly Ile Thr Phe Pro Val Asn
                20                  25                  30

Ala Tyr Gly Trp Tyr Arg Gln Ala Pro Gly Lys Gln Arg Asp Leu Val
            35                  40                  45

Ala Ile Ile Ser Ala Gly Gly Thr Thr Asn Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Tyr
                     85                  90                  95

Leu Gln Arg Arg Ile Gly Met Leu Arg Asp Tyr Trp Gly Gln Gly Thr
                100                 105                 110

Gln Val Thr Val Ser Ser
            115
```

```
<210> SEQ ID NO 177
<211> LENGTH: 118
<212> TYPE: PRT
<213> ORGANISM: Artificial Sequence
<220> FEATURE:
<223> OTHER INFORMATION: Synthetic Construct

<400> SEQUENCE: 177

Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gly Leu Glu Leu Val
        35                  40                  45

Ala Ile Ile Ser Ala Gly Gly Thr Thr Asn Tyr Ala Asp Ser Val Lys
    50                  55                  60

Gly Arg Phe Ala Ile Ser Lys Asp Asn Val Asn Asn Thr Val Tyr Leu
65                  70                  75                  80

Gln Met Asn Ser Leu Thr Ser Glu Asp Thr Gly Val Tyr Tyr Cys Tyr
                85                  90                  95

Leu Gln Arg Arg Ile Gly Met Leu Arg Asp Tyr Trp Gly Gln Gly Thr
            100                 105                 110

Gln Val Thr Val Ser Ser
        115

<210> SEQ ID NO 178
<211> LENGTH: 118
<212> TYPE: PRT
<213> ORGANISM: Artificial Sequence
<220> FEATURE:
<223> OTHER INFORMATION: Synthetic Construct

<400> SEQUENCE: 178

Gln Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Pro Val Asn
            20                  25                  30

Ala Tyr Gly Trp Tyr Arg Gln Ala Pro Gly Lys Gly Leu Glu Leu Val
        35                  40                  45

Ala Ile Ile Ser Ala Gly Gly Thr Thr Asn Tyr Ala Asp Ser Val Lys
    50                  55                  60

Gly Arg Phe Ala Ile Ser Lys Asp Asn Val Asn Asn Thr Val Tyr Leu
65                  70                  75                  80

Gln Met Asn Ser Leu Thr Ser Glu Asp Thr Gly Val Tyr Tyr Cys Tyr
                85                  90                  95

Leu Gln Arg Arg Ile Gly Met Leu Arg Asp Tyr Trp Gly Gln Gly Thr
            100                 105                 110

Gln Val Thr Val Ser Ser
        115

<210> SEQ ID NO 179
<211> LENGTH: 119
<212> TYPE: PRT
<213> ORGANISM: Artificial Sequence
<220> FEATURE:
<223> OTHER INFORMATION: Synthetic Construct

<400> SEQUENCE: 179

Gln Val Gln Leu Val Glu Ser Gly Gly Gly Leu Val Gln Pro Gly Gly
```

```
                1               5                  10                  15
        Ser Leu Arg Leu Ser Cys Ala Ala Ser Gly Ser Ile Ser Ser Ile Arg
                        20                  25                  30

His Met Arg Trp Tyr Arg Gln Ala Pro Gly Lys Gln Arg Glu Leu Val
                        35                  40                  45

Ala Thr Val Ser Asn Asp Gly Ser Ala Tyr Tyr Ala Gly Ser Val Lys
                    50                  55                  60

Gly Arg Phe Thr Ile Ser Arg Asp Asn Ser Lys Asn Thr Leu Leu Tyr
        65                  70                  75                  80

Leu Gln Met Asn Ser Leu Arg Ala Glu Asp Thr Ala Val Tyr Ile Cys
                        85                  90                  95

Asn Ala Asp Thr Trp Gly Trp Pro Gly Ala Asp Tyr Trp Gly Gln Gly
                        100                 105                 110

Thr Gln Val Thr Val Ser Ser
                    115

<210> SEQ ID NO 180
<211> LENGTH: 119
<212> TYPE: PRT
<213> ORGANISM: Artificial Sequence
<220> FEATURE:
<223> OTHER INFORMATION: Synthetic Construct

<400> SEQUENCE: 180

Gln Val Gln Leu Val Glu Ser Gly Gly Gly Leu Val Gln Ala Gly Gly
        1               5                   10                  15

Ser Leu Arg Leu Ser Cys Ala Ala Ser Gly Ser Ile Ser Ser Ile Arg
                        20                  25                  30

His Met Arg Trp Tyr Arg Gln Ala Pro Gly Lys Gly Leu Glu Leu Val
                        35                  40                  45

Ala Thr Val Ser Asn Asp Gly Ser Ala Tyr Tyr Leu Gly Ser Val Lys
                    50                  55                  60

Gly Arg Phe Thr Ile Ser Arg Thr Asn Ala Lys Asn Thr Leu Leu Tyr
        65                  70                  75                  80

Leu Gln Met Asn Ser Leu Lys Pro Glu Asp Ser Ala Leu Tyr Ile Cys
                        85                  90                  95

Asn Ala Asp Thr Trp Gly Trp Pro Gly Ala Asp Tyr Trp Gly Gln Gly
                        100                 105                 110

Thr Gln Val Thr Val Ser Ser
                    115

<210> SEQ ID NO 181
<211> LENGTH: 119
<212> TYPE: PRT
<213> ORGANISM: Artificial Sequence
<220> FEATURE:
<223> OTHER INFORMATION: Synthetic Construct

<400> SEQUENCE: 181

Gln Val Gln Leu Val Glu Ser Gly Gly Gly Leu Val Gln Pro Gly Gly
        1               5                   10                  15

Ser Leu Arg Leu Ser Cys Ala Ala Ser Gly Ser Ile Ser Ser Ile Arg
                        20                  25                  30

His Met Arg Trp Tyr Arg Gln Ala Pro Gly Lys Gly Leu Glu Leu Val
                        35                  40                  45

Ala Thr Val Ser Asn Asp Gly Ser Ala Tyr Tyr Leu Gly Ser Val Lys
                    50                  55                  60
```

```
Gly Arg Phe Thr Ile Ser Arg Thr Asn Ala Lys Asn Thr Leu Leu Tyr
 65                  70                  75                  80

Leu Gln Met Asn Ser Leu Lys Pro Glu Asp Ser Ala Leu Tyr Ile Cys
                 85                  90                  95

Asn Ala Asp Thr Trp Gly Trp Pro Gly Ala Asp Tyr Trp Gly Gln Gly
            100                 105                 110

Thr Gln Val Thr Val Ser Ser
            115
```

<210> SEQ ID NO 182
<211> LENGTH: 112
<212> TYPE: PRT
<213> ORGANISM: Artificial Sequence
<220> FEATURE:
<223> OTHER INFORMATION: Synthetic Construct

<400> SEQUENCE: 182

```
Gln Val Gln Leu Val Glu Ser Gly Gly Gly Leu Val Gln Pro Gly Gly
 1               5                  10                  15

Ser Leu Arg Leu Ser Cys Val Val Ser Gly Arg Thr Leu Glu Ser Tyr
             20                  25                  30

Val Met Ala Trp Phe Arg Gln Ala Pro Gly Lys Glu Arg Glu Ala Val
         35                  40                  45

Ala Ser Ile Asn Trp Ser Ser Gly Arg Leu Ile Tyr Ala Asp Phe Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Gly Arg Tyr Trp Gly Gln Gly Thr Gln Val Thr Val Ser Ser
            100                 105                 110
```

<210> SEQ ID NO 183
<211> LENGTH: 112
<212> TYPE: PRT
<213> ORGANISM: Artificial Sequence
<220> FEATURE:
<223> OTHER INFORMATION: Synthetic Construct

<400> SEQUENCE: 183

```
Gln Val Gln Leu Val Glu Ser Gly Gly Gly Leu Val Gln Pro Gly Gly
 1               5                  10                  15

Ser Leu Arg Leu Ser Cys Val Val Ser Gly Arg Thr Leu Glu Ser Tyr
             20                  25                  30

Val Met Ala Trp Phe Arg Gln Ala Pro Gly Lys Gly Leu Glu Ala Val
         35                  40                  45

Ala Ser Ile Asn Trp Ser Ser Gly Arg Leu Ile Tyr Ala Asp Phe Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Ala Ala Gly Arg Tyr Trp Gly Gln Gly Thr Gln Val Thr Val Ser Ser
            100                 105                 110
```

<210> SEQ ID NO 184
<211> LENGTH: 112
<212> TYPE: PRT
<213> ORGANISM: Artificial Sequence
<220> FEATURE:
<223> OTHER INFORMATION: Synthetic Construct

<400> SEQUENCE: 184

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Gly Leu Glu Ala Val
        35                  40                  45

Ala Ser Ile Asn Trp Ser Ser Gly Arg Leu Ile Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110
```

<210> SEQ ID NO 185
<211> LENGTH: 112
<212> TYPE: PRT
<213> ORGANISM: Artificial Sequence
<220> FEATURE:
<223> OTHER INFORMATION: Synthetic Construct

<400> SEQUENCE: 185

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Gly Leu Glu Ala Val
        35                  40                  45

Ala Ser Ile Asn Trp Ser Ser Gly Arg Leu Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110
```

<210> SEQ ID NO 186
<211> LENGTH: 112
<212> TYPE: PRT
<213> ORGANISM: Artificial Sequence
<220> FEATURE:
<223> OTHER INFORMATION: Synthetic Construct

<400> SEQUENCE: 186

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Leu Glu Ser Tyr
            20                  25                  30

Val Met Ala Trp Phe Arg Gln Ala Pro Gly Lys Glu Arg Glu Ala Val
        35                  40                  45

Ala Ser Ile Asn Trp Ser Ser Gly Arg Leu Ile Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Arg Tyr Trp Gly Gln Gly Thr Gln Val Thr Val Ser Ser
            100                 105                 110

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 187

Gly Ser Ile Ser Ser Ile Arg His
1               5

<210> SEQ ID NO 188
<211> LENGTH: 7
<212> TYPE: PRT
<213> ORGANISM: Artificial Sequence
<220> FEATURE:
<223> OTHER INFORMATION: Synthetic Construct

<400> SEQUENCE: 188

Val Ser Asn Asp Gly Ser Ala
1               5

<210> SEQ ID NO 189
<211> LENGTH: 12
<212> TYPE: PRT
<213> ORGANISM: Artificial Sequence
<220> FEATURE:
<223> OTHER INFORMATION: Synthetic Construct

<400> SEQUENCE: 189

Asn Ala Asp Thr Trp Gly Trp Pro Gly Ala Asp Tyr
1               5                   10

<210> SEQ ID NO 190
<211> LENGTH: 8
<212> TYPE: PRT
<213> ORGANISM: Artificial Sequence
<220> FEATURE:
<223> OTHER INFORMATION: Synthetic Construct

<400> SEQUENCE: 190

Gly Arg Thr Leu Glu Ser Tyr Val
1               5

<210> SEQ ID NO 191
<211> LENGTH: 8
<212> TYPE: PRT
<213> ORGANISM: Artificial Sequence
<220> FEATURE:
<223> OTHER INFORMATION: Synthetic Construct

<400> SEQUENCE: 191

Ile Asn Trp Ser Ser Gly Arg Leu
1               5

<210> SEQ ID NO 192
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 192

Ala Ala Gly Arg Tyr
1               5

<210> SEQ ID NO 193
<211> LENGTH: 8
<212> TYPE: PRT
<213> ORGANISM: Artificial Sequence
<220> FEATURE:
<223> OTHER INFORMATION: Synthetic Construct

<400> SEQUENCE: 193

Gly Ile Thr Phe Pro Val Asn Ala
1               5

<210> SEQ ID NO 194
<211> LENGTH: 7
<212> TYPE: PRT
<213> ORGANISM: Artificial Sequence
<220> FEATURE:
<223> OTHER INFORMATION: Synthetic Construct

<400> SEQUENCE: 194

Ile Ser Ala Gly Gly Thr Thr
1               5

<210> SEQ ID NO 195
<211> LENGTH: 12
<212> TYPE: PRT
<213> ORGANISM: Artificial Sequence
<220> FEATURE:
<223> OTHER INFORMATION: Synthetic Construct

<400> SEQUENCE: 195

Tyr Leu Gln Arg Arg Ile Gly Met Leu Arg Asp Tyr
1               5                   10

<210> SEQ ID NO 196
<211> LENGTH: 311
<212> TYPE: PRT
<213> ORGANISM: Artificial Sequence
<220> FEATURE:
<223> OTHER INFORMATION: Synthetic Construct

<400> SEQUENCE: 196

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
                20                  25                  30

Asp Ala Ala Leu Leu Ala Thr Gln Met Asp Arg Val Asn Ala Ile Pro
            35                  40                  45

Phe Thr Tyr Glu Gln Leu Asp Val Leu Lys His Lys Leu Asp Glu Leu
        50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
                100                 105                 110

Ser Pro Gln Ala Pro Arg Arg Pro Leu Pro Gln Val Ala Thr Leu Ile
```

-continued

```
            115                 120                 125
Asp Arg Phe Val Lys Gly Arg Gly Gln Leu Asp Lys Asp Thr Leu Asp
        130                 135                 140

Thr Leu Thr Ala Phe Tyr Pro Gly Tyr Leu Cys Ser Leu Ser Pro Glu
145                 150                 155                 160

Glu Leu Ser Ser Val Pro Pro Ser Ser Ile Trp Ala Val Arg Pro Gln
                165                 170                 175

Asp Leu Asp Thr Cys Asp Pro Arg Gln Leu Asp Val Leu Tyr Pro Lys
                180                 185                 190

Ala Arg Leu Ala Phe Gln Asn Met Asn Gly Ser Glu Tyr Phe Val Lys
            195                 200                 205

Ile Gln Ser Phe Leu Gly Gly Ala Pro Thr Glu Asp Leu Lys Ala Leu
        210                 215                 220

Ser Gln Gln Asn Val Ser Met Asp Leu Ala Thr Phe Met Lys Leu Arg
225                 230                 235                 240

Thr Asp Ala Val Leu Pro Leu Thr Val Ala Glu Val Gln Lys Leu Leu
                245                 250                 255

Gly Pro His Val Glu Gly Leu Lys Ala Glu Glu Arg His Arg Pro Val
                260                 265                 270

Arg Asp Trp Ile Leu Arg Gln Arg Gln Asp Asp Leu Asp Thr Leu Gly
            275                 280                 285

Leu Gly Leu Gln Gly Gly Ile Pro Asn Gly Tyr Leu Val Leu Asp Leu
        290                 295                 300

Ser Met Gln Glu Ala Leu Ser
305                 310
```

CYTOKINE-ALBUMIN BINDING MOIETY FUSION PROTEINS AND USES THEREOF

CROSS-REFERENCE TO RELATED APPLICATIONS

This application is a National Stage of International Application No. PCT/US2019/037558, filed Jun. 17, 2019; which claims the benefit of U.S. Provisional Application No. 62/686,481, filed Jun. 18, 2018, and U.S. Provisional Application No. 62/809,496, filed Feb. 22, 2019; the disclosure of each of which is hereby incorporated by reference in its entirety.

REFERENCE TO A SEQUENCE LISTING

The present specification is being filed with a Sequence Listing in Computer Readable Form (CRF), which is entitled 216A002US01_SEQ_LIST_ST25.txt of 235,280 bytes in size and created Apr. 14, 2021; the content of which is incorporated herein by reference in its entirety.

FIELD OF THE APPLICATION

The present application relates to fusion proteins, methods of making thereof, and methods of treating a disease or disorder by administering a fusion protein.

BACKGROUND OF THE APPLICATION

Cytokine therapy is an effective strategy for stimulating the immune system to induce immune response against a disease (such as a cancer or infection). However, cytokines that are administered to patients generally have a short half-life. For example, interleukin-21 stimulates various immune cells (such as T, B and NK cells) and enhances anti-tumor activity. It was reported that a recombinant IL-21 has a half-life of about one to three hours following intravenous administration. See Schmidt H, Clin Cancer Res. 2010 Nov. 1; 16 (21):5312-9.

Therefore, there is a need for developing new cytokine therapeutics that effectively treating a disease.

The disclosures of all publications, patents, patent applications and published patent applications referred to herein are hereby incorporated herein by reference in their entirety.

BRIEF SUMMARY OF THE APPLICATION

The present application provides fusion proteins comprising: a) a cytokine, and b) an albumin binding moiety (such as an sdAb that binds to albumin). In some embodiments, the cytokine is selected from the group consisting of IL-21, IL-7, IL-15, IL-15 bound to IL-15Rα or fragment thereof, IL-33, and IL-22. In some embodiments, the fusion protein further comprises an antigen binding moiety.

The present application also provides fusion proteins comprising: a) a cytokine fused to an albumin binding moiety ("cytokine-ALBBM"), and b) an antigen binding moiety, wherein the linkage between the cytokine-ALBBM and the antigen binding moiety is optionally cleavable. In some embodiments, the cytokine is selected from the group consisting of IL-21, IL-7, IL-15, IL-15 bound to IL-15Rα or fragment thereof, IL-33, and IL-22. In some embodiments, the antigen binding moiety is fused to the C-terminus of the cytokine-ALBBM. In some embodiments, the antigen binding moiety is fused to the N-terminus of the cytokine-ALBBM. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the antigen binding moiety binds to a tumor antigen. In some embodiments, the tumor antigen is selected from the group consisting of mesothelin ("MSLN"), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, the antigen binding moiety is an antibody or fragment thereof. In some embodiments, the antigen binding moiety comprises a single domain antibody (sdAb). In some embodiments, antigen binding moiety comprises a $V_HH$ single domain antibody. In some embodiments, the sdAb binds to mesothelin.

In some embodiments according to any one of the fusion proteins described above, the cytokine is IL-21. In some embodiments, the IL-21 comprises an amino acid sequence of SEQ ID NO: 1, 2, 126, 171, or 172 or a variant thereof comprising at least about 80% (such as at least about any of 80%, 85%, 90%, 91%, 92%, 93%, 94%, 95%, 96%, 97%, 98%, or 99%) sequence identity to SEQ ID NO: 1, 2, 126, 171, or 172.

In some embodiments according to any one of the fusion proteins described above, the albumin binding moiety binds to a human serum albumin (HSA) and/or a cynomolgus monkey serum albumin (CMSA).

In some embodiments according to any one of the fusion proteins described above, the albumin binding moiety comprises an albumin binding domain (ABD).

In some embodiments according to any one of the fusion proteins described above, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11.

In some embodiments according to any one of the fusion proteins described above, the albumin binding moiety comprises a single domain antibody (sdAb). In some embodiments, the sdAb is a $V_HH$ single domain antibody.

In some embodiments according to any one of the fusion proteins described above, the albumin binding moiety is fused to the C-terminus of the cytokine.

In some embodiments according to any one of the fusion proteins described above, the albumin binding moiety is fused to the N-terminus of the cytokine.

In some embodiments according to any one of the fusion proteins described above, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159.

The present application also provides pharmaceutical compositions comprising any of the fusion protein described above.

The present application also provides methods of treating a disease or condition in an individual comprising administering to the individual any of the fusion proteins pharmaceutical compositions described above. In some embodiments, the method further comprises administering a second agent.

The present application also provides methods of treating a disease or condition in an individual comprising administering to the individual a) a fusion protein comprising i) a cytokine and ii) a half-life extending domain fused to the cytokine; and b) a second agent. In some embodiments, the half-life extending domain is an albumin binding moiety. In some embodiments, the half-life extending domain is an albumin. In some embodiments, the half-life extending domain is an Fc fragment. In some embodiments, the Fc fragment is selected from the group consisting of an IgG1, IgG2, IgG3, and IgG4 Fc fragments or a variant thereof. In some embodiments, the Fc fragment is an IgG1 Fc fragment or variant thereof. In some embodiments, the IgG1 Fc fragment or variant thereof comprises a mutation at position 297, wherein the amino acid at position 297 is mutated to alanine, aspartic acid or glycine. In some embodiments, the individual is a human. In some embodiments, the disease or condition is selected from the group consisting of a cancer, an inflammatory condition, and an infection.

In some embodiments according to any one of the methods described above, the disease or condition is an inflammatory disease. In some embodiments, the cytokine is IL-22. In some embodiments, the disease is selected from the group consisting of ulcerative colitis, Crohn's disease, or ulcerative ileitis, and intestinal graft vs host disease.

In some embodiments according to any one of the methods described above, the disease or condition is a cancer. In some embodiments, the cancer is a solid or liquid tumor. In some embodiments, the cancer is selected from the group consisting of mesothelioma, lung cancer, breast cancer, ovarian cancer, pancreatic cancer, lymphoma, leukemia, head and neck cancer, liver cancer, esophageal cancer, gastric cancer, and colorectal cancer. In some embodiments, the cancer is selected from the group consisting of mesothelioma, lung cancer, ovarian cancer, and gastric cancer. In some embodiments, the cytokine is selected from the group consisting of IL-21, IL-7, IL-15, IL-15 bound to IL-15Rα or fragment thereof, and IL-33.

In some embodiments according to any one of the methods described above, the fusion protein is administered about once every three weeks to about twice a week.

In some embodiments according to any one of the methods described above, the amount of fusion protein for each administration is about 100 ng/kg to about 10 mg/kg.

In some embodiments according to any one of the methods described above, the fusion protein is administered parenterally into the individual. In some embodiments, the fusion protein is administered intravenously or subcutaneously into the individual.

In some embodiments according to any one of the methods described above, the fusion protein is administered for at least about one week to six months for each treatment cycle.

In some embodiments according to any one of the methods described above, the second agent comprises a therapeutic antibody, an immune checkpoint inhibitor, a second cytokine, a chemotherapeutic agent, a tyrosine kinase inhibitor, or an immune cell. In some embodiments, the second agent is a therapeutic antibody. In some embodiments, the therapeutic antibody binds to a tumor antigen. In some embodiments, the tumor antigen is selected from the group consisting of mesothelin (MSLN), GPA33, Her-2 (ERBB2), EGFR, and CD20 (MS4A1). In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, the tumor antigen is mesothelin. In some embodiments, the second agent is an anti-mesothelin antibody or fragment thereof. In some embodiments, the anti-mesothelin antibody or fragment thereof comprises a single chain antibody comprising an anti-mesothelin heavy chain variable region (anti-MSLN $V_H$), wherein: a) the anti-MSLN $V_H$ comprises a CDR1 comprising the amino acid sequence of SEQ ID NO: 46, a CDR2 comprising the amino acid sequence of SEQ ID NO: 47, and a CDR3 comprising the amino acid sequence of SEQ ID: NO: 48, or a variant thereof comprising up to a total of 3, 2, or 1 amino acid substitutions in the CDRs; or b) the anti-MSLN $V_H$ comprises a CDR1 comprising the amino acid sequence of SEQ ID NO: 49, a CDR2 comprising the amino acid sequence of SEQ ID NO: 50, and a CDR3 comprising the amino acid sequence of GRY, or a variant thereof comprising up to a total of 3, 2, or 1 amino acid substitutions in the CDRs. In some embodiments, the second agent that binds to mesothelin is administered about once per month to about twice per week. In some embodiments, the amount of the second agent for each administration is about 100 ng/kg to about 100 mg/kg. In some embodiments, the second agent is an immune checkpoint modulator. In some embodiments, the immune checkpoint modulator is an inhibitor of an immune checkpoint protein selected from the group consisting of PD-L1, CTLA4, PD-L2, PD-1, CD47, TIGIT, GITR, TIM3, LAG3, CD27, 4-1BB, and B7H4. In some embodiments, the immune checkpoint protein is PD-1. In some embodiments, the second agent is an anti-PD-1 antibody or fragment thereof. In some embodiments, the amount of the second agent for each administration is about 1 µg/kg to about 100 mg/kg. In some embodiments, the second agent is a second cytokine. In some embodiments, the cytokine in the fusion protein is IL-21, and wherein the second cytokine is selected from the group consisting of IL-7, IL-15, IL15 bound to IL15Rα or half-life extended variants thereof. In some embodiments, the second agent is an immune cell. In some embodiments, the immune cell comprises T cells or NK cells. In some embodiments, the immune cell comprises T cells expressing a chimeric antigen receptor (CAR), T cells expressing a modified T cell receptor (TCR), or T cells isolated from a tumor. In some embodiments, the second agent is a tyrosine kinase inhibitor. In some embodiments, the second agent is administered parenterally or orally into the individual. In some embodiments, the second agent is administered parenterally into the individual. In some embodiments, the second agent is administered intravenously into the individual.

In some embodiments according to any one of the methods described above, the fusion protein and the second agent are administered simultaneously, concurrently or sequentially into the individual.

BRIEF DESCRIPTION OF THE DRAWINGS

FIG. 6C shows ADCC activities of PBMCs against N87 cells in the presence of P390, P394, P461/P462, and P461/P463 at different dosages in combination with 3 ng/mL P303.

FIGS. 9A, 9F, and 9G depict SDS-PAGE pictures that shows the staining of IL-21-anti-HSA fusion protein P394 (i.e., AWT-P394) and P593 (i.e., AWT-P593) and P748. In FIGS. 9F and 9G, arrows indicate intact target protein, and asterisk indicates cleaved protein.

FIG. 10E depicts comparison of the $T_{onset}$ of anti-albumin antibody AWT-P342 and its humanized version AWT-P610. FIG. 10D depicts the binding of anti-HSA antibody AWT-367 and its humanized anti-AWT-P494 with human, monkey or mouse albumin. FIG. 10E depicts KD of the binding of AWT-P367 or AWT-494 with human, monkey or mouse albumin.

DETAILED DESCRIPTION OF THE APPLICATION

Figure 1:
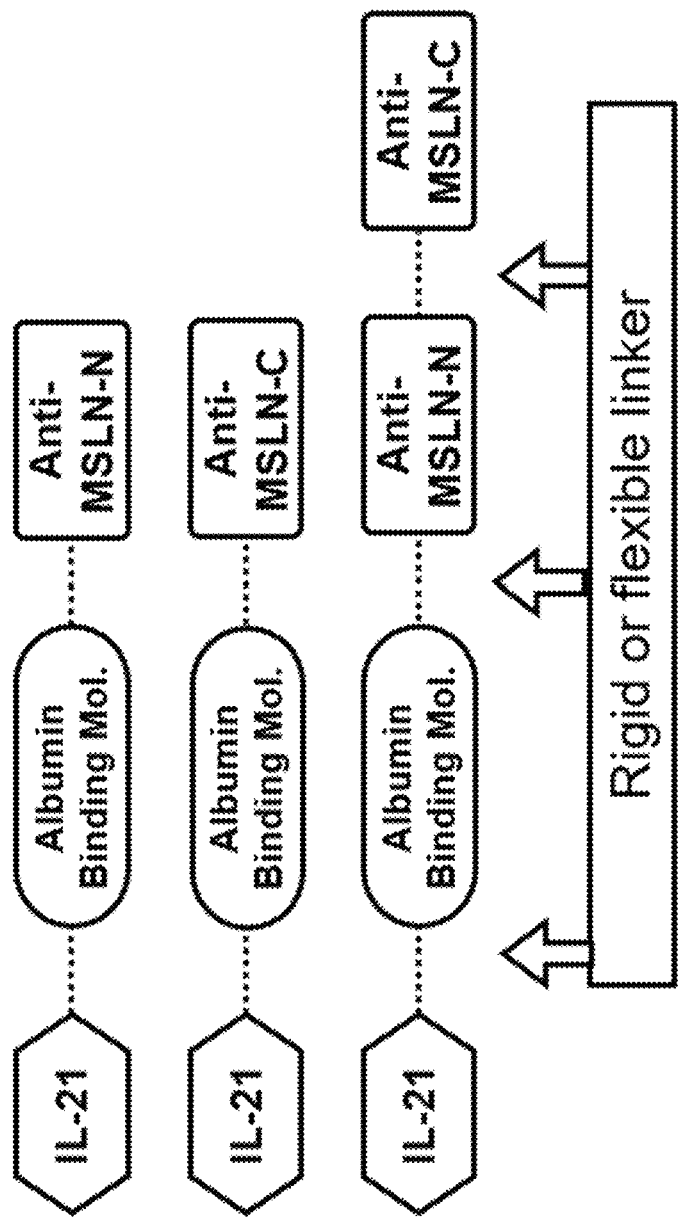
FIG. 1 depicts exemplary IL-21 fusion proteins provided herein.

The present application is related to fusion proteins that comprise a cytokine and a half-life extending domain. In some embodiments, the cytokine is selected from the group consisting of IL-21, IL-7, IL-15, IL-15 bound to IL-15Rα or fragment thereof, IL-33, and IL-22. In some embodiments, the fusion protein comprises a) a cytokine fused to an albumin binding moiety ("cytokine-ALBBM"), and b) an antigen binding moiety; the linkage between the cytokine-ALBBM and the antigen binding moiety is optionally cleavable.

The present application further provides methods of treating diseases or disorders (such as a cancer or an inflammatory disease) comprising administering a fusion protein as described above. In some embodiments, the method comprises administering a) a fusion protein comprising i) a cytokine, and ii) a half-life extending domain, and b) a second agent. Exemplary second agents include, and are not limited to, a therapeutic agent, an immune checkpoint inhibitor, a second cytokine, a tyrosine kinase inhibitor, a chemotherapeutic agent, or an immune cell.

Also provided are compositions, kits and articles of manufacture comprising the bispecific antibodies described herein and methods of making thereof.

I. Definitions

The term "antibody" is used in its broadest sense and encompasses various antibody structures, including but not limited to monoclonal antibodies, polyclonal antibodies, multispecific antibodies (e.g., bispecific antibodies), full-length antibodies and antigen-binding fragments thereof, so long as they exhibit the desired antigen-binding activity. The term "antibody moiety" refers to a full-length antibody or an antigen-binding fragment thereof.

An "isolated" antibody (or construct) is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator; or (3) to homogeneity by SDS-PAGE under non-reducing or reducing conditions using Coomassie Blue or, preferably, silver stain. Isolated antibody (or construct) includes the antibody in situ within recombinant cells since at least one component of the antibody's natural environment will not be present. Ordinarily, however, an isolated polypeptide, antibody, or construct will be prepared by at least one purification step.

A full-length antibody comprises two heavy chains and two light chains. The variable regions of the light and heavy chains are responsible for antigen binding. The variable domains of the heavy chain and light chain may be referred to as "$V_H$" and "$V_L$", respectively. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μheavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The terms "full-length antibody", "intact antibody", or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain variable domain (such as $V_H H$) and an Fc region. The constant domains may be native sequence constant domains (e.g., human native sequence constant domains) or amino acid sequence variants thereof. In some cases, the intact antibody may have one or more effector functions.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites. Heavy-chain only antibodies from the Camelid species have a single heavy chain variable region, which is referred to as "V$_H$H". V$_H$H is thus a special type of VH.

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the V$_H$ and V$_L$ antibody domains connected into a single polypeptide chain. In some embodiments, the scFv polypeptide further comprises a polypeptide linker between the V$_H$ and V$_L$ domains which enables the scFv to form the desired structure for antigen binding. For a review of scFv, see Plückthun in *The Pharmacology of Monoclonal Antibodies*, vol. 113, Rosenburg and Moore eds., Springer-Verlag, New York, pp. 269-315 (1994).

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody," "single domain antibody," or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "V$_H$Hs" (Variable domain of the heavy chain of the Heavy chain antibody). Camelid sdAb is one of the smallest known antigen-binding antibody fragments (see, e.g., Hamers-Casterman et al., Nature 363: 446-8 (1993); Greenberg et al., Nature 374:168-73 (1995); Hassanzadeh-Ghassabeh et al., Nanomedicine (Lond), 8:1013-26 (2013)). A basic V$_H$H has the following structure from the N-terminus to the C-terminus: FR1-CDR1-FR2-CDR2-FR3-CDR3-1R4, in which FR1 to FR4 refer to framework regions 1 to 4, respectively, and in which CDR1 to CDR3 refer to the complementarity determining regions 1 to 3.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 (or CDR3) displays the most diversity of the three HVRs, and is believed to play a unique role in conferring fine specificity to antibodies. See, e.g., Hamers-Casterman et al., Nature 363:446-448 (1993); Sheriff et al., Nature Struct. Biol. 3:733-736 (1996).

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., *J. Mol. Biol.*, 273: 927-948 (1997); MacCallum et al., J. Mol. Biol. 262:732-745 (1996); Abhinandan and Martin, *Mol. Immunol.*, 45: 3832-3839 (2008); Lefranc M. P. et al., *Dev. Comp. Immunol.*, 27: 55-77 (2003); and Honegger and Plückthun, *J. Mol. Biol.*, 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, *Mol. Immunol.*, 45: 3832-3839 (2008); Ehrenmann F et al., *Nucleic Acids Res.*, 38: D301-D307 (2010); and Adolf-Bryfogle J. et al., *Nucleic Acids Res.*, 43: D432-D438 (2015). The contents of the references cited in this paragraph are incorporated herein by reference in their entireties for use in the present application and for possible inclusion in one or more claims herein.

TABLE 1

CDR DEFINITIONS

| | Kabat[1] | Chothia[2] | MacCallum[3] | IMGT[4] | AHo[5] |
|---|---|---|---|---|---|
| V$_H$ CDR1 | 31-35 | 26-32 | 30-35 | 27-38 | 25-40 |
| V$_H$ CDR2 | 50-65 | 53-55 | 47-58 | 56-65 | 58-77 |
| V$_H$ CDR3 | 95-102 | 96-101 | 93-101 | 105-117 | 109-137 |
| V$_L$ CDR1 | 24-34 | 26-32 | 30-36 | 27-38 | 25-40 |
| V$_L$ CDR2 | 50-56 | 50-52 | 46-55 | 56-65 | 58-77 |
| V$_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the CDR residues as herein defined.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., Nucleic Acids Research 32(5):1792-1797, 2004; Edgar, R. C., BMC Bioinformatics 5(1):113, 2004).

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "constant domain" refers to the portion of an immunoglobulin molecule having a more conserved amino acid sequence relative to the other portion of the immunoglobulin, the variable domain, which contains the antigen-binding site. The constant domain contains the $C_H1$, $C_H2$ and $C_H3$ domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

The "CH1 domain" of a human IgG Fc region (also referred to as "C1" of "H1" domain) usually extends from about amino acid 118 to about amino acid 215 (EU numbering system).

"Hinge region" is generally defined as a region in IgG corresponding to Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec Immunol. 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

The term "Fc region" or "fragment crystallizable region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Fc receptor" or "FcR" describes a receptor that binds the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody or fragment thereof "competes" for binding to a target antigen with a second antibody or fragment thereof when the first antibody or fragment thereof inhibits the target antigen binding of the second antibody of fragment thereof by at least about 50% (such as at least about any one of 55%, 60%, 65%, 70%, 75%, 80%, 85%, 90%, 95%, 98% or 99%) in the presence of an equimolar concentration of the first antibody or fragment thereof, or vice versa. A high throughput process for "binning" antibodies based upon their cross-competition is described in PCT Publication No. WO 03/48731.

As use herein, the terms "specifically binds," "specifically recognizing," and "is specific for" refer to measurable and reproducible interactions, such as binding between a target and an antibody or antibody moiety, which is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, the extent of binding of an antibody to an unrelated target is less than about 10% of the binding of the antibody to the target as measured, e.g., by a radioimmunoassay (RIA). In some embodiments, an antibody that specifically binds a target has a dissociation constant ($K_D$) of $\leq 10^{-5}$ M, $\leq 10^{-6}$ M, $\leq 10^{-7}$M, $\leq 10^{-8}$M, $\leq 10^{-9}$M, $\leq 10^{-10}$ M, $\leq 10^{-11}$ M, or $\leq 10^{-12}$ M. In some embodiments, an antibody specifically binds an epitope on a protein that is conserved among the protein from different species. In some embodiments, specific binding can include, but does not require exclusive binding. Binding specificity of the antibody or antigen-binding domain can be determined experimentally by methods known in the art. Such methods comprise, but are not limited to Octet, Western blots, ELISA-, RIA-, ECL-, IRMA-, EIA-, BIACORE™-tests and peptide scans.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair. Binding affinity can be indicated by $K_d$, $K_{off}$, $K_{on}$, or $K_a$. The term "$K_{off}$", as used herein, is intended to refer to the off rate constant for dissociation of an antibody (or antigen-binding domain) from the antibody/antigen complex, as determined from a kinetic selection set up, expressed in units of $s^{-1}$. The term "$K_{on}$", as used herein, is intended to refer to the on rate constant for association of an antibody (or antigen-binding domain) to the antigen to form the antibody/antigen complex, expressed in units of $M^{-1} s^{-1}$. The term equilibrium dissociation constant "$K_D$" or "$K_d$", as used herein, refers to the dissociation constant of a particular antibody-antigen interaction, and describes the concentration of antigen required to occupy one half of all of the antibody-binding domains present in a solution of antibody molecules at equilibrium, and is equal to $K_{off}/K_{on}$, expressed in units of M. The measurement of $K_a$ presupposes that all binding agents are in solution. In the case where the antibody is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$, expressed in units of $M^{-1}$. The dissociation constant ($K_D$ or $K_d$) is used as an indicator showing affinity of antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (Mols). An antibody or antigen-binding fragment thereof that specifically binds to a target may have a dissociation constant ($K_a$) of, for example, $\leq 10^{-5}$ M, $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M.

Half maximal inhibitory concentration ($IC_{50}$) is a measure of the effectiveness of a substance (such as an antibody) in inhibiting a specific biological or biochemical function. It indicates how much of a particular drug or other substance (inhibitor, such as an antibody) is needed to inhibit a given biological process (e.g., the binding between albumin and CD155, or component of a process, i.e. an enzyme, cell, cell receptor or microorganism) by half. The values are typically expressed as molar concentration. $IC_{50}$ is comparable to an "$EC_{50}$" for agonist drug or other substance (such as an antibody). $EC_{50}$ also represents the plasma concentration required for obtaining 50% of a maximum effect in vivo. As used herein, an "$IC_{50}$" is used to indicate the effective concentration of an antibody (such as an anti-albumin sdAb) needed to neutralize 50% of the antigen bioactivity (such as albumin bioactivity) in vitro. $IC_{50}$ or $EC_{50}$ can be measured by bioassays such as inhibition of ligand binding by FACS analysis (competition binding assay), cell based cytokine release assay, or amplified luminescent proximity homogeneous assay (AlphaLISA).

As used herein, the term "cytokine" is understood to mean any protein or peptide, analog or functional fragment thereof, which is capable of stimulating or inducing a cytocidal immune response against a preselected cell-type, for example, a cancer cell or a virally-infected cell, in a mammal. Accordingly, it is contemplated that a variety of cytokines can be incorporated into this application. Useful cytokines include, for example, tumor necrosis factors (TNFs), interleukins (ILs), lymphokines (Ls), colony stimulating factors (CSFs), interferons (IFNs) including species variants, truncated analogs thereof which are capable of stimulating or inducing such cytocidal immune responses. Useful tumor necrosis factors include, for example, TNFα. Useful lymphokines include, for example, LT. Useful colony stimulating factors include, for example, GM-CSF and M-CSF. Useful interleukins include, for example, IL-2, IL-4, IL-5, IL-7, IL-12, IL-15, IL-18, IL-21, IL22, and IL-33. Useful interferons, include, for example, IFN-α, IFN-α and IFN-γ. The term "cytokine" is also understood to encompass any variant of a wildtype cytokine (such as IL-21, IL-7, IL-15, etc.) that comprises modification and maintains at least a significant portion (such as at least about 50%) of any of its desired function.

The term "truncated IL-21", as used herein, refers to a protein or peptide comprising an IL-21 that has a deletion of one or more amino acids at one or both of C- and N-terminus of a wildtype IL-21. A fusion protein comprising a truncated IL-21 described herein can have other moieties or domains such as an antigen-binding moiety, a linker, a signal sequence, or an albumin-binding moiety, although the IL-21 in the fusion protein is a truncated form that has at least one amino acid less than a wildtype IL-21. In some embodiments, the wildtype IL-21 has an amino acid sequence of SEQ ID NO: 1.

An "isolated" nucleic acid molecule encoding a construct, antibody, or antigen-binding fragment thereof described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies described herein is in a form other than in the form or setting in which it is found in nature. Isolated nucleic acid molecules therefore are distinguished from nucleic acid encoding the polypeptides and antibodies described herein existing naturally in cells. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that has the same function or biological activity as screened or selected for in the originally transformed cell is included herein.

As used herein, "treatment" or "treating" is an approach for obtaining beneficial or desired results, including clinical results. For purposes of this application, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the application contemplate any one or more of these aspects of treatment.

In the context of cancer, the term "treating" includes any or all of: inhibiting growth of cancer cells, inhibiting replication of cancer cells, lessening of overall tumor burden and ameliorating one or more symptoms associated with the disease.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to that of a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of an individual. In some examples, a reference is obtained from one or more healthy individuals who are not the individual or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in an individual that may be predisposed to the disease but has not yet been diagnosed with the disease.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

The terms "subject," "individual," and "patient" are used interchangeably herein to refer to a mammal, including, but not limited to, human, bovine, horse, feline, canine, rodent, or primate. In some embodiments, the individual is a human.

An "effective amount" of an agent refers to an amount effective, at dosages and for periods of time necessary, to achieve the desired therapeutic or prophylactic result. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

A "therapeutically effective amount" of a substance/molecule of the application, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to an individual to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to an individual. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

It is understood that embodiments of the application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II-A. Fusion Proteins Comprising an Albumin Binding Moiety

Provided herein are fusion proteins comprising: a) a cytokine, and b) an albumin binding moiety (such as an sdAb that binds to albumin) In some embodiments, the fusion protein comprises a) a cytokine selected from the group consisting of IL-21, IL-7, IL-15, IL-15 bound to IL-15Rα or fragment thereof, IL-33, and IL-22, and b) an albumin binding moiety (such as an sdAb that binds to albumin) In some embodiments, the albumin binding moiety comprises an albumin binding domain (ABD). In some embodiments, the albumin binding moiety comprises a single domain antibody (sdAb). In some embodiments, the albumin binding moiety is fused to the C-terminus of the cytokine. In some embodiments, the albumin binding moiety is fused to the N-terminus of the cytokine. In some embodiments, the cytokine and the albumin binding moiety are connected via a first linker (such as of about one to thirty amino acids). In some embodiments, the albumin binding moiety is a single domain antibody (such as a $V_H H$ antibody). An sdAb with relatively small molecular weight may help increase cancer penetration of the fusion protein, thereby making it better suited to treat certain cancers, e.g., solid tumors.

In some embodiments, there is provided a fusion protein comprising: a) an IL-21, and b) an albumin binding moiety (such as an sdAb that binds to albumin). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises an anti-albumin antibody (such as a single domain antibody (sdAb), such as a $V_H H$ single domain antibody). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-21 is a truncated IL-21. In some embodiments, the truncated IL-21 comprises an amino acid sequence of SEQ ID NO: 126, 171, or 172. In some embodiments, the first linker is a rigid linker. In some embodiments, the first linker is selected from the group consisting of SEQ ID NO: 21, 22, and 24. In some embodiments, the first linker is a flexible linker. In some embodiments, the first linker is selected from the group consisting of GSG and SEQ ID NOs: 12-14.

In some embodiments, there is provided a fusion protein comprising: a) an IL-21, and b) an albumin binding moiety (such as an sdAb that binds to albumin), wherein the IL-21 comprises an amino acid sequence of SEQ ID NO: 1, 2, 126, 171, or 172 or a variant thereof comprising at least about 80% (such as at least about any of 80%, 85%, 90%, 91%, 92%, 93%, 94%, 95%, 96%, 97%, 98%, or 99%) sequence identity to SEQ ID NO: 1, 2, 126, 171, or 172, and wherein the albumin binding moiety comprises an albumin binding domain. In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-21 is a truncated IL-21. In some embodiments, the truncated IL-21 comprises an amino acid sequence of SEQ ID NO: 126, 171, or 172. In some embodiments, the first linker is a rigid linker. In some embodiments, the first linker is selected from the group consisting of SEQ ID NO: 21, 22, and 24. In some embodiments, the first linker is a flexible linker. In some embodiments, the first linker is selected from the group consisting of GSG and SEQ ID NOs: 12-14.

In some embodiments, there is provided a fusion protein comprising: a) an IL-21, and b) an albumin binding moiety (such as an sdAb that binds to albumin), wherein the IL-21 comprises an amino acid sequence of SEQ ID NO: 1, 2, 126, 171, or 172 or a variant thereof comprising at least about 80% (such as at least about any of 80%, 85%, 90%, 91%, 92%, 93%, 94%, 95%, 96%, 97%, 98%, or 99%) sequence identity to SEQ ID NO: 1, 2, 126, 171, or 172, and wherein the albumin binding moiety comprises an anti-albumin antibody or fragment thereof (such as a single domain antibody, such as an $V_H H$ antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-21 is a truncated IL-21. In some embodiments, the truncated IL-21 comprises an amino acid sequence of SEQ ID NO: 126, 171, or 172. In some embodiments, the first linker is a rigid linker. In some embodiments, the first linker is selected from the group consisting of SEQ ID NO: 21, 22, and 24. In some embodiments, the first linker is a flexible linker. In some embodiments, the first linker is selected from the group consisting of GSG and SEQ ID NOs: 12-14.

In some embodiments, there is provided a fusion protein comprising: a) an IL-7, and b) an albumin binding moiety (such as an sdAb that binds to albumin). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises an anti-albumin antibody (such as a single domain antibody (sdAb), such as a $V_HH$ single domain antibody). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the first linker is a rigid linker. In some embodiments, the first linker is selected from the group consisting of SEQ ID NO: 21, 22, and 24. In some embodiments, the first linker is a flexible linker. In some embodiments, the first linker is selected from the group consisting of GSG and SEQ ID NOs: 12-14.

In some embodiments, there is provided a fusion protein comprising: a) an IL-7, and b) an albumin binding moiety (such as an sdAb that binds to albumin), wherein the IL-7 comprises an amino acid sequence of any one of SEQ ID NOs: 96-98 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 96-98, and wherein the albumin binding moiety comprises an albumin binding domain. In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159.

In some embodiments, there is provided a fusion protein comprising: a) an IL-7, and b) an albumin binding moiety (such as an sdAb that binds to albumin), wherein the IL-7 comprises an amino acid sequence of any one of SEQ ID NOs: 96-98 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 96-98, and wherein the albumin binding moiety comprises an anti-albumin antibody or fragment thereof (such as a single domain antibody, such as an $V_HH$ antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159.

In some embodiments, there is provided a fusion protein comprising: a) an IL-15, and b) an albumin binding moiety (such as an sdAb that binds to albumin). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises an anti-albumin antibody (such as a single domain antibody (sdAb), such as a $V_HH$ single domain antibody). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the cytokine is IL-15Rα or IL-15 bound to IL-15Rα or fragment thereof, and wherein the IL-15Rα or IL-15 bound to IL-15Rα or fragment thereof comprises an amino acid sequence of any one of SEQ ID NOs: 101-108, or a variant thereof comprising at least about 80% sequence identity to any one of SEQ ID NOs: 101-108. In some embodiments, the cytokine comprises IL-15 and IL-15Rα. In some embodiments, the IL-15 and IL-15Rα are connected via a linker ("linker between the IL-15 and IL-15Rα"). In some embodiments, the linker between the IL-15 and IL-15Rα is cleavable. In some embodiments, the linker between the IL-15 and IL-15Rα is non-cleavable.

In some embodiments, there is provided a fusion protein comprising: a) an IL-15, and b) an albumin binding moiety (such as an sdAb that binds to albumin), wherein the IL-15 comprises an amino acid sequence of any one of SEQ ID NO: 99, 100, or 127 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 99, 100, or 127, and wherein the albumin binding moiety comprises an albumin binding domain. In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the cytokine is IL-15Rα or IL-15 bound to IL-15Rα or fragment thereof, and wherein the IL-15Rα or IL-15 bound to IL-15Rα or fragment thereof comprises an amino acid sequence of any one of SEQ ID NOs: 101-108, or a variant thereof comprising at least about 80% sequence identity to any one of SEQ ID NOs: 101-108. In some embodiments, the cytokine comprises IL-15 and IL-15Ra. In some embodiments, the IL-15 and IL-15Rα are connected via a linker ("linker between the IL-15 and IL-15Rα"). In some embodiments, the linker between the IL-15 and IL-15Ra is cleavable. In some embodiments, the linker between the IL-15 and IL-15Rα is non-cleavable.

In some embodiments, there is provided a fusion protein comprising: a) an IL-15, and b) an albumin binding moiety (such as an sdAb that binds to albumin), wherein the IL-15 comprises an amino acid sequence of any one of SEQ ID NO: 99, 100, or 127 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 99, 100, or 127, and wherein the albumin binding moiety comprises an anti-albumin antibody or fragment thereof (such as a single domain antibody, such as an V$_H$H antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the cytokine is IL-15Rα or IL-15 bound to IL-15Rα or fragment thereof, and wherein the IL-15Rα or IL-15 bound to IL-15Rα or fragment thereof comprises an amino acid sequence of any one of SEQ ID NOs: 101-108, or a variant thereof comprising at least about 80% sequence identity to any one of SEQ ID NOs: 101-108. In some embodiments, the cytokine comprises IL-15 and IL-15Rα. In some embodiments, the IL-15 and IL-15Rα are connected via a linker ("linker between the IL-15 and IL-15Rα"). In some embodiments, the linker between the IL-15 and IL-15Rα is cleavable. In some embodiments, the linker between the IL-15 and IL-15Rα is non-cleavable.

In some embodiments, there is provided a fusion protein comprising a) a cytokine comprising an IL-15R sushi domain, and b) an albumin binding moiety (such as an sdAb that binds to albumin). In some embodiments, the IL-15R sushi domain comprises or consists of an amino acid sequence of any one of SEQ ID NO: 127-128 or a variant thereof comprising at least 80% (such as at least about any one of 80%, 85%, 90%, 95%, 96%, 97%, 98%, or 99%) sequence identity to any one of SEQ ID NO: 127-128. In some embodiments, the fusion protein does not comprise an IL-15. In some embodiments, the fusion protein further comprises an IL-15. In some embodiments, the IL-15 and IL-15R sushi domain are connected via a linker ("linker between the IL-15 and IL-15R sushi domain"). In some embodiments, the linker between the IL-15 and IL-15R sushi domain is cleavable. In some embodiments, the linker between the IL-15 and IL-15 sushi domain is non-cleavable.

In some embodiments, there is provided a fusion protein comprising: a) an IL-15 bound to IL-15Rα comprising an IL-15 and an IL-15Rα, and b) an albumin binding moiety (such as an sdAb that binds to albumin) In some embodiments, the albumin binding moiety is fused to one of the IL-15 or the IL-15Rα. In some embodiments, the albumin binding moiety is fused to both the IL-15 and the IL-15Rα. In some embodiments, the albumin binding moiety is fused to the N- and/or C-terminus of IL-15Rα. In some embodiments, the albumin binding moiety is fused to the N- and/or C-terminus of IL-15. In some embodiments, the albumin binding moiety is fused to the C-terminus of IL-15 and/or IL-15Rα. In some embodiments, the albumin binding moiety is fused to the N-terminus of IL-15 and/or IL-15Rα. In some embodiments, the IL-15 is non-covalently bound to the IL-15Rα. In some embodiments, the IL-15 is fused to the IL-15Rα. In some embodiments, the IL-15 is fused to the N-terminus of the IL-15Rα. In some embodiments, the IL-15 is fused to the C-terminus of the IL-15Rα. In some embodiments, the albumin binding moiety is further fused to the N- or C-terminus of a second cytokine. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises an anti-albumin antibody (such as a single domain antibody (sdAb), such as a $V_HH$ single domain antibody). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-15 and the IL-15Rα are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159. In some embodiments, IL-15 bound to IL-15Rα or fragment thereof comprises an amino acid sequence of any one of SEQ ID NOs: 101-108, or a variant thereof comprising at least about 80% sequence identity to any one of SEQ ID NOs: 101-108. In some embodiments, the IL-15 and IL-15Rα are connected via a linker ("linker between the IL-15 and IL-15Rα"). In some embodiments, the linker between the IL-15 and IL-15Rα is cleavable. In some embodiments, the linker between the IL-15 and IL-15Rα is non-cleavable.

In some embodiments, there is provided a fusion protein comprising: a) an IL-15 bound to IL-15Rα comprising an IL-15 and an IL-15Rα, and b) an albumin binding moiety (such as an sdAb that binds to albumin), wherein the fusion protein comprises said IL-15, IL-15Ra and albumin binding moiety from N-terminal to C-terminal in an order selected from the group consisting of (1) the albumin binding moiety, the IL-15, the IL-15Rα; (2) the albumin binding moiety, the IL-15Rα, the IL-15; (3) the IL-15, the IL-15Rα, the albumin binding moiety; (4) the IL-15Rα, the IL-15, the albumin binding moiety. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises an anti-albumin antibody (such as a single domain antibody (sdAb), such as a $V_HH$ single domain antibody). In some embodiments, the cytokine (IL-15 or IL-15Rα) and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-15 and the IL-15Ra are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159. In some embodiments, IL-15 bound to IL-15Rα or fragment thereof comprises an amino acid sequence of any one of SEQ ID NOs: 101-108, or a variant thereof comprising at least about 80% sequence identity to any one of SEQ ID NOs: 101-108. In some embodiments, the IL-15 and IL-15Rα are connected via a linker ("linker between the IL-15 and IL-15Rα"). In some embodiments, the linker between the IL-15 and IL-15Rα is cleavable. In some embodiments, the linker between the IL-15 and IL-15Rα is non-cleavable.

In some embodiments, there is provided a fusion protein comprising: a) an IL-15 bound to IL-15Rα comprising an IL-15 and an IL-15Rα, and b) an albumin binding moiety (such as an sdAb that binds to albumin), wherein the IL-15 thereof comprises an amino acid sequence of any one of SEQ ID NO: 99, 100, or 127 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 99, 100, or 127, and wherein the albumin binding moiety comprises an albumin binding domain. In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-15 is non-covalently bound to the IL-15Ra. In some embodiments, the IL-15 is fused to the IL-15Rα. In some embodiments, the IL-15 is fused to the N-terminus of the IL-15Rα. In some embodiments, the IL-15 is fused to the C-terminus of the IL-15Rα. In some embodiments, the fusion protein comprises said IL-15, IL-15Ra and albumin binding moiety from N-terminal to C-terminal in an order selected from the group consisting of (1) the albumin binding moiety, the IL-15, the IL-15Rα; (2) the albumin binding moiety, the IL-15Rα, the IL-15; (3) the IL-15, the IL-15Rα, the albumin binding moiety; (4) the IL-15Rα, the IL-15, the albumin binding moiety. In some embodiments, the IL-15 and the IL-15Rα are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159. In some embodiments, IL-15 bound to IL-15Rα or fragment thereof comprises an amino acid sequence of any one of SEQ ID NOs: 101-108, or a variant thereof comprising at least about 80% sequence identity to any one of SEQ ID NOs: 101-108. In some embodiments, the IL-15 and IL-15Rα are connected via a linker ("linker between the IL-15 and IL-15Rα"). In some embodiments, the linker between the IL-15 and IL-15Rα is cleavable. In some embodiments, the linker between the IL-15 and IL-15Rα is non-cleavable.

In some embodiments, there is provided a fusion protein comprising: a) an IL-15 bound to IL-15Rα comprising an IL-15 and an IL-15Rα, and b) an albumin binding moiety (such as an sdAb that binds to albumin), wherein the IL-15 comprises an amino acid sequence of any one of SEQ ID NO: 99, 100, or 127 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 99, 100, or 127, and wherein the albumin binding moiety comprises an anti-albumin antibody or fragment thereof (such as a single domain antibody, such as an V$_H$H antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-15 is non-covalently bound to the IL-15Rα. In some embodiments, the IL-15 is fused to the IL-15Rα. In some embodiments, the IL-15 is fused to the N-terminus of the IL-15Rα. In some embodiments, the IL-15 is fused to the C-terminus of the IL-15Rα. In some embodiments, the fusion protein comprises said IL-15, IL-15Rα and albumin binding moiety from N-terminal to C-terminal in an order selected from the group consisting of (1) the albumin binding moiety, the IL-15, the IL-15Rα; (2) the albumin binding moiety, the IL-15Rα, the IL-15; (3) the IL-15, the IL-15Rα, the albumin binding moiety; (4) the IL-15Rα, the IL-15, the albumin binding moiety. In some embodiments, the IL-15 and the IL-15Rα are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159. In some embodiments, IL-15 bound to IL-15Rα or fragment thereof comprises an amino acid sequence of any one of SEQ ID NOs: 101-108, or a variant thereof comprising at least about 80% sequence identity to any one of SEQ ID NOs: 101-108. In some embodiments, the IL-15 and IL-15Rα are connected via a linker ("linker between the IL-15 and IL-15Rα"). In some embodiments, the linker between the IL-15 and IL-15Rα is cleavable. In some embodiments, the linker between the IL-15 and IL-15Rα is non-cleavable.

In some embodiments, there is provided a fusion protein comprising: a) an IL-15 bound to IL-15Rα comprising an IL-15 and an IL-15Rα, and b) an albumin binding moiety (such as an sdAb that binds to albumin), wherein the IL-15Rα thereof comprises an amino acid sequence of any one of SEQ ID NOs: 101-108 (such as SEQ ID NOs: 103-104) or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 101-108 (such as SEQ ID NOs: 103-104), and wherein the albumin binding moiety comprises an albumin binding domain. In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-15 is non-covalently bound to the IL-15Rα. In some embodiments, the IL-15 is fused to the IL-15Rα. In some embodiments, the IL-15 is fused to the N-terminus of the IL-15Rα. In some embodiments, the IL-15 is fused to the C-terminus of the IL-15Rα. In some embodiments, the fusion protein comprises said IL-15, IL-15Rα and albumin binding moiety from N-terminal to C-terminal in an order selected from the group consisting of (1) the albumin binding moiety, the IL-15, the IL-15Rα; (2) the albumin binding moiety, the IL-15Rα, the IL-15; (3) the IL-15, the IL-15Rα, the albumin binding moiety; (4) the IL-15Rα, the IL-15, the albumin binding moiety. In some embodiments, the IL-15 and the IL-15Rα are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159.

In some embodiments, there is provided a fusion protein comprising: a) an IL-15 bound to IL-15Rα comprising an IL-15 and an IL-15Rα, and b) an albumin binding moiety (such as an sdAb that binds to albumin), wherein the IL-15Rα comprises an amino acid sequence of any one of SEQ ID NOs: 101-108 (such as SEQ ID NOs: 103-104) or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 101-108 (such as SEQ ID NOs: 103-104), and wherein the albumin binding moiety comprises an anti-albumin antibody or fragment thereof (such as a single domain antibody, such as an V$_H$H antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-15 is non-covalently bound to the IL-15Rα. In some embodiments, the IL-15 is fused to the IL-15Rα. In some embodiments, the IL-15 is fused to the N-terminus of the IL-15Rα. In some embodiments, the IL-15 is fused to the C-terminus of the IL-15Rα. In some embodiments, the fusion protein comprises said IL-15, IL-15Rα and albumin binding moiety from N-terminal to C-terminal in an order selected from the group consisting of (1) the albumin binding moiety, the IL-15, the IL-15Rα; (2) the albumin binding moiety, the IL-15Rα, the IL-15; (3) the IL-15, the IL-15Rα, the albumin binding moiety; (4) the IL-15Rα, the IL-15, the albumin binding moiety. In some embodiments, the IL-15 and the IL-15Rα are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159.

In some embodiments, there is provided a fusion protein comprising: a) an IL-15 bound to IL-15Rα comprising an IL-15 and an IL-15Rα, and b) an albumin binding moiety (such as an sdAb that binds to albumin), wherein the IL-15 comprises an amino acid sequence of any one of SEQ ID NO: 99, 100, or 127 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 99, 100, or 127, wherein the IL-15Rα comprises an amino acid sequence of any one of SEQ ID NOs: 101-108 (such as SEQ ID NOs: 103-104) or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 101-108 (such as SEQ ID NOs: 103-104), and wherein the albumin binding moiety comprises an anti-albumin antibody or fragment thereof (such as a single domain antibody, such as an $V_H H$ antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the IL-15 is non-covalently bound to the IL-15Rα. In some embodiments, the IL-15 is fused to the IL-15Rα. In some embodiments, the IL-15 is fused to the N-terminus of the IL-15Rα. In some embodiments, the IL-15 is fused to the C-terminus of the IL-15Rα. In some embodiments, the fusion protein comprises said IL-15, IL-15Rα and albumin binding moiety from N-terminal to C-terminal in an order selected from the group consisting of (1) the albumin binding moiety, the IL-15, the IL-15Rα; (2) the albumin binding moiety, the IL-15Rα, the IL-15; (3) the IL-15, the IL-15Rα, the albumin binding moiety; (4) the IL-15Rα, the IL-15, the albumin binding moiety. In some embodiments, the IL-15 and the IL-15Rα are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159.

In some embodiments, there is provided a fusion protein comprising: a) an IL-33, and b) an albumin binding moiety (such as an sdAb that binds to albumin). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises an anti-albumin antibody (such as a single domain antibody (sdAb), such as a $V_H H$ single domain antibody). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, there is no linker between the cytokine and the albumin binding moiety.

In some embodiments, there is provided a fusion protein comprising: a) an IL-33, and b) an albumin binding moiety (such as an sdAb that binds to albumin), wherein the IL-33 comprises an amino acid sequence of any one of SEQ ID NO: 109 and 155-157 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 109 and 155-157, and wherein the albumin binding moiety comprises an albumin binding domain. In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, there is no linker between the cytokine and the albumin binding moiety.

In some embodiments, there is provided a fusion protein comprising: a) an IL-33, and b) an albumin binding moiety (such as an sdAb that binds to albumin), wherein the IL-33 comprises an amino acid sequence of any one of SEQ ID NO: 109 and 155-157 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 109 and 155-157, and wherein the albumin binding moiety comprises an anti-albumin antibody or fragment thereof (such as a single domain antibody, such as an $V_H H$ antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, there is no linker between the cytokine and the albumin binding moiety.

In some embodiments, there is provided a fusion protein comprising: a) an IL-22, and b) an albumin binding moiety (such as an sdAb that binds to albumin). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises an anti-albumin antibody (such as a single domain antibody (sdAb), such as a $V_H H$ single domain antibody). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159.

In some embodiments, there is provided a fusion protein comprising: a) an IL-22, and b) an albumin binding moiety (such as an sdAb that binds to albumin), wherein the IL-22 comprises an amino acid sequence of any one of SEQ ID NOs: 109-110 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NO: 99, 100, or 127, and wherein the albumin binding moiety comprises an albumin binding domain. In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159.

In some embodiments, there is provided a fusion protein comprising: a) an IL-22, and b) an albumin binding moiety (such as an sdAb that binds to albumin), wherein the IL-22 comprises an amino acid sequence of any one of SEQ ID NOs: 109-110 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 109-110, and wherein the albumin binding moiety comprises an anti-albumin antibody or fragment thereof (such as a single domain antibody, such as an $V_HH$ antibody). In some embodiments, the cytokine is fused to the C-terminus of the albumin binding moiety. In some embodiments, the cytokine is fused to the N-terminus of the albumin binding moiety. In some embodiments, the albumin binding moiety is fused to both the N-terminus and the C-terminus of the cytokine. In some embodiments, a second cytokine, either the same as the first cytokine or different, is fused to the other terminus of the albumin binding moiety. In some embodiments, the albumin binding moiety binds to a human serum albumin (HSA) and/or a cynomolgus monkey serum albumin (CMSA). In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159.

Fusion Proteins Comprising an Antigen Binding Moiety

Also provided herein are fusion proteins comprising: a) a cytokine fused to an albumin binding moiety ("cytokine-ALBBM"), and b) an antigen binding moiety, wherein the linkage between the cytokine-ALBBM and the antigen binding moiety is optionally cleavable. In some embodiments, the antigen binding moiety binds to a tumor antigen. Such fusion proteins provide various advantages. For example, in some embodiments, the antigen binding moiety that binds to a tumor antigen enables the local delivery of the cytokine to cancer proximity, leading to lower off-target toxicity and increased efficacy.

Certain advantages are offered by such fusion proteins due to their tertiary structure and overall configuration design. For example, in some embodiments, the cytokine (such as IL-21) is fused to the C-terminus of the albumin binding moiety via a cleavable linker (such as an MMP sensitive linker), and the antigen binding moiety is fused to the N-terminus of the albumin binding moiety. The cytokine (such as IL-21) in the fusion protein may be temporarily blocked from interacting with the cytokine receptor (such as IL-21R) since its N-terminus (close to C-terminus in tertiary structure) may be required for their interaction. When the fusion protein binds to a tumor antigen, the cytokine (such as IL-21) can be released from the fusion protein if the linker is cleavable by MMP and become active, since cancer cell are known to secret various MMPs. An MMP sensitive linker ensures that cancers which typically have higher MMP activities have higher exposure to the active cytokine. Thus, unnecessary toxicity and side effects of the cytokine (such as IL-21) can be avoided. In addition, by preventing the interaction between the cytokine (such as IL-21) and the cytokine receptor (such as IL-21Ra) on peripheral immune cells, the efficiency of cancer delivery of the fusion protein can be increased.

In some embodiments, the albumin binding moiety is a single domain antibody (such as a $V_HH$ antibody). In some embodiments, the antigen binding moiety is a single domain antibody (such as a $V_HH$ antibody). In some embodiments, the albumin binding moiety and the antigen binding moiety are both single domain antibodies (such as $V_HH$ antibodies).

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is fused to the N-terminus of the cytokine, and wherein the antigen binding moiety is linked to the N-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises a single domain antibody (sdAb). In some embodiments, the sdAb is a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the antigen binding moiety binds to a tumor antigen. In some embodiments, the tumor antigen is selected from the group consisting of mesothelin (MSLN), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, the antigen binding moiety is an antibody or fragment thereof. In some embodiments, the antigen binding moiety comprises a single domain antibody (sdAb). In some embodiments, antigen binding moiety comprises a $V_HH$ single domain antibody. In some embodiments, the sdAb binds to mesothelin.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is fused to the N-terminus of the cytokine, and wherein the antigen binding moiety is linked to the C-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises a single domain antibody (sdAb). In some embodiments, the sdAb is a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the antigen binding moiety binds to a tumor antigen. In some embodiments, the tumor antigen is selected from the group consisting of mesothelin (MSLN), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, the antigen binding moiety is an antibody or fragment thereof. In some embodiments, the antigen binding moiety comprises a single domain antibody (sdAb). In some embodiments, antigen binding moiety comprises a $V_HH$ single domain antibody. In some embodiments, the sdAb binds to mesothelin.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is fused to the C-terminus of the cytokine, and wherein the antigen binding moiety is linked to the C-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises a single domain antibody (sdAb). In some embodiments, the sdAb is a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the antigen binding moiety binds to a tumor antigen. In some embodiments, the tumor antigen is selected from the group consisting of mesothelin (MSLN), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, the antigen binding moiety is an antibody or fragment thereof. In some embodiments, the antigen binding moiety comprises a single domain antibody (sdAb). In some embodiments, antigen binding moiety comprises a $V_HH$ single domain antibody. In some embodiments, the sdAb binds to mesothelin.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is fused to the C-terminus of the cytokine, and wherein the antigen binding moiety is linked to the N-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the albumin binding moiety comprises an albumin binding domain (ABD). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises a single domain antibody (sdAb). In some embodiments, the sdAb is a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the antigen binding moiety binds to a tumor antigen. In some embodiments, the tumor antigen is selected from the group consisting of mesothelin (MSLN), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, the antigen binding moiety is an antibody or fragment thereof. In some embodiments, the antigen binding moiety comprises a single domain antibody (sdAb). In some embodiments, antigen binding moiety comprises a $V_HH$ single domain antibody. In some embodiments, the sdAb binds to mesothelin.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is an albumin binding domain (ABD), and wherein the antigen binding moiety is a single domain antibody that binds to a tumor antigen (such as a $V_HH$ antibody that binds to a tumor antigen). In some embodiments, the albumin binding moiety is fused to the N- or C-terminus of the cytokine. In some embodiments, the antigen binding moiety is linked to the N- or C-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the tumor antigen is selected from the group consisting of mesothelin (MSLN), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, antigen binding moiety comprises a $V_HH$ single domain antibody. In some embodiments, the sdAb binds to mesothelin.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is a single domain antibody ("anti-albumin dsAb", such as an anti-albumin $V_HH$ antibody), and wherein the antigen binding moiety is a single domain antibody that binds to a tumor antigen (such as a $V_HH$ antibody that binds to a tumor antigen). In some embodiments, the albumin binding moiety is fused to the N- or C-terminus of the cytokine. In some embodiments, the antigen binding moiety is linked to the N- or C-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the anti-albumin sdAb is a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the tumor antigen is selected from the group consisting of mesothelin (MSLN), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, antigen binding moiety comprises a $V_HH$ single domain antibody. In some embodiments, the sdAb binds to mesothelin.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is an albumin binding domain or a single domain antibody ("anti-albumin dsAb", such as an anti-albumin $V_HH$ antibody), and wherein the antigen binding moiety is an anti-mesothelin single domain antibody (such as an anti-MSLN $V_HH$ antibody). In some embodiments, the albumin binding moiety is fused to the N- or C-terminus of the cytokine. In some embodiments, the antigen binding moiety is linked to the N- or C-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80%

(such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises a single domain antibody (sdAb) comprising a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is an albumin binding domain or a single domain antibody ("anti-albumin dsAb", such as an anti-albumin $V_HH$ antibody), and wherein the antigen binding moiety is a single domain antibody that binds to a tumor antigen, wherein the cytokine is IL-21. In some embodiments, the albumin binding moiety is fused to the N- or C-terminus of the cytokine. In some embodiments, the antigen binding moiety is linked to the N- or C-terminus of the cytokine-ALBBM. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises a single domain antibody (sdAb) comprising a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159. In some embodiments, the tumor antigen is selected from the group consisting of mesothelin (MSLN), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA. In some embodiments, antigen binding moiety comprises a $V_HH$ single domain antibody. In some embodiments, the sdAb binds to mesothelin.

In some embodiments, there is provided a fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable, wherein the albumin binding moiety is an albumin binding domain or a single domain antibody ("anti-albumin dsAb", such as an anti-albumin $V_HH$ antibody), and wherein the antigen binding moiety comprises an anti-mesothelin single domain antibody comprising an anti-mesothelin heavy chain variable region (anti-MSLN $V_H$), wherein: a) the anti-MSLN $V_H$ comprises a CDR1 comprising the amino acid sequence of SEQ ID NO: 46 or a variant thereof comprising up to 3, 2, or 1 substitution in CDR1, a CDR2 comprising the amino acid sequence of SEQ ID NO: 47 or a variant thereof comprising up to 3, 2, or 1 substitution in CDR2, and a CDR3 comprising the amino acid sequence of SEQ ID: NO: 48 or a variant thereof comprising up to 3, 2, or 1 substitution in CDR3; or b) the anti-MSLN $V_H$ comprises a CDR1 comprising the amino acid sequence of SEQ ID NO: 49 or a variant thereof comprising up to 3, 2, or 1 substitution in CDR1, a CDR2 comprising the amino acid sequence of SEQ ID NO: 50 or a variant thereof comprising up to 3, 2, or 1 substitution in CDR2, and a CDR3 comprising the amino acid sequence of GRY or a variant thereof comprising up to 3, 2, or 1 substitution in CDR3. In some embodiments, the albumin binding moiety is fused to the N- or C-terminus of the cytokine. In some embodiments, the antigen binding moiety is linked to the N- or C-terminus of the cytokine-ALBBM. In some embodiments, the cytokine is selected from the group consisting of IL-21, IL-7, IL-15, IL-15 bound to IL-15Rα or fragment thereof, IL-33, and IL-22. In some embodiments, the albumin binding moiety binds to a human serum albumin (HSA) and/or a cynomolgus monkey serum albumin (CMSA). In some embodiments, the albumin binding domain comprises an amino acid sequence selected from the group consisting of SEQ ID NOs: 3-11 or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 3-11. In some embodiments, the albumin binding moiety comprises a single domain antibody (sdAb) comprising a $V_HH$ single domain antibody. In some embodiments, the cytokine and the albumin binding moiety are connected via a first linker. In some embodiments, the first linker has a length of about one to thirty amino acids. In some embodiments, the first linker is selected from the group consisting of GSG and SEQ ID NOs: 12-26 and 158-159. In some embodiments, the antigen binding moiety is fused to the cytokine-ALBBM via a second linker. In some embodiments, the second linker has a length of about one to thirty amino acids. In some embodiments, the second linker is cleavable. In some embodiments, the cleavable linker is a matrix met alloprotease, legumain, matriptase, or urokinase sensitive. In some embodiments, the second linker is selected from the group consisting of GSG and SEQ ID NOs: 12-45 and 158-159.

In some embodiments, the fusion protein comprises an amino acid sequence of any one of SEQ ID NOs: 120-125, 129-154, and 160-167, or a variant thereof comprising at least about 80% (such as at least about any of 80%, 85%, 90%, 91%, 92%, 93%, 94%, 95%, 96%, 97%, 98%, or 99%) sequence identity to any one of SEQ ID NOs: 120-125, 129-154, and 160-167.

A. Fusion Protein Properties

1 Serum Half-Life

In some embodiments, the serum half-life of the fusion protein is at least about 15 days, about 14 days, about 13 days, about 12 days, about 11 days, about 10 days, about 9 days, about 8 days, about 7 days, about 6 days, about 5 days, about 4 days, about 3 days, about 2 days, about 24 hrs, about 24 hrs, about 20 hrs, about 18 hrs, about 16 hrs, about 14 hrs, about 12 hrs, about 10 hrs, about 8 hrs, about 6 hrs, about 4 hrs, about 3 hrs, about 2 hrs, or about 1 hr when administered to an individual. The fusion protein can be administered via various routes, for example, intravenously, orally, subcutaneously or intraperitoneally.

In some embodiments, the serum half-life of the fusion protein is longer (such as at least about 20%, 30%, 40%, 50%, 60%, 70%, 80%, or 90% longer) than that of a reference protein. In some embodiments, the serum half-life of the fusion protein is at least 1-fold, 2-fold, 3-fold, 4-fold, 5-fold, 6-fold, 7-fold, 8-fold, 9-fold, 10-fold, 12-fold, 15-fold, 20-fold, 25-fold, 30-fold, 35-fold, 40-fold, 45-fold, or 50-fold of that of the reference protein. In some embodiments, the reference protein comprises the same cytokine and/or the same antigen binding moiety but does not have the albumin binding moiety. In some embodiments, the same cytokine and the same antigen binding moiety is fused in same order as the fusion protein and/or via the same linker.

2 Stability

In some embodiments, the fusion protein has a higher stability than a reference protein. In some embodiments, the reference protein comprises the same cytokine and/or the same antigen binding moiety but does not have the albumin binding moiety. In some embodiments, the same cytokine and the same antigen binding moiety is fused in same order as the fusion protein and/or via the same linker.

In some embodiments, the stability comprises a thermal stability.

In some embodiments, the stability is assessed by the extent to which the fusion protein retains an acceptable degree of chemical structure or biological function after storage under defined conditions. In some embodiments, the fusion protein has a high stability even if it does not maintain 100% of its chemical structure or biological function after storage for a defined amount of time. In some embodiments, maintenance of about 90%, about 95%, about 96%, about 97%, about 98% or about 99% of structure or function of a fusion protein as described herein after storage for a defined amount of time may be regarded as having a high stability.

Stability can be measured, inter alia, by determining the percentage of native (non-aggregated or degraded) fusion protein that remains in the formulation (liquid or reconstituted) after storage for a defined amount of time at a defined temperature. The percentage of native fusion protein can be determined by, inter alia, size exclusion chromatography (e.g., size exclusion high performance liquid chromatography [SE-HPLC]), such that native means non-aggregated and non-degraded. In some embodiments, at least about 90% (such as at least about 90%, 91%, 92%, 93%, 94%, 95%, 96%, 97%, 98%, 99% or 100%) of the native form of the fusion protein can be detected in the formulation after storage for a defined amount of time at a given temperature. In some embodiments, at least about 90% (such as at least about 90%, 91%, 92%, 93%, 94%, 95%, 96%, 97%, 98%, 99% or 100%) of the native form of the fusion protein can be detected in the formulation after at least about 6 hrs, at least about 8 hrs, at least about 10 hrs, at least about 12 hrs, at least about 14 hrs, at least about 16 hrs, at least about 18 hrs, at least about 20 hrs, at least about 22 hrs, at least about 24 hrs, at least about 26 hrs, at least about 28 hrs, at least about 30 hrs, at least about 32 hrs, at least about 34 hrs, at least about 36 hrs, at least about 38 hrs, at least about 40 hrs, at least about 42 hrs, at least about 44 hrs, at least about 46 hrs, or at least about 48 hrs under room temperature (about 25° C.).

Stability can be measured, inter alia, by determining the percentage of fusion protein that forms in an aggregate within the formulation (liquid or reconstituted) after storage for a defined amount of time at a defined temperature, wherein stability is inversely proportional to the percent aggregate that is formed. The percentage of aggregated fusion protein can be determined by, inter alia, size exclusion chromatography (e.g., size exclusion high performance liquid chromatography [SE-HPLC]). In some embodiment, there is less than about 10% (preferably less than about 5%) of the fusion protein present as an aggregate in the formulation after storage for a defined amount of time at a given temperature. In some embodiments, the fusion protein described herein has substantially no aggregation, for example, at most about 6%, 5%, 4%, 3%, 2%, 1%, 0.5%, or 0.1% of the fusion protein can be detected in an aggregate in the formulation after storage for a defined amount of time at a given temperature, for example, after at least about 6 hrs, at least about 8 hrs, at least about 10 hrs, at least about 12 hrs, at least about 14 hrs, at least about 16 hrs, at least about 18 hrs, at least about 20 hrs, at least about 22 hrs, at least about 24 hrs, at least about 26 hrs, at least about 28 hrs, at least about 30 hrs, at least about 32 hrs, at least about 34 hrs, at least about 36 hrs, at least about 38 hrs, at least about 40 hrs, at least about 42 hrs, at least about 44 hrs, at least about 46 hrs, or at least about 48 hrs under room temperature (about 25° C.).

Measuring the binding affinity of the fusion protein to its target(s) may also be used to assess stability. For example, a fusion protein of the present application may be regarded as stable if, after storage at e.g., room temperature (about 25° C.) for a defined amount of time (e.g., 6 hrs, 12 hrs, 24 hrs, 36 hrs, 48 hrs), the cytokine and/or the antigen-binding domain have an affinity that is at least 50%, 55%, 60%, 65%, 70%, 75%, 80%, 85%, 90%, 95%, or even more of the binding affinity of the antibody prior to said storage. Binding affinity may be determined by any method, such as e.g., ELISA or plasmon resonance. The binding of the fusion protein to such a cell may be measured directly, such as via FACS analysis.

3 Clinical Properties

In some embodiments, the fusion protein described herein has improved clinical properties relative to a reference protein. In some embodiments, the fusion protein exhibit improved cytotoxicity activity, compared to that of the reference protein. In some embodiments, the fusion protein exhibits higher anti-tumor effects (such as reducing tumor burden, improving survival, etc.), compared to that of the reference protein. In some embodiments, the reference protein comprises the same cytokine and/or the same antigen binding moiety but does not have the albumin binding moiety. In some embodiments, the same cytokine and the same antigen binding moiety is fused in same order as the fusion protein and/or via the same linker.

Cytotoxicity

Cytotoxicity (such as ADCC activity) of the fusion protein described herein against a cell can be tested with many assays. For example, cancer cell line expressing the antigen that can be recognized by the fusion protein and effector cells (e.g., PBMC cells) are mixed together in a 96-well plate. Varying concentrations of fusion protein is added into each well. After incubation, EC50 (representing ADCC activity) can be calculated.

In some embodiments, the fusion protein exhibits improved ADCC activity against a cell, compared to that of the reference protein. In some embodiments, the EC50 of the fusion protein specific for the cell is no more than about 50%, 40%, 30%, 20%, 10%, or less than the reference protein. In some embodiments, the cell is a tumor cell. In some embodiments, the tumor cell is derived from a mesothelioma, lung cancer, breast cancer, ovarian cancer, pancreatic cancer, lymphoma, leukemia, head and neck cancer, liver cancer, esophageal cancer, gastric cancer, and colorectal cancer. In some embodiments, the reference protein comprises the same cytokine and/or the same antigen binding moiety but does not have the albumin binding moiety. In some embodiments, the same cytokine and the same antigen binding moiety is fused in same order as the fusion protein and/or via the same linker.

Treating a Cancer

In some embodiments, the fusion protein treats a cancer (for example, by inhibiting tumor growth) in an individual. In some embodiments, the fusion exhibited enhanced antitumor effect against a cancer, compared to that of a reference protein. For example, in some embodiments, the administration of the fusion protein resulted in a reduced tumor burden (such as at least about 10%, 20%, 30%, 40% or 50% less tumor volume) as compared to that of the reference protein. In some embodiments, the cancer is selected from the group comprising a mesothelioma, lung cancer, breast cancer, ovarian cancer, pancreatic cancer, lymphoma, leukemia, head and neck cancer, liver cancer, esophageal cancer, gastric cancer, and colorectal cancer. In some embodiments, the reference protein comprises the same cytokine and/or the same antigen binding moiety but does not have the albumin binding moiety. In some embodiments, the same cytokine and the same antigen binding moiety is fused in same order as the fusion protein and/or via the same linker.

B. Linker

In some embodiments, the fusion proteins described herein comprise a first linker between the cytokine and the albumin binding moiety. In some embodiments, the fusion proteins described herein comprise a second linker between the cytokine fused to an albumin binding moiety ("cytokine-ALBBM") and the antigen binding moiety.

In some embodiments, the first linker is a rigid linker. In some embodiments, the first linker is selected from the group consisting of SEQ ID NO: 21, 22, and 24.

In some embodiments, the first linker is a flexible linker. In some embodiments, the first linker is selected from the group consisting of GSG and SEQ ID NOs: 12-14.

In some embodiments, the first linker is a non-cleavable linker.

In some embodiments, the first linker has a length of about one to forty (such as one to thirty-five, one to thirty, one to twenty-five, one to twenty, four to twenty, or four to sixteen) amino acids.

In some embodiments, the first linker is selected from the group consisting of GSG and SEQ ID NOs: 12-26 and 158-159.

In some embodiments, the second linker is a rigid linker. In some embodiments, the second linker is selected from the group consisting of SEQ ID NO: 21, 22, and 24.

In some embodiments, the second linker is a flexible linker. In some embodiments, the second linker is selected from the group consisting of GSG and SEQ ID NOs: 12-14.

In some embodiments, the second linker is a cleavable linker. In some embodiments, the second linker is a matrix met alloprotease, legumain, matriptase, or urokinase sensitive.

In some embodiments, the second linker is selected from the group consisting of GSG and SEQ ID NOs: 12-45 and 158-159. In some embodiments, the second linker is selected from the group consisting of SEQ ID NOs: 27-45.

In some embodiments, the second linker has a length of about one to forty (such as one to thirty-five, one to thirty, one to twenty-five, one to twenty, four to twenty, four to sixteen, four to twelve, or five to nine) amino acids.

In some embodiments, the first and/or second linker does not comprise a Gly-Gly-Gly-Gly-Ser sequence. In some embodiments, the first and/or second linker is not a GS linker.

The length, the degree of flexibility and/or other properties of the first and/or second linker(s) used in the fusion proteins may have some influence on properties, including but not limited to the affinity, specificity or avidity for one or more components (such as the cytokine, the albumin-binding molecule, and/or the antigen binding moiety) to bind its target. For example, longer linkers may be selected to ensure that two adjacent domains do not sterically interfere with one another. In some embodiment, a linker (such as peptide linker) comprises flexible residues (such as glycine and serine) so that the adjacent domains are free to move relative to each other. For example, a glycine-serine doublet can be a suitable peptide linker. In some embodiments, the linker is a non-peptide linker. In some embodiments, the linker is a peptide linker.

Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

Non-Peptide Linkers

Coupling of the components described above may be accomplished by any chemical reaction that will bind the two molecules so long as both components retain their respective activities, i.e. binding to cytokine receptor, albumin, or the target antigen, respectively. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents may be useful in coupling protein molecules in this context. For example, representative coupling agents can include organic compounds such as thioesters, carbodimide, succinimide esters, diisocyanate, glutaraldehyde, diazobenzenes and hexamethylene diamines. This listing is not intended to be exhaustive of the various classes of coupling agents known in the art but, rather, is exemplary of the more common coupling agents (see Killen and Lindstrom, Jour. Immun 133:1335-2549 (1984); Jansen et al., Immunological Reviews 62:185-216 (1982); and Vitetta et al., Science 238:1098 (1987)).

Linkers that can be applied in the present application are described in the literature (see, for example, Ramakrishnan, S. et al., Cancer Res. 44:201-208 (1984) describing use of MBS (M-maleimidobenzoyl-N-hydroxysuccinimide ester). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus may lead to fusion proteins with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form antibody fusion protein with increased stability. Disulfide linkages, are in general, less stable than other linkages because the disulfide linkage is cleaved in vitro, resulting in less antibody fusion protein available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Peptide Linkers

The peptide linker may have a naturally occurring sequence, or a non-naturally occurring sequence. For example, a sequence derived from the hinge region of heavy chain only antibodies may be used as the linker. See, for example, WO1996/34103.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the domains to each other can be provided by, e.g., genetic engineering. Methods for preparing fused and operatively linked fusion protein components and expressing them in mammalian cells or bacteria are well-known in the art (e.g. WO 99/54440, Ausubel, Current Protocols in Molecular Biology, Green Publishing Associates and Wiley Interscience, N.Y. 1989 and 1994 or Sambrook et al., Molecular Cloning: A Laboratory Manual, Cold Spring Harbor Laboratory Press, Cold Spring Harbor, N.Y., 2001).

The peptide linker can be a stable linker, which is not cleavable by protease, especially by Matrix met alloproteinases (MMPs).

The linker can also be a flexible linker. Exemplary flexible linkers include glycine polymers $(G)_n$, glycine-serine polymers (including, for example, $(GS)_n$, $(GSGS)_n$ (SEQ ID NO: 19), $(GGSG)_n$ (SEQ ID NO: 20), $(GGGGS)_n$ (SEQ ID NO: 14), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11 173-142 (1992)). The ordinarily skilled artisan will recognize that design of an antibody fusion protein can include linkers that are all or partially flexible, such that the linker can include a flexible linker portion as well as one or more portions that confer less flexible structure to provide a desired antibody fusion protein structure.

C. Cytokines

The fusion proteins described herein comprise a cytokine. In some embodiments, the cytokine is selected from the group consisting of IL-21, IL-7, IL-15, IL-15 bound to IL-15Rα or fragment thereof, IL-33, and IL-22.

IL-21

IL-21 is a type I cytokine produced by T cells and natural killer T cells that has pleiotropic actions on a wide range of immune and non-immune cell types. This cytokine has diverse effects on a broad range of cell types including, but not limited to, $CD4^+$ and $CD8^+$ T cells, B cells, macrophages, monocytes, and dendritic cells (DCs). The functional receptor for IL-21 is composed of the IL-21 receptor (IL-21R) and the common cytokine receptor γ chain (γc), which is also a subunit of the receptors for IL-2, IL-4, IL-7, IL-9, and IL-15.

Activation of the cytotoxic programs in NK cells and CD8 T cells is key for cancer immunotherapy, and consequently early studies provided compelling evidence that IL-21 is a promising immunotherapeutic agent for this disease. IL-21 promotes maturation, enhances cytotoxicity, and induces production of IFN-γ and perforin by NK cells. Correspondingly, cytolytic activity induced by IL-21 significantly inhibits the growth of B16 melanoma. Moreover, IL-21 together with IL-15 expands antigen-specific $CD8^+$ T-cell numbers and their effector function, resulting in tumor regression. Leonard et al. F1000Res. 2016 Feb. 26; 5. pii: F1000 Faculty Rev-224.

In some embodiments, the cytokine is IL-21. In some embodiments, the IL-21 is a wild-type IL-21. In some embodiments, the IL-21 is derived from a human IL-21. In some embodiments, the IL-21 is a human wildtype IL-21. In some embodiments, the IL-21 is a truncated IL-21.

In some embodiments, the IL-21 comprises an amino acid sequence of SEQ ID NO: 1, 2, 126, 171, or 172 or a variant thereof comprising at least 80% (such as at least about any one of 80%, 85%, 90%, 95%, 96%, 97%, 98%, or 99%) sequence identity to SEQ ID NO: 1, 2, 126, 171, or 172.

In some embodiments, the IL-21 is a truncated IL-21. In some embodiments, the truncated IL-21 comprises an amino acid sequence of SEQ ID NO: 126, 171, or 172.

In some embodiments, the IL-21 variant lacks one or more amino acids between and including L123 and S133 at the C-terminus. In some embodiments, the IL-21 variant lacks any one amino acid between and including L123 and 5133 at the C-terminus. In some embodiments, the IL-21 variant lacks any two amino acids between and including L123 and S133 at the C-terminus. In some embodiments, the IL-21 variant lacks any three amino acids between and including L123 and S133 at the C-terminus. In some embodiments, the IL-21 variant lacks any four amino acids between and including L123 and S133 at the C-terminus. In some embodiments, the IL-21 variant lacks any five amino acids between and including L123 and S133 at the C-terminus. In some embodiments, the IL-21 variant lacks any six amino acids between and including L123 and S133 at the C-terminus. In some embodiments, the IL-21 variant lacks any seven amino acids between and including L123 and S133 at the C-terminus. In some embodiments, the IL-21 variant lacks any eight amino acids between and including L123 and S133 at the C-terminus. In some embodiments, the IL-21 variant lacks any nine amino acids between and including L123 and S133 at the C-terminus. In some embodiments, the IL-21 variant lacks any ten amino acids between and including L123 and S133 at the C-terminus. In some embodiments, the IL-21 variant lacks all eleven amino acids between and including L123 and S133 at the C-terminus.

In some embodiments, the IL-21 variant lacks the 11 amino acids at the C-terminus of SEQ ID NO: 1. In some embodiments, the IL-21 variant lacks the 10 amino acids at the C-terminus of SEQ ID NO: 1. In some embodiments, the IL-21 variant lacks the 9 amino acids at the C-terminus of SEQ ID NO: 1. In some embodiments, the IL-21 variant lacks the 8 amino acids at the C-terminus of SEQ ID NO: 1. In some embodiments, the IL-21 variant lacks the 7 amino acids at the C-terminus of SEQ ID NO: 1. In some embodiments, the IL-21 variant lacks the 6 amino acids at the C-terminus of SEQ ID NO: 1. In some embodiments, the IL-21 variant lacks the 5 amino acids at the C-terminus of SEQ ID NO: 1. In some embodiments, the IL-21 variant lacks the 4 amino acids at the C-terminus of SEQ ID NO: 1. In some embodiments, the IL-21 variant lacks the 3 amino acids at the C-terminus of SEQ ID NO: 1. In some embodiments, the IL-21 variant lacks the 2 amino acids at the C-terminus of SEQ ID NO: 1. In some embodiments, the IL-21 variant lacks the 1 amino acid at the C-terminus of SEQ ID NO: 1.

In some embodiments, the IL-21 variant lacks the 14, 13, or 12 amino acids at the C-terminus of SEQ ID NO: 1.

In some embodiments, the IL-21 variant lacks at least 9-10, 9-11, 10-12, or 12-15 consecutive amino acids at the C-terminus of SEQ ID NO: 1. In some embodiments, the IL-21 variant lacks at least 9-14, 10-14, 11-14, or 12-14 consecutive amino acids at the C-terminus of SEQ ID NO: 1.

In some embodiments, the IL-21 variant provided herein has an amino acid sequence of SEQ ID NO: 2, which lacks the 10 amino acids at the C-terminus and represents a sequence of Q1 to L123 of SEQ ID NO: 1.

IL-7

IL-7 is one of the members of IL-2 superfamily. IL-2 superfamily includes IL-2, IL-4, IL-7, IL-9, IL-15 and IL-21. It binds to receptors with a common γ chain subunit. In addition to a common γ chain subunit, the receptor for IL-7 (IL-7R) requires an IL-7R a chain in order for binding to take place. See Lin et al., Anticancer Res. 2017 March; 37(3):963-967.

Interleukin-7 (IL-7) is required for T cell development in mice and humans and is produced by stromal tissues rather than activated lymphocytes. Under normal conditions, IL-7 is a limiting resource for T cells, but it accumulates during lymphopenic conditions. IL-7 signals through a heterodimeric receptor consisting of the IL-7 receptor α-chain (IL-7Ra) and the common cytokine receptor γ-chain (γc). IL-7 has also been recently demonstrated to regulate lymphoid tissue inducer (LTi) cells, which induce the development of secondary lymphoid organs and can induce tertiary lymphoid tissue postnatally in settings of chronic inflammation. In animals, IL-7 therapy enhances the effectiveness of adoptive immunotherapy for cancer, enhances vaccine responses and enhances viral clearance in the setting of acute and chronic infections. See Mackall et al., *Nature Reviews Immunology* volume 11, pages 330-342 (2011).

In some embodiments, the cytokine is IL-7. In some embodiments, the IL-7 is a wild-type IL-7. In some embodiments, the IL-7 is derived from a human IL-7. In some embodiments, the IL-7 is a human wildtype IL-7.

In some embodiments, the IL-7 comprises an amino acid sequence of any one of SEQ ID NOs: 96-98 or a variant thereof comprising at least 80% (such as at least about any one of 80%, 85%, 90%, 95%, 96%, 97%, 98%, or 99%) sequence identity to any one of SEQ ID NOs: 96-98.

IL-15, IL-15 Rα, and IL-15 Bound to IL-15Rα

The heterotrimeric receptor of IL-15 shares the IL-2R/IL-15Rβ (CD122) and common gamma (γc) chain (CD132) with the IL-2 receptor. IL-15 and IL-2 share certain functions that include the stimulation of T cell proliferation, the generation of cytotoxic T lymphocytes, stimulation of immunoglobulin synthesis by B cells and the generation and persistence of NK cells. However, in many adaptive immune responses, IL-2 and IL-15 also have distinct and often competing roles. Unlike IL-2, IL-15 is not required for the maintenance of T regulatory cells (Tregs) that can attenuate antitumor immune responses. IL-2 in contrast to IL-15 inhibits T cell responses through activation-induced cell death (AICD) of CD8+ effector T cells. However, IL-15 is required for the differentiation of NK, effector CD8+ and memory phenotype CD8+ T cells. In addition, based on pre-clinical studies, their toxicities appear to be different, with little vascular capillary leak observed with IL-15 in contrast to IL-2. In summary, IL-15 primarily stimulates the proliferation and cytotoxic functions of CD8 T cells and NK cells leading to enhanced anti-tumor responses. However, while initially showing promise as a cancer therapeutic, the efficacy of IL-15 was limited by its short in vivo half-life. Steel et al., *Trends Pharmacol Sci.* 2012 January; 33(1): 35-41. See Robinson et al, *Immunol Lett.* 2017 October; 190: 159-168.

In some cases, the efficacy of IL-15 as a treatment is limited by the availability of IL-15Rα, which plays an integral part in stabilizing and increasing the biological activity of IL-15. Since unassociated IL-15 isn't found naturally in vivo, IL-15 bound to IL-15Rα resembles the physiological form of IL-15 and has a higher affinity for IL-15Rβ/γC than free IL-15. See Robinson et al, *Immunol Lett.* 2017 October; 190: 159-168.

In some embodiments, the cytokine is or comprises IL-15. In some embodiments, the IL-15 is a wild-type IL-15. In some embodiments, the IL-15 is derived from a human IL-15. In some embodiments, the IL-15 is a human wildtype IL-15.

In some embodiments, the cytokine is or comprises IL-15Rα. In some embodiments, the IL-15Rα is a wild-type IL-15Rα. In some embodiments, the IL-15Rα is derived from a human IL-15Rα. In some embodiments, the IL-15Rα is a human wildtype IL-15Rα. In some embodiments, the IL-15Rα is a sushi domain of soluble IL-15 receptor (i.e. IL-15R sushi domain). In some embodiments, the IL-15R sushi domain comprises or consists of an amino acid sequence of any one of SEQ ID NO: 127-128 or a variant thereof comprising at least 80% (such as at least about any one of 80%, 85%, 90%, 95%, 96%, 97%, 98%, or 99%) sequence identity to any one of SEQ ID NO: 127-128.

In some embodiments, the cytokine is IL-15 bound to IL-15Rα or fragment thereof. In some embodiments, the IL-15 bound to IL-15Rα or fragment thereof comprises a wild-type IL-15 and/or a wildtype IL-15Rα. In some embodiments, the IL-15 bound to IL-15Rα or fragment thereof comprises an IL-15 derived from a human IL-15 and/or an IL-15Rα derived from a human IL-15Rα. In some embodiments, the IL-15 bound to IL-15Rα or fragment thereof comprises a human wildtype IL-15 and/or a human wildtype IL-15Rα. In some embodiments, the IL-15 bound to IL-15Rα or fragment thereof comprises an IL-15 derived from a mouse IL-15 and/or an IL-15Rα derived from a mouse IL-15Rα. In some embodiments, the IL-15 bound to IL-15Rα or fragment thereof comprises a mouse wildtype IL-15 and/or a mouse wildtype IL-15Rα. In some embodiments, the IL-15 bound to IL-15Rα or fragment thereof is a sushi domain of soluble IL-15 receptor (i.e. IL-15R sushi domain). In some embodiments, the IL-15R sushi domain comprises or consists of an amino acid sequence of any one of SEQ ID NO: 127-128 or a variant thereof comprising at least 80% (such as at least about any one of 80%, 85%, 90%, 95%, 96%, 97%, 98%, or 99%) sequence identity to any one of SEQ ID NO: 127-128.

In some embodiments, the IL-15 is non-covalently bound to the IL-15Rα. In some embodiments, the IL-15 is fused to the IL-15Rα. In some embodiments, the IL-15 is fused to the N-terminus of the IL-15Rα. In some embodiments, the IL-15 is fused to the C-terminus of the IL-15Rα. In some embodiments, the fusion protein comprises said IL-15, IL-15Rα and albumin binding moiety from N-terminal to C-terminal in an order selected from the group consisting of (1) the albumin binding moiety, the IL-15, the IL-15Rα; (2) the albumin binding moiety, the IL-15Rα, the IL-15; (3) the IL-15, the IL-15Rα, the albumin binding moiety; (4) the IL-15Rα, the IL-15, the albumin binding moiety. In some embodiments, the IL-15 and the IL-15Rα are fused via a second linker. In some embodiments, the second linker is a cleavable linker. In some embodiments, the second linker is selected from the group consisting of SEQ ID NOs: 27-45. In some embodiments, the second linker has a sequence of SEQ ID NO: 27. In some embodiments, the second linker is a non-cleavable linker. In some embodiments, the second linker is selected from the group consisting of GSG and SEQ ID NOs: 12-26 and 158-159.

In some embodiments, the IL-15 or IL-15 bound to IL-15Rα comprises a human IL-15 comprising an amino acid sequence of any one of SEQ ID NO: 99, 100, or 127 or a variant thereof comprising at least 80% (such as at least about any one of 80%, 85%, 90%, 95%, 96%, 97%, 98%, or 99%) sequence identity to any one of SEQ ID NO: 99, 100, or 127.

In some embodiments, the IL-15 or IL-15 bound to IL-15Rα comprises a human IL-15 comprising a N72D mutation. See Han et al., Cytokine. 2011 December; 56(3): 804-810.

In some embodiments, the IL-15Rα or the IL-15 bound to IL-15Rα comprises a human IL-15Rα comprising an amino acid sequence of any one of SEQ ID NOs: 101-108 (such as SEQ ID NOs: 103-104) or a variant thereof comprising at least 80% (such as at least about any one of 80%, 85%, 90%, 95%, 96%, 97%, 98%, or 99%) sequence identity to any one of SEQ ID NOs: 101-108 (such as SEQ ID NOs: 103-104).

IL-33

Interleukin-33 (IL-33) is a member of the IL-1 family. It was originally described as an inducer of type 2 immune responses, activating T helper 2 ($T_H2$) cells and mast cells. Now, evidence is accumulating that IL-33 also potently stimulates group 2 innate lymphoid cells (ILC2s), regulatory T ($T_{reg}$) cells, $T_H1$ cells, $CD8^+$ T cells and natural killer (NK) cells. This pleiotropic nature is reflected in the role of IL-33 in tissue and metabolic homeostasis, infection, inflammation, cancer and diseases of the central nervous system.

IL-33 has a broad expression in stromal and barrier tissue, which renders it a ubiquitous and crucial immune modulator that shapes type 1, type 2 and regulatory immune responses. Although lacking a secretion sequence and sequestered in the nucleus, IL-33 is released and processed into highly active forms by various proteases. IL-33 contributes to cytokine networks that not only control pathogen removal but also support tissue repair mediated by group 2 innate lymphoid cells and regulatory T cells. The role of IL-33 is expected to continue to expand, modulating both protective and pathological immune responses. Delivering or blocking IL-33 is emerging as a promising therapeutic strategy for maintaining immune homeostasis and protecting against infectious and inflammatory diseases. See Liew, *Nature Reviews Immunology* volume 16, pages 676-689 (2016).

In some embodiments, the cytokine is IL-33. In some embodiments, the IL-33 is a wild-type IL-33. In some embodiments, the IL-33 is derived from a human IL-33. In some embodiments, the IL-33 is a human wildtype IL-33.

In some embodiments, the IL-33 comprises an amino acid sequence of any one of SEQ ID NO: 109 and 155-157 or a variant thereof comprising at least 80% (such as at least about any one of 80%, 85%, 90%, 95%, 96%, 97%, 98%, or 99%) sequence identity to any one of SEQ ID NO: 109 and 155-157.

In some embodiments, the IL-33 comprises one or more mutations selected from C208S, C227S, C232S and C259S. See Cohen et al., *Nature Communications* volume 6, Article number: 8327 (2015).

IL-22

Interleukin-22 (IL-22) is a recently described IL-10 family cytokine that is produced by T-helper (Th)-17 cells, γ6 T cells, NKT cells and newly described innate lymphoid cells (ILCs). The human IL22 gene is located at chromosome 12q15 in the vicinity of the genes encoding IFN-γ and IL-26. The active, secreted form of the cytokine is a 146 amino acid protein.

The IL-22 receptor (IL-22R) is a Type 2 cytokine receptor and member of the IL-10 family of receptors along with the receptors for IL-10, IL-19, IL-20, IL-24, IL-26, IL-28 and IL-29. It is composed of two heterodimeric subunits, IL-22R1 and IL-10R2. Studies suggest that initial binding of IL-22 to the IL-22R1 subunit enables secondary binding of the IL-10R2 subunit, thereby enabling downstream signaling.

IL-22 has a variety of functions, most notably its trophic effect on non-hematopoietic cells, especially epithelial cells. IL-22 is involved in epithelial regeneration and pathology in several organs depending on the context and/or cytokine milieu. Its involvement in a variety of diseases makes it an attractive target for clinical development. See Dudakov et al., *Annu Rev Immunol.* 2015 Mar. 21; 33: 747-785.

In some embodiments, the cytokine is IL-22. In some embodiments, the IL-22 is a wild-type IL-22. In some embodiments, the IL-22 is derived from a human IL-22. In some embodiments, the IL-22 is a human wildtype IL-22.

In some embodiments, the IL-22 comprises an amino acid sequence of any of SEQ ID NOs: 110-111 or a variant thereof comprising at least 80% (such as at least about any one of 80%, 85%, 90%, 95%, 96%, 97%, 98%, or 99%) sequence identity to any of SEQ ID NOs: 110-111.

Cytokine Variants

In some embodiments, a cytokine variant can be in the fusion protein provided herein. Variations may be a substitution, deletion, or insertion of one or more codons encoding the cytokine polypeptide that results in a change in the amino acid sequence as compared with the human wide-type cytokine protein Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 10 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In some embodiments, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the full-length or mature native sequence.

Amino acid sequence insertions include amino- and/or carboxyl-terminal fusions ranging in length from one residue or multiple residues, as well as intrasequence insertions of single or multiple amino acid residues.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity (e.g., binding to cytokine receptor) to identify mutants that retain activity. Following mutagenesis, the encoded protein can be expressed and the activity of the protein can be determined.

Conservative (e.g., within an amino acid group with similar properties and/or side chains) substitutions may be made, so as to maintain or not significantly change the properties of the cytokine. Amino acids may be grouped according to similarities in the properties of their side chains (see, e.g., Lehninger, Biochemistry 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce a polypeptide.

D. Albumin Binding Moiety

The fusion proteins described herein comprise an albumin-binding molecule. Albumin-binding molecules and methods by which they are linked to proteins of interest are described, for example, in WO 1991/01743, WO 2001/45746, WO 2002/076489, WO 2004/041865, or US20070269422A1, the contents of which are herein incorporated by reference.

The albumin-binding molecule can be any of the albumin-binding molecule described, for instance, in WO1991/01743, WO2001/45746, WO2002/076489, WO2004/041865, US20070269422A1; US20160152686A1; Dennis et al. (2002), JBC 277(38): 35035-35043.

In some embodiments, the albumin-binding molecule binds to a human serum albumin (HSA), a cynomolgus monkey serum albumin (CMSA), and/or a mouse serum albumin (MSA).

In some embodiments, the albumin binding moiety binds to an albumin (such as an HAS) with a $K_D$ of between about 1-1000 nM (such as between about 1-900 nM, 1-800 nM, 1-700 nM, 1-600 nM, 1-500 nM, 1-400 nM, 1-300 nM, 1-200 nM, 1-100 nM, 1-50 nM, 1-25 nM, 0.1-1 nM. In some embodiments, the albumin-binding protein comprises an albumin-binding domain (ABD) of Streptococcal protein G (SPG). See, e.g., Nygren et al. J. Mol. Recogn. (1988) 1(2): 69-74.

1 Albumin Binding Domain (ABD)

In some embodiments, the albumin binding moiety comprises an albumin binding domain (ABD). In some embodiments, the albumin-binding molecule comprises an ABD of SPG strain G148. In some embodiments, the albumin-binding molecule comprises the C-terminal albumin-binding domain 3 (ABD3) of SPG strain G148. See, e.g., Nilvebrant and Hober (2013), Comput. Struct. Biotechol. J., 6: e201303009.

In some specific embodiments, the ABD has an amino acid sequence of LAEAKVLANRELDKYGVSDYYKN-LINNAKTVEGVKALIDEILAALP (SEQ ID NO: 3), which has a $K_D$ to HSA of about 1.2 nM.

In some embodiments, an ABD having relatively lower affinity to HSA than the ABD of SEQ ID NO: 3 is preferred. Accordingly, variants of SEQ ID NO: 3 that have lower affinity to HSA are included in the present disclosure.

In some specific embodiments, the ABD has an amino acid sequence of any one of SEQ ID NOs: 4-11.

Variations may be a substitution, deletion, or insertion of one or more codons encoding the ABD polypeptide of any one of SEQ ID NOs: 3-11 that results in a change in the amino acid sequence. Amino acid substitutions can be the result of replacing one amino acid with another amino acid having similar or different structural and/or chemical properties. Standard techniques known to those of skill in the art can be used to introduce mutations in the nucleotide sequence encoding a molecule provided herein, including, for example, site-directed mutagenesis and PCR-mediated mutagenesis which results in amino acid substitutions.

The variation allowed may be determined by systematically making insertions, deletions, or substitutions of amino acids in the sequence and testing the resulting variants for activity and in some embodiments, variants having a lower affinity to HSA are selected. Certain such kind of variants are exemplified in Table 3.

2 Anti-Albumin Antibody or Fragment Thereof

According to the present invention, the albumin binding moiety can also be anti-albumin antibody or antigen binding fragment thereof. In some embodiments, the anti-albumin antibody or antigen binding fragment thereof is an anti-HSA antibody or antigen binding fragment thereof.

A few isoforms of HSA are listed in Table 2 below (see for example, UniProtKB-P02768 (ALBU_HUMAN)). In some embodiments, the anti-albumin antibody or antigen binding fragment thereof binds to any one of SEQ ID NO: 52-55.

TABLE 2

| | |
|---|---|
| Isoform 1 | MKWVTFISLLFLFSSAYSRGVFRRDAHKSEVAHRFKDLGEENFKALV LIAFAQYLQQCPFEDHVKLVNEVTEFAKTCVADESAENCDKSLHTLF GDKLCTVATLRETYGEMADCCAKQEPERNECFLQHKDDNPNLPRLV RPEVDVMCTAFHDNEETFLKKYLYEIARRHPYFYAPELLFFAKRYKA AFTECCQAADKAACLLPKLDELRDEGKASSAKQRLKCASLQKFGER AFKAWAVARLSQRFPKAEFAEVSKLVTDLTKVHTECCHGDLLECAD DRADLAKYICENQDSISSKLKECCEKPLLEKSHCIAEVENDEMPADLP SLAADFVESKDVCKNYAEAKDVFLGMFLYEYARRHPDYSVVLLLRL AKTYETTLEKCCAAADPHECYAKVFDEFKPLVEEPQNLIKQNCELFE QLGEYKFQNALLVRYTKKVPQVSTPTLVEVSRNLGKVGSKCCKHPE AKRMPCAEDYLSVVLNQLCVLHEKTPVSDRVTKCCTESLVNRRPCF SALEVDETYVPKEFNAETFTFHADICTLSEKERQIKKQTALVELVKH KPKATKEQLKAVMDDFAAFVEKCCKADDKETCFAEEGKKLVAASQ AALGL (SEQ ID NO: 52) |
| Isoform 2 | MKWVTFISLLFLFSSAYSRGVFRRDAHKSEVAHRFKDLGEENFKAW AVARLSQRFPKAEFAEVSKLVTDLTKVHTECCHGDLLECADDRADL AKYICENQDSISSKLKECCEKPLLEKSHCIAEVENDEMPADLPSLAAD FVESKDVCKNYAEAKDVFLGMFLYEYARRHPDYSVVLLLRLAKTYE TTLEKCCAAADPHECYAKVFDEFKPLVEEPQNLIKQNCELFEQLGEY KFQNALLVRYTKKVPQVSTPTLVEVSRNLGKVGSKCCKHPEAKRMP CAEDYLSVVLNQLCVLHEKTPVSDRVTKCCTESLVNRRPCFSALEVD ETYVPKEFNAETFTFHADICTLSEKERQIKKQTALVELVKHKPKATK EQLKAVMDDFAAFVEKCCKADDKETCFAEEGKKLVAASQAALGL (SEQ ID NO: 53) |
| Isoform 3 | MKWVTFISLLFLFSSAYSRGVFRRDAHKSEVAHRFKDLGEENFKALV LIAFAQYLQQCPFEDHVKLVNEVTEFAKTCVADESAENCDKSLHTLF GDKLCTVATLRETYGEMADCCAKQEPERNECFLQHKDDNPNLPRLV RPEVDVMCTAFHDNEETFLKKYLYETTLEKCCAAADPHECYAKVFD EFKPLVEEPQNLIKQNCELFEQLGEYKFQNALLVRYTKKVPQVSTPT LVEVSRNLGKVGSKCCKHPEAKRMPCAEDYLSVVLNQLCVLHEKTP VSDRVTKCCTESLVNRRPCFSALEVDETYVPKEFNAETFTFHADICTL SEKERQIKKQTALVELVKHKPKATKEQLKAVMDDFAAFVEKCCKA DDKETCFAEEGKKLVAASQAALGL (SEQ ID NO: 54) |
| Mature HSA | DAHKSEVAHRFKDLGEENFKALVLIAFAQYLQQCPFEDHVKLVNEV TEFAKTCVADESAENCDKSLHTLFGDKLCTVATLRETYGEMADCCA KQEPERNECFLQHKDDNPNLPRLVRPEVDVMCTAFHDNEETFLKKY LYEIARRHPYFYAPELLFFAKRYKAAFTECCQAADKAACLLPKLDEL RDEGKASSAKQGLKCASLQKFGERAFKAWAVARLSQRFPKAEFAEV SKLVTDLTKVHTECCHGDLLECADDRADLAKYICENQDSISSKLKEC CEKPLLEKSHCIAEVENDEMPADLPSLAADFVGSKDVCKNYAEAKD VFLGMFLYEYARRHPDYSVVLLLRLAKTYETTLEKCCAAADPHECY AKVFDEFKPLVEEPQNLIKQNCELFEQLGEYKFQNALLVRYTKKVPQ VSTPTLVEVSRNLGKVGSKCCKHPEAKRMPCAEDCLSVFLNQLCVL HEKTPVSDRVTKCCTESLVNGRPCFSALEVDETYVPKEFNAETFTFH ADICTLSEKERQIKKQTALVELVKHKPKATKEQLKAVMDDFAAFVE KCCKADDKETCFAEEGKKLVAASQAALGL (SEQ ID NO: 55) |

The anti-albumin antibodies or fragments thereof may be from any animal origin including birds and mammals (e.g., human, murine, donkey, sheep, rabbit, goat, guinea pig, camel, horse, or chicken). In certain embodiments, the antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In certain embodiments, the anti-albumin antibodies are fully human antibodies, such as fully human antibodies that immunospecifically bind a cancer antigen. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies when administered to the subject.

The anti-albumin antibodies provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. In some embodiments, the antibodies provided herein are monospecific for a given epitope of a polypeptide and do not immunospecifically bind to other epitopes.

The anti-albumin antibodies provided herein may be monoclonal antibodies or derived from monoclonal antibodies. The anti-albumin antibodies can be, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies or their humanized versions, Fab fragments, F(ab') fragments, disulfide-linked Fvs (sdFv), anti-idiotypic (anti-Id) antibodies, and epitope-binding fragments of any of the above.

In particular, the anti-albumin antibodies provided herein include immunoglobulin molecules and immunologically active portions of immunoglobulin molecules, i.e., molecules that contain an antigen binding site that immunospecifically binds to an albumin (such as an HSA). The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In some embodiments, the anti-albumin antibody is an IgG antibody, such as an IgG1 antibody.

Variants and derivatives of anti-albumin antibodies including antibody fragments that retain the ability to specifically bind to an epitope of albumin are also included in the present disclosure. Exemplary fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')2 (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, anti-HSA antibody provided herein comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in *The Pharmacology of Monoclonal Antibodies*, vol. 113, Rosenburg and Moore eds. Springer-Verlag, New York, pp. 269-315 (1994).

In certain circumstances there are advantages of using anti-albumin antibody fragments, rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. Fab, Fv, and scFv antibody fragments can all be expressed in and secreted from *E. coli* or yeast cells, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., 1992, Bio/Technology 10:163-67). According to another approach, F(ab')$_2$ fragments can be isolated directly from recombinant host cell culture. Fab and F(ab')$_2$ fragments with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above. Such linear antibodies may be monospecific or multi-specific, such as bispecific.

Single Domain Antibody (sdAb)

In some embodiments, the antibody fragment is a single domain antibody (sdAb).

In some embodiments, the sdAb is a $V_HH$ single domain antibody.

In some embodiments, the sdAb binds to the albumin (such as an HSA) with a $K_D$ of between about 1-1000 nM (such as between about 1-900 nM, 1-800 nM, 1-700 nM, 1-600 nM, 1-500 nM, 1-400 nM, 1-300 nM, 1-200 nM, 1-100 nM, 1-50 nM, 1-25 nM, or 0.1-1 nM). In other embodiments, the sdAb binds to the albumin (such as an HSA) with a $K_D$ of between about 10-800 nM (such as between about 20-500 nM, 50-300 nM or 100-200 nM).

In some embodiments, the sdAb binds to the albumin (such as an HSA) with a $K_D$ of between about 1-1000 nM (such as between about 1-900 nM, 1-800 nM, 1-700 nM, 1-600 nM, 1-500 nM, 1-400 nM, 1-300 nM, 1-200 nM, 1-100 nM, 1-50 nM, 1-25 nM, or 0.1-1 nM) at a pH of about 5.5 and/or at a pH of about 7.5. In some embodiments, the sdAb binds to the albumin (such as an HSA) with a $K_D$ of between about 1-200 nM at a pH of about 5.5 and at a pH of about 7.5.

In some embodiments, the single-domain antibody or fragment thereof comprises a CDR1 comprising the amino acid sequence of any one of SEQ ID NOs: 69, 72, 75, 78, 81, 84, 87, 90, and 93, or a variant thereof comprising up to about 3 amino acid substitutions; a CDR2 comprising the amino acid sequence of any one of SEQ ID NOs: 70, 73, 76, 79, 82, 85, 88, 91, and 94, or a variant thereof comprising up to about 3 amino acid substitutions; and a CDR3 comprising the amino acid sequence of any one of SEQ ID NOs: 71, 74, 77, 80, 83, 86, 89, 92, and 95, or a variant thereof comprising up to about 3 amino acid substitutions.

In some embodiments, the single-domain antibody or fragment thereof comprises any one of the following: (1) a CDR1 comprising the amino acid sequence of SEQ ID NO: 69, or a variant thereof comprising up to about 3 amino acid substitutions; a CDR2 comprising the amino acid sequence of SEQ ID NO: 70, or a variant thereof comprising up to about 3 amino acid substitutions; and a CDR3 comprising the amino acid sequence of SEQ ID NO: 71, or a variant thereof comprising up to about 3 amino acid substitutions; (2) a CDR1 comprising the amino acid sequence of SEQ ID NO: 72, or a variant thereof comprising up to about 3 amino acid substitutions; a CDR2 comprising the amino acid sequence of SEQ ID NO: 73, or a variant thereof comprising up to about 3 amino acid substitutions; and a CDR3 comprising the amino acid sequence of SEQ ID NO: 74, or a variant thereof comprising up to about 3 amino acid substitutions; (3) a CDR1 comprising the amino acid sequence of SEQ ID NO: 75, or a variant thereof comprising up to about 3 amino acid substitutions; a CDR2 comprising the amino acid sequence of SEQ ID NO: 76, or a variant thereof comprising up to about 3 amino acid substitutions; and a CDR3 comprising the amino acid sequence of SEQ ID NO: 77, or a variant thereof comprising up to about 3 amino acid substitutions; (4) a CDR1 comprising the amino acid sequence of SEQ ID NO: 78, or a variant thereof comprising up to about 3 amino acid substitutions; a CDR2 comprising the amino acid sequence of SEQ ID NO: 79, or a variant thereof comprising up to about 3 amino acid substitutions; and a CDR3 comprising the amino acid sequence of SEQ ID NO: 80, or a variant thereof comprising up to about 3 amino acid substitutions; (5) a CDR1 comprising the amino acid sequence of SEQ ID NO: 81, or a variant thereof comprising up to about 3 amino acid substitutions; a CDR2 comprising the amino acid sequence of SEQ ID NO: 82, or a variant thereof comprising up to about 3 amino acid substitutions; and a CDR3 comprising the amino acid sequence of SEQ ID NO: 83, or a variant thereof comprising up to about 3 amino acid substitutions; (6) a CDR1 comprising the amino acid sequence of SEQ ID NO: 84, or a variant thereof comprising up to about 3 amino acid substitutions; a CDR2 comprising the amino acid sequence of SEQ ID NO: 85, or a variant thereof comprising up to about 3 amino acid substitutions; and a CDR3 comprising the amino acid sequence of SEQ ID NO: 86, or a variant thereof comprising up to about 3 amino acid substitutions; (7) a CDR1 comprising the amino acid sequence of SEQ ID NO: 87, or a variant thereof comprising up to about 3 amino acid substitutions; a CDR2 comprising the amino acid sequence of SEQ ID NO: 88, or a variant thereof comprising up to about 3 amino acid substitutions; and a CDR3 comprising the amino acid sequence of SEQ ID NO: 89, or a variant thereof comprising up to about 3 amino acid substitutions; (8) a CDR1 comprising the amino acid sequence of SEQ ID NO: 90, or a variant thereof comprising up to about 3 amino acid substitutions; a CDR2 comprising the amino acid sequence of SEQ ID NO: 91, or a variant thereof comprising up to about 3 amino acid substitutions; and a CDR3 comprising the amino acid sequence of SEQ ID NO: 92, or a variant thereof comprising up to about 3 amino acid substitutions; or (9) a CDR1 comprising the amino acid sequence of SEQ ID NO: 93, or a variant thereof comprising up to about 3 amino acid substitutions; a CDR2 comprising the amino acid sequence of SEQ ID NO: 94, or a variant thereof comprising up to about 3 amino acid substitutions; and a CDR3 comprising the amino acid sequence of SEQ ID NO: 95, or a variant thereof comprising up to about 3 amino acid substitutions.

In some embodiments, the single-domain antibody or fragment thereof comprises an amino acid sequence selected from the group consisting of SEQ ID NOs: 60-68 and 168-170. In some embodiments, the single-domain antibody or fragment thereof comprises an amino acid sequence having about or at least about 80% (such as at least about any of 80%, 85%, 90%, 91%, 92%, 93%, 94%, 95%, 96%, 97%, 98%, or 99%) sequence identity to an amino acid sequence selected from the group consisting of SEQ ID NOs: 60-68 and 168-170. In some embodiments, the single-domain antibody or fragment thereof comprises a $V_HH$ domain comprising the amino acid sequence of any one of SEQ ID NOs: 60-68 and 168-170, or a variant thereof having at least about 80% (such as at least about any of 80%, 85%, 90%, 91%, 92%, 93%, 94%, 95%, 96%, 97%, 98%, or 99%) sequence identity to any one of SEQ ID NOs: 60-68 and 168-170.

In some embodiments, the single-domain antibody or fragment thereof that binds to albumin comprises a CDR1, a CDR2, a CDR3, respectively comprising the amino acid sequence of a CDR1, a CDR2, and a CDR3 within a heavy chain variable domain having the sequence set forth in any of SEQ ID NOs: 60-68 and 168-170.

E. Antigen Binding Moiety

In some embodiments, the fusion protein further comprises an antigen binding moiety, and wherein the antigen binding moiety is fused to the N- or C-terminus of the cytokine fused to the albumin binding moiety ("cytokine-ALBBM").

In some embodiments, the antigen binding moiety binds to a tumor antigen. I some embodiments, the tumor is a solid or liquid tumor. In some embodiments, the tumor is a cancer selected from the group consisting of mesothelioma, lung cancer, breast cancer, ovarian cancer, pancreatic cancer, lymphoma, leukemia, head and neck cancer, liver cancer, esophageal cancer, gastric cancer, and colorectal cancer. In some embodiments, the cancer expresses a high level of the tumor antigen. For example, in some embodiments, the cancer expresses a level of at least 2-fold, 5-fold, 10-fold, 20-fold, 30-fold, 40-fold, or 50-fold of that of a reference tissue. In some embodiments, the reference tissue is a tissue that does not comprise a cancer cell in the same individual.

In some embodiments, the tumor antigen is selected from the group consisting of mesothelin ("MSLN"), GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA.

In some embodiments, the antigen binding moiety is an antibody (such as a full length antibody) or antigen binding fragment thereof. In some embodiments, the antibodies or antigen binding fragments thereof provided herein can immunospecifically bind to a polypeptide, a polypeptide fragment, or an epitope of an antigen expressed on a cancer cell. In one embodiment, the antibodies bind to a human cancer antigen. In some embodiments, the antibodies or antigen binding fragments thereof provided herein bind to the extracellular domain (ECD) of a cancer antigen. In certain embodiments, the antibodies bind to an epitope in the ECD of a cancer antigen. In some embodiments, the cancer antigen is expressed on a solid or liquid tumor cancer cell.

Antibodies that bind to a cancer antigen provided herein can be, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies or their humanized variants, Fab fragments, F(ab') fragments, disulfide-linked Fvs (sdFv), anti-idiotypic (anti-Id) antibodies, and epitope-binding fragments of any of the above.

In some embodiments, antibodies provided herein include immunoglobulin molecules and immunologically active portions of immunoglobulin molecules, i.e., molecules that contain an antigen binding site that immunospecifically binds to a cancer antigen (e.g., a solid or liquid tumor cancer antigen). The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, such as an IgG1 antibody.

Variants and derivatives of antibodies including antibody fragments that retain the ability to specifically bind to an epitope of a cancer antigen are also included in the present disclosure. Exemplary fragments include Fab fragments; Fab'; F(ab')₂; a bispecific Fab; a single chain Fab chain comprising a variable region, also known as, a sFv; a disulfide-linked Fv, or dsFv; a camelized VH; a bispecific sFv; a diabody; and a triabody. Derivatives of antibodies also include one or more CDR sequences of an antibody combining site. The CDR sequences may be linked together on a scaffold when two or more CDR sequences are present. In certain embodiments, an antibody provided herein comprises a single-chain Fv ("scFv"). Various techniques have been developed for the production of antibody fragments as briefly described in the above section.

In some embodiments, the antigen binding moiety is a single variable domain antibody (sdAb) (such as a $V_HH$ antibody) that bind to a tumor antigen. Certain types of organisms, the camelids and cartilaginous fish, possess high affinity single V-like domains mounted on an Fc equivalent domain structure as part of their immune system. (Woolven et al., 1999, Immunogenetics 50: 98-101; and Streltsov et al., 2004, Proc Natl Acad Sci USA. 101:12444-49). The V-like domains (called $V_HH$ in camelids and V-NAR in sharks) typically display long surface loops, which allow penetration of cavities of target antigens. They also stabilize isolated VH domains by masking hydrophobic surface patches.

Anti-Mesothelin Single Domain Antibody (Anti-MSLN dsAb)

In some embodiments, the antigen binding moiety is an anti-mesothelin single domain antibody ("anti-MSLN dsAb").

The anti-MSLN antibodies (e.g., sdAbs) provided herein can bind to any of the isoforms of mesothelin or any fragments thereof (such as any one of SEQ ID NOs 56-59). In some embodiments, the anti-MSLN antibody provided herein binds to any one of SEQ ID NOs: 56-59 or a fragment thereof.

In some embodiments, the anti-MSLN dsAb comprises an anti-mesothelin heavy chain variable region (anti-MSLN $V_H$), wherein: a) the anti-MSLN $V_H$ comprises a CDR1 comprising the amino acid sequence of SEQ ID NO: 46, a CDR2 comprising the amino acid sequence of SEQ ID NO: 47, and a CDR3 comprising the amino acid sequence of SEQ ID: NO: 48, or a variant thereof comprising up to a total of 5, 4, 3, 2, or 1 amino acid substitutions in the CDRs; or b) the anti-MSLN $V_H$ comprises a CDR1 comprising the amino acid sequence of SEQ ID NO: 49, a CDR2 comprising the amino acid sequence of SEQ ID NO: 50, and a CDR3 comprising the amino acid sequence of GRY, or a variant thereof comprising up to a total of 5, 4, 3, 2, or 1 amino acid substitutions in the CDRs.

In some embodiments, the anti-MSLN dsAb comprises an anti-mesothelin heavy chain variable region (anti-MSLN $V_H$), wherein: a) the anti-MSLN $V_H$ comprises a CDR1 comprising the amino acid sequence of SEQ ID NO: 46 or a variant thereof comprising up to 3, 2, or 1 substitution in CDR1, a CDR2 comprising the amino acid sequence of SEQ ID NO: 47 or a variant thereof comprising up to 3, 2, or 1 substitution in CDR2, and a CDR3 comprising the amino acid sequence of SEQ ID: NO: 48 or a variant thereof comprising up to 3, 2, or 1 substitution in CDR3; or b) the anti-MSLN $V_H$ comprises a CDR1 comprising the amino acid sequence of SEQ ID NO: 49 or a variant thereof comprising up to 3, 2, or 1 substitution in CDR1, a CDR2 comprising the amino acid sequence of SEQ ID NO: 50 or a variant thereof comprising up to 3, 2, or 1 substitution in CDR2, and a CDR3 comprising the amino acid sequence of GRY or a variant thereof comprising up to 3, 2, or 1 substitution in CDR3. In some embodiments, the anti-MSLN dsAb comprises an anti-mesothelin heavy chain variable region (anti-MSLN $V_H$), wherein: a) the anti-MSLN $V_H$ comprises a CDR1 comprising the amino acid sequence of SEQ ID NO: 187 or a variant thereof comprising up to 3, 2, or 1 substitution in CDR1, a CDR2 comprising the amino acid sequence of SEQ ID NO: 188 or a variant thereof comprising up to 3, 2, or 1 substitution in CDR2, and a CDR3 comprising the amino acid sequence of SEQ ID: NO: 189 or a variant thereof comprising up to 3, 2, or 1 substitution in CDR3. In some embodiments, the anti- MSLN dsAb comprises an anti-mesothelin heavy chain variable region (anti-MSLN $V_H$), wherein: a) the anti-MSLN $V_H$ comprises a CDR1 comprising the amino acid sequence of SEQ ID NO: 190 or a variant thereof comprising up to 3, 2, or 1 substitution in CDR1, a CDR2 comprising the amino acid sequence of SEQ ID NO: 191 or a variant thereof comprising up to 3, 2, or 1 substitution in CDR2, and a CDR3 comprising the amino acid sequence of SEQ ID: NO: 192 or a variant thereof comprising up to 3, 2, or 1 substitution in CDR3. In some embodiments, the anti-MSLN dsAb comprises an anti-mesothelin heavy chain variable region (anti-MSLN $V_H$), wherein: a) the anti-MSLN $V_H$ comprises a CDR1 comprising the amino acid sequence of SEQ ID NO: 193 or a variant thereof comprising up to 3, 2, or 1 substitution in CDR1, a CDR2 comprising the amino acid sequence of SEQ ID NO: 194 or a variant thereof comprising up to 3, 2, or 1 substitution in CDR2, and a CDR3 comprising the amino acid sequence of SEQ ID: NO: 195 or a variant thereof comprising up to 3, 2, or 1 substitution in CDR3.

In some embodiments, the anti-MSLN sdAb comprises a CDR1, a CDR2, a CDR3, respectively comprising the amino acid sequence of a CDR1, a CDR2, and a CDR3 within a heavy chain variable domain having the sequence set forth in any of SEQ ID NOs: 173-186.

F. Fusion Protein Variants

In some embodiments, amino acid sequence variants of the fusion proteins provided herein are contemplated. For example, it may be desirable to improve the binding affinity and/or other biological properties of the fusion protein in a whole or any component(s) of the fusion protein Amino acid sequence variants of a fusion protein may be prepared by introducing appropriate modifications into the nucleic acid sequence encoding the fusion protein, or by peptide synthesis. Such modifications include, for example, deletions from, and/or insertions into and/or substitutions of residues within the amino acid sequences of the fusion protein. Any combination of deletion, insertion, and substitution can be made to arrive at the final construct, provided that the final construct possesses the desired characteristics.

1 Substitution, Insertion, Deletion and Variants

In some embodiments, fusion protein variants having one or more amino acid substitutions are provided. Sites of interest for substitutional mutagenesis include the HVRs and FRs of albumin-binding molecule and/or antigen binding moiety. Conservative substitutions are shown in Table 3. More substantial changes are provided under the heading of "exemplary substitutions," and as further described below in reference to amino acid side chain classes Amino acid substitutions may be introduced into the component of the fusion protein and the products screened for a desired activity, e.g., retained/improved antigen binding, decreased immunogenicity, or improved ADCC or CDC. Also see subsection "1. Amino acid sequence variants" under section "V. Methods of preparation."

TABLE 3

Amino acid substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |

TABLE 3-continued

Amino acid substitutions

| Original Residue | Exemplary Substitutions | Preferred Substitutions |
| --- | --- | --- |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (α-CDRs), with the resulting variant $V_H$ or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

2 Derivatives

In some embodiments, a fusion protein provided herein may be further modified to contain additional non-proteinaceous moieties that are known in the art and readily available. The moieties suitable for derivatization of the fusion protein include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the fusion protein may vary, and if more than one polymer are attached, they can be the same or different molecules. In general, the number and/or type of polymers used for derivatization can be determined based on considerations including, but not limited to, the particular properties or functions of the fusion protein to be improved, whether the fusion protein derivative will be used in a therapy under defined conditions, etc.

In some embodiments, conjugates of a fusion protein and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the fusion protein nonproteinaceous moiety are killed.

II-B. Fusion Proteins Comprising a Truncated IL-21

The present application also provides a fusion protein comprising a human IL-21 variant that comprises a truncated human IL-21. Without being bound to theory, it is discovered that a fusion protein comprising a truncated form of IL-21 that lack 1-11 amino acids at the C-terminus has an improved stability than the wildtype counterpart and a truncated counterpart that lack 12 or more amino acids at the C-terminus. It is contemplated that fusion proteins comprising a truncated IL-21 as described herein are not limited to fusion proteins that comprise an anti-albumin binding moiety.

In some embodiments, there is provided a fusion protein that comprises a) a truncated IL-21 that lacks about 1-11 amino acids at the C-terminus of the wildtype IL-21, and b) a second moiety (such as a single domain antibody moiety). In some embodiments, the IL-21 is derived from human. In some embodiments, there is provided a fusion protein that comprises a) a truncated IL-21 that comprises an amino acid sequence of SEQ ID NO: 126, 171, or 172, and b) a second moiety. In some embodiments, the truncated IL-21 lacks one or more amino acids between and including L123 and S133 at the C-terminus. In some embodiments, the truncated IL-21 lacks any one, any two, any three, any four, any five, any six, any seven, any eight, any nine, any ten, or all the eleven amino acids between and including L123 and S133 at the C-terminus of the IL-21 having a sequence set forth in SEQ ID NO: 1. In some embodiments, the IL-21 variant lacks the 11, 10, 9, 8, 7, 6, 5, 4, 3, 2, or 1 amino acid at the C-terminus of SEQ ID NO: 1. In some embodiments, the truncated IL-21 lacks about 5-11, 6-11, 7-11, 8-11, 9-11, or 10-11 amino acids (e. g., consecutive amino acids) at the C-terminus of SEQ ID NO: 1.

In some embodiments, the fusion protein has a molecular weight of at least about 15 kDa, 18 kDa, 20 kDa, 22 kDa, 25 kDa, 28 kDa. In some embodiments, the fusion protein has a molecular weight of no more than about 1000 kDa, 500 kDa, 250 kDa, 100 kDa, 70 kDa, 50 kDa, 40 kDa, or 30 kDa. In some embodiments, the fusion protein has a molecular weight of about 15 kDa to about 1000 kDa, about 15 kDa to about 500 k Da, about 15 kDa to about 100 kDa, about 15 kDa to about 70 kDa, about 20 kDa to about 50 kDa, about 25 kDa to about 30 kDa, or about 28 kDa.

In some embodiments, the second moiety comprises a half-life extending moiety. In some embodiments, the half-life extending moiety is an albumin binding moiety (e.g., an albumin binding antibody moiety, e.g., a single domain albumin binding antibody moiety). In some embodiments, the half-life extending moiety is an Fc domain (e.g., an IgG1 Fc domain).

In some embodiments, the second moiety comprises an antigen binding moiety. In some embodiments, the antigen binding moiety has a molecular weight of less than about 50 kDa, 40 kDa, 30 kDa, 20 kDa or 15 kDa. In some embodiments, the antigen binding moiety comprises a single domain antibody moiety. In some embodiments, the antigen binding moiety comprises a single domain antibody moiety that specifically binds to albumin.

In some embodiments, the second moiety is fused to the N-terminus of the truncated IL-21. In some embodiments, the second moiety is fused to the C-terminus of the truncated IL-21.

In some embodiments, the second moiety is fused to the truncated IL-21 via a linker (can be either adjacent to IL-21 or not adjacent to IL-21). In some embodiments, the second moiety is fused to N- or C-terminus of the truncated IL-21 via a linker. In some embodiments, the linker is a rigid linker. In some embodiments, the linker is a flexible linker.

III. Pharmaceutical Compositions

Further provided by the present application are pharmaceutical compositions comprising any one of fusion proteins described herein, and optionally a pharmaceutically acceptable carrier. Pharmaceutical compositions can be prepared by mixing a fusion protein described herein having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

The pharmaceutical composition is preferably to be stable, in which the fusion protein described herein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month, and/or stable at 2-8° C. for at least 2 years. Where the formulation is to be stored at 30° C., generally the formulation should be stable for at least 2 years at 30° C., and/or stable at 40° C. for at least 6 months. For example, the extent of aggregation during storage can be used as an indicator of protein stability. In some embodiments, the stable formulation of fusion proteins described herein may comprise less than about 10% (preferably less than about 5%) of the fusion protein present as an aggregate in the formulation.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers (e.g. sodium chloride), stabilizers, metal complexes (e.g. Zn-protein complexes); chelating agents such as EDTA and/or non-ionic surfactants.

Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

Buffers are used to control the pH in a range which optimizes the therapeutic effectiveness, especially if stability is pH dependent. Buffers are preferably present at concentrations ranging from about 50 mM to about 250 mM. Suitable buffering agents for use in the present application include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). The addition of a preservative may, for example, facilitate the production of a multi-use (multiple-dose) formulation. Suitable preservatives for use in the present application include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1% to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellulose and carboxymethyl cellulose. Anionic detergents that can be used include sodium lauryl sulfate, dioctyl sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intra-arterial, intralesional or intraarticular routes, topical administration, inhalation or by sustained release or extended-release means. In some embodiments, the pharmaceutical composition is administered locally, such as intratumorally, or intravitreally.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The pharmaceutical compositions herein may also contain more than one active compound as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

The antibody fusion protein disclosed herein can be formulated as immunoliposomes. Liposomes containing the antibody fusion protein are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

In some embodiments, the pharmaceutical composition is contained in a single-use vial, such as a single-use sealed vial. In some embodiments, the pharmaceutical composition is contained in a multi-use vial. In some embodiments, the pharmaceutical composition is contained in bulk in a container. In some embodiments, the pharmaceutical composition is cryopreserved.

IV. Methods of Treatments

One aspect of the present application provides methods of treating a disease or condition in an individual using the fusion proteins or pharmaceutical compositions described herein. For example, the fusion proteins described herein comprise: a) a cytokine, and b) an albumin binding moiety (such as an sdAb that binds to albumin). In some embodiments, the fusion protein comprises a) a cytokine selected from the group consisting of IL-21, IL-7, IL-15, IL-15 bound to IL-15Rα or fragment thereof, IL-33, and IL-22, and b) an albumin binding moiety (such as an sdAb that binds to albumin) In some embodiments, the albumin binding moiety comprises an albumin binding domain or a single domain antibody (sdAb) that binds to albumin as described herein. In some embodiments, the method further comprises administering a second agent.

Another aspect of the present application provides methods of treating a disease or condition in an individual comprising administering to the individual a) a fusion protein comprising i) a cytokine and ii) a half-life extending domain fused to the cytokine; and b) a second agent. In some embodiments, the half-life extending domain is fused to the C-terminus of the cytokine. In some embodiments, the half-life extending domain is fused to the N-terminus of the cytokine. In some embodiments, the cytokine and the half-life extending domain are connected via a linker. In some embodiments, the linker has a length of one to forty (such as one to thirty-five, one to thirty, one to twenty-five, one to twenty, four to twenty, or four to sixteen) amino acids. In some embodiments, the linker is selected from the group consisting of GSG and SEQ ID NOs: 12-26 and 158-159. In some embodiments, the cytokine is selected from the group consisting of IL-21, IL-7, IL-15, IL-15 bound to IL-15Rα or fragment thereof, IL-33, and IL-22. In some embodiments, the cytokine is IL-21. In some embodiments, the half-life extending domain is an albumin binding moiety (such as an albumin binding domain or an anti-albumin single domain antibody). In some embodiments, the half-life extending domain is an albumin. In some embodiments, the half-life extending domain is an Fc fragment. In some embodiments, the Fc fragment is selected from the group consisting of an IgG1, IgG2, IgG3, and IgG4 Fc fragments or a variant thereof. In some embodiments, the Fc fragment is an IgG1 Fc fragment or variant thereof. In some embodiments, the IgG1 Fc fragment or variant thereof comprises a mutation at position 297, wherein the amino acid at position 297 is mutated to alanine, aspartic acid or glycine. In some embodiments, the individual is a human.

In some embodiments, the second agent comprises a therapeutic antibody, an immune checkpoint inhibitor, a second cytokine, a chemotherapeutic agent, a tyrosine kinase inhibitor or an immune cell.

In some embodiments, the second agent is a therapeutic antibody. In some embodiments, the therapeutic antibody binds to a tumor antigen. In some embodiments, the tumor antigen is selected from the group consisting of mesothelin, GPA33, Her-2, EGFR, and CD20. In some embodiments, the tumor antigen is selected from the group consisting of CEA, MUC16, MUC1, AFP, EPCAM, CD19, CD21, CD22, CD30, CD33, CD37, CD45, PSMA, and BCMA.

In some embodiments, the tumor antigen is mesothelin. In some embodiments, the second agent is an anti-mesothelin antibody or fragment thereof. In some embodiments, the anti-mesothelin antibody or fragment thereof comprises a single chain antibody comprising an anti-mesothelin heavy chain variable region (anti-MSLN $V_H$), wherein the anti-MSLN $V_H$ comprises a CDR1, a CDR2, and a CDR3, wherein: a) the CDR1 comprising the amino acid sequence of SEQ ID NO: 46, the CDR2 comprising the amino acid sequence of SEQ ID NO: 47, and the CDR3 comprising the amino acid sequence of SEQ ID: NO: 48, or a variant thereof comprising up to a total of 3, 2, or 1 amino acid substitutions in the CDRs; or b) the CDR1 comprising the amino acid sequence of SEQ ID NO: 49, the CDR2 comprising the amino acid sequence of SEQ ID NO: 50, and the CDR3 comprising the amino acid sequence of GRY, or a variant thereof comprising up to a total of 3, 2, or 1 amino acid substitutions in the CDRs.

In some embodiments, the second agent is an immune checkpoint modulator. In some embodiments, the immune checkpoint modulator is an inhibitor of an immune checkpoint protein selected from the group consisting of PD-L1, CTLA4, PD-L2, PD-1, CD47, TIGIT, GITR, TIM3, LAG3, 4-1BB, CD27 and B7H4. In some embodiments, the immune checkpoint protein is PD-1. In some embodiments, the second agent is an anti-PD-1 antibody or fragment thereof.

In some embodiments, the second agent is a second cytokine. In some embodiments, the cytokine in the fusion protein is IL-21, and wherein the second cytokine is selected from the group consisting of IL-7, IL-15, IL15 bound to IL15Rα or half-life extended variants thereof.

In some embodiments, the second agent is an immune cell. In some embodiments, the immune cell comprises T cells or NK cells. In some embodiments, the immune cell comprises T cells expressing a chimeric antigen receptor (CAR), T cells expressing a modified T cell receptor (TCR), or T cells isolated from a tumor.

In some embodiments, the second agent is a tyrosine kinase inhibitor.

In some embodiments, the second agent is a chemotherapeutic agent (such as sorafenib).

In some embodiments, there is provided a method of treating a disease or condition in an individual comprising administering to the individual a) a fusion protein comprising i) IL-21 and ii) a half-life extending domain fused to the cytokine; and b) a second agent. In some embodiments, the half-life extending domain is fused to N-terminus of the cytokine. In some embodiments, the half-life extending domain is fused to C-terminus of the cytokine. In some embodiments, the second agent comprises a therapeutic antibody (such as a therapeutic antibody that binds to a tumor antigen such as CD20 or mesothelin), an immune checkpoint inhibitor (such as an anti-PD-1 antibody), a second cytokine, a chemotherapeutic agent, a tyrosine kinase inhibitor, or an immune cell. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the fusion protein further comprises an antigen binding moiety (such as described above). In some embodiments, the antigen binding moiety binds to a tumor antigen (such as mesothelin). In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer. In some embodiments, the individual is a human.

In some embodiments, there is provided a method of treating a disease or condition in an individual comprising administering to the individual a) a fusion protein comprising i) IL-7 and ii) a half-life extending domain fused to the cytokine; and b) a second agent. In some embodiments, the half-life extending domain is fused to N-terminus of the cytokine. In some embodiments, the half-life extending domain is fused to C-terminus of the cytokine. In some embodiments, the second agent comprises a therapeutic antibody (such as a therapeutic antibody that binds to a tumor antigen such as CD20 or mesothelin), an immune checkpoint inhibitor (such as an anti-PD-1 antibody), a second cytokine, a chemotherapeutic agent, a tyrosine kinase inhibitor, or an immune cell. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the fusion protein further comprises an antigen binding moiety (such as described above). In some embodiments, the antigen binding moiety binds to a tumor antigen (such as mesothelin). In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer. In some embodiments, the individual is a human.

In some embodiments, there is provided a method of treating a disease or condition in an individual comprising administering to the individual a) a fusion protein comprising i) IL-15 and ii) a half-life extending domain fused to the cytokine; and b) a second agent. In some embodiments, the half-life extending domain is fused to N-terminus of the cytokine. In some embodiments, the half-life extending domain is fused to C-terminus of the cytokine. In some embodiments, the second agent comprises a therapeutic antibody (such as a therapeutic antibody that binds to a tumor antigen such as CD20 or mesothelin), an immune checkpoint inhibitor (such as an anti-PD-1 antibody), a second cytokine, a chemotherapeutic agent, a tyrosine kinase inhibitor, or an immune cell. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the fusion protein further comprises an antigen binding moiety (such as described above). In some embodiments, the antigen binding moiety binds to a tumor antigen (such as mesothelin). In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer. In some embodiments, the individual is a human.

In some embodiments, there is provided a method of treating a disease or condition in an individual comprising administering to the individual a) a fusion protein comprising i) IL-15 bound to IL-15Rα or a fragment thereof and ii) a half-life extending domain fused to the cytokine; and b) a second agent. In some embodiments, the half-life extending domain is fused to N-terminus of the cytokine. In some embodiments, the half-life extending domain is fused to C-terminus of the cytokine. In some embodiments, the second agent comprises a therapeutic antibody (such as a therapeutic antibody that binds to a tumor antigen such as CD20 or mesothelin), an immune checkpoint inhibitor (such as an anti-PD-1 antibody), a second cytokine, a chemotherapeutic agent, a tyrosine kinase inhibitor, or an immune cell. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the fusion protein further comprises an antigen binding moiety (such as described above). In some embodiments, the antigen binding moiety binds to a tumor antigen (such as mesothelin). In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer. In some embodiments, the individual is a human.

In some embodiments, there is provided a method of treating a disease or condition in an individual comprising administering to the individual a) a fusion protein comprising i) IL-33 and ii) a half-life extending domain fused to the cytokine; and b) a second agent. In some embodiments, the half-life extending domain is fused to N-terminus of the cytokine. In some embodiments, the half-life extending domain is fused to C-terminus of the cytokine. In some embodiments, the second agent comprises a therapeutic antibody (such as a therapeutic antibody that binds to a tumor antigen such as CD20 or mesothelin), an immune checkpoint inhibitor (such as an anti-PD-1 antibody), a second cytokine, a chemotherapeutic agent, a tyrosine kinase inhibitor, or an immune cell. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the fusion protein further comprises an antigen binding moiety (such as described above). In some embodiments, the antigen binding moiety binds to a tumor antigen (such as mesothelin). In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer. In some embodiments, the individual is a human.

In some embodiments, there is provided a method of treating a cancer in an individual comprising administering to the individual a fusion protein comprising an IL-21 as described above. For example in some embodiments, the fusion protein comprises a) IL-21, and b) an albumin binding moiety (such as an sdAb that binds to albumin), wherein the albumin binding moiety is fused to the N- or C-terminus of the IL-21 or the variant thereof. In some embodiments, the fusion protein comprises a) IL-21 fused to an albumin binding moiety ("IL-21-ALBBM") and b) an antigen binding moiety, wherein the linkage between the cytokine-ALBBM and the antigen binding moiety is optionally cleavable. In some embodiments, the antigen binding moiety binds to a tumor antigen (such as mesothelin). In some embodiments, there is provided a method of treating a cancer in an individual comprising administering to the individual a fusion protein comprising i) IL-21, and ii) a half-life extending domain, wherein the half-life extending domain is fused to the N- or C-terminus of IL-21. In some embodiments, the method further comprises a second agent (such as a therapeutic antibody that binds to a tumor antigen such as CD20 or mesothelin, a chemotherapeutic agent such as sorafenib, an immunomodulator such as an anti-PD-1 antibody). In some embodiments, the cancer expresses a high level of a tumor antigen. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer. In some embodiments, the individual is a human.

In some embodiments, there is provided a method of treating a cancer in an individual comprising administering to the individual a fusion protein comprising an IL-7 as described above. For example in some embodiments, the fusion protein comprises a) IL-7, and b) an albumin binding moiety (such as an sdAb that binds to albumin), wherein the albumin binding moiety is fused to the N- or C-terminus of the IL-7 or the variant thereof. In some embodiments, the fusion protein comprises a) IL-7 fused to an albumin binding moiety ("IL-7-ALBBM") and b) an antigen binding moiety, wherein the linkage between the cytokine-ALBBM and the antigen binding moiety is optionally cleavable. In some embodiments, the antigen binding moiety binds to a tumor antigen (such as mesothelin). In some embodiments, there is provided a method of treating a cancer in an individual comprising administering to the individual a fusion protein comprising i) IL-7, and ii) a half-life extending domain, wherein the half-life extending domain is fused to the N- or C-terminus of IL-7. In some embodiments, the method further comprises a second agent. In some embodiments, the cancer expresses a high level of a tumor antigen. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the cancer is selected from the group consisting of mesothelioma, lung cancer, ovarian cancer, and gastric cancer. In some embodiments, the individual is a human.

In some embodiments, there is provided a method of treating a cancer in an individual comprising administering to the individual a fusion protein comprising an IL-15 as described above. For example in some embodiments, the fusion protein comprises a) IL-15, and b) an albumin binding moiety (such as an sdAb that binds to albumin), wherein the albumin binding moiety is fused to the N- or C-terminus of the IL-15 or the variant thereof. In some embodiments, the fusion protein comprises a) IL-15 fused to an albumin binding moiety ("IL-15-ALBBM") and b) an antigen binding moiety, wherein the linkage between the cytokine-ALBBM and the antigen binding moiety is optionally cleavable. In some embodiments, the antigen binding moiety binds to a tumor antigen (such as mesothelin). In some embodiments, there is provided a method of treating a cancer in an individual comprising administering to the individual a fusion protein comprising i) IL-15, and ii) a half-life extending domain, wherein the half-life extending domain is fused to the N- or C-terminus of IL-15. In some embodiments, the method further comprises a second agent. In some embodiments, the cancer expresses a high level of a tumor antigen. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the cancer is selected from the group consisting of mesothelioma, lung cancer, ovarian cancer, and gastric cancer. In some embodiments, the individual is a human.

In some embodiments, there is provided a method of treating a cancer in an individual comprising administering to the individual a fusion protein comprising an IL-15 bound to IL-15Rα as described above. For example in some embodiments, the fusion protein comprises a) IL-15 bound to IL-15Rα, and b) an albumin binding moiety (such as an sdAb that binds to albumin), wherein the albumin binding moiety is fused to the N- or C-terminus of the IL-15 bound to IL-15Rα or the variant thereof. In some embodiments, the fusion protein comprises a) IL-15 bound to IL-15Rα fused to an albumin binding moiety ("IL-15 bound to IL-15Rα-ALBBM") and b) an antigen binding moiety, wherein the linkage between the cytokine-ALBBM and the antigen binding moiety is optionally cleavable. In some embodiments, the antigen binding moiety binds to a tumor antigen (such as mesothelin). In some embodiments, there is provided a method of treating a cancer in an individual comprising administering to the individual a fusion protein comprising i) IL-15 bound to IL-15Rα, and ii) a half-life extending domain, wherein the half-life extending domain is fused to the N- or C-terminus of IL-15 bound to IL-15Rα. In some embodiments, the method further comprises a second agent. In some embodiments, the cancer expresses a high level of a tumor antigen. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the cancer is selected from the group consisting of mesothelioma, lung cancer, ovarian cancer, and gastric cancer. In some embodiments, the individual is a human.

In some embodiments, there is provided a method of treating a cancer in an individual comprising administering to the individual a fusion protein comprising an IL-33 as described above. For example in some embodiments, the fusion protein comprises a) IL-33, and b) an albumin binding moiety (such as an sdAb that binds to albumin), wherein the albumin binding moiety is fused to the N- or C-terminus of the IL-33 or the variant thereof. In some embodiments, the fusion protein comprises a) IL-33 fused to an albumin binding moiety ("IL-33-ALBBM") and b) an antigen binding moiety, wherein the linkage between the cytokine-ALBBM and the antigen binding moiety is optionally cleavable. In some embodiments, the antigen binding moiety binds to a tumor antigen (such as mesothelin). In some embodiments, there is provided a method of treating a cancer in an individual comprising administering to the individual a fusion protein comprising i) IL-33, and ii) a half-life extending domain, wherein the half-life extending domain is fused to the N- or C-terminus of IL-33. In some embodiments, the method further comprises a second agent. In some embodiments, the cancer expresses a high level of a tumor antigen. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the cancer is selected from the group consisting of mesothelioma, lung cancer, ovarian cancer, and gastric cancer. In some embodiments, the individual is a human.

In some embodiments, there is provided a method of treating an inflammatory disease in an individual comprising administering to the individual a fusion protein, wherein the fusion protein comprises a) IL-22, and b) an albumin binding moiety (such as an sdAb that binds to albumin), wherein the albumin binding moiety is fused to the N- or C-terminus of the IL-22 or the variant thereof. In some embodiments, the albumin binding moiety is an albumin binding domain or an anti-albumin single domain antibody such as those described herein. In some embodiments, there is provided a method of treating an inflammatory disease in an individual comprising administering to the individual a fusion protein, wherein the fusion protein comprises a) IL-22, and ii) a half-life extending domain. In some embodiments, the half-life extending domain is an antibody of fragment thereof, an albumin, a binding protein (such as an albumin binding protein or an IgG binding protein), an antibody derivative, or a polyamino sequence. In some embodiments, the disease is selected from the group consisting of ulcerative colitis, Crohn's disease, or ulcerative ileitis, and intestinal graft vs host disease. In some embodiments, the individual is a human.

In some embodiments, there is provided a method of treating a mesothelioma in an individual comprising administering to the individual a fusion protein comprising a cytokine as described above. For example in some embodiments, the fusion protein comprises a) a cytokine, and b) an albumin binding moiety (such as an sdAb that binds to albumin), wherein the albumin binding moiety is fused to the N- or C-terminus of the cytokine. In some embodiments, the fusion protein comprises a) a cytokine fused to an albumin binding moiety ("cytokine-ALBBM") and b) an antigen binding moiety, wherein the linkage between the cytokine-ALBBM and the antigen binding moiety is optionally cleavable. In some embodiments, the cytokine is selected from the group consisting of IL-21, IL-7, IL-15, IL-15 bound to IL-15Rα or fragment thereof, IL-33, and IL-22. In some embodiments, the antigen binding moiety binds to a tumor antigen (such as mesothelin). In some embodiments, there is provided a method of treating a mesothelioma in an individual comprising administering to the individual a fusion protein comprising i) cytokine, and ii) a half-life extending domain, wherein the half-life extending domain is fused to the N- or C-terminus of cytokine. In some embodiments, the method further comprises a second agent (such as an anti-mesothelin antibody). In some embodiments, the half-life extending domain is an antibody of fragment thereof, an albumin, a binding protein (such as an albumin binding protein or an IgG binding protein), an antibody derivative, or a polyamino sequence as described herein.

In some embodiments, there is provided a method of treating a lung cancer in an individual comprising administering to the individual a fusion protein comprising a cytokine as described above. For example in some embodiments, the fusion protein comprises a) a cytokine, and b) an albumin binding moiety (such as an sdAb that binds to albumin), wherein the albumin binding moiety is fused to the N- or C-terminus of the cytokine. In some embodiments, the fusion protein comprises a) a cytokine fused to an albumin binding moiety ("cytokine-ALBBM") and b) an antigen binding moiety, wherein the linkage between the cytokine-ALBBM and the antigen binding moiety is optionally cleavable. In some embodiments, the cytokine is selected from the group consisting of IL-21, IL-7, IL-15, IL-15 bound to IL-15Rα or fragment thereof, IL-33, and IL-22. In some embodiments, the antigen binding moiety binds to a tumor antigen. In some embodiments, there is provided a method of treating a lung cancer in an individual comprising administering to the individual a fusion protein comprising i) cytokine, and ii) a half-life extending domain, wherein the half-life extending domain is fused to the N- or C-terminus of cytokine. In some embodiments, the method further comprises a second agent. In some embodiments, the half-life extending domain is an antibody of fragment thereof, an albumin, a binding protein (such as an albumin binding protein or an IgG binding protein), an antibody derivative, or a polyamino sequence as described herein.

In some embodiments, there is provided a method of treating an ovarian cancer in an individual comprising administering to the individual a fusion protein comprising a cytokine as described above. For example in some embodiments, the fusion protein comprises a) a cytokine, and b) an albumin binding moiety (such as an sdAb that binds to albumin), wherein the albumin binding moiety is fused to the N- or C-terminus of the cytokine. In some embodiments, the fusion protein comprises a) a cytokine fused to an albumin binding moiety ("cytokine-ALBBM") and b) an antigen binding moiety, wherein the linkage between the cytokine-ALBBM and the antigen binding moiety is optionally cleavable. In some embodiments, the cytokine is selected from the group consisting of IL-21, IL-7, IL-15, IL-15 bound to IL-15Rα or fragment thereof, IL-33, and IL-22. In some embodiments, the antigen binding moiety binds to a tumor antigen. In some embodiments, there is provided a method of treating an ovarian cancer in an individual comprising administering to the individual a fusion protein comprising i) cytokine, and ii) a half-life extending domain, wherein the half-life extending domain is fused to the N- or C-terminus of cytokine. In some embodiments, the method further comprises a second agent. In some embodiments, the half-life extending domain is an antibody of fragment thereof, an albumin, a binding protein (such as an albumin binding protein or an IgG binding protein), an antibody derivative, or a polyamino sequence as described herein.

In some embodiments, there is provided a method of treating a gastric cancer in an individual comprising administering to the individual a fusion protein comprising a cytokine as described above. For example in some embodiments, the fusion protein comprises a) a cytokine, and b) an albumin binding moiety (such as an sdAb that binds to albumin), wherein the albumin binding moiety is fused to the N- or C-terminus of the cytokine. In some embodiments, the fusion protein comprises a) a cytokine fused to an albumin binding moiety ("cytokine-ALBBM") and b) an antigen binding moiety, wherein the linkage between the cytokine-ALBBM and the antigen binding moiety is optionally cleavable. In some embodiments, the cytokine is selected from the group consisting of IL-21, IL-7, IL-15, IL-15 bound to IL-15Rα or fragment thereof, IL-33, and IL-22. In some embodiments, the antigen binding moiety binds to a tumor antigen. In some embodiments, there is provided a method of treating a gastric cancer in an individual comprising administering to the individual a fusion protein comprising i) cytokine, and ii) a half-life extending domain, wherein the half-life extending domain is fused to the N- or C-terminus of cytokine. In some embodiments, the method further comprises a second agent. In some embodiments, the half-life extending domain is an antibody of fragment thereof, an albumin, a binding protein (such as an albumin binding protein or an IgG binding protein), an antibody derivative, or a polyamino sequence as described herein.

In some embodiments, there is provided a method of treating a cancer in an individual comprising administering to the individual a) a fusion protein comprising an IL-21 as described above and b) a second cytokine selected from the group consisting of IL-7, IL-15, IL15 bound to IL15Rα or half-life extended variants thereof. For example, in some embodiments, the fusion protein comprises a) IL-21, and b) an albumin binding moiety (such as an sdAb that binds to albumin), wherein the albumin binding moiety is fused to the N- or C-terminus of the IL-21 or the variant thereof. In some embodiments, the fusion protein comprises a) IL-21 fused to an albumin binding moiety ("IL-21-ALBBM") and b) an antigen binding moiety, wherein the linkage between the cytokine-ALBBM and the antigen binding moiety is optionally cleavable. In some embodiments, the antigen binding moiety binds to a tumor antigen (such as mesothelin). In some embodiments, there is provided a method of treating a cancer in an individual comprising administering to the individual a) a fusion protein comprising i) IL-21, and ii) a half-life extending domain, wherein the half-life extending domain is fused to the N- or C-terminus of IL-21; b) a second agent selected from the group consisting of IL-7, IL-15, IL15 bound to IL15Rα or half-life extended variants thereof. In some embodiments, the half-life extending domain is an antibody of fragment thereof, an albumin, a binding protein (such as an albumin binding protein or an IgG binding protein), an antibody derivative, or a polyamino sequence as described herein. In some embodiments, the first extended half-life cytokine is fused to the second extended half-life cytokine via a peptide linker, which is optionally protease cleavable. In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer. In some embodiments, the individual is a human.

Fusion Proteins for Treating a Disease

In some embodiments, the fusion protein for treating a disease or condition comprises any of the fusion proteins described herein (such as in Section II). In some embodiments, the fusion protein comprises i) a cytokine and ii) a half-life extending domain fused to the cytokine. In some embodiments, the half-life extending domain is fused to the C-terminus of the cytokine. In some embodiments, the half-life extending domain is fused to the N-terminus of the cytokine. In some embodiments, the cytokine and the half-life extending domain are connected via a linker. In some embodiments, the linker can be any linker described herein (such as in Section II-B). In some embodiments, the cytokine is selected from the group consisting of IL-21, IL-7, IL-15, IL-15 bound to IL-15Rα or fragment thereof, IL-33, and IL-22. In some embodiments, the cytokine is IL-21.

Half-Life Extending Domain

In some embodiments, the fusion proteins for treating a disease or condition as described herein comprise a half-life extending domain.

In some embodiments, the fusion protein provided herein comprises a half-life extension domain selected from the group consisting of antibodies and fragments thereof, albumin, albumin-binding proteins, IgG-binding proteins, and polyamino acid sequences. It is contemplated that other mechanisms for extending the half-life of the fusion protein available in the art may also be employed.

a) Antibodies and Fragments Thereof

By linking a cytokine to an antibody or fragment thereof that is capable of FcRn-mediated recycling, clearance of the cytokine from a subject can be reduced or otherwise delayed, thereby prolonging the half-life of the administered cytokine.

In some embodiments, the half-life extension domain comprises an antibody or fragment thereof. In some embodiments, the antibody or fragment thereof is any antibody or fragment thereof that is capable of FcRn-mediated recycling, such as any heavy chain polypeptide or portion thereof (e.g., Fc domain or fragment thereof) that is capable of FcRn-mediated recycling. It is recognized in the art that FcRn-mediated recycling requires binding of the FcRn receptor to the Fc region of the antibody or fragment thereof. For instance, studies have shown that residues I253, S254, H435, and Y436 (numbering according to the Kabat EU index numbering system) are important for the interaction between the human Fc region and the human FcRn complex. See, e.g., Firan, M., et al., Int. Immunol. 13 (2001) 993-1002; Shields, R. L., et al, J. Biol. Chem. 276 (2001) 6591-6604). Various mutants of residues 248-259, 301-317, 376-382, and 424-437 (numbering according to the Kabat EU index numbering system) have also been examined and reported. Yeung, Y. A., et al. (J. Immunol. 182 (2009) 7667-7671.

In some embodiments, the antibody or fragment thereof comprises either a heavy chain polypeptide or a light chain polypeptide. In some embodiments, the antibody or fragment thereof comprises a portion of either a heavy chain polypeptide or a light chain polypeptide. In some embodiments, the antibody or fragment thereof comprises an Fc domain or fragment thereof. In some embodiments, the antibody or fragment thereof comprises a CH2 and CH3 domain or a fragment thereof. In some embodiments, the antibody or fragment thereof comprises the constant domain of the heavy chain polypeptide. In some embodiments, the antibody or fragment thereof comprises the constant domain of the light chain polypeptide. In some embodiments, the antibody or fragment thereof comprises a heavy chain polypeptide or fragment thereof (e.g., an Fc domain or fragment thereof). In some embodiments, the antibody or fragment thereof comprises a light chain polypeptide.

In some embodiments, the antibody of fragment thereof comprises an Fc domain or fragment thereof. In some embodiments, the Fc fragment is selected from the group consisting of an IgG1, IgG2, IgG3, and IgG4 Fc fragments or a variant thereof. In some embodiments, the Fc fragment is an IgG1 Fc fragment or variant thereof. In some embodiments, the IgG1 Fc fragment or variant thereof comprises a mutation at position 297. In some embodiments, the amino acid at position 297 is asparagine. In some embodiments, the amino acid at position 297 (e.g., asparagine) is mutated to alanine, aspartic acid or glycine.

In some embodiments, the cytokine of the fusion protein forms a dimer by the half-life extension domain of one copy of the cytokine forming a disulfide bond with the corresponding half-life extension domain of a second copy of the cytokine.

b) Albumin

Albumin is a natural carrier protein that has an extended serum half-life of approximately three weeks due to its size and its susceptibility to FcRn-mediated recycling, which prevents intracellular degradation. Thus, linking a cytokine to albumin can greatly extend the half-life of the cytokine. This approach has been taken to extend the plasma half-life of therapeutically beneficial proteins. See, e.g., WO 2001/079271A1 and WO 2003/59934A2, the contents of which are herein incorporated by reference. A few isoforms of HSA were listed in Table 2.

In some embodiments, the fusion protein comprises a half-life extension domain that comprises an albumin polypeptide or a fragment or variant thereof (hereinafter referred to as "albumin" or "albumin polypeptide"). As used herein, the terms "albumin" and "albumin polypeptide" includes fragments of albumin as well as variants of albumin. The albumin polypeptide comprises an amino-terminus and a carboxy-terminus. The albumin polypeptide can be any albumin polypeptide, including any fragment or variant thereof, such as any albumin polypeptide described in WO 2001/079271A1; WO 2003/59934A2; US20160152686A1; WO 2012/059486; WO 2011/124718; US20070048282, the contents of which are herein incorporated by reference. In some embodiments, the albumin polypeptide is HSA.

c) Binding Proteins

Additional strategies for extending the half-life of the cytokines or variants thereof in serum include linking the cytokine to certain binding proteins, such as albumin-binding proteins as described above or IgG-binding proteins. The binding proteins can be any protein that binds to a serum protein having a prolonged half-life, such as albumin or IgG. Albumin and IgG are polypeptides that are known to have long half-lives in serum.

In some embodiments, the half-life extension domain comprises an albumin-binding protein. In some embodiments, the fusion protein comprises more than one albumin-binding protein, each of which can be any of the albumin-binding proteins described herein.

In some embodiments, the albumin-binding protein is a single-domain antibody or fragment thereof, such as a Nanobody, that binds to or otherwise associates with albumin, such as those described herein. See, e.g., WO 2004041865A2 and US20070269422A1, the contents of which are herein incorporated by reference.

Another example of a binding protein is an IgG-binding protein. IgG-binding proteins have been reported. For an overview of IgG-binding proteins, including specific IgG-binding proteins and their applications, see, e.g., Choe et al. (2016) Materials 9(12): 994, the contents of which are herein incorporated by reference.

d) Antibody Derivatives

The cytokines described herein may alternatively be linked to various antibody derivatives including, but not limited to, an scFv, an scFc, a dual-variable domain (DVD), and antibody derivatives based on the CrossMab approach. See, e.g., Klein et al. (2012), MAbs, 4(6): 653-663; US20070071675A1. The antibody derivatives include antibody derivatives engineered as bispecific antibodies or fragments thereof. As such, in some embodiments, a half-life extension domain can comprise any antibody derivative, variant, or fusion product thereof including, but not limited to an scFv, an scFc, a dual-variable domain (DVD), antibody derivatives based on the CrossMab approach, and bispecific antibodies or fragments thereof.

e) Polyamino Acid Sequences

An additional strategy for extending the half-life of fusion proteins in serum is by linking the fusion protein to a polyamino acid sequence. As such, in some embodiments, the half-life extension domain comprises a polyamino acid sequence. The polyamino acid sequence can be any polyamino acid sequence capable of extending the half-life of the fusion protein in serum when it is linked to the fusion protein. Examples of polyamino acid sequences include PAS polypeptides and XTEN polypeptides.

f) PEGylation and Glycosylation

Additional strategies for extending the half-life of the cytokines provided herein include PEGylation and the engineering of additional glycosylation sites. Each of these strategies is discussed in further detail below.

"PEGylation" refers to a process of covalent or non-covalent attachment or amalgamation of polyethylene glycol (PEG) polymer chains to molecules and macrostructures, such as a drug, therapeutic protein, polypeptide, antibody, antibody fragment, antibody derivative, or to any of the fusion proteins or components thereof provided herein (e.g., the half-life extension domain of a fusion protein and/or the cytokine or functional fragment thereof of the fusion protein). The benefits of PEGylation include, for example, (1) markedly improved circulating half-lives in vivo due to either evasion of renal clearance as a result of the polymer increasing the apparent size of the molecule to above the glomerular filtration limit, and/or through evasion of cellular clearance mechanisms, (2) reduced antigenicity and immunogenicity of the molecule to which PEG is attached, (3) improved pharmacokinetics, (4) improved solubility, (5) improved formulation and dosing options, (6) improved bioavailability via reduced losses at subcutaneous injection sites, (7) improved thermal and mechanical stability of the PEGylated molecule.

Methods for the pegylation of various molecules and macrostructures are well known in the art. See, e.g., US20140256636A1; Fee and Damodaran (2010) European Pharmaceutical Review, 15(1): 18-26; Chapman et al. (1999) Nature Biotechnol., 17: 780-783; Yang et al. (2003), Protein Eng., 16(10): 761-770; Chapman, Adv. Drug. Deliv. Rev. (2002), 54(4): 531-545, the contents of which are herein incorporated by reference.

"Glycosylation" refers to the addition of saccharides or glycosyl groups to a polypeptide. Glycosylation of polypeptides is typically either N-linked or O-linked. N-linked refers to the attachment of a carbohydrate moiety to the side chain of an asparagine residue. The tripeptide sequences asparagine-X-serine (N-X-S) and asparagine-X-threonine (N-X-T), where X is any amino acid except proline (P), are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars (e.g., N-acetylgalactosamine, galactose, or xylose) to a hydroxyamino acid, most commonly serine or threonine, although 5-hydroxyproline or 5-hydroxylysine may also be used.

Naturally-occurring glycosylation has been shown to increase the molecular stability of proteins. See, e.g., Sola et al. (2007), Cell. Mol. Life Sci., 64(16): 2133-2152. It has also been shown that the engineering of additional glycosylation sites can stabilize a variety of protein therapeutics against most major physiochemical instabilities. See, e.g., Sola and Griebenow (2009), J. Pharm. Sci., 98(4): 1223-1245. Among the pharmaceutically relevant protein instabilities that have been shown to be improved by glycosylation are, for example, oxidation; cross-linking; pH-, chemical-, thermal-, and freezing-induced denaturation/unfolding; precipitation; kinetic activation; and aggregation. Id.

Addition of glycosylation sites to the fusion protein is conveniently accomplished by altering the amino acid sequence such that one or more of the above-described tripeptide sequences (for N-linked glycosylation sites) is created in the amino acid sequence of the fusion protein (e.g., in the amino acid sequence of the half-life extension domain and/or the cytokine or functional fragment thereof). The alteration may also be made by the addition to, or substitution of, one or more serine or threonine residues in the amino acid sequence of the fusion protein (e.g., in the amino acid sequence of the half-life extension domain and/or the cytokine or functional fragment thereof) (for O-linked glycosylation sites).

g) Heterodimerization Modifications

The half-life extension domains described herein may include one or more modifications that promote heterodimerization of two different half-life extension domains. In some embodiments comprising a first half-life extension domain and a second half-life extension domain, it is desirable to promote heterodimerization of the first and second half-life extension domains such that production of the fusion protein in its correct heterodimeric form is produced efficiently. As such, one or more amino acid modifications can be made to the first half-life extension domain and one or more amino acid modifications can be made to the second half-life extension domain using any strategy available in the art, including any strategy as described in Klein et al. (2012), MAbs, 4(6): 653-663.

One strategy for promoting heterodimerization of two different half-life extension domains is an approach termed the "knobs-into-holes." In some embodiments, the fusion protein comprises a first half-life extension domain and a second half-life extension domain, each of which comprises a CH3 domain. In some embodiments, the half-life extension domain comprising a CH3 domain is a heavy chain polypeptide or a fragment thereof (e.g., an Fc domain or fragment thereof). The CH3 domains of the two half-life extension domains can be altered by the "knobs-into-holes" technology, which is described in detail with several examples in, e.g., WO 1996/027011; Ridgway, J. B. et al., Protein Eng. (1996) 9(7): 617-621; Merchant, A. M., et al., Nat. Biotechnol. (1998) 16(7): 677-681. See also Klein et al. (2012), MAbs, 4(6): 653-663. Using the knob-into-holes method, the interaction surfaces of the two CH3 domains are altered to increase the heterodimerization of the two half-life extension domains containing the two altered CH3 domains. This occurs by introducing a bulky residue into the CH3 domain of one of the half-life extension domains, which acts as the "knob." Then, in order to accommodate the bulky residue, a "hole" is formed in the other half-life extension domain that can accommodate the knob. Either of the altered CH3 domains can be the "knob" while the other can be the "hole." The introduction of a disulfide bridge further stabilizes the heterodimers (Merchant, A. M., et al., Nat. Biotechnol. (1998) 16(7); Atwell, S., et al., J. Mol. Biol. (1997) 270(1): 26-35) as well as increases yield. Exemplary sequences that will facilitate the acts as "knob" and "hole" are disclosed in, for example, include sequences included in the sequence of SEQ ID NO: 164-167. In some embodiments, the CH3 domain has one or more mutations selected from Y349C, T366S, L368A, Y407V, S354C, T366W.

Another strategy for promoting heterodimerization of two different half-life extension domains is by stabilizing ionic interactions that favor heterodimerization through altering charged residues. In some embodiments, the fusion protein comprises a first half-life extension domain and a second half-life extension domain, each of which comprises a CH3 domain. In some embodiments, the half-life extension domain comprising a CH3 domain is a heavy chain polypeptide or a fragment thereof (e.g., an Fc domain or fragment thereof). It has been observed that altering the charge polarities between two different Fc domains can result in ionic interactions such that heterodimerization is favored while homodimerization is suppressed. See, e.g., WO 2006/106905A1; Gunasekaran et al. (2010), J. Biol. Chem. 285 (25): 19637-19646. For example, it was observed that negatively charged E356 pairs of an Fc domain pairs with positively charged K439 of another Fc domain, negatively charged E357, E357, and D399 of a first Fc domain pairs with positively charged K439, K370, and K409, respectively, of a second Fc domain See WO 2006/106905A1; Gunasekaran et al. (2010), J. Biol. Chem. 285(25): 19637-19646. As such, by introducing at least two of the mutations of E356K, E357K, and D399K in a first Fc domain, and the mutations K370E, K409D, and K439E into a second Fc domain, efficient heterodimerization can be achieved while suppressing homodimer formation. Id. Efficient heterodimerization has been achieved by introducing K392D and K409D mutations in a first Fc chain, and by introducing D399K and E356K mutations in a second Fc chain. Gunasekaran et al. (2010), J. Biol. Chem. 285(25): 19637-19646.

Another strategy for promoting heterodimerization of two different half-life extension domains is by using structure- and sequence-based approaches to identify alterations that could promote heterodimerization and/or suppress homodimerization. Among the ways of identifying alterations that promote heterodimerization is by performing structural calculations to determine the energies of paired variant combinations for residues that interact across the CH3-CH3 dimer interface, as was the approach taken in Moore et al. (2011), MAbs 3(6): 546-557, the contents of which are herein incorporated by reference. Moore et al. identified the pairs that were predicted to have lower energy in the heterodimer form relative to the homodimer form as a starting point for further analysis. It was observed that a heterodimerization yield of 89% could be achieved by introducing S364H and F405A mutations in a first Fc domain and by introducing Y349T and T394F mutations in a second Fc domain. Id.

Disease or Disorder

The methods described herein can be used to treat a disease or disorder. In some embodiments, the disease or condition is selected from the group consisting of a cancer, an inflammatory condition, and an infection.

In some embodiments, the disease or condition is an inflammatory disease. In some embodiments, the disease is selected from the group consisting of ulcerative colitis, Crohn's disease, or ulcerative ileitis, and intestinal graft vs host disease.

In some embodiments, the disease or condition is a cancer. In some embodiments, the cancer is a solid or liquid tumor. In some embodiments, the cancer is selected from the group consisting of mesothelioma, lung cancer, breast cancer, ovarian cancer, pancreatic cancer, lymphoma (non-Hodgkin's lymphoma), leukemia (such as acute myeloid leukemia), head and neck cancer, liver cancer, renal cancer, kidney cancer, esophageal cancer, gastric cancer, and colorectal cancer. In some embodiments, the cancer is selected from the group consisting of mesothelioma, lung cancer, ovarian cancer, and gastric cancer.

Dosing Regimen

The fusion proteins and/or second agents may be administered to the individual using any suitable dosage and routes of administration. In some embodiments, the fusion protein and/or the second agent is administered parenterally into the individual. The route of administration is in accordance with known and accepted methods, such as by single or multiple bolus or infusion over a period of time in a suitable manner, e.g., injection or infusion by subcutaneous, intravenous, intraperitoneal, intramuscular, intra-arterial, intralesional, intraarticular, intratumoral, or oral routes.

In some embodiments, the fusion protein and the second agent are administered simultaneously, concurrently or sequentially into the individual.

The determination of the appropriate dosage or route of administration is well within the skill of an ordinary artisan. Animal experiments provide reliable guidance for the determination of effective doses for human diagnostic applications. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

In some embodiments, the fusion protein is administered about once every three weeks to about twice a week (such as about once every three weeks to about once every two weeks, about once every two weeks to about once every week, about once every week to about twice a week). In some embodiments, the fusion protein is administered no less than about once every three weeks, about once every two weeks, about once every week, about twice a week. In some embodiments, the fusion protein is administered no more than about once every three weeks, about once every two weeks, about once every week, about twice a week. In some embodiments, the fusion protein is administered about once every three weeks, about once every two weeks, about once every week, about twice a week.

In some embodiments, the fusion protein is administered for at least about one week to six months (such as one week to two, three, or four weeks, one week to one, two, three, four, five, or six months, one month to two, three, four, five, or six months, three month to four, five, or six month) for each treatment cycle.

In some embodiments, the amount of fusion protein for each administration is about 100 ng/kg to about 10 mg/kg (for example about 100 ng/kg to about 500 ng/kg, about 500 ng/kg to about 1 µg/kg, about 1 µg/kg to about 5 µg/kg, about 5 µg/kg to about 10 µg/kg, about 10 µg/kg to about 50 µg/kg, about 50 µg/kg to about 100 µg/kg, about 100 µg/kg to about 500 µg/kg, about 500 µg/kg to about 1 mg/kg, about 1 mg/kg to about 5 mg/kg, about 5 mg/kg to about 10 mg/kg).

In some embodiments, the second agent (such as a therapeutic antibody that binds to mesothelin or an inhibitor of PD-1) is administered about once per month to about twice per week (such as about once per month to twice, three times or four times a month, about once every two weeks, about once every three weeks, about once every week, or twice each week).

In some embodiments, the amount of the second agent (such as a therapeutic antibody that binds to mesothelin or an inhibitor of PD-1) for each administration is about 100 ng/kg to about 100 mg/kg (for example about 100 ng/kg to about 500 ng/kg, about 500 ng/kg to about 1 µg/kg, about 1 µg/kg to about 5 µg/kg, about 5 µg/kg to about 10 µg/kg, about 10 µg/kg to about 50 µg/kg, about 50 µg/kg to about 100 µg/kg, about 100 µg/kg to about 500 µg/kg, about 500 µg/kg to about 1 mg/kg, about 1 mg/kg to about 5 mg/kg, about 5 mg/kg to about 10 mg/kg, about 10 mg/kg to about 50 mg/kg, or about 50 mg/kg to about 100 mg/kg).

V. Methods of Preparation

The fusion proteins described herein and the components of the fusion proteins described herein (such as albumin binding moieties, cytokines or variants thereof, antigen binding moieties) may be prepared by any of the known protein expression and purification methods in the art.

In some embodiments, the present application provides isolated nucleic acids encoding one or more of the polypeptide chains of any one of the fusion proteins, albumin binding moieties, cytokines or variants thereof, or antigen binding moieties. In some embodiments, the isolated nucleic acid comprises the nucleic acid sequence encoding any of the amino acid sequences of GRY, and SEQ ID NOs: 46-50 and 60-95.

In some embodiments, the isolated nucleic acid is inserted into a vector, such as an expression vector, a viral vector, or a cloning vector. For expression of the nucleic acids, the vector may be introduced into a host cell to allow expression of the nucleic acids within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art. For example, the promoter sequences may be selected to promote the transcription of the polynucleotide in the vector. Suitable promoter sequences include, without limitation, T7 promoter, T3 promoter, SP6 promoter, beta-actin promoter, EF1a promoter, CMV promoter, and SV40 promoter. Enhancer sequences may be selected to enhance the transcription of the nucleic acids. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell. In some embodiments, the isolated nucleic acids further comprise a nucleic acid sequence encoding a signal peptide.

In some embodiments, there is provided an isolated host cell containing the vector described above. The host cells containing the vector may be useful in expression or cloning of the isolated nucleic acids. Suitable host cells can include, without limitation, prokaryotic cells, fungal cells, yeast cells, or higher eukaryotic cells such as mammalian cells. The expression of antibodies and antigen-binding fragments in prokaryotic cells such as E. coli is well established in the art. For a review, see for example Pluckthun, A. BioTechnology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560. Higher eukaryotic cells, in particular, those derived from multicellular organisms can be used for expression of glycosylated polypeptides. Suitable higher eukaryotic cells include, without limitation, invertebrate cells and insect cells, and vertebrate cells.

The vector can be introduced to the host cell using any suitable methods known in the art, including, but not limited to, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In some embodiments, the host cells comprise a first vector encoding a first polypeptide and a second vector encoding a second polypeptide. In some embodiments, the host cells comprise a single vector comprising isolated nucleic acids encoding a first polypeptide and a second polypeptide.

In some embodiments, the present application provides methods of expressing any of the fusion proteins, albumin binding moieties, cytokines or variants thereof, or antigen binding moieties described herein, comprising culturing the isolated host cell containing the vector and recovering the fusion proteins, albumin binding moieties, cytokines or variants thereof, or antigen binding moieties from the cell culture. The isolated host cells are cultured under conditions that allow expression of the isolated nucleic acids inserted in the vectors. Suitable conditions for expression of polynucleotides may include, without limitation, suitable medium, suitable density of host cells in the culture medium, presence of necessary nutrients, presence of supplemental factors, suitable temperatures and humidity, and absence of microorganism contaminants A person with ordinary skill in the art can select the suitable conditions as appropriate for the purpose of the expression.

The expressed polypeptide(s) can be collected using any suitable methods. The polypeptide(s) can be expressed intracellularly, in the periplasmic space or be secreted outside of the cell into the medium. If the polypeptide is expressed intracellularly, the host cells containing the polypeptide may be lysed and polypeptide may be isolated from the lysate by removing the unwanted debris by centrifugation or ultrafiltration. If the polypeptide is secreted into periplasmic space of *E. coli*, the cell paste may be thawed in the presence of agents such as sodium acetate (pH 3.5), EDTA, and phenylmethylsulfonylfluoride (PMSF) for about 30 min, and cell debris can be removed by centrifugation (Carter et al., BioTechnology 10:163-167 (1992)). If the polypeptide is secreted into the medium, the supernatant of the cell culture may be collected and concentrated using a commercially available protein concentration filter, for example, an Amincon or Millipore Pellicon ultrafiltration unit. A protease inhibitor and/or an antibiotic may be included in the collection and concentration steps to inhibit protein degradation and/or growth of contaminated microorganisms.

The expressed polypeptide(s) can be further purified by a suitable method, such as without limitation, affinity chromatography, hydroxyapatite chromatography, size exclusion chromatography, gel electrophoresis, dialysis, ion exchange fractionation on an ion-exchange column, ethanol precipitation, reverse phase HPLC, chromatography on silica, chromatography on heparin sepharose, chromatography on an anion or cation exchange resin (such as a polyaspartic acid column), chromatofocusing, SDS-PAGE, and ammonium sulfate precipitation (see, for review, Bonner, P. L., Protein purification, published by Taylor & Francis. 2007; Janson, J. C., et al, Protein purification: principles, high resolution methods and applications, published by Wiley-VCH, 1998).

In some embodiments, the polypeptides can be purified by affinity chromatography. In some embodiments, protein A chromatography or protein A/G (fusion protein of protein A and protein G) chromatography can be useful for purification of polypeptides comprising a component derived from antibody CH2 domain and/or CH3 domain and/or VH and/or $V_HH$ (Lindmark et al., *J. Immunol. Meth.* 62:1-13 (1983)); Zettlit, K. A., *Antibody Engineering*, Part V, 531-535, 2010; Fridy et al. 2015. *Analytical Biochemistry* 477, 92-94; Henry et al. 2016. *PLoS One.* 2016; 11(9): e0163113). In some embodiments, protein G chromatography can be useful for purification of polypeptides and/or polypeptide complexes comprising IgG γ3 heavy chain (Guss et al., EMBO J. 5:1567 1575 (1986)). In some embodiments, protein L chromatography can be useful for purification of polypeptides and/or polypeptide complexes comprising κ light chain (Sudhir, P., Antigen engineering protocols, Chapter 26, published by Humana Press, 1995; Nilson, B. H. K. at al, J. Biol. Chem., 267, 2234-2239 (1992)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX resin (J. T. Baker, Phillipsburg, N.J.) is useful for purification.

VI. Articles of Manufacture and Kits

In some embodiments of the invention, there is provided an article of manufacture containing materials useful for the treatment of a disease or condition (such as a cancer or an inflammatory disease) in an individual, for administering a fusion protein into the individual. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is a fusion protein described herein. The label or package insert indicates that the composition is used for treating the particular condition. The label or package insert will further comprise instructions for administering the fusion protein to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a disease or condition (such as a cancer or an inflammatory disease).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a disease or condition (such as a cancer or an inflammatory disease) described herein, for administering a fusion protein into an individual, optionally in combination with the articles of manufacture. Kits of the invention include one or more containers comprising a fusion protein composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising a fusion protein. In some embodiments, the kit comprises a) a composition comprising a fusion protein, and b) an effective amount of at least one other agent as described herein. In some embodiments, the kit comprises a) a composition comprising a fusion protein, and b) instructions for administering the fusion protein composition to an individual for treatment. In some embodiments, the kit comprises a) a composition comprising a fusion protein, b) an effective amount of at least one other agent as described herein, and c) instructions for administering the fusion protein composition and the other agent(s) to an individual for treatment. The fusion protein and the other agent(s) can be present in separate containers or in a single container. For example, the kit may comprise one distinct composition or two or more compositions wherein one composition comprises a fusion protein and another composition comprises another agent.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the fusion protein compositions generally include information as to dosage, dosing schedule, and route of administration for the intended treatment. The containers may be unit doses, bulk packages (e.g., multi-dose packages) or subunit doses. For example, kits may be provided that contain sufficient dosages of a fusion protein as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the fusion protein and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXEMPLARY EMBODIMENTS

Embodiment 1

A fusion protein comprising: a) a cytokine, and b) an albumin binding moiety (such as an sdAb that binds to albumin), wherein the cytokine is selected from the group consisting of IL-21, IL-7, IL-15, IL-15 bound to IL-15Rα or fragment thereof, IL-33, and IL-22.

Embodiment 2

A fusion protein comprising: a) a cytokine fused to an albumin binding moiety ("cytokine-ALBBM"), and b) an antigen binding moiety, wherein the linkage between the cytokine-ALBBM and the antigen binding moiety is optionally cleavable.

Embodiment 3

The fusion protein of embodiment 2, wherein the cytokine is selected from the group consisting of IL-21, IL-7, IL-15, IL-15 bound to IL-15Rα or fragment thereof, IL-33, and IL-22.

Embodiment 4

The fusion protein of any one of embodiments 1-3, wherein the cytokine is IL-21.

Embodiment 5

The fusion protein of embodiment 4, wherein the IL-21 comprises an amino acid sequence of SEQ ID NO: 1, 2, 126, 171, or 172 or a variant thereof comprising at least about 80% sequence identity to SEQ ID NO: 1, 2, 126, 171, or 172.

Embodiment 6

The fusion protein of any one of embodiments 1-5, wherein the albumin binding moiety binds to a human serum albumin (HSA) and/or a cynomolgus monkey serum albumin (CMSA).

Embodiment 7

The fusion protein of any one of embodiments 1-6, wherein the albumin binding moiety comprises an albumin binding domain (ABD).

Embodiment 8

The fusion protein of any one of embodiments 1-7, wherein the albumin binding domain comprises an amino acid sequence selected from the group consisting of SEQ ID NOs: 3-11 or a variant thereof comprising at least about 80% sequence identity to any one of SEQ ID NOs: 3-11.

Embodiment 9

The fusion protein of any one of embodiments 1-6, wherein the albumin binding moiety comprises a single domain antibody (sdAb).

Embodiment 10

The fusion protein of embodiment 9, wherein the sdAb is a $V_H H$ single domain antibody.

Embodiment 11

The fusion protein of any one of embodiments 1-10, wherein the albumin binding moiety is fused to the C-terminus of the cytokine.

Embodiment 12

The fusion protein of any one of embodiments 1-10, wherein the albumin binding moiety is fused to the N-terminus of the cytokine.

Embodiment 13

The fusion protein of any one of embodiments 1-12, wherein the cytokine and the albumin binding moiety are connected via a first linker.

Embodiment 14

The fusion protein of embodiment 13, wherein the first linker has a length of about one to thirty amino acids.

Embodiment 15

The fusion protein of embodiment 13 or 14, wherein the first linker is selected from the group consisting of GSG and SEQ ID NOs: 12-26 and 158-159.

Embodiment 16

The fusion protein of any one of embodiments 2-15, wherein the antigen binding moiety is fused to the C-terminus of the cytokine-ALBBM.

Embodiment 17

The fusion protein of any one of embodiments 2-15, wherein the antigen binding moiety is fused to the N-terminus of the cytokine-ALBBM.

Embodiment 18

The fusion protein of any one of embodiments 2-17, wherein the antigen binding moiety is fused to the cytokine-ALBBM via a second linker.

Embodiment 19

The fusion protein of embodiment 18, wherein the second linker has a length of about one to thirty amino acids.

Embodiment 20

The fusion protein of embodiment 18 or 19, wherein the second linker is cleavable.

Embodiment 21

The fusion protein of embodiment 20, wherein the cleavable linker is a matrix met alloprotease, legumain, matriptase, or urokinase sensitive.

Embodiment 22

The fusion protein of any one of embodiments 18-21, wherein the second linker is selected from the group consisting of GSG and SEQ ID NOs: 12-45 and 158-159.

Embodiment 23

The fusion protein of any one of embodiments 2-22, wherein the antigen binding moiety binds to a tumor antigen.

Embodiment 24

The fusion protein of embodiment 23, wherein the tumor antigen is selected from the group consisting of mesothelin ("MSLN"), GPA33, Her-2, EGFR, and CD20.

Embodiment 25

The fusion protein of embodiment 23, wherein the tumor antigen is selected from the group consisting of CEA, MUC16, MUC1, AFP, EPCAM, CD19, CD21, CD22, CD30, CD33, CD37, CD45, PSMA, and BCMA.

Embodiment 26

The fusion protein of any one of embodiments 2-25, wherein the antigen binding moiety is an antibody or fragment thereof.

Embodiment 27

The fusion protein of any one of embodiments 2-26, wherein the antigen binding moiety comprises a single domain antibody (sdAb).

Embodiment 28

The fusion protein of embodiment 27, wherein antigen binding moiety comprises a $V_HH$ single domain antibody.

Embodiment 29

The fusion protein of embodiment 27, wherein the sdAb binds to mesothelin.

Embodiment 30

A pharmaceutical composition comprising the fusion protein of any one of embodiments 1-29.

Embodiment 31

A method of treating a disease or condition in an individual comprising administering to the individual the fusion protein of any one of embodiments 1-29 or the pharmaceutical composition of embodiment 30.

Embodiment 32

The method of embodiment 31, further comprising administering a second agent.

Embodiment 33

A method of treating a disease or condition in an individual comprising administering to the individual a) a fusion protein comprising i) a cytokine and ii) a half-life extending domain fused to the cytokine; and b) a second agent.

Embodiment 34

The method of embodiment 33, wherein the half-life extending domain is an albumin binding moiety.

Embodiment 35

The method of embodiment 33, wherein the half-life extending domain is an albumin.

Embodiment 36

The method of embodiment 33, wherein the half-life extending domain is an Fc fragment.

Embodiment 37

The method of embodiment 36, wherein the Fc fragment is selected from the group consisting of an IgG1, IgG2, IgG3, and IgG4 Fc fragments or a variant thereof.

Embodiment 38

The method of embodiment 37, wherein the Fc fragment is an IgG1 Fc fragment or variant thereof.

Embodiment 39

The method of embodiment 38, wherein the IgG1 Fc fragment or variant thereof comprises a mutation at position 297, wherein the amino acid at position 297 is mutated to alanine, aspartic acid or glycine.

Embodiment 40

The method of any one of embodiments 31-39, wherein the individual is a human.

Embodiment 41

The method of any one of embodiments 31-40, wherein the disease or condition is selected from the group consisting of a cancer, an inflammatory condition, and an infection.

Embodiment 42

The method of embodiment 41, wherein the disease or condition is an inflammatory disease.

Embodiment 43

The method of embodiment 42, wherein the cytokine is IL-22.

Embodiment 44

The method of embodiment 42 or 43, wherein the disease is selected from the group consisting of ulcerative colitis, Crohn's disease, or ulcerative ileitis, and intestinal graft vs host disease.

Embodiment 45

The method of embodiment 41, wherein the disease or condition is a cancer.

Embodiment 46

The method of embodiment 45, wherein the cancer is a solid or liquid tumor.

Embodiment 47

The method of embodiment 45, wherein the cancer is selected from the group consisting of mesothelioma, lung cancer, breast cancer, ovarian cancer, pancreatic cancer, lymphoma, leukemia, head and neck cancer, liver cancer, esophageal cancer, gastric cancer, and colorectal cancer.

Embodiment 48

The method of embodiment 47, wherein the cancer is selected from the group consisting of mesothelioma, lung cancer, ovarian cancer, and gastric cancer.

Embodiment 49

The method of any one of embodiments 45-48, wherein the cytokine is selected from the group consisting of IL-21, IL-7, IL-15, IL-15 bound to IL-15Rα or fragment thereof, and IL-33.

Embodiment 50

The method of any one of embodiments 31-49, wherein the fusion protein is administered about once every three weeks to about twice a week.

Embodiment 51

The method of any one of embodiments 31-50, wherein the amount of fusion protein for each administration is about 100 ng/kg to about 10 mg/kg.

Embodiment 52

The method of any one of embodiments 31-51, wherein the fusion protein is administered parenterally into the individual.

Embodiment 53

The method of embodiment 52, wherein the fusion protein is administered intravenously or subcutaneously into the individual.

Embodiment 54

The method of any one of embodiments 31-53, wherein the fusion protein is administered for at least about one week to six months for each treatment cycle.

Embodiment 55

The method of any one of embodiments 32-54, wherein the second agent comprises a therapeutic antibody, an immune checkpoint inhibitor, a second cytokine, a chemotherapeutic agent, a tyrosine kinase inhibitor, or an immune cell.

Embodiment 56

The method of embodiment 55, wherein the second agent is a therapeutic antibody.

Embodiment 57

The method of embodiment 56, wherein the therapeutic antibody binds to a tumor antigen.

Embodiment 58

The method of embodiment 57, wherein the tumor antigen is selected from the group consisting of mesothelin (MSLN), GPA33, Her-2 (ERBB2), EGFR, and CD20 (MS4A1).

Embodiment 59

The method of embodiment 57, wherein the tumor antigen is selected from the group consisting of CEA, MUC16, MUC1, AFP, EPCAM, CD19, CD21, CD22, CD30, CD33, CD37, CD45, PSMA, and BCMA.

Embodiment 60

The method of embodiment 59, wherein the tumor antigen is mesothelin.

Embodiment 61

The method of embodiment 60, wherein the second agent is an anti-mesothelin antibody or fragment thereof.

Embodiment 62

The method of embodiment 61, wherein the anti-mesothelin antibody or fragment thereof comprises a single chain antibody comprising an anti-mesothelin heavy chain variable region (anti-MSLN VH), wherein:
  a) the anti-MSLN VH comprises a CDR1 comprising the amino acid sequence of SEQ ID NO: 46, a CDR2 comprising the amino acid sequence of SEQ ID NO: 47, and a CDR3 comprising the amino acid sequence of SEQ ID: NO: 48, or a variant thereof comprising up to a total of 3, 2, or 1 amino acid substitutions in the CDRs; or b) the anti-MSLN VH comprises a CDR1 comprising the amino acid sequence of SEQ ID NO: 49, a CDR2 comprising the amino acid sequence of SEQ ID NO: 50, and a CDR3 comprising the amino acid sequence of GRY, or a variant thereof comprising up to a total of 3, 2, or 1 amino acid substitutions in the CDRs.

Embodiment 63

The method of any one of embodiments 60-62, wherein the second agent that binds to mesothelin is administered about once per month to about twice per week.

Embodiment 64

The method of any one of embodiments 60-63, wherein the amount of the second agent for each administration is about 100 ng/kg to about 100 mg/kg.

Embodiment 65

The method of embodiment 55, wherein the second agent is an immune checkpoint modulator.

Embodiment 66

The method of embodiment 65, wherein the immune checkpoint modulator is an inhibitor of an immune checkpoint protein selected from the group consisting of PD-L1, CTLA4, PD-L2, PD-1, 4-1BB, CD47, TIGIT, GITR, TIM3, LAG3, CD27 and B7H4.

Embodiment 67

The method of embodiment 66, wherein the immune checkpoint protein is PD-1.

Embodiment 68

The method of embodiment 67, wherein the second agent is an anti-PD-1 antibody or fragment thereof.

Embodiment 69

The method of embodiment 67 or 68, wherein the amount of the second agent for each administration is about 1 μg/kg to about 100 mg/kg.

Embodiment 70

The method of embodiment 55, wherein the second agent is a second cytokine.

Embodiment 71

The method of embodiment 70, wherein the cytokine in the fusion protein is IL-21, and wherein the second cytokine is selected from the group consisting of IL-7, IL-15, IL15 bound to IL15Rα or half-life extended variants thereof.

Embodiment 72

The method of embodiment 55, wherein the second agent is an immune cell.

Embodiment 73

The method of embodiment 72, wherein the immune cell comprises T cells or NK cells.

Embodiment 74

The method of embodiment 73, wherein the immune cell comprises T cells expressing a chimeric antigen receptor (CAR), T cells expressing a modified T cell receptor (TCR), or T cells isolated from a tumor.

Embodiment 75

The method of embodiment 55, wherein the second agent is a tyrosine kinase inhibitor.

Embodiment 76

The method of any one of embodiments 32-75, wherein the second agent is administered parenterally or orally into the individual.

Embodiment 77

The method of embodiment 76, wherein the second agent is administered parenterally into the individual.

Embodiment 78

The method of embodiment 77, wherein the second agent is administered intravenously into the individual.

Embodiment 79

The method of any one of embodiments 32-78, wherein the fusion protein and the second agent are administered simultaneously, concurrently or sequentially into the individual.

EXAMPLES

The examples below are intended to be purely exemplary of the application and should therefore not be considered to limit the application in any way. The following examples and detailed description are offered by way of illustration and not by way of limitation.

Example 1: Exemplary IL-21 Fusion Proteins

This example illustrates certain exemplary IL-21 fusion proteins provided herein. It is to be understood that the exemplary IL-21 fusion proteins described in this example are not intended to represent the full scope of the present invention.

The IL-21-(HSA binding molecule)-(anti-MSLN) is used herein to present certain exemplary IL-fusion proteins, which comprise 1) an IL-21 or a variant thereof, e.g., a truncated IL-21; 2) a peptide (e.g., an ABD or an sdAb) that binds to human serum albumin (HSA); 3) one or more antibody or antigen binding fragment thereof targeting tumor antigen mesothelin (MSLN), 4) a first linker (L1) composed of 4-20 amino acids which connects C-terminus of IL-21 and N-terminus of αHSA; and 5) a second linker (L2) composed of 4-20 amino acids which connects C-terminus of αHSA and N-terminus of anti-MSLN.

The IL-21 can have an amino acid sequence of SEQ ID NO: 1. Alternatively, the IL-21 can be a truncated human IL-21 having an amino acid sequence of SEQ ID NO: 2.

See sequence listing for a few options for an HSA binding peptide (SEQ ID NO: 3 to SEQ ID NO: 11).

Exemplary L1 and L2 linkers can be independently selected GSG and SEQ ID NOs: 12-45 and 158-159.

In certain exemplary IL-21 fusion proteins, the anti-MSLN functional module comprises two single domain antibodies (sdAbs) targeting different domains of mesothelin, and the two sdAbs are connected by a third linker composed of 4-20 amino acids (L3). The L3 linker can be selected from SEQ ID NOs: 14 and 19-22.

The design of the exemplary IL-21 fusion proteins of the present example contemplates all possible combinations of various components of the IL-21 fusion proteins described above.

Example 2: Generation of Anti-MSLN Single Domain Antibodies

Two different antigen peptides were used to immunize llama to produce anti-MSLN single domain antibodies (VHH antibodies). The first antigen peptide (MSLN antigen 1) represents the cell membrane anchored MSLN. The second antigen peptide (MSLN antigen 2) represents the C-terminus of cell membrane anchored MSLN. The sequences of these two peptides are as follows:

MSLN Antigen 1 (MSLN Cleaved Form)

(SEQ ID NO: 196)
EVEKTACPSGKKAREIDESLIFYKKWELEACVDAALLATQMDRVNAIPF

TYEQLDVLKHKLDELYPQGYPESVIQHLGYLFLKMSPEDIRKWNVTSLE

TLKALLEVNKGHEMSPQAPRRPLPQVATLIDRFVKGRGQLDKDTLDTLT

AFYPGYLCSLSPEELSSVPPSSIWAVRPQDLDTCDPRQLDVLYPKARLA

FQNMNGSEYFVKIQSFLGGAPTEDLKALSQQNVSMDLATFMKLRTDAVL

PLTVAEVQKLLGPHVEGLKAEERHRPVRDWILRQRQDDLDTLGLGLQGG

IPNGYLVLDLSMQEALS

MSLN Antigen 2 (MSLN C-Terminus)
VQKLLGPHVEGLKAEERHRPVRDWILRQRQD-DLDTLGLGLQGGIPNGYLV (SEQ ID NO: 197)

After immunization, peripheral mononuclear cells (PBMC) were isolated for RNA extraction. VHH antibody phage display libraries were constructed with mRNA/cDNA that encodes the antibody genes. The constructed phage display libraries were screened through multiple rounds of affinity binding with antigen. Positive clones were identified through ELISA. Antibody genes of the positive clones were sequenced and cloned into UCOE vector (EMD Millipore) for CHO cell expression.

Exemplary anti-MSLN single domain (VHH) antibodies are listed in Table 4 below. CDR sequences of the exemplary anti-MSLN single domain antibodies are listed in Table 5 below.

TABLE 4

| sdAb name | | VHH Sequences |
|---|---|---|
| Anti-MSLN-3 | R3-B08(D5) or R3D5 | QVQLVESGGGLVQAGGSLRLSCAASGSISSIRHMRW YRQAPGKQRELVATVSNDGSAYYLGSVKGRFTISRT NAKNTLLYLQMNSLKPEDSALYICNADTWGWPGAD YWGQGTQVTVSS (SEQ ID NO: 173) |
| Anti-MSLN-6 | R3-E08(C7) or R3C7 | QVQLVESGGGLVEAGDSLRLSCVVSGRTLESYVMA WFRQAPGKEREAVASINWSSGRLIYADFVKGRFTISR DYEKNTIYLSMNNLKPEDTAVYYCAAGRYWGQGTQ VTVSS (SEQ ID NO: 174) |
| Anti-MSLN-9 | R2-G06(G12) or R2G12 | QVQLVESGGGLVQAGGSLRLSCAASGITFPVNAYGW YRQAPGKQRDLVAIISAGGTTNYADSVKGRFAISKD NVNNTVYLQMNSLTSEDTGVYYCYLQRRIGMLRDY WGQGTQVTVSS (SEQ ID NO: 175) |
| Anti-MSLN-35 (humanized) | R2G12 v1.1 | QVQLVESGGGLVQPGGSLRLSCAASGITFPVNAYGW YRQAPGKQRDLVAIISAGGTTNYADSVKGRFTISRDN SKNTLYLQMNSLRAEDTAVYYCYLQRRIGMLRDYW GQGTQVTVSS (SEQ ID NO: 176) |
| Anti-MSLN-36 (humanized) | R2G12 v1.2 | QVQLVESGGGLVQAGGSLRLSCAASGITFPVNAYGW YRQAPGKGLELVAIISAGGTTNYADSVKGRFAISKDN VNNTVYLQMNSLTSEDTGVYYCYLQRRIGMLRDYW GQGTQVTVSS (SEQ ID NO: 177) |
| Anti-MSLN-37 (humanized) | R2G12 v1.3 | QVQLVESGGGLVQPGGSLRLSCAASGITFPVNAYGW YRQAPGKGLELVAIISAGGTTNYADSVKGRFAISKDN VNNTVYLQMNSLTSEDTGVYYCYLQRRIGMLRDYW GQGTQVTVSS (SEQ ID NO: 178) |
| Anti-MSLN-38 (humanized) | R3D5 v1.1 | QVQLVESGGGLVQPGGSLRLSCAASGSISSIRHMRW YRQAPGKQRELVATVSNDGSAYYAGSVKGRFTISRD NSKNTLLYLQMNSLRAEDTAVYICNADTWGWPGAD YWGQGTQVTVSS (SEQ ID NO: 179) |

TABLE 4-continued

| sdAb name | | VHH Sequences |
|---|---|---|
| Anti-MSLN-39 (humanized) | R3D5 v1.2 | QVQLVESGGGLVQAGGSLRLSCAASGSISSIRHMRW YRQAPGKGLELVATVSNDGSAYYLGSVKGRFTISRT NAKNTLLYLQMNSLKPEDSALYICNADTWGWPGAD YWGQGTQVTVSS (SEQ ID NO: 180) |
| Anti-MSLN-40 (humanized) | R3D5 v1.3 | QVQLVESGGGLVQPGGSLRLSCAASGSISSIRHMRW YRQAPGKGLELVATVSNDGSAYYLGSVKGRFTISRT NAKNTLLYLQMNSLKPEDSALYICNADTWGWPGAD YWGQGTQVTVSS (SEQ ID NO: 181) |
| Anti-MSLN-41 (humanized) | R3C7 v1.1 | QVQLVESGGGLVQPGGSLRLSCVVSGRTLESYVMA WFRQAPGKEREAVASINWSSGRLIYADFVKGRFTISR DNSKNTLYLQMNSLRPEDTAVYYCAAGRYWGQGT QVTVSS (SEQ ID NO: 182) |
| Anti-MSLN-42 (humanized) | R3C7 v1.2 | QVQLVESGGGLVQPGGSLRLSCVVSGRTLESYVMA WFRQAPGKGLEAVASINWSSGRLIYADFVKGRFTISR DNSKNTLYLQMNSLRPEDTAVYYCAAGRYWGQGT QVTVSS (SEQ ID NO: 183) |
| Anti-MSLN-43 (humanized) | R3C7 v1.3 | QVQLVESGGGLVQPGGSLRLSCAASGRTLESYVMA WFRQAPGKGLEAVASINWSSGRLIYADFVKGRFTISR DNSKNTLYLQMNSLRPEDTAVYYCAAGRYWGQGT QVTVSS (SEQ ID NO: 184) |
| Anti-MSLN-44 (humanized) | R3C7 v1.4 | QVQLVESGGGLVQPGGSLRLSCAASGRTLESYVMA WFRQAPGKGLEAVASINWSSGRLIYADSVKGRFTISR DNSKNTLYLQMNSLRAEDTAVYYCAAGRYWGQGT QVTVSS (SEQ ID NO: 185) |
| Anti-MSLN-45 (humanized) | R3C7 v1.5 | QVQLVESGGGLVQPGGSLRLSCAASGRTLESYVMA WFRQAPGKEREAVASINWSSGRLIYADSVKGRFTISR DNSKNTLYLQMNSLRAEDTAVYYCAAGRYWGQGT QVTVSS (SEQ ID NO: 186) |

TABLE 5

| Sequence | sdAb Name |
|---|---|
| [CDR1]GSISSIRH (SEQ ID NO: 187) [CDR2]VSNDGSA (SEQ ID NO: 188) [CDR3]NADTWGWPGADY (SEQ ID NO: 189) | Anti-MSLN-3 |
| [CDR1]GRTLESYV (SEQ ID NO: 190) [CDR2]INWSSGRL (SEQ ID NO: 191) [CDR3]AAGRY (SEQ ID NO: 192) | Anti-MSLN-6 |
| [CDR1]GITFPVNA (SEQ ID NO: 193) [CDR2]ISAGGTT (SEQ ID NO: 194) [CDR3]YLQRRIGMLRDY (SEQ ID NO: 195) | Anti-MSLN-9 |

Example 3: Molecular Cloning of the IL-21 Fusion Protein

Oligonucleotide Synthesis

An exemplary oligonucleotide synthesis procedure is described below. cDNA sequences encoding human IL-21 full length (SEQ ID NO: 1), human IL-21 truncated (SEQ ID NO: 2), G148-ABD-wt (SEQ ID NO: 3), low immunogenicity G148-ABD variants (SEQ ID NOs: 4-11), humanized sdAb targeting HSA, and humanized sdAb targeting MSLN (e.g., those listed in Table 4) were obtained by gene synthesis using GeneArt Gene Synthesis (ThermoFisher Scientific) or gBlocks Gene Fragments (Integrated DNA Technologies) with NgoMIV restriction enzyme site and Kozak sequence added to 5' and SalI restriction enzyme site added to 3'. The codon usage of these genes was optimized for expression in Chinese hamster ovary (CHO) cells. Synthesized oligonucleotides were inserted into UCOE expression vector CET1019-AS-Puro (CS221284, Millipore Sigma) by NgoMIV/SalI digest-ligation method.

Construction of IL-21 Fusion Protein Expression Vector

Figure 2:
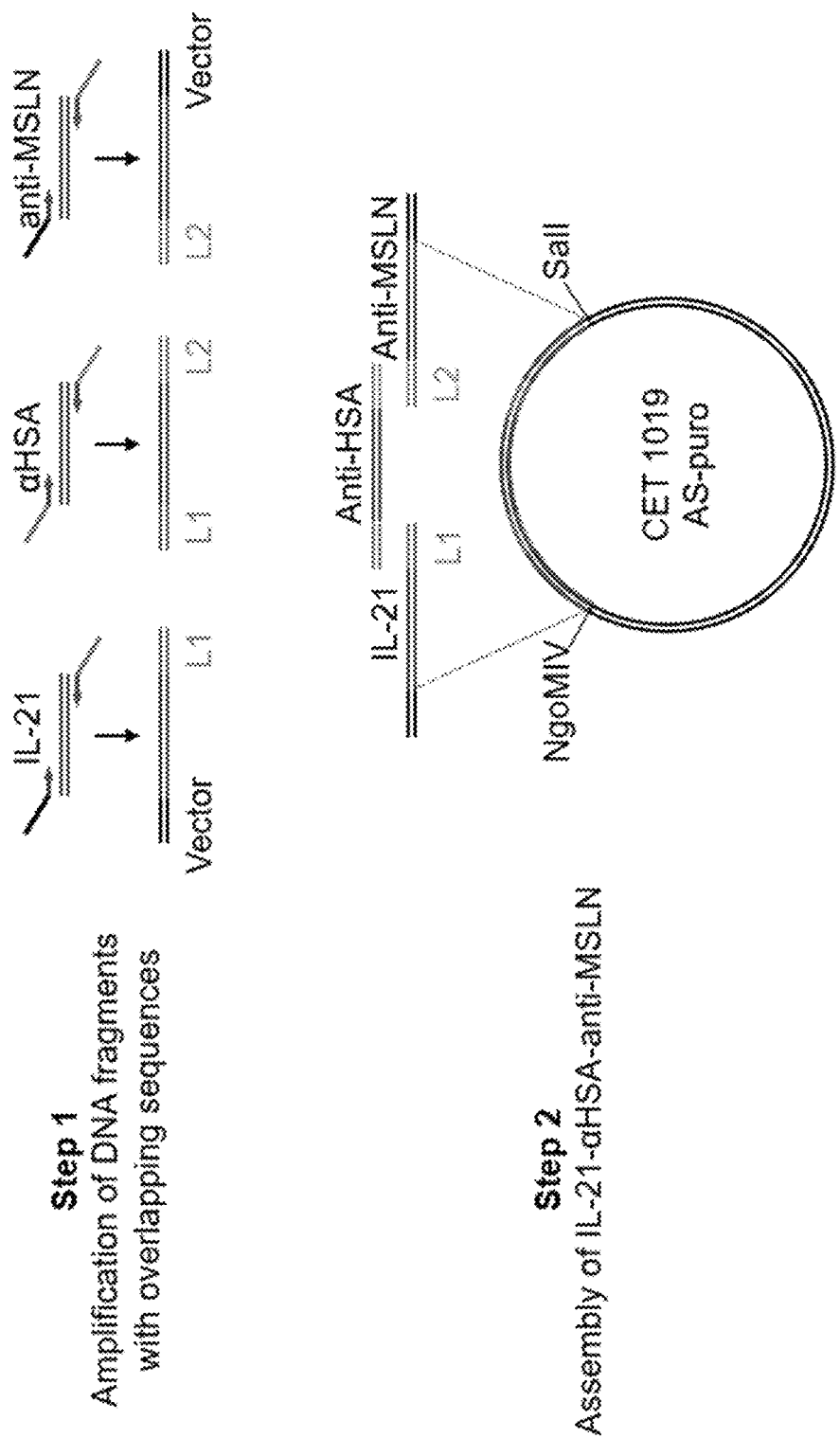
FIG. 2 depicts assembly of an exemplary IL-21 fusion protein expression vector wherein the albumin binding molecule is an anti-HSA antibody.

Construction of IL-21 fusion protein expression vector is exemplified herein. C-terminus of IL-21 was fused to N-terminus of albumin binding domain or albumin binding sdAb (αHSA) via a peptide linker (L1), and the C-terminus of albumin binding domain or albumin binding sdAb was fused with mesothelin binding sdAb (anti-MSLN) via a second peptide linker (L2). The DNA sequences encoding these polypeptides can be seamlessly assembled together by Gibson Assembly (Synthetic Genomics) or similar in vitro recombination method. To produce DNA fragments with overlapping sequence to its neighboring fragments for Gibson Assembly reaction, 20-40 base pair (bp) overlapping sequences encoding L1 or L2 linker peptide or CET1019-AS-Puro vector sequence were introduced at the 5' ends of the primers (see FIG. 2, Step 1). After amplification, the PCR products were purified and harvested by gel extraction using PureLink Gel Extraction Kit (ThermoFisher Scientific). The purified DNA fragments of desired gene-linker-vector combination were mixed and assembled together by Gibson Assembly Master Mix (New England BioLabs) or NEBuilder HiFi DNA Assembly Master Mix (New England BioLabs) according to the manufacturer's protocol (see FIG. 2, Step 2).

Figure 3:
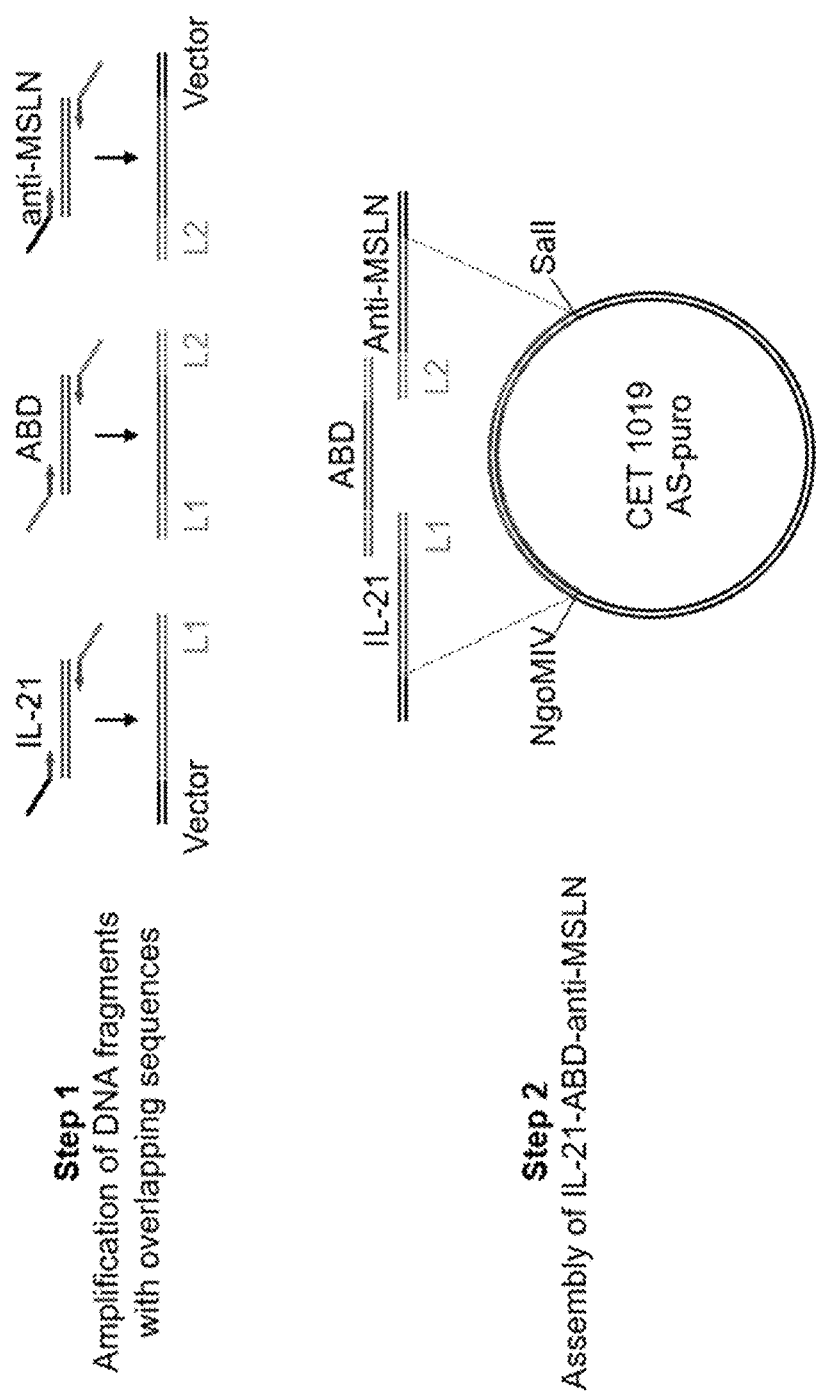
FIG. 3 depicts assembly of an exemplary IL-21 fusion protein expression vector wherein the albumin binding molecule is an ABD that binds to HSA.

Similarly, FIG. 3 illustrates the construction of an exemplary IL-21 fusion protein provided herein when the albumin binding molecule is an ABD.

A 6His tag can be optionally fused to the C-terminus of anti-MSLN sdAb. In such cases, the DNA sequence encoding 6His was used as overlapping sequence for designing the reverse primer for amplification of anti-MSLN and the forward primer for amplification of CET1019 AS-puro vector backbone.

After assembly reaction, 2 μl of the assembly product was used for transformation of NEB 5-alpha Competent *E. coli* cells (New England BioLabs) according to the manufacturer's protocol. Colonies from Amp selection plates were picked for subsequent mini-prep using PureLink Quick Plasmid Miniprep Kit (ThermoFisher Scientific) and DNA sequencing verification (ELIM Biopharmaceuticals).

Example 4: Expression and Purification of the IL-21 Fusion Protein

DNA sequences encoding the IL-21 fusion protein is transiently expressed in ExpiCHO cells. Briefly, on Day −1, CHO cells are seeded at 3-4×10e6 cells/ml in 25 ml of transient transfection medium (BALANCD® TRANSFECTORY™ CHO, Irvine Scientific, #91147), plus 4 mM glutamine in a 125 ml non-baffled flask. On Day 0, 22.5 μg plasmid DNA is mixed with 112.5 μg PEI in 1.5 ml transient transfection medium and is incubated at RT for 7 minutes. The mixture is then slowly added to the cells. The cells are fed once on Day 1 with 1) 0.5 mM Valproic acid (50 ul to 25 ml), 2) 10% post-TF supplement (Irvine Scientific #91148), 3) 1.5 ml Glucose stock (200 g/L), and 4) 5% IS Feed with 50 g/L TC Yeastolyte. CHO cells are harvested on Day 8 for purification over affinity column.

Example 5: In Vitro NK Cell Proliferation Assay

Human NK cells are isolated using a negative selection kit—Kit II (all beads are from Miltenyi Biotech, Bergisch Gladbach, Germany) Purification is performed manually or with an AutoMACS (Miltenyi). The purity of the cells is always controlled by fluorescence-activated cell sorting (FACS) and is more than 90%. The isolated NK cells are treated with the fusion proteins provided herein including those described above in Example 1. The proliferation of NK cells is monitored with CD69 signal using FACS analysis.

Example 6: In Vitro Cytotoxicity Assay

Human lung carcinoma cell A549 is mixed with freshly isolated human PBMC and incubated with 0, 5, 10, and 50 ng/mL of purified IL-21 fusion protein. In the case an MMP cleavable linker is used, a parallel set of experiment is set up with MMP9 added to activate IL-21. The mixed culture is incubated for up to 72 hour and MTS method is used to determine the percentage of the lyzed target cells in the study.

Example 7: In Vivo Efficacy Study

Neu mice are implanted with A549 cancer cells on Day 0. After tumors grow to approximate 50-100 mm$^3$, mice are randomized and treated with the IL-fusion protein provided herein and a control (e.g., an isotype control antibody in PBS) every other day. IL-21 fusion proteins provided herein are expected to show better efficacy at the same dose or achieve a similar efficacy at much lower dose when compared with IL-21 combination study (the study of combination treatment with IL-21 and a second agent).

Tumor sizes and body weights are measured at baseline before dosing. Tumor sizes and body weights are measured 3 times per week for two weeks post treatment. Terminal blood samples are collected for PK/PD analysis.

Example 8. Generation of Anti-HSA Single Domain Antibodies

Human serum albumin (HSA) expressed from rice (Sigma, #A9731) was used to immunize llama to produce anti-HSA single domain antibodies (VHH antibodies). After immunization, peripheral mononuclear cells (PBMCs) were isolated for RNA extraction. VHH antibody phage display libraries were constructed with mRNA/cDNA that encodes the antibody genes. The constructed phage display libraries were screened through multiple rounds of affinity binding with antigen. Positive clones were identified through Octet affinity measurement (ForteBio, Octet RED96). Antibody genes of the positive clones were sequenced and cloned into UCOE vector (EMD Millipore, #CS221284) for Chinese Hamster Ovary (CHO) cell expression.

Nine exemplary novel anti-HSA single domain (VHH) antibodies are generated according to the method described above. See SEQ ID NOs: 60-68. The CDR sequences of these 9 exemplary novel VHH antibodies are listed in sequence listing table as SEQ ID Nos: 69-95. Among the 9 antibodies, one antibody (P367) interacts with human, cynomolgus monkey and mouse serum albumin. The rest of antibodies interact with both human and cynomolgus monkey serum albumin.

Example 9 Molecular Cloning of the IL-21-Anti-HSA Fusion Protein

Construction of IL-21-anti-HSA fusion protein expression vector is exemplified herein. cDNA sequences encoding human IL-21 full length (SEQ ID NO: 1) were obtained by gene synthesis using GeneArt Gene Synthesis (ThermoFisher Scientific). The codon usage of these genes was optimized for expression in Chinese hamster ovary (CHO) cells. C-terminus of human IL-21 was fused to N-terminus of anti-HSA VHH antibody via a peptide linker. The DNA sequences encoding human IL21, a polypeptide linker and an anti-HSA VHH antibody can be seamlessly assembled together by assembly cloning (New England BioLabs, #E5520S) or similar in vitro recombination method. Oligonucleosides of IL-21-anti-HSA fusion were inserted into UCOE expression vector CET1019-AS-Puro (EMD Millipore, #CS221284) for CHO cell expression.

Table 6 lists the sequences of human IL-21.

TABLE 6

| Interleukin 21 | | |
|---|---|---|
| Name | SEQ ID | Sequence |
| Human IL21 full length | SEQ ID NO: 1 | QGQDRHMIRMRQLIDIVDQLKNYVNDLVPEFLPAPEDV ETNCEWSAFSCFQKAQLKSANTGNNERIINVSIKKLKRK PPSTNAGRRQKHRLTCPSCDSYEKKPPKEFLERFKSLLQ KMIHQHLSSRTHGSEDS |

TABLE 6-continued

Interleukin 21

| Name | SEQ ID | Sequence | |
|---|---|---|---|
| Human IL21 truncated (10aa) | SEQ ID NO: 2 | QGQDRHMIRMRQLIDIVDQLKNYVNDLVPEFLPAPEDV ETNCEWSAFSCFQKAQLKSANTGNNERIINVSIKKLKRK PPSTNAGRRQKHRLTCPSCDSYEKKPPKEFLERFKSLLQ KMIHQHL | |
| Human IL21 truncated (11aa) | SEQ ID NO: 126 | QGQDRHMIRMRQLIDIVDQLKNYVNDLVPEFLPAPEDV ETNCEWSAFSCFQKAQLKSANTGNNERIINVSIKKLKRK PPSTNAGRRQKHRLTCPSCDSYEKKPPKEFLERFKSLLQ KMIHQH | |

Table 7 lists exemplary polypeptide linkers for human IL-21-anti-HSA fusion proteins.

TABLE 7

| Name | SEQ ID | Sequence | |
|---|---|---|---|
| GSG linker, n = 1 | | GSG | Non-cleavable |
| GSG linker, n = 2-6 | 12 | (GSG)n (SEQ ID NO: 12) | |
| G3S linker, n = 1-6 | 13 | (G3S)n (SEQ ID NO: 13) | |
| G4S linker, n = 1-6 | 14 | (G4S)n (SEQ ID NO: 14) | |
| EAAAK linker, n = 1-6 | 15 | (EAAAK)n (SEQ ID NO: 15) | |
| PAPAP linker, n = 1-6 | 16 | (PAPAP)n (SEQ ID NO: 16) | |
| VLVH. Linker | 17 | IKRTVAAP (SEQ ID NO: 17) | |
| SIRPα linker | 18 | RAKPS (SEQ ID NO: 18) | |
| UPA linker | 28 | SGRSA (SEQ ID NO: 28) | Cleavable |
| MMP linker | 29 | PVGLIG (SEQ ID NO: 29) | |

Example 10 Expression and Purification of the IL-21 Fusion Protein

DNA sequences encoding the IL-21 fusion protein is transiently expressed in ExpiCHO cells. Briefly, on Day −1, ExpiCHO-S cells (Gibco™, #A29127) are seeded at 3-4× 10e6 cells/mL with ExpiCHO expression medium (Gibco™, #A2910001) in vented Erlenmeyer shake flask and placed on 125 rpm orbital shaker in 37° C. incubator with 8% $CO_2$. On Day 0, plasmid DNA is mixed with Expifectamine CHO Reagent (Gibco™, #A29129). The mixture is then slowly added to the cells. After 16 hours, cells are transferred to 32° C. incubator with 5% $CO_2$. The cells are fed twice on Day 1 and Day 5 with ExpiCHO™ Feed (Gibco™, #A29129). CHO cells are harvested on Day 8-12 for purification over affinity column.

Figure 4:
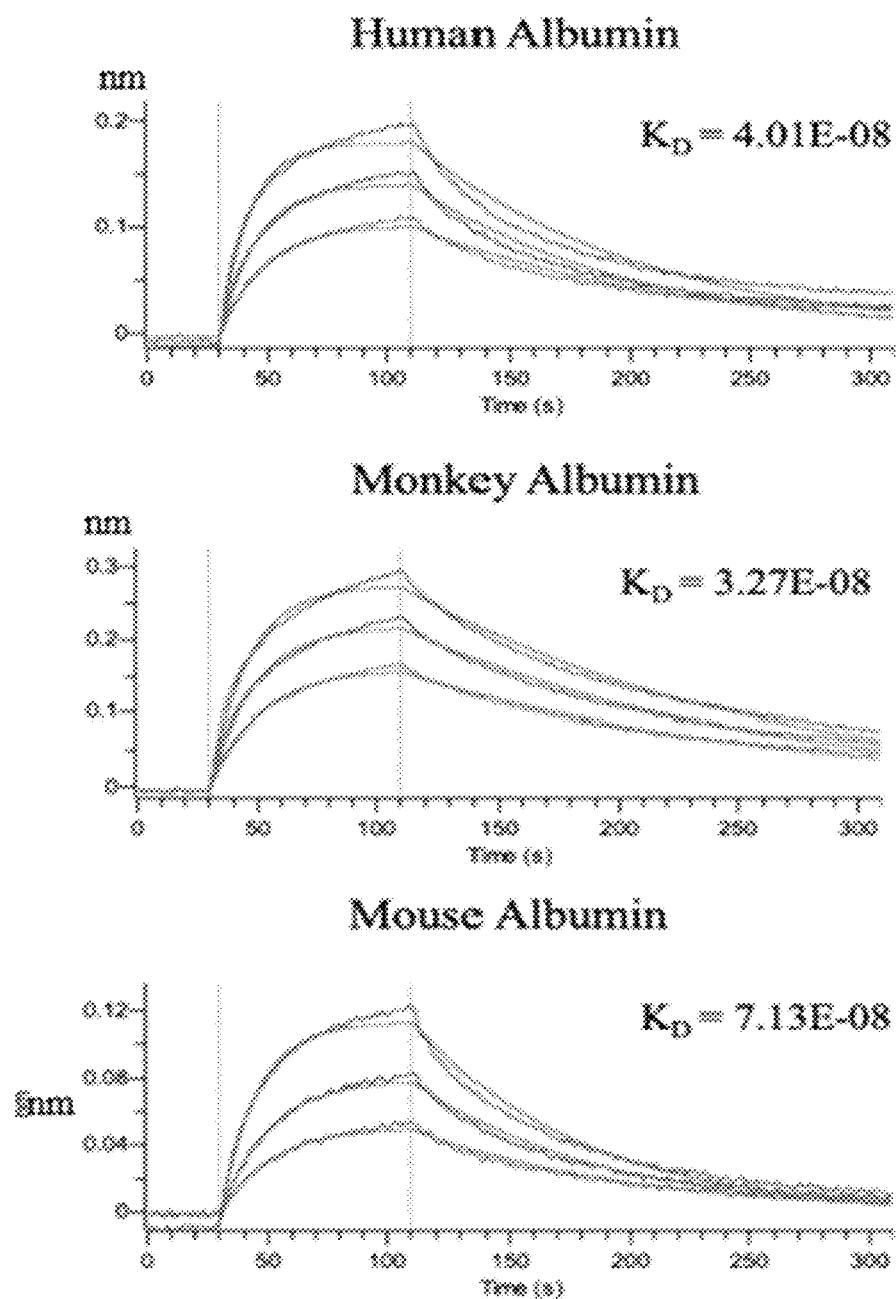
FIG. 4 shows KD of anti-HSA antibody P367 when interacting with human, monkey or mouse serum albumin P394-hgG1 Fc fusion protein was loaded onto protein A biosensor and dip into human, monkey or mouse serum albumin Colored lines represent the binding response for different concentration of serum albumin at 400 nM (dark blue), 200 nM (dark red) and 100 nM (light blue). Experimental data was analyzed with global fitting (red) to determine KD.

As shown in FIG. 4, Anti-HSA antibody P367 interacts with human, monkey or mouse serum albumin P367-IgG1 Fc fusion protein was loaded onto protein A biosensor and dip into human, monkey or mouse serum albumin. Colored lines represent the binding response for different concentration of serum albumin at 400 nM (dark blue), 200 nM (dark red) and 100 nM (light blue). Primary experimental data is analyzed with global fitting (red) to determine $K_D$.

Example 11: Anti-HSA Conjugate Interleukin 21 Signaling Potency is Similar to Recombinant IL21

Pfeiffer cells were maintained in RPMI-1640 containing 10% fetal bovine serum and penicillin/streptomycin. 100,000 Pfeiffer cells were treated with the indicated concentration of recombinant human IL-21 (rhIL-21), P390 (mouse IL-21-anti-HSA, with a sequence of SEQ ID NO: 120), or P394 (human IL-21-anti-HSA, with a sequence of SEQ ID NO:121) for 30 minutes at 37 C, 5% $CO_2$ in Hanks Balanced Salt Solution containing 10 mM HEPES. Phospho-STAT3 was measured using a phospho-STAT3 (Tyr705) homogeneous time resolved fluorescence (HTRF) assay (Cisbio) according to the manufacturer's instructions. The signal ratio of 665 nm/620 nm was multiplied by 1000, plotted and fit using a dose response curve (Graphpad Prism) to calculate the EC50.

Figure 5:
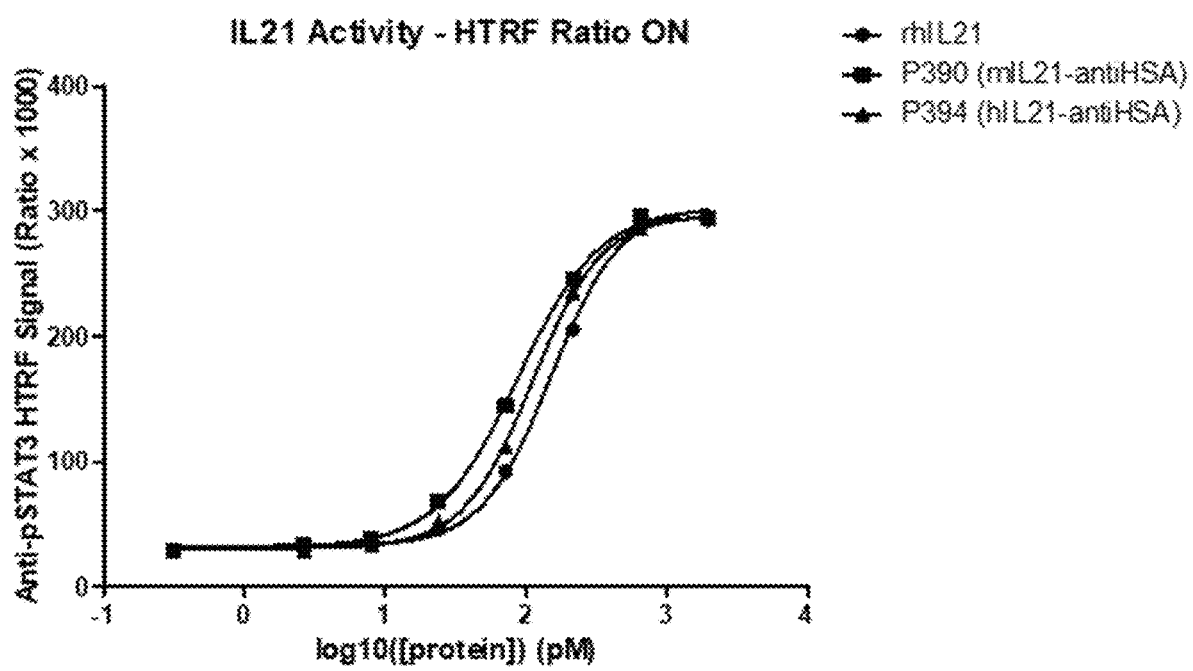
FIG. 5 shows anti-HSA IL-21 conjugate P390 and P394 signaling potency as compared to recombinant IL-21.

As shown in FIG. 5 and Table 8, IL-21-anti-HSA conjugates showed equivalent cell based potency relative to recombinant human IL-21

TABLE 8

EC50 of Different IL-21 variant

| Molecule | EC50 (pM) |
|---|---|
| rhIL21 | 150 |
| P390 | 88 |
| P394 | 111 |

Example 12. ADCC Assay

NCI-N87 and NCI-H226 cancer cell lines were maintained in RPMI-1640 containing 10% fetal bovine serum and penicillin/streptomycin. On day 0, 10,000 NCI-N87 cells/well and 5,000 NCI-H226 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO$_2$, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303 is an anti-MSLN antibody; P394 is a human IL-21-anti-HSA fusion protein; P390 is a mouse IL-21-anti-HSA fusion protein; P461/P462 is a human IL-15/IL-15Rα-anti-HSA fusion protein).

Figure 6A:
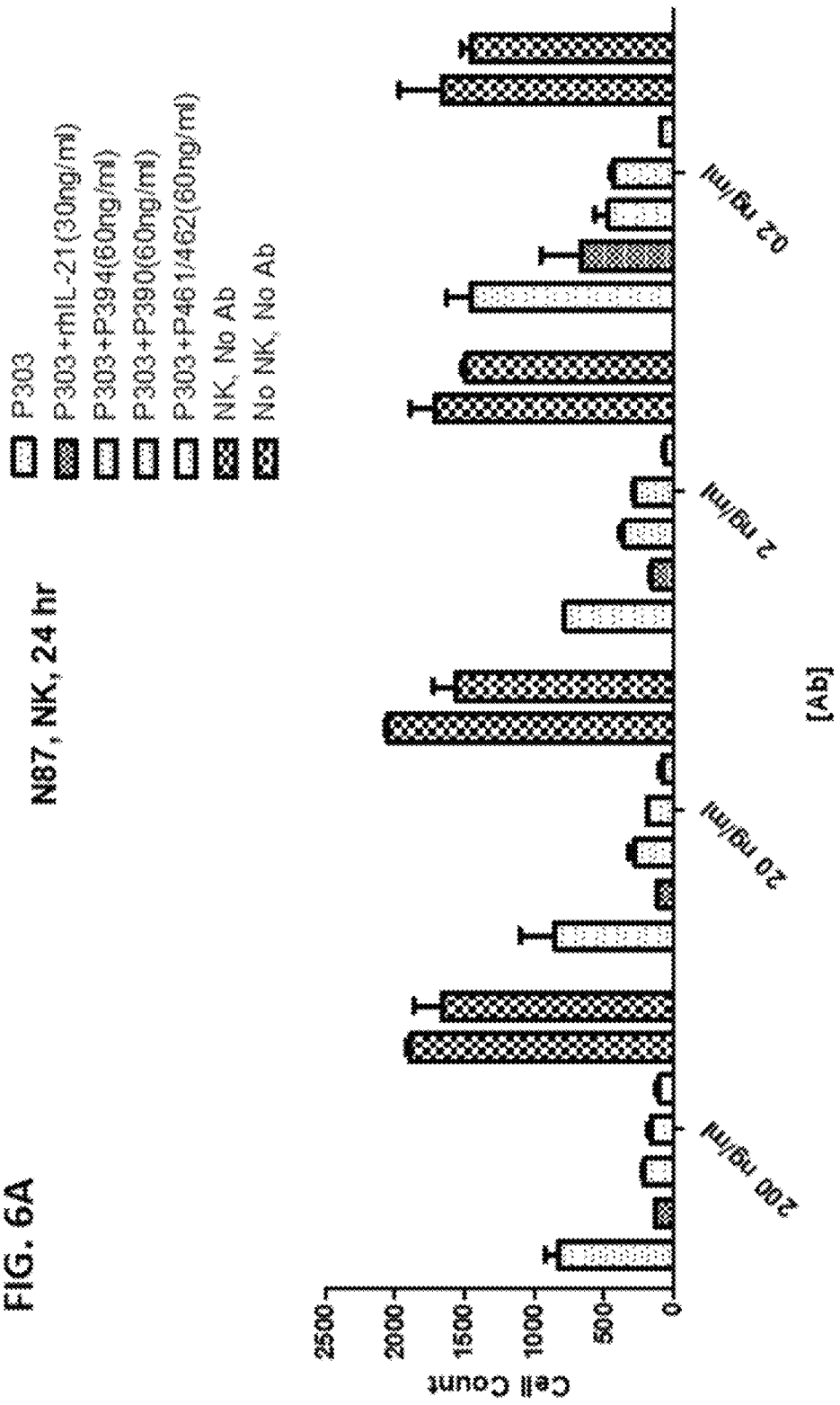
FIG. 6A shows ADCC activities of PBMCs against N87 cells in the presence of P390, P394, and P461/P462 in combination with anti-mesothelin antibody P303.
Figure 6B:
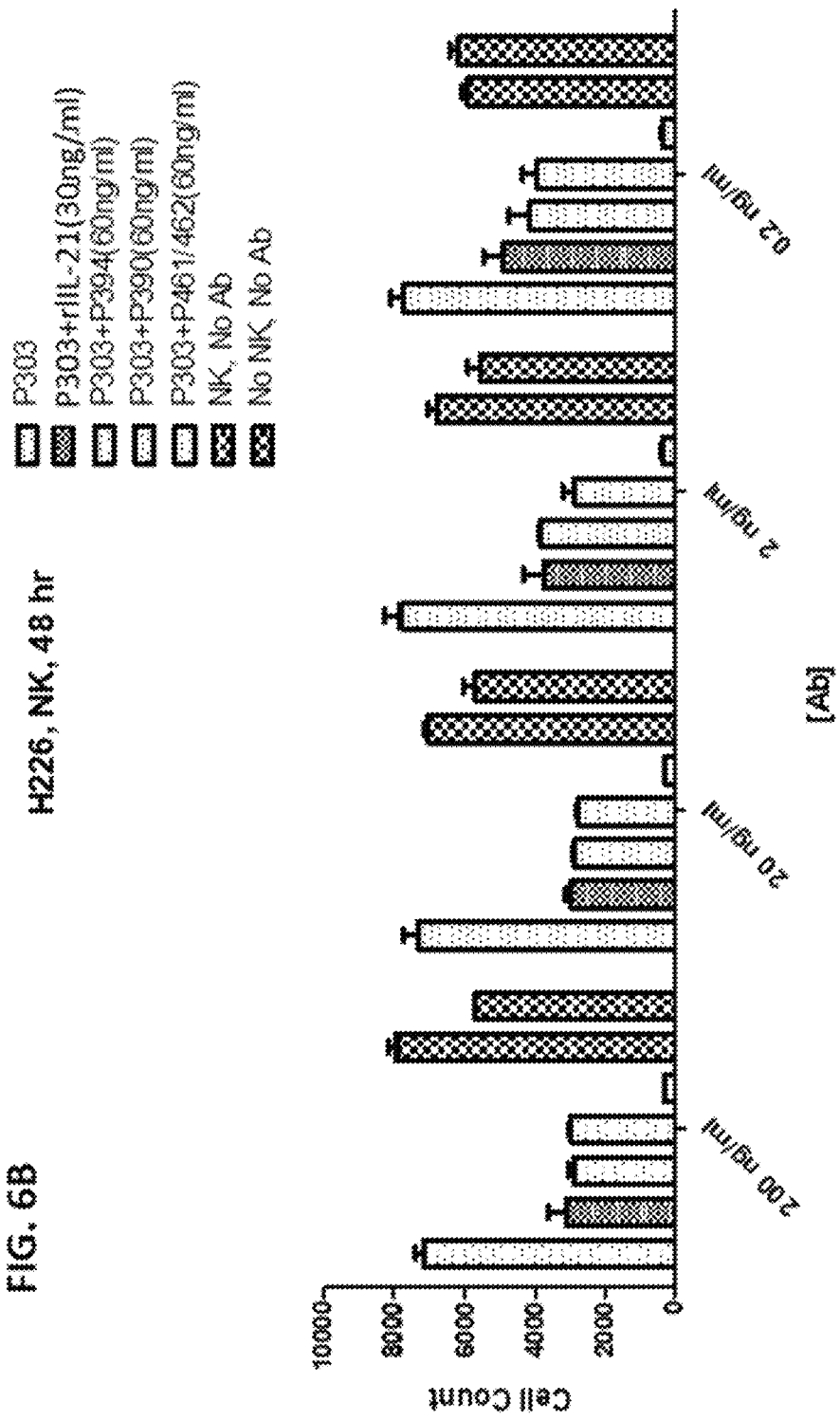
FIG. 6B shows ADCC activities of PBMCs against H226 cells in the presence of P390, P394, and P461/P462 in combination with anti-mesothelin antibody P303 against H226 cells.

As shown in FIG. 6A and FIG. 6B, mIL-21 and hIL-21 anti-HSA fusion proteins enhanced NK cell ADCC activity when combined with anti-MSLN antibodies. The magnitude of enhanced ADCC was similar between IL-21 anti-HSA fusion proteins and rhIL-21.

Example 13. ADCC Dose Response

NCI-N87 and NCI-H226 cancer cell lines were maintained in RPMI-1640 containing 10% fetal bovine serum and penicillin/streptomycin. On day 0, 10,000 NCI-N87 cells/well and 5,000 NCI-H226 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Anti-MSLN antibody P303 was added into each well at either 3 ng/ml (NCI-N87 cells) or 20 ng/ml (NCI-H226 cells). Plates were incubated for 48 hrs at 37 C, 5% CO$_2$, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P303 is an anti-MSLN antibody; P394 is a human IL-21-anti-HSA fusion protein; P390 is a mouse IL-21-anti-HSA fusion protein; P461/P462 (SEQ ID NOs: 123 and 124) and P461/P463 (SEQ ID NOs: 123 and 125) are both human IL-15/IL-15Rα-anti-HSA fusion proteins; rhIL-15 is a recombinant human IL-15.)

Figure 6D:
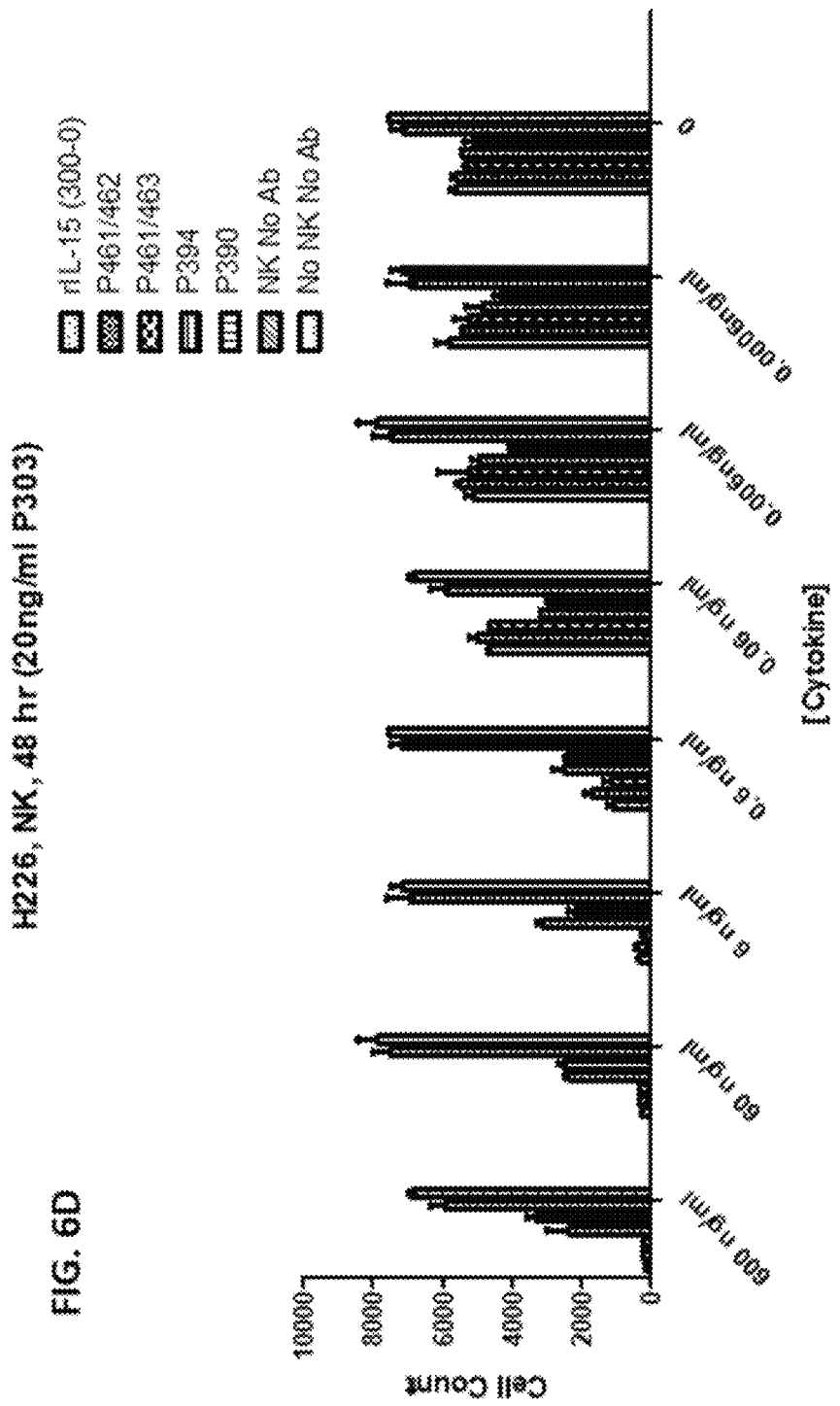
FIG. 6D shows ADCC activities of PBMCs against H226 cells in the presence of P390, P394, P461/P462, and P461/P463 at different dosages in combination with 20 ng/mL P303.

As shown in FIGS. 6C and 6D, Both IL-21-anti-HSA and IL-15-anti-HSA show full ADCC efficacy down to 0.6 ng/ml or lower when combined with anti-MSLN antibody.

Example 14. Activity of Full Length and Truncated IL-21 Fusion Proteins, Fusion Proteins with Different Linkers and N-Terminal and C-Terminal IL-21 Fusion Proteins Part A.

Pfeiffer cells were maintained in RPMI-1640 containing 10% fetal bovine serum and penicillin/streptomycin. 100,000 Pfeiffer cells were treated with the indicated concentration of recombinant human IL-21 (rhIL-21), P394 (human IL-21-GSG4 (SEQ ID NO: 12)-anti-HSA, with a sequence of SEQ ID NO:121), P593 (human IL-21(1-122)-A(EAAAK)4A (SEQ ID NO: 24)-anti-HSA), P636 (human IL-21(1-119)-GSG4 (SEQ ID NO: 12)-anti-HSA), P637 (human IL-21(1-120)-GSG4 (SEQ ID NO: 12)-anti-HSA), P744 (human IL-21(1-122)-A(EAAAK)4A (SEQ ID NO: 24)-anti-HSA), P748 (anti-HSA-A(EAAAK)4A (SEQ ID NO: 24)-human IL-21 (1-122), P750 (human IL-21-GSG4 (SEQ ID NO: 12)-anti-HSA), P751 (human IL-21-A (EAAAK)4A (SEQ ID NO: 24)-anti-HSA) and P783 (human IL-21 (1-122)-A(EAAAK)4A (SEQ ID NO: 24)-anti-HSA) for 30 minutes at 37 C, 5% CO2 in Hanks Balanced Salt Solution containing 10 mM HEPES. Phospho-STAT3 was measured using a phospho-STAT3 (Tyr705) homogeneous time resolved fluorescence (HTRF) assay (Cisbio) according to the manufacturer's instructions. The signal ratio of 665 nm/620 nm was multiplied by 1000, plotted and fit using a dose response curve (Graphpad Prism) to calculate the EC50.

Figure 7A:
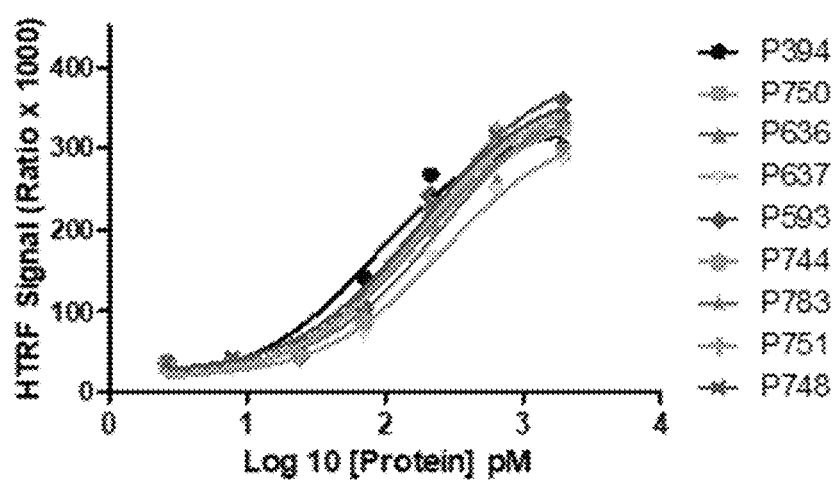
FIG. 7A shows STATS signaling by IL-21-anti-HSA fusion protein variants P394, P593, P636, P637, P744, P748, P750, P751 and P783.

All fusion proteins show similar IL-21R signaling activity, suggesting that truncation variants tested, different linkers tested and C-terminal vs N-terminal IL-21 fusion tested do not impact IL-21 signaling (FIG. 7A).

Part B.

NCI-N87 cancer cell lines were maintained in RPMI-1640 containing 10% fetal bovine serum and penicillin/streptomycin. On day 0, 10,000 NCI-N87 cells/well and 5,000 NCI-H226 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1 (Biotek). Lower cell counts indicated better NK mediated cell killing. (P394 (human IL-21-GSG4 (SEQ ID NO: 12)-anti-HSA, with a sequence of SEQ ID NO:121), P593 (human IL-21 (1-122)-A(EAAAK)4A (SEQ ID NO: 24)-anti-HSA), P636 (human IL-21(1-119)-GSG4-anti-HSA), P637 (human IL-21(1-120)-GSG4 (SEQ ID NO: 12)-anti-HSA), P744 (human IL-21(1-122)-A(EAAAK)4A-anti-HSA), (SEQ ID NO: 24) P748 (anti-HSA-A(EAAAK)4A (SEQ ID NO: 24)-human IL-21(1-122), P750 (human IL-21-(GSG)4 (SEQ ID NO: 12)-anti-HSA), P751 (human IL-21-A (EAAAK)4A (SEQ ID NO: 24)-anti-HSA) and P783 (human IL-21 (1-122)-A(EAAAK)4A (SEQ ID NO: 24)-anti-HSA)).

Figure 7B:
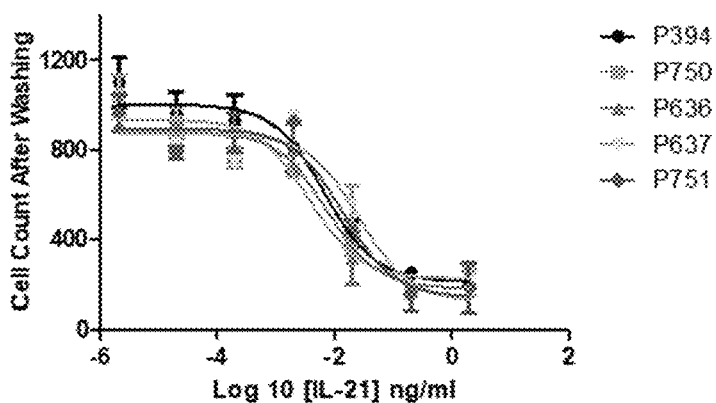
FIG. 7B and FIG. 7C show NK cell mediated ADCC on NCI-N87 tumor cells when titrating IL-21-anti-HSA fusion protein variants P394, P593, P636, P637, P744, P748, P750, P751 and P783 at a fixed dose of anti-MSLN antibody (P303).
Figure 7C:
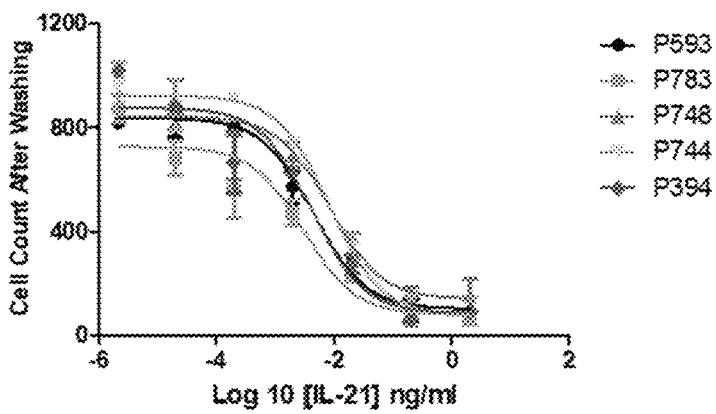

All fusion proteins show similar ADCC function when combined with an anti-MSLN antibody, suggesting that truncation variants tested (WT vs. C-terminal truncations), different linkers tested (GSG4 (SEQ ID NO: 12) vs A(EAAAK)4A) (SEQ ID NO: 24) and C-terminal vs N-terminal IL-21 fusion tested do not impact IL-21 activation of NK cells (FIGS. 7B and 7C).

Example 15. Pharmacokinetic Evaluation of IL-21-Anti-HSA Fusion Proteins

Balb/cJ mice were intraperitoneally injected with rhIL-21, P325 or P394 diluted in 100 ul PBS. Following a pre-dose bleed, mice were bled 0.5, 2, 6, 24, 48, 72, 96 hrs after compound injection for P394 or 0.25, 0.5, 1, 2, 6, 24, 48, 72 hrs after compound injection for rhIL-21 and P325. Blood was placed in a microtainer (BD) with EDTA to prevent clotting. IL-21 protein was quantified using an IL-21 ELISA (Life Technologies) according to the manufacturer's instructions with each compound serving as its own standard.

Figure 8:
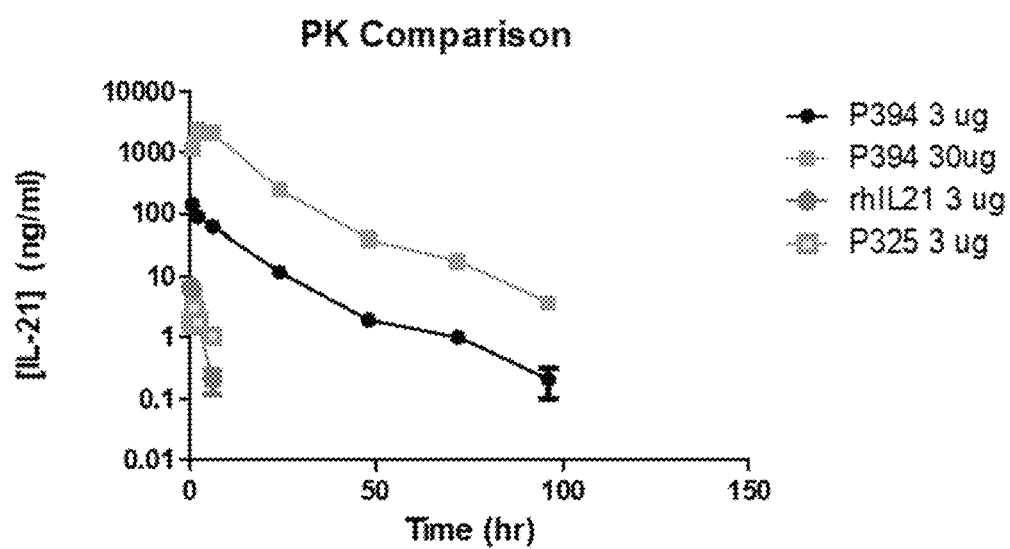
FIG. 8 shows depicts a comparison of pharmacokinetics in mice of 3 μg of recombinant human IL-21, 3 μg of P325 (human IL-21-irrelevant nanobody) and 3 or 30 μg of P394 (human IL-21-anti-HSA).

Pharmacokinetic evaluation in mice of 3 μg recombinant human IL-21, 3 μg P325 (human IL-21-irrelevant nanobody) and 3 or 30 μg P394 (human IL-21-anti-HSA) showed increased half-life and exposure of P394 demonstrating the impact of IL-21 conjugation with anti-HSA. (FIG. 8)

Conjugating anti-HSA to IL-21 increases in vivo half-life and exposure.

Example 16. Characterization of IL-21 Fusion Proteins

Part A. HPLC and SDS-PAGE

Figure 9A:
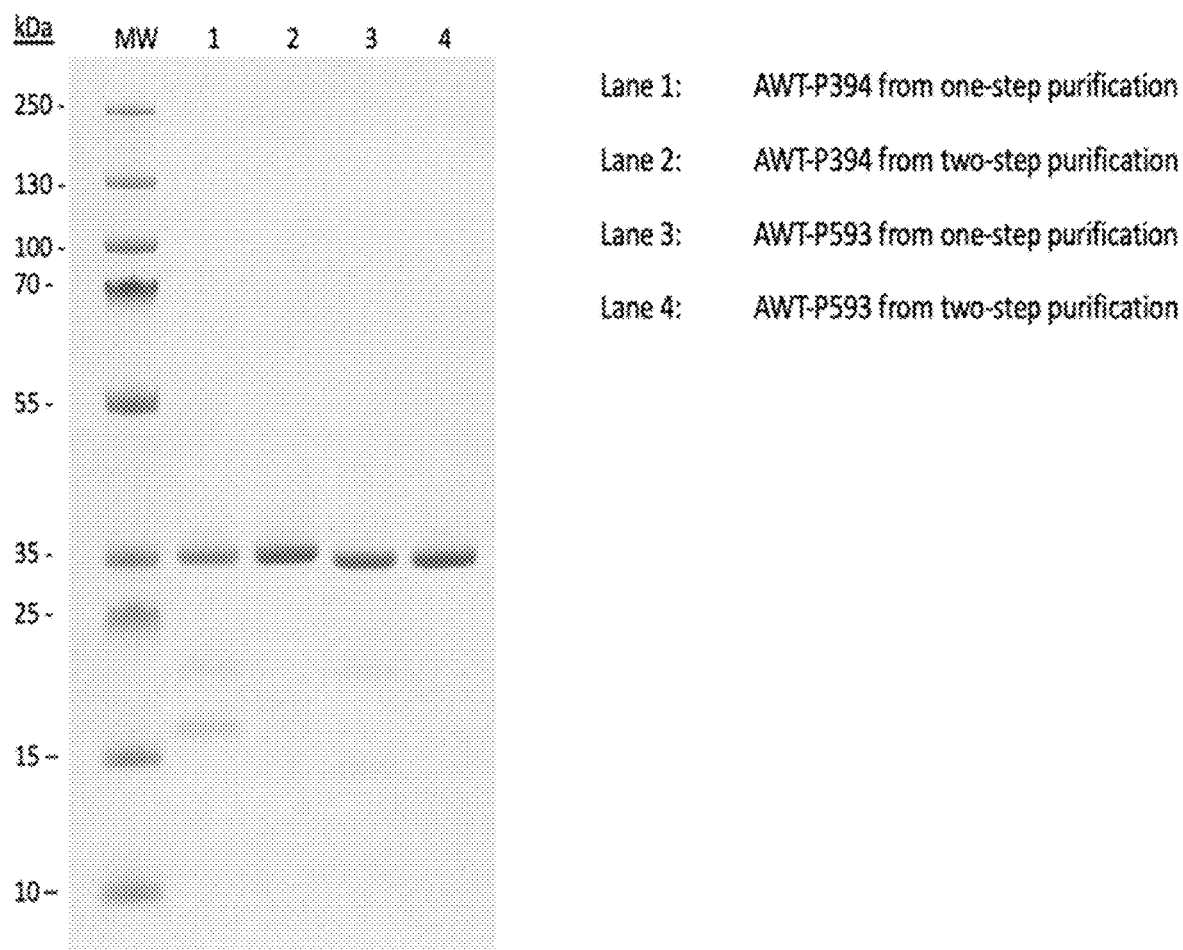

After the purification of IL-21 fusion proteins, their sizes and purity were determined by SDS-PAGE and/or high-performance liquid chromatography (HPLC). For SDS-PAGE, NuPAGE 4-12% Bis-Tris Protein Gels precast gel (Thermofisher) were used and approximately 1 μg of protein were loaded into each well. After electrophoresis, the proteins on the protein gel were fixed and stained with InstantBlue Protein Stain (Expedeon). As shown in FIG. 9A, combined with optimized linker, truncated IL-21(1-122)-A(EAAAK)4A (SEQ ID NO: 24)-anti-HSA fusion protein (AWT-593) shows reduced degradation (Lane 3) compared with full length IL-21-(GSG)4 (SEQ ID NO: 12)-anti-HSA fusion protein (AWT-P394, Lane 1).

Moreover, as shown in FIGS. 9F and 9G, P748, anti-HSA-A(EAAAK)4A (SEQ ID NO: 24)-IL21(1-122) (P748) (Lane 1 in FIG. 9G) showed ever more reduced degradation than P593 (Lane 3 in FIG. 9F) and P394 (Lane 1 in FIG. 9F), which suggests that a fusion of IL21 which to the c-terminus of anti-HSA antibody reduces protein cleavage during production.

Figure 9B:
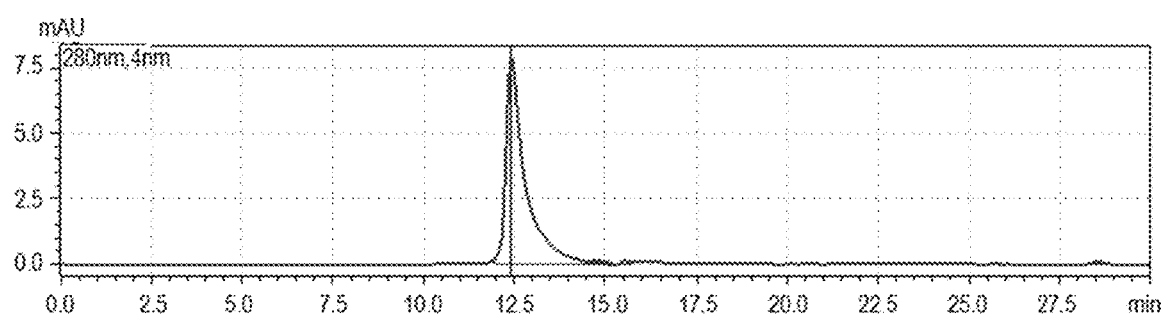
FIG. 9B depicts a representative chromatogram of AWT-P394 IL21-anti HSA fusion protein.

For HPLC, the analysis was performed on a Shimadzu LC-2030C HPLC System. Approximately 5 μg of samples were injected onto an AdvanceBio 300 Å, 2.7 μM, 4.6×300 mm Size Exclusion Column (Agilent) at 0.25 mL/min using 25 mM Sodium Phosphate, 500 mM Sodium Chloride buffer, pH 6.5. Data was analyzed using Post-run by LabSolutions software (Shimadzu). A single peak composed of >95% of the total protein sample can be detected at 12.5 minutes. FIG. 9B shows representative chromatogram of AWT-P394 IL-21-anti HSA fusion protein.

Part B. Formulation

Figure 9C:
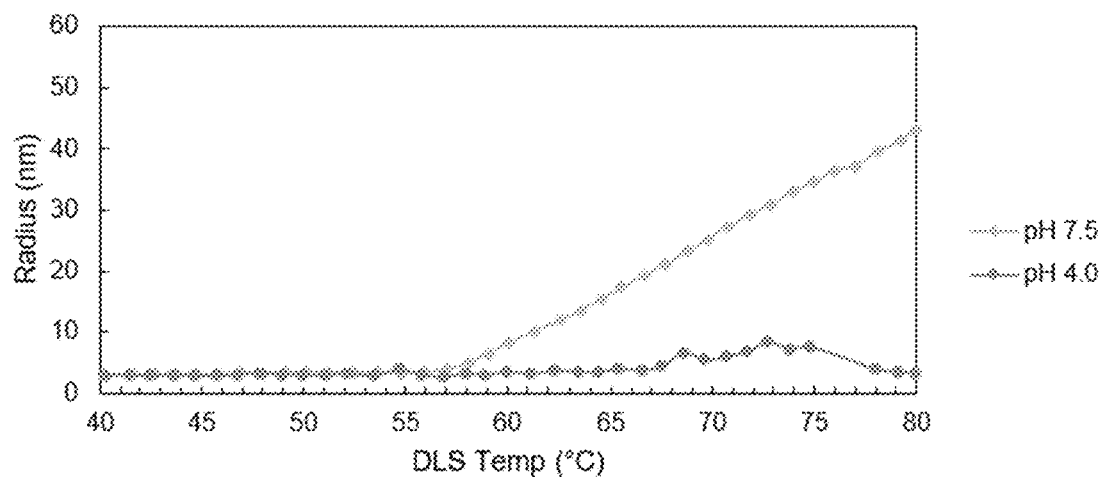
FIG. 9C depicts comparison of $T_{onset}$ of AWT-P593 at pH 4.0 and pH 7.5.

To rapidly evaluate the best formulation condition and the stability of different molecular designs, two-step purified IL-21 fusion proteins were buffer exchanged into different buffers composing various amount of histidine (5-20 mM) and NaCl (0-100 mM) at different pH (3-7), with 0.02% Tween 80. The protein samples were gradually heated from 40° C. to 80° C. and the real-time protein size distribution of each sample was determined by dynamic light scattering (DLS) using DynaPro Plate Reader III (Wyatt Technology). After two-step purification, more than 99% of IL-21-anti HSA fusion proteins are smaller than 10 nM. During the temperature ramp, the minimum temperature required to induce aggregation in a protein formulation was determined as $T_{onset}$. The best formulation that gives highest $T_{onset}$ (>80° C.) in all tested condition was 5 mM Histidine, 25 mM NaCl and 0.02% Tween 80 at pH 4.0. See FIGS. 9C-9D.

Figure 9D:
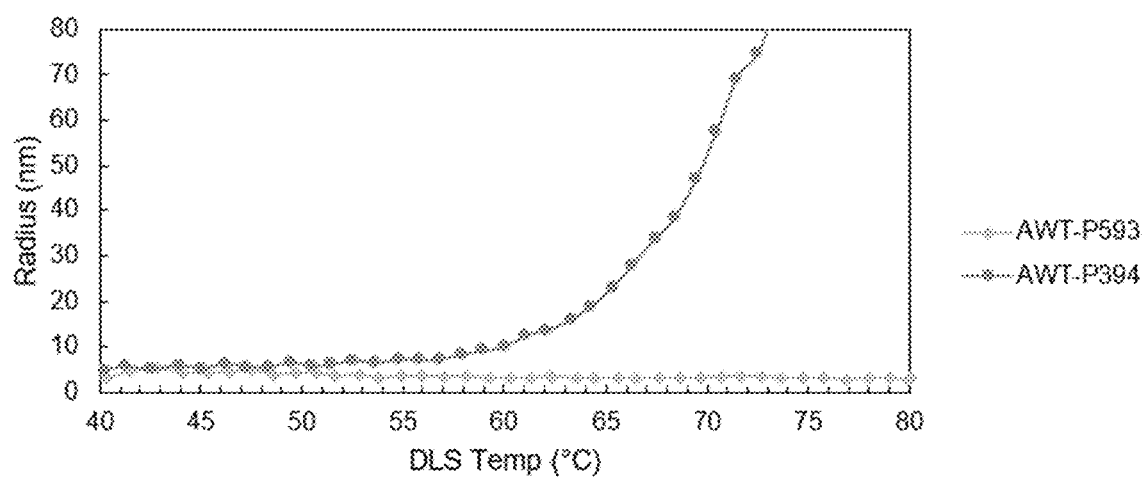
FIG. 9D depicts of the $T_{onset}$ of AWT-P394 and AWT-P593.

As shown in FIG. 9D, the combination of IL-21 truncation and linker optimization also contributes to the improvement of protein stability. Compared with full length human IL-21-(GSG)4-anti HSA fusion protein, truncated IL-21 with optimized linker significantly (AWT-P593) increased the $T_{onset}$, indicating a greatly improved stability in the indicated formulation condition.

Part C. Binding Affinity

Figure 9E:
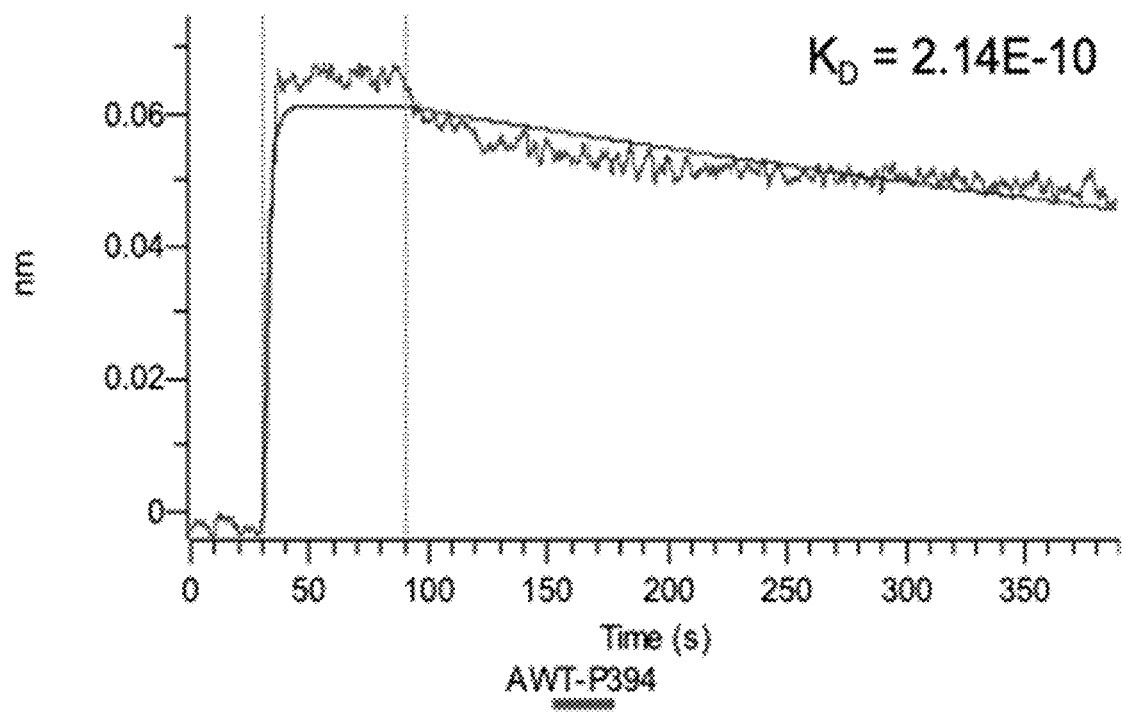
FIG. 9E depicts binding of human IL021 receptor to IL-21-anti-HSA fusion protein AWT-P394 or AWT-P593.
Figure 9E:
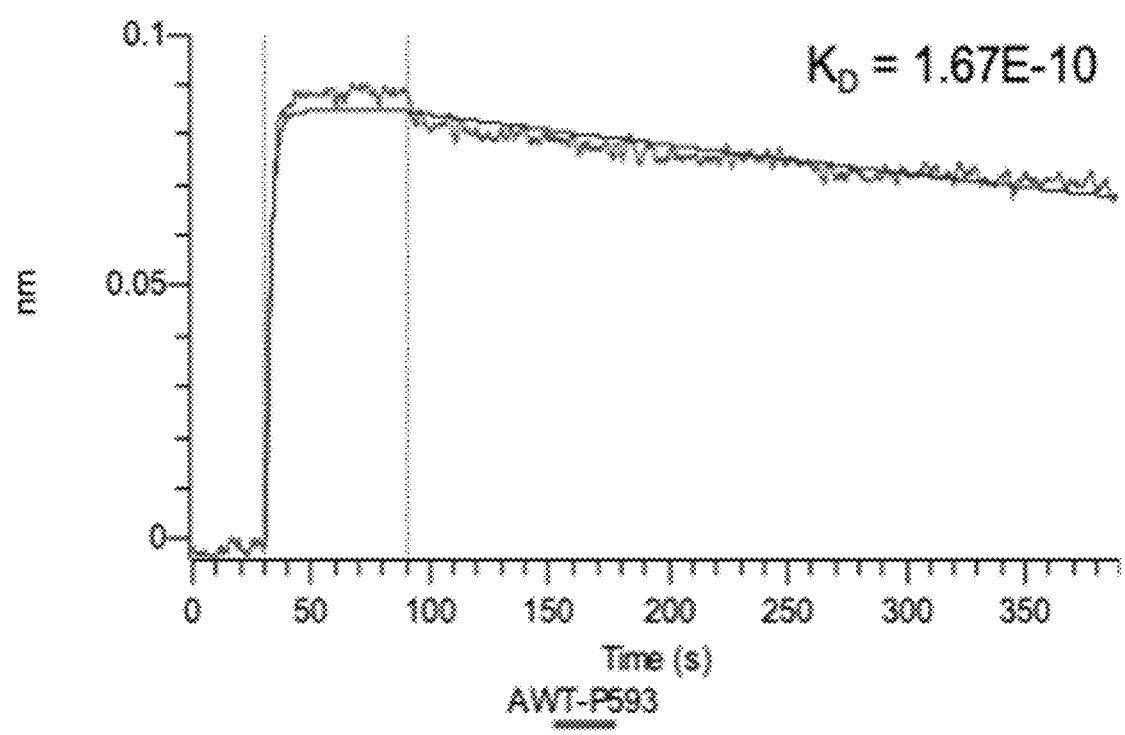

Binding of human IL-21 receptor to IL-21-anti-HSA fusion protein AWT-P394 or AWT-P593. An Octet RED96 (ForteBio) was used to characterize the interaction. Briefly, human IL-21 receptor-hgG1 Fc fusion proteins were loaded onto AHC biosensor and dip into AWT-P394 or AWT-P593 at 100 nM concentration. Primary experimental data was analyzed with global fitting to determine the $K_D$. See FIG. 9E.

Example 17. Anti-HSA Antibodies

Albumin is the most abundant protein in human serum and it has a half-live of three weeks. The long half-life of serum albumin is largely attributed to the protection from neonatal Fc receptor (FcRn). Serum albumin can be up-taken by somatic cells through a process named fluid phase pinocytosis. Pinocytotic vesicles subsequently fuse with endosomal compartment, where the pH is in a range of 4.5-6.5. If the proteins in the vesicle are released from their receptors, they would be further sorted for lysosomal degradation. The binding between serum albumin and FcRn only occurs at acidic pH (<6.5), allowing FcRn to rescue albumin from endosome and recycle them back to serum (Grevys et al., 2018). Therefore, as an albumin dependent half-life extending moiety, anti-HSA antibodies need to retain their binding affinity at both neutral and acidic pH.

Figure 10A:
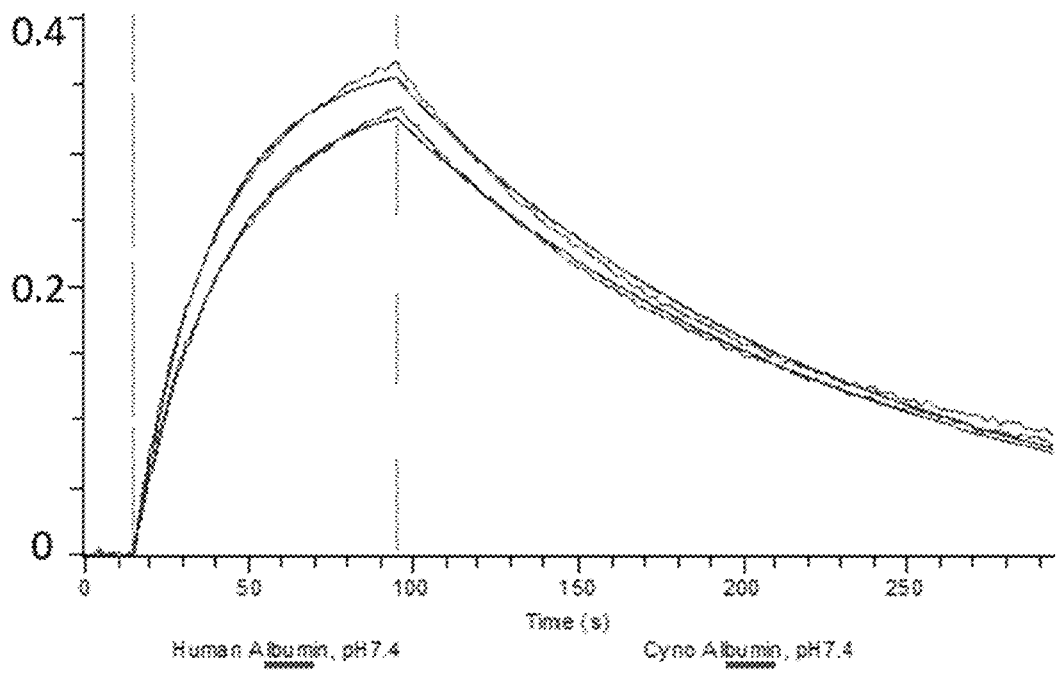
FIG. 10A depicts comparison of the $T_{onset}$ of AWT-P593 at pH 4.0 and pH 7.5.
Figure 10A:
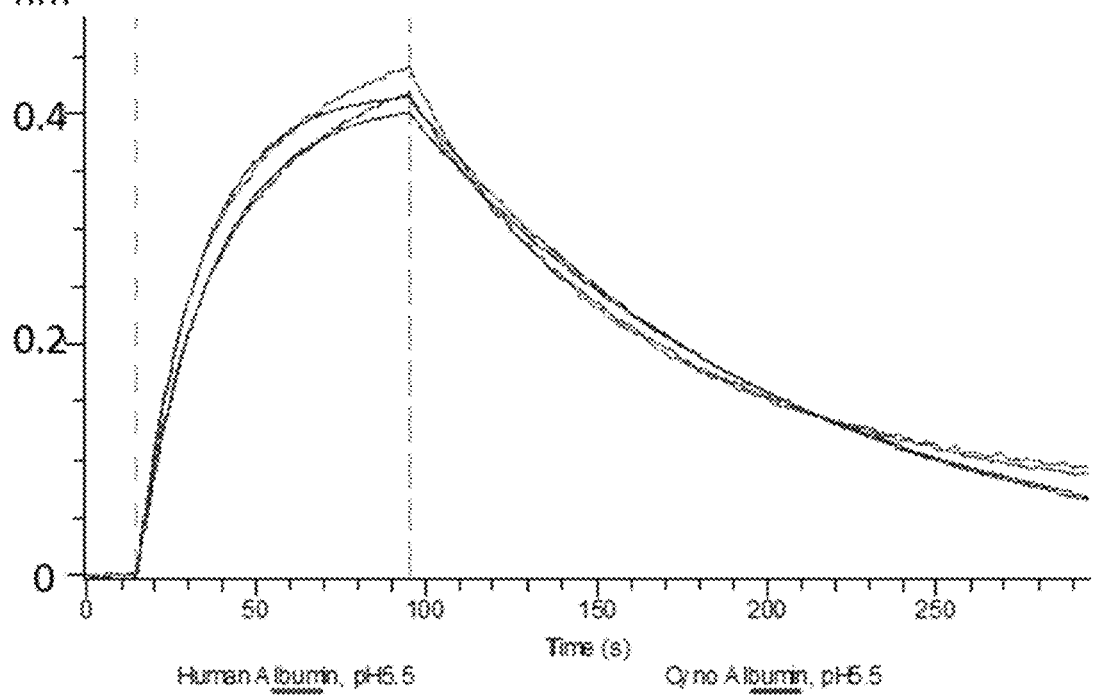

An Octet RED96 (ForteBio) was used to characterize the interaction between AWT-610 and human or monkey serum albumin at pH 7.4 and pH 5.5. Briefly, AWT-P610-hgG1 Fc fusion protein was loaded onto protein A biosensor and dip into human (blue colored line) or monkey (dark red colored line) serum albumin at pH 7.4 (left graph) or pH 5.5 (right graph). See FIG. 10A.

Primary experimental data was analyzed with global fitting (red) to determine the $K_D$. Specifically, three different anti-HSA antibodies interact with both human and monkey serum albumin at pH 7.4 and pH 5.5. The binding was measured using Octet RED96 (ForteBio) and the $K_D$ was determined by global fitting using Octet Data Analysis HT software. Table 9 shows the calculated KD of three different Anwita anti-HSA antibodies at both pH 5.5 and pH 7.4. In general, the antibodies show a slightly increase in binding affinity to human serum albumin at pH 5.5.

TABLE 9

| Antibody | Binding Condition | KD (M) Human SA | KD (M) Cyno SA |
|---|---|---|---|
| AWT-P367 | pH7.4 | $29.6 \times 10^{-9}$ | $18.9 \times 10^{-9}$ |
|  | pH5.5 | $9.6 \times 10^{-9}$ | $20.5 \times 10^{-9}$ |
| AWT-P342 | pH7.4 | $33.2 \times 10^{-9}$ | $28.1 \times 10^{-9}$ |
|  | pH5.5 | $15.5 \times 10^{-9}$ | $11.0 \times 10^{-9}$ |
| AWT-P610 | pH7.4 | $43.0 \times 10^{-9}$ | $49.6 \times 10^{-9}$ |
|  | pH5.5 | $39.8 \times 10^{-9}$ | $47.1 \times 10^{-9}$ |

Figure 10B:
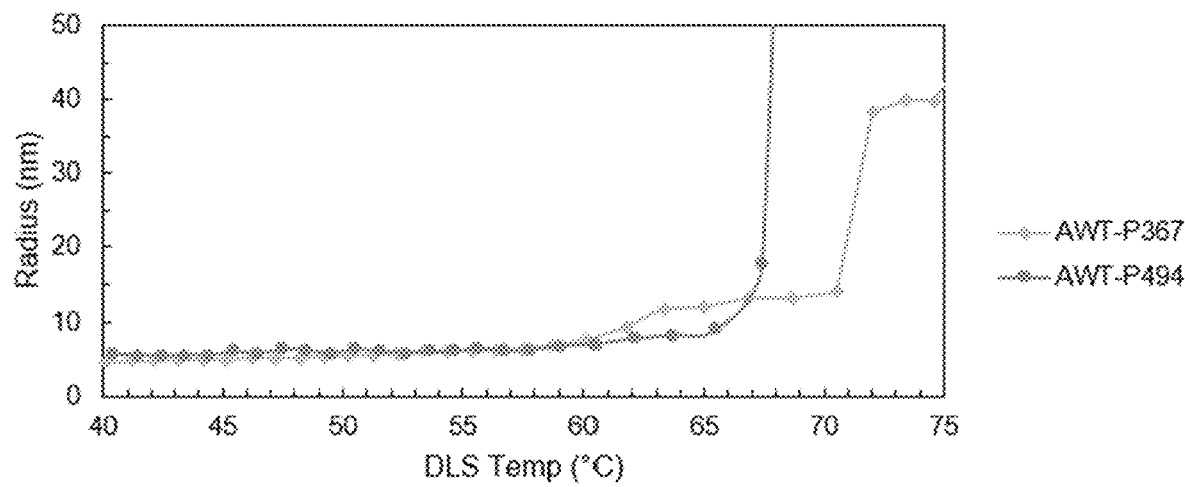
FIG. 10B depicts comparison of the $T_{onset}$ of AWT-P394 and AWT-P593.

The $T_{onset}$ of anti-HSA antibodies AWT-P367 and its humanized version AWT-P494 was assessed. AWT-P367 and AWT-P494 were buffer exchanged into 1×PBS pH 7.4. The protein samples were gradually heated from 40° C. to 80° C. and the real-time protein size distribution of each sample was determined by dynamic light scattering (DLS) using DynaPro Plate Reader III (Wyatt Technology). As shown in FIG. 10B, AWT-P494 shows slighted increased $T_{onset}$ compared with AWT-P367.

Figure 10C:
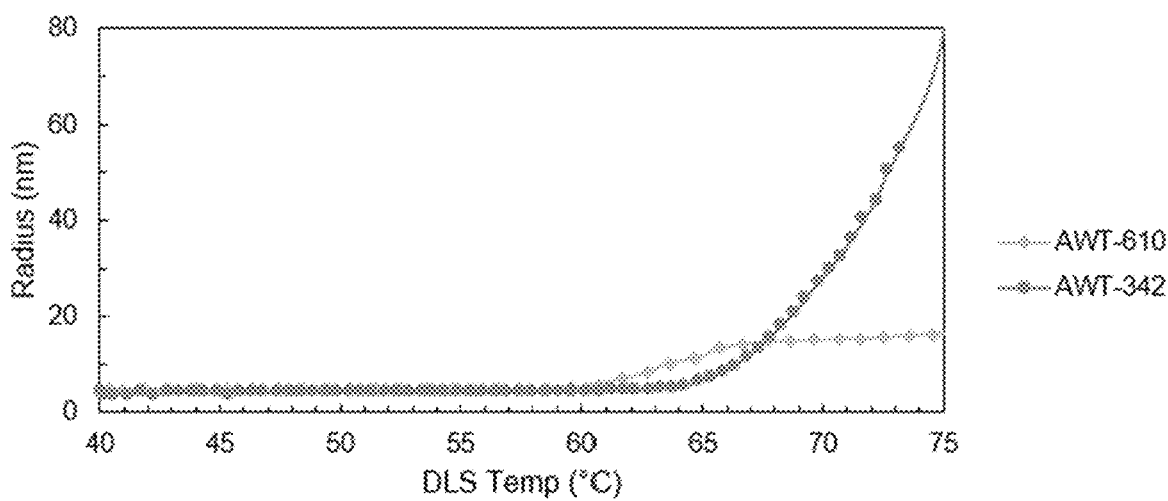
FIG. 10C depicts the binding of humanized anti-AWT-P610 (i.e., P610) with human serum albumin or monkey serum albumin at pH 7.4 and pH 5.5.

The $T_{onset}$ of anti-HSA antibodies AWT-P342 and its fully humanized version AWT-P610 was assessed. AWT-P342 and AWT-P610 were buffer exchanged into 1×PBS pH 7.4. The protein samples were gradually heated from 40° C. to 80° C. and the real-time protein size distribution of each sample was determined by dynamic light scattering (DLS) using DynaPro Plate Reader III (Wyatt Technology). As shown in FIG. 10C, AWT-P610 shows decreased $T_{onset}$ compared with AWT-P342.

Figure 10D:
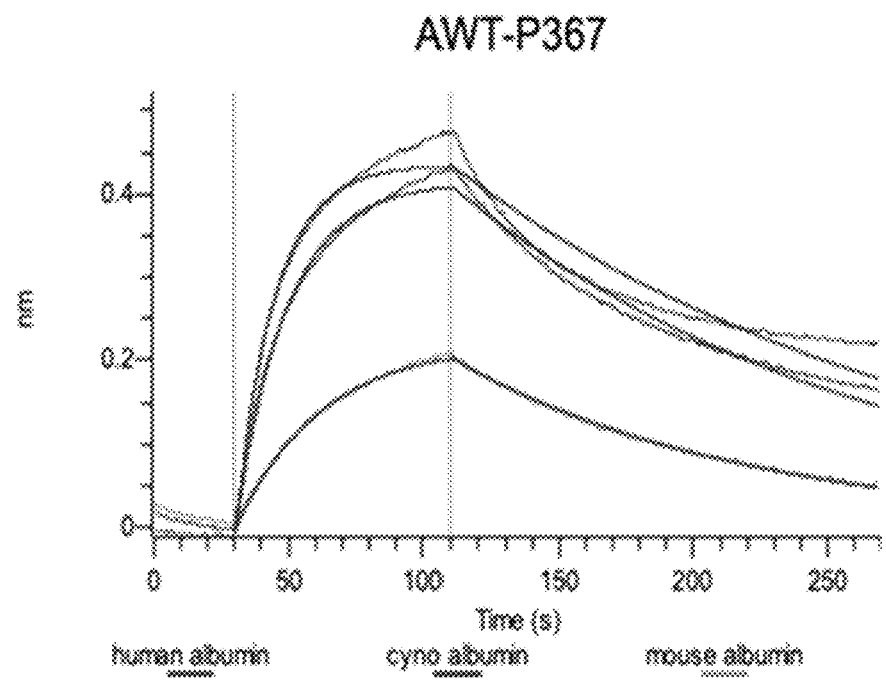
FIG. 10D depicts comparison of the $T_{onset}$ of anti-albumin antibody AWT-P367 and its humanized version AWT-P494.
Figure 10D:
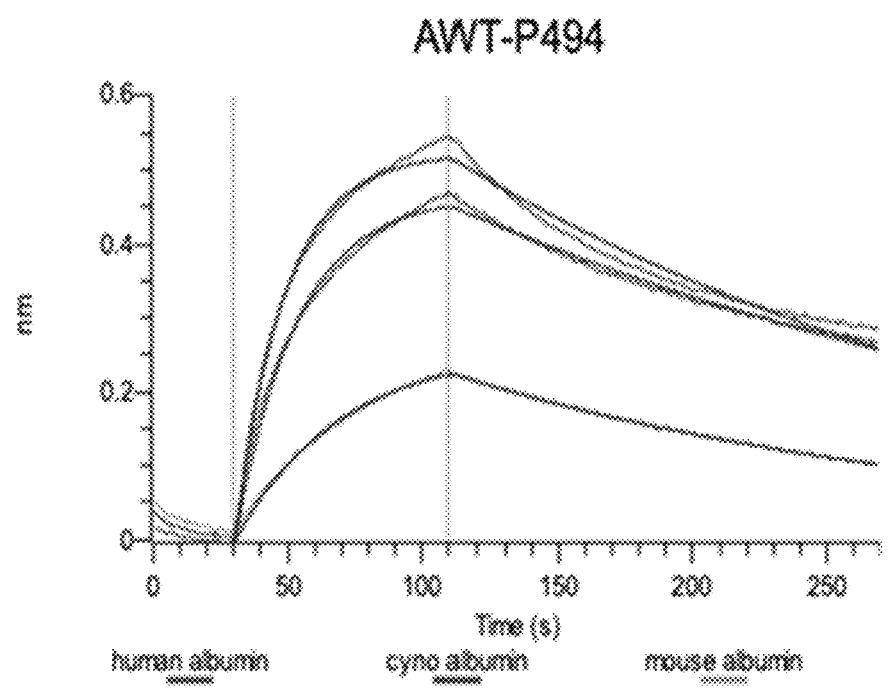

An Octet RED96 (ForteBio) was used to characterize the interaction between anti-HSA antibody AWT-P367 or its humanized version AWT-P494 to human, monkey or mouse albumin. Briefly, AWT-P367 or AWT-P494 were loaded onto AHC biosensor and dip into human, monkey or mouse serum albumin at 200 nM concentration. Primary experimental data was analyzed with global fitting to determine the $K_D$. As shown in FIGS. 10D-10E, the binding affinity of humanized anti-HSA antibody AWT-P494 is similar to its original clone AWT-P367.

Example 18: Anti-Mesothelin Antibody, Cytokine, or Cytokine Fusion Protein for Inhibiting Cancer Cells NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1™ (Biotek). Lower cell counts indicated better NK mediated cell killing. (P303-R3C7 anti-MSLN antibody. P303F-R3C7 anti-mesothelin antibody with reduced fucosylation. P394-human IL-21-anti-HSA. P390-mouse IL-21-anti-HSA. P431/435-human IL-21-anti-HSA-IgG1-R3C7. P479-anti-HSA-Human-IL-15 RA Sushi/IL-15. P480)-anti-HSA-Human-IL-15 RA Sushi/IL-15, rhIL-21-recombinant human IL-21, rhIL-15-recombinant human IL-15).

Figure 11:
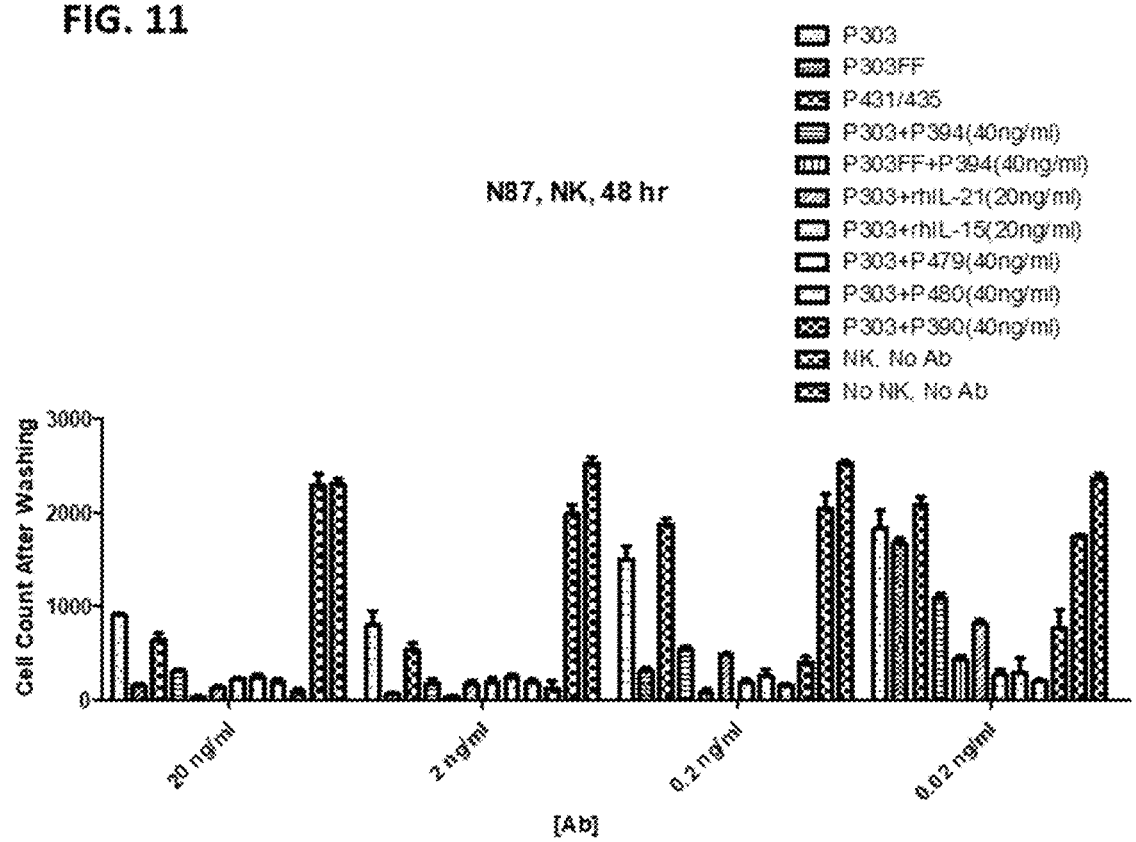
FIG. 11 depicts remaining cell numbers of N87 cells after treatment of NK cells alone or in combination with study drug as shown in the figure.

As shown in FIG. 11, rhIL-21, mIL-21 (P390) and hIL-21 (P394) anti-HSA fusion proteins enhanced NK cell ADCC activity to a similar extent when combined with anti-MSLN antibody P303 (R3C7) compared to P303 alone. Moreover, rhIL-15 and hIL-15/IL-15RA anti-HSA fusion proteins (P479 and P480) enhanced NK cell ADCC activity to a similar extent when combined with anti-MSLN antibody P303 (R3C7) compared to P303 alone. Cytokine-anti-HSA fusion proteins maintained full ADCC activity compared to the equivalent recombinant cytokines.

Example 19: Anti-Mesothelin Antibody Alone or in Combination with Herceptin for Inhibiting Cancer Cells NCI-N87 cancer cell line was maintained in RPMI-1640) containing 10% fetal bovine serum and penicillin/streptomycin. On day 0, 10.000 NCI-N87 cells/well were plated in culture medium in a 96-well flat bottom plate. On day 1. NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1™ (Biotek). Lower cell counts indicated better NK mediated cell killing. (P303F-Anwita anti-mesothelin antibody with reduced fucosylation. P380-human IL-33-anti-HSA. P394-human IL-21-anti-HSA).

Figure 12:
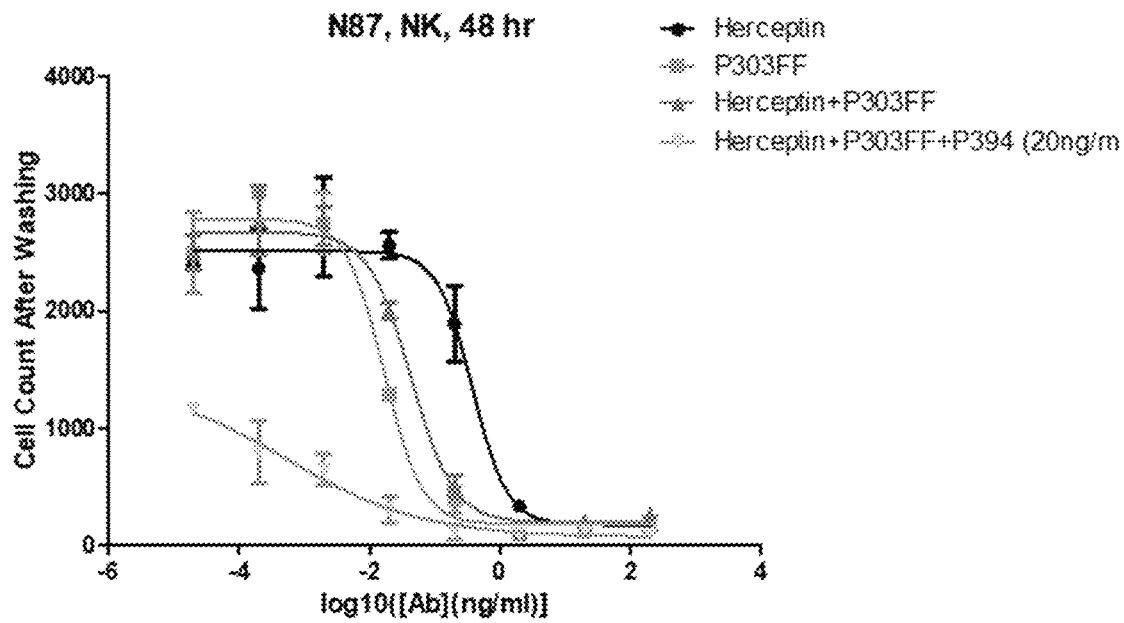
FIG. 12 depicts remaining cell numbers of N87 cells after treatment of NK cells alone or in combination with a) Herceptin alone, b) P303FF (i.e., P303F) alone, c) Herceptin and P303FF, or d) Herceptin, P303FF, and IL-21-anti-HSA fusion protein P394.

As shown in FIG. 12. P303F (R3C7 anti-mesothelin antibody) was more potent than Herceptin in NK cell ADCC and the combination of P303F and Herceptin was similar to P303F alone. Addition of P394 (human IL-21-anti-HSA) to P303F and Herceptin resulted in significantly improved ADCC function and improved potency.

Example 20: Cytokine Fusion Proteins for Inhibiting Cancer Cells

Pfeiffer cancer cell line was maintained in RPMI-1640 containing 10% fetal bovine serum and penicillin/streptomycin. On day 1, 10.000 Pfeiffer cells/well were plated in culture medium in a 96-well flat bottom plate. NK cells were isolated from human buffy coat using RosetteSep NK Isolation kit (Stemcell Technologies), and 30,000 NK cells/well were added to the cancer cells together with the indicated treatment. Plates were incubated for 24 hrs at 37 C, 5% CO2, and cells were then stained with luM propidium iodide for FACS analysis. Pfeiffer cells were separated from NK cells based on FSC and SSC gating and total Pfeiffer cell counts were determined. Pfeiffer dead cells were determined using PI stain. Total live cells were calculated by subtracting PI positive from total Pfeiffer cell count in. Lower live cell counts indicated better NK mediated cell killing. (p394-human IL-21-anti-HSA. P480)-anti-HSA-Human-IL-15 RA Sushi/IL-15).

Figure 13:
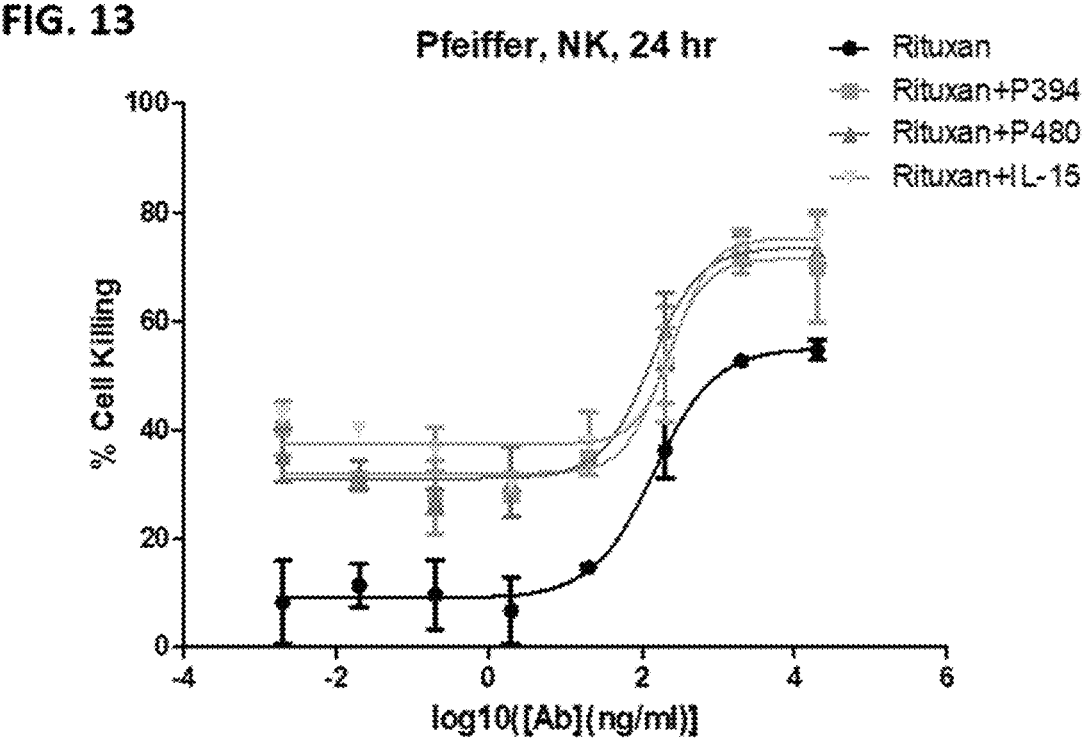
FIG. 13 depicts percentage of dead Pfeiffer cells after treatment of NK cells in combination with a) rituxan, b) rituxan and P394, c) rituxan and IL-15 fusion protein P480, or d) rituxan and IL-15.

As shown in FIG. 13, human IL-21-anti-HSA fusion protein (P394), human IL-15/IL-15R sushi-anti-HSA fusion protein (P480), and rhIL-15 enhanced NK cell ADCC activity against diffuse large B cell lymphoma cell line Pfeiffer when combined with Rituxan.

Example 21: Anti-Mesothelin Antibody Alone or in Combination with Cytokine Fusion Proteins for Inhibiting Cancer Cells NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 24 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1™ (Biotek). Lower cell counts indicated better NK mediated cell killing. (P303F-Anwita anti-mesothelin IgG1 antibody R3C7 with reduced fucosylation, P480-anti-HSA-Human-IL-15 RA Sushi/IL-15, rhIL-21-recombinant human IL-21, rhIL-15-recombinant human IL-15).

Figure 14:
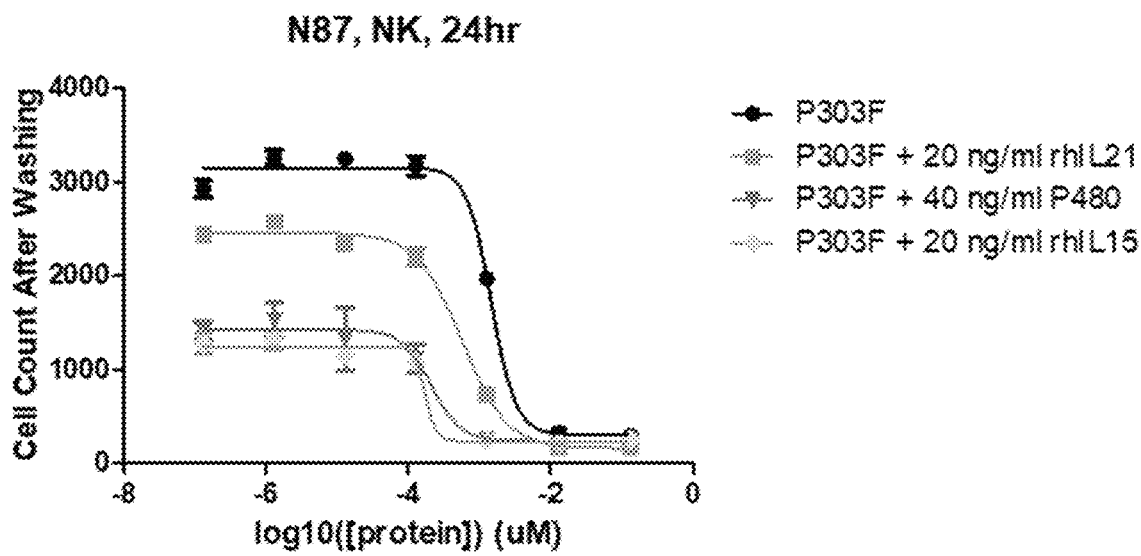
FIG. 14 depicts remaining cell numbers of N87 cells after treatment of NK cells in combination with a) P303F, b) P303F and recombinant human IL-21 (i.e., rhIL-21), c) P303F and P480, or d) P303F and recombination human IL-15 (i.e., rhIL-15).

As shown in FIG. 14, rhIL-15 and IL-15-anti-HSA (P480)) enhanced NK cell ADCC activity when combined with anti-MSLN antibody P303F better than P303F and P303F with rhIL-21. P480 (IL-15/IL-15R sushi-anti-HSA) enhanced NK mediated ADCC with similar potency and magnitude compared to rhIL-15 suggesting full IL-15 activity was retained in the antibody fusion protein.

Example 23: IL-15-Anti-HSA Fusion Protein for Inhibiting Cancer Cells

NCI-N87 cancer cell line was maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1™ (Biotek). Lower cell counts indicated better NK mediated cell killing. (P303-Anwita anti-mesothelin antibody R3C7, P480-anti-HSA-Human-IL-15 RA Sushi/IL-15, P597-anti-HSA-Human-IL-15 RA Sushi-peptide linker-IL-15, rhIL-15-recombinant human IL-15).

Figure 15:
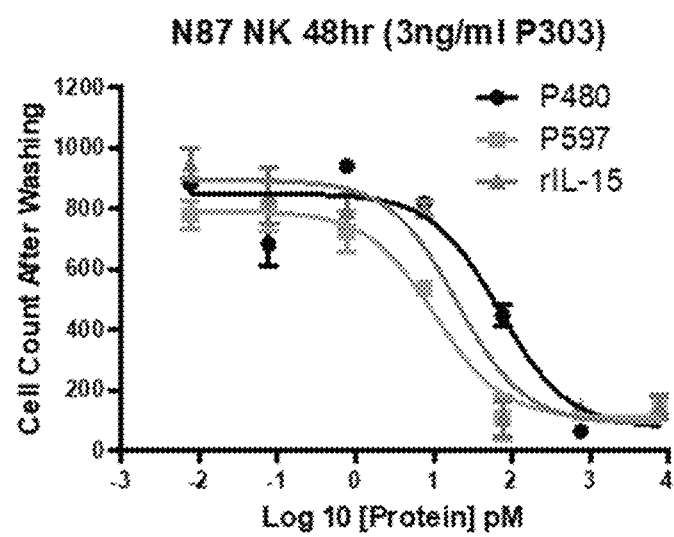
FIG. 15 depicts remaining cell numbers of N87 cells after treatment of NK cells in combination with a) P480, b) P597, or c) rIL-15 (upper panel) and IC50 of three drugs (lower panel).

As shown in FIG. 15, anti-HSA fusion protein P597, with a peptide linker between IL-15R sushi and IL-15, improved ADCC activity compared to P480, an anti-HSA fusion protein without a linker (after cleavage of the F2A linker[1]) between IL-15R sushi and IL-15. The ADCC potency of P597 was similar to rhIL-15, suggesting full IL-15 activity was retained in the fusion protein.

The F2A linker used in P480 is a cleavable linker with high cleavage efficiency (>90%). After protein synthesis, IL 15 is cleaved. However, due to the high affinity between IL. 15 and IL. 15RA sushi, they will still remain bound as a single protein.

Example 24: IL-21 Fusion Proteins for Inhibiting Cancer Cells

NCI-N87 and H226 cancer cell lines were maintained in RPMI-1640 containing 10% fetal bovine serum and penicillin/streptomycin. On day 0, 10,000 NCI-N87 cells/well, 5000 H226 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1™ (Biotek). Lower cell counts indicated better NK mediated cell killing. (P129-Anwita anti-mesothelin antibody R2G12. P126-human IL-21-R2G12-IgG1 fusion. P107-human IL-21-IgG1 fusion, P325-human IL-21-R2D2 fusion. P286/288-human IL-21-R3C7-IgG1-R2G12 fusion.)

Figure 16:
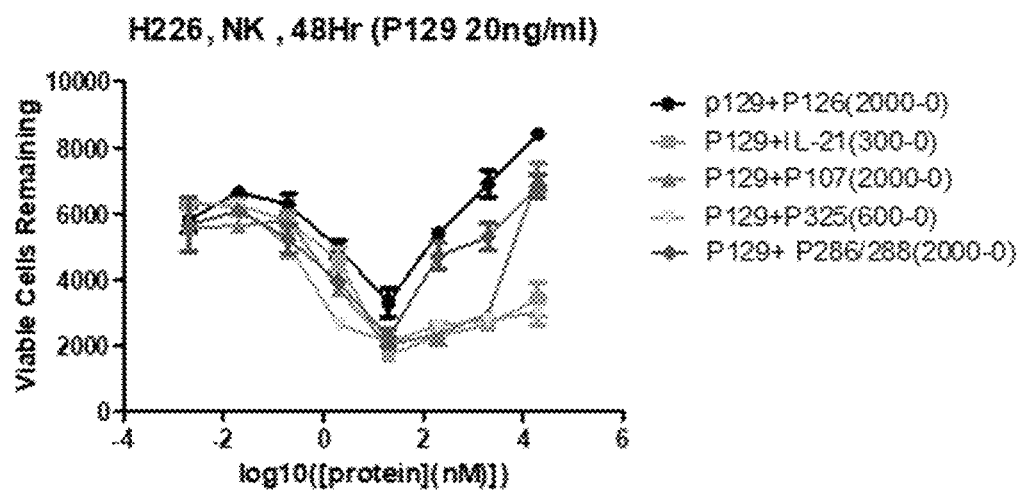
FIG. 16 depicts remaining cell numbers of H226 cells after treatment of NK cells in combination with a) anti-mesothelin antibody P129 (i.e., R2G12) and P126, (i.e., human IL-21-R2G12-IgG1 fusion), b) P129 and IL-21, c) P129 and P107 (human IL-21-IgG1 fusion), d) P129 and P325 (human IL-21-R2D2 fusion), or e) P129 and P286/288 (human IL-21-R3C7-IgG1-R2G12).

As shown in FIG. 16, lower concentrations of IL-21-Fc fusion proteins (P107. P126. P288/286) enhanced NK cell ADCC activity when combined with anti-MSLN antibody P129 (i.e., R2G12). However, at higher concentrations (>100 nM). IL-21-Fc fusion proteins (P107. P126. P288/286) inhibited NK cell ADCC activity when combined with anti-MSLN antibody P129 (R2G12). This inhibition was not observed for IL-21 or IL-21 fusion protein without the Fc domain (P325).

Example 25: IL-21-Anti-HSA Fusion Proteins in Combination with Anti-Mesothelin Antibodies for Inhibiting Cancer Cells NCI-N87 cancer cells were maintained in RPMI-1640 containing 10% fetal bovine serum and penicillin/streptomycin. On day 0, 10.000 NCI-N87 cells/well were plated in culture medium in a 96-well flat bottom plate. On day 1. NK cells were isolated from human buffy coat using RosetteSep NK Isolation kit (Stemcell Technologies), and 100.000 NK cells/well were added to the cancer cells together with the indicated treatment. Plates were incubated for 48 hrs at 37 C, 5% CO2, and cells were then fixed with 4% paraformaldehyde and nuclei stained with Sytox Orange. The number of remaining cancer cells was calculated by counting the number of cancer cell nuclei remaining in each well using the Cytation 1™ (Biotek). Lower cell counts indicated better NK mediated cell killing. (P197-Anwita anti-mesothelin antibody R2G12. P390-mouse IL-21-anti-HSA. P394-human IL-21-anti-HSA).

Figure 17:
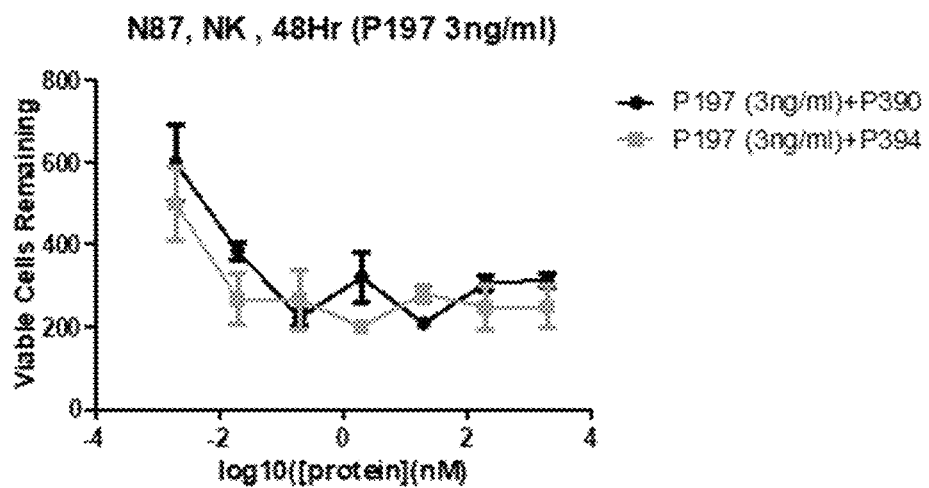
FIG. 17 depicts remaining cell numbers of N87 cells after treatment of NK cells in combination with a) P197 and P390; or b) P197 and P394.

As shown in FIG. 17, both mouse and human IL-21-anti-HSA fusion proteins (P390 and P394) enhance NK cell ADCC activity potently when combined with anti-MSLN antibody P197 (R2G12).

Example 26: Cytokine Production of PBMCs after Incubation with Cytokine or Cytokine-Anti-HSA Fusion Protein Frozen PBMC cells isolated from human buffy coat were thawed and grew in RPMI-1640 containing 10% fetal bovine serum and penicillin/streptomycin. On day 1, 30,000 PBMC cells/well were added to a 96-well plate with the indicated treatment. Plates were incubated over night at 37 C, 5% CO$_2$. On day 2, medium was collected and centrifuged to pellet the PBMC cells. 25 ul of medium were tested in the IFNgamma and IL-6 ELISA assay for cytokine release. (P394-human IL-21-anti-HSA, P597-anti-HSA-Human-IL-15 RA Sushi (plus)-IL-15).

Figure 18A:
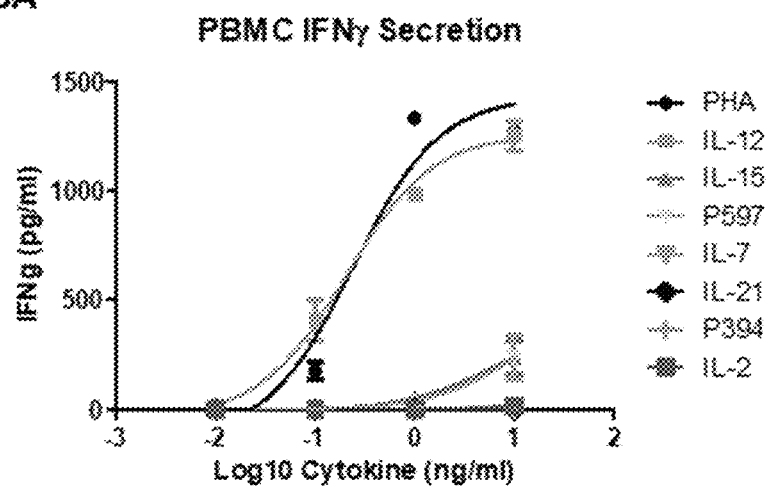
FIGS. 18A-18B depict levels of IFN-gamma (FIG. 18A) and IL-6 (FIG. 18B) secreted by PBMC after incubation with different drugs as shown.
Figure 18B:
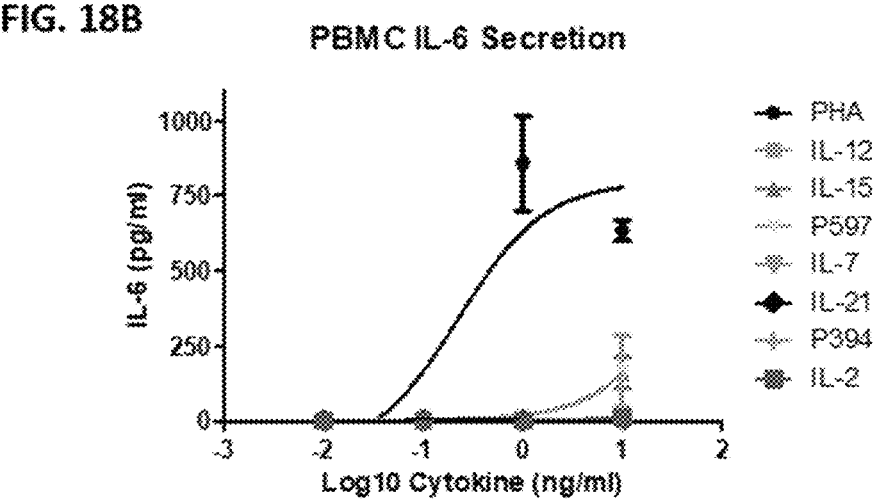

As shown in FIGS. 18A-18B, positive control phytohemagglutinin (PHA) stimulates robust IFNg and IL-6 secretion from PBMCs. PBMCs do not secrete IFNg or IL-6 in response to rIL-21 or IL-21-anti-HSA fusion protein P394 stimulation. Both rIL-15 and IL-15-anti-HSA fusion protein P597 stimulate IFNg and IL-6 secretion by PBMCs to a similar extent, suggesting the fusion protein has similar activity to the recombinant protein. IL-12 stimulates IFNg secretion, but not IL-6 secretion, by PBMCs. IL-7 and IL-2 stimulate minimal levels of IFNg and IL-6 secretion.

Example 27. IL-21-Anti-HSA Fusion Protein, Anti-HSA-IL-15Ra-IL-15 Fusion Protein and Anti-CTLA4 Alone or in Combination for Treating Cancer Part A.

MC38 cells were cultured and maintained in DMEM media supplemented with 10% FBS+glutamax+NEAA+sodium pyruvate+Pen/Strep. Cells were trypsinized, washed with media, and counted. Cells were then washed with PBS, and $0.5 \times 10^6$ cells (in 50 ul PBS) were injected subcutaneously into anesthetized C57BL/6 mice (Taconic) using an 18-gauge needle. Stock study drug was diluted to the appropriate concentration in PBS on the day of dosing, and animals were dosed IP with PBS, 25 µg P394 (human IL-21-anti-HSA), 100 µg anti-CTLA-4, or 25 µg P394 in combination with 100 µg anti-CTLA-4 in 100 ul PBS twice per week for a total of 5 doses. Tumor measurements (length (L) and width (W)) were collected twice per week using digital calipers, and the tumor volume was calculated (L×W×W)/2.

Figure 19A:
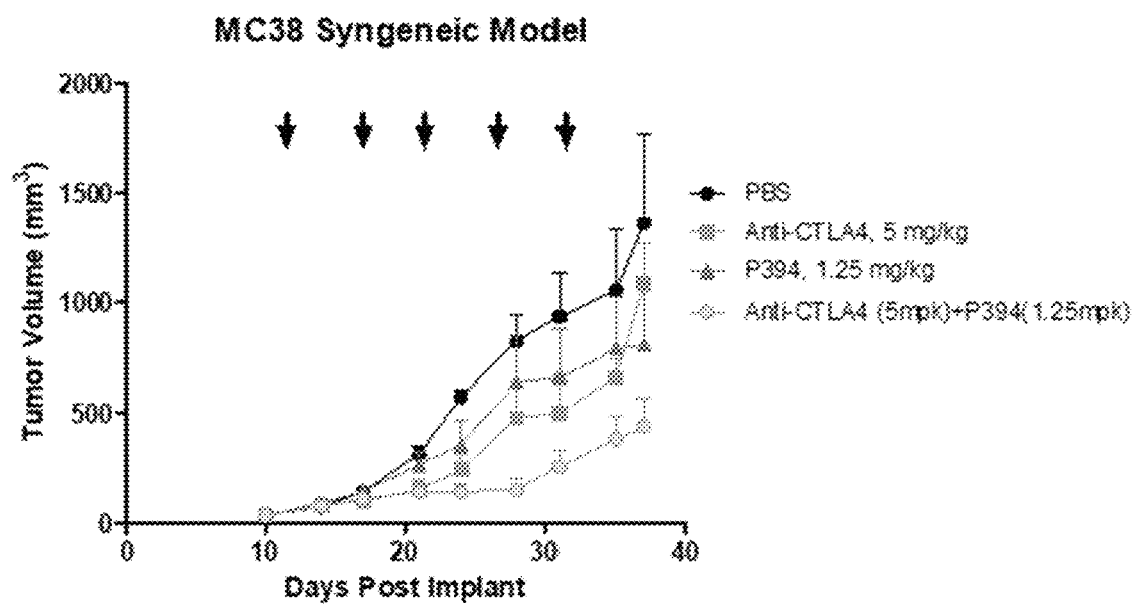
FIGS. 19A-19B depict the change in tumor volume in an MC38 mouse syngeneic tumor model when dosed with anti-CTLA-4, IL-21-anti-HSA fusion protein (P394), anti-HSA-IL-15Ra/IL-15 fusion protein (P597) or combinations of these agents.

As shown in FIG. 19A, P394 and anti-CTLA-4 monotherapy are able to decrease tumor growth relative to PBS control. Combination of P394 and anti-CTLA-4 further decreases tumor growth relative to P394 and anti-CTLA-4 monotherapies.

Part B.

MC38 cells were cultured and maintained in DMEM media supplemented with 10% FBS+glutamax+NEAA+sodium pyruvate+Pen/Strep. Cells were trypsinized, washed with media, and counted. Cells were then washed with PBS, and 0.5×10⁶ cells (in 50 ul PBS) were injected subcutaneously into anesthetized C57BL/6 mice (Taconic) using an 18-gauge needle. Stock study drug was diluted to the appropriate concentration in PBS on the day of dosing, and animals were dosed IP with PBS, 100 µg anti-CTLA-4, 100 µg anti-CTLA-4 with 25 µg P394 (human IL-21-anti-HSA), 100 µg anti-CTLA-4 with 5 µg P597 (anti-HSA-IL-15Ra-IL-15), or 100 µg anti-CTLA-4 with 25 µg P394 and 5 µg P597 in 100 ul PBS twice per week for a total of 5 doses. Tumor measurements (length (L) and width (W)) were collected twice per week using digital calipers, and the tumor volume was calculated (L×W×W)/2.

Figure 19B:
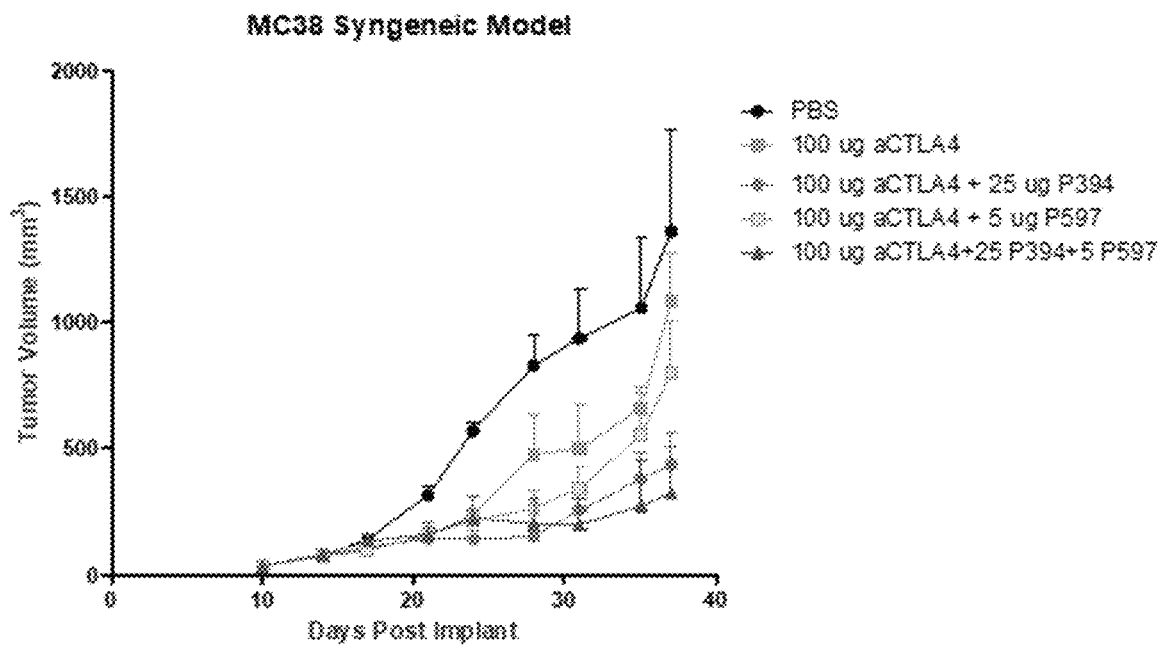

As shown in FIG. 19B, while anti-CTLA-4, anti-CTLA-4 with P394 and anti-CTLA-4 with P597 all reduce tumor growth, the triple combination of anti-CTLA-4 with P394 and P597 reduced tumor growth the most of all combinations tested.

Example 28. IL-21-Anti-HSA Fusion Protein and Anti-HSA-IL-15Ra-IL-15 Fusion Protein Alone or in Combination for Treating Cancer MC38 cells were cultured and maintained in DMEM media supplemented with 10% FBS+glutamax+NEAA+sodium pyruvate+Pen/Strep. Cells were trypsinized, washed with media, and counted. Cells were then washed with PBS, and 0.5×10⁶ cells (in 50 ul PBS) were injected subcutaneously into anesthetized C57BL/6 mice (Taconic) using an 18-gauge needle. Stock study drug was diluted to the appropriate concentration in PBS on the day of dosing, and animals were dosed IP with PBS, 25 µg P394 (human IL-21-anti-HSA), 5 µg P597 (anti-HSA-IL-15Ra-IL-15), or 25 µg P394 in combination with 5 µg P597 in 100 ul PBS twice per week for a total of 5 doses. Tumor measurements (length (L) and width (W)) were collected twice per week using digital calipers, and the tumor volume was calculated (L×W×W)/2.

Figure 20:
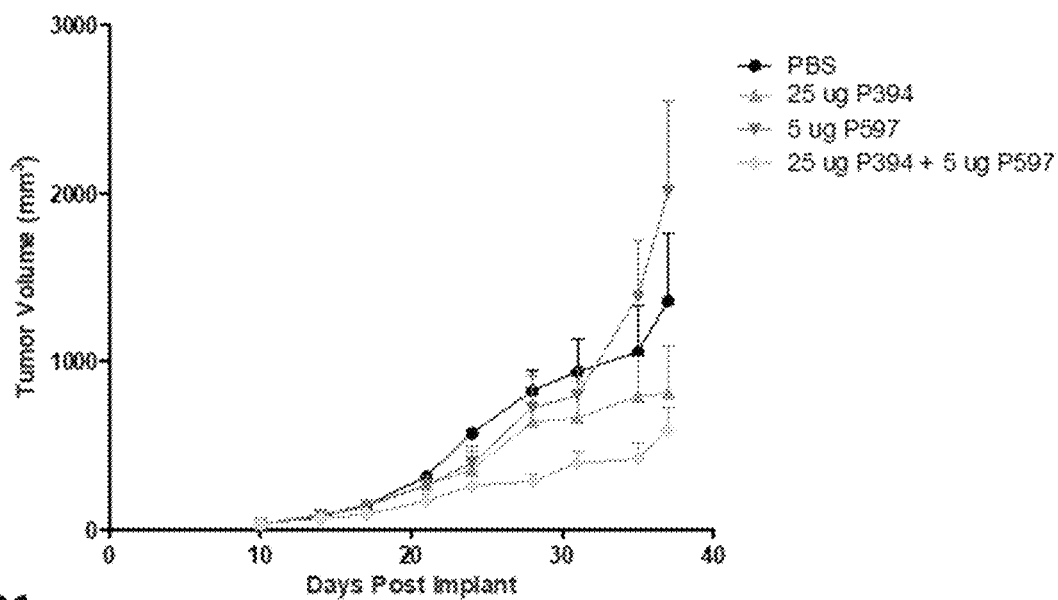
FIG. 20 depicts the change in tumor volume in an MC38 syngeneic mouse tumor model after treatment with IL-21-anti-HSA fusion protein (P394), anti-HSA-IL-15Ra/IL-15 fusion protein (P597) or a combination of these agents.

P394 and P597 monotherapy reduce tumor growth relative to PBS control. Combination therapy of P394 plus P597 reduces tumor growth further relative to P394 and P597 monotherapy (FIG. 20).

Example 29: In Vivo Antitumor Activity Assay in Syngeneic Mouse Model

MC38 murine colon cancer cells (3×10⁶ cells) were implanted subcutaneously into the flanks of C57BL/6 mice on day 0. On days 4, 8, 12 and 16, mice were treated with either PBS, 100 µg anti-PD-1, 25 µg P390 (mIL-21-anti-HSA), 100 µg anti-PD-1 and 25 µg P390, or 100 µg anti-PD-1 and 5 µg P390. Tumor size was measured using calipers on the indicated days and tumor volume calculated.

Figure 21:
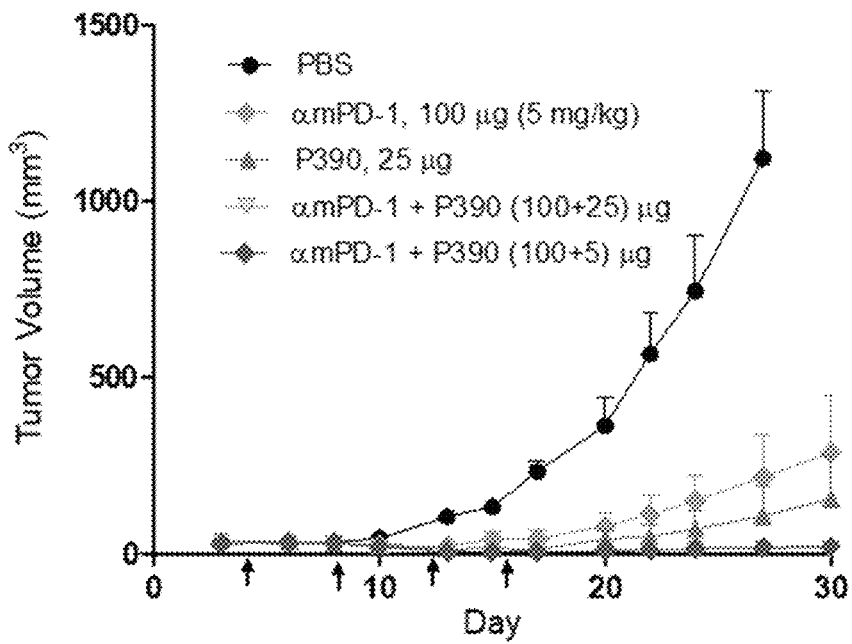
FIG. 21 depicts change of tumor volume in animal model of MC38 syngeneic model after treatment with a) 100 μg of anti-PD-1 antibody, b) 25 μg of P390, c) 100 μg of anti-PD-1 antibody and 25 μg of P390 or d) 100 μg of anti-PD-1 antibody and 5 μg of P390.

As shown in FIG. 21, Mouse IL-21-anti-HSA (P390) monotherapy significantly slows tumor growth. Combination of mouse IL-21-anti-HSA (P390) and anti-PD-1 eliminates or shrinks tumors in all mice.

Example 30: Anti-Mesothelin Antibodies and/or IL-21-Anti-HSA Fusion Protein in Treating Cancer NCI-N87 cells were cultured and maintained in RPMI media supplemented with 10% FBS+glutamax+Pen/Strep. Cells were trypsinized, washed with media, and counted. Cells were then washed with PBS, and 3×10⁶ cells (in 100 ul PBS) were injected subcutaneously into anesthetized NSG mice (Jackson) using a 23-gauge needle. After 6 days, 10×10⁶ human PBMCs were injected into the tail vein in 100 ul PBS per mouse. Stock study drug was diluted to the appropriate concentration in PBS on the day of dosing, and animals were dosed IP with 100 µg P303F (anti-mesothelin antibody), 25 µg P394 (human IL-21-anti-HSA) or a combination of 100 µg P303F with either 25 µg or 5 µg P394 twice per week for a total of 5 doses. Tumor measurements (length (L) and width (W)) were collected twice per week using digital calipers, and the tumor volume was calculated (L×W×W)/2.

Figure 22:
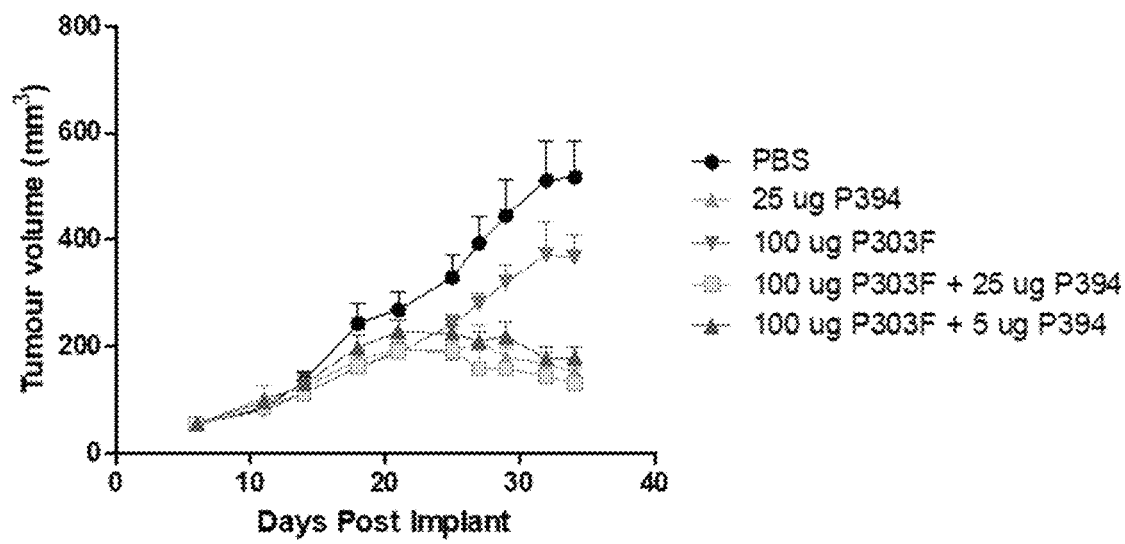
FIG. 22 depicts change of tumor volume in animal model of NSG mice with N87 tumors after treatment with a) 25 μg of P394, b) 100 μg of P303F, c) 100 μg of P303F and 25 μg of P394, or d) 100 μg of P303F and 5 μg of P394.

As shown in FIG. 22. P303F reduces tumor growth relative to the control. All mice receiving P394 alone or in combination with P303F had significantly reduced tumor growth relative to PBS control or P303F alone.

Example 31: IL-21-Anti-HSA Fusion Protein Alone or in Combination with Herceptin for Treating Cancer NCI-N87 cells were cultured and maintained in RPMI media supplemented with 10% FBS+glutamax+Pen/Strep. Cells were trypsinized, washed with media, and counted. Cells were then washed with PBS, and 3×10⁶ cells (in 100 ul PBS) were injected subcutaneously into anesthetized NSG mice (Jackson) using a 23-gauge needle. After 6 days, 10×10⁶ human PBMCs were injected into the tail vein in 100 ul PBS per mouse. Stock study drug was diluted to the appropriate concentration in PBS on the day of dosing, and animals were dosed IP with 20 µg Herceptin (anti-HER2 antibody), 25 µg P394 (human IL-21-anti-HSA) or a combination of 20 µg Herceptin with either 25 µg or 5 µg P394 twice per week for a total of 5 doses. Tumor measurements (length (L) and width (W)) were collected twice per week using digital calipers, and the tumor volume was calculated (L×W×W)/2.

Figure 23:
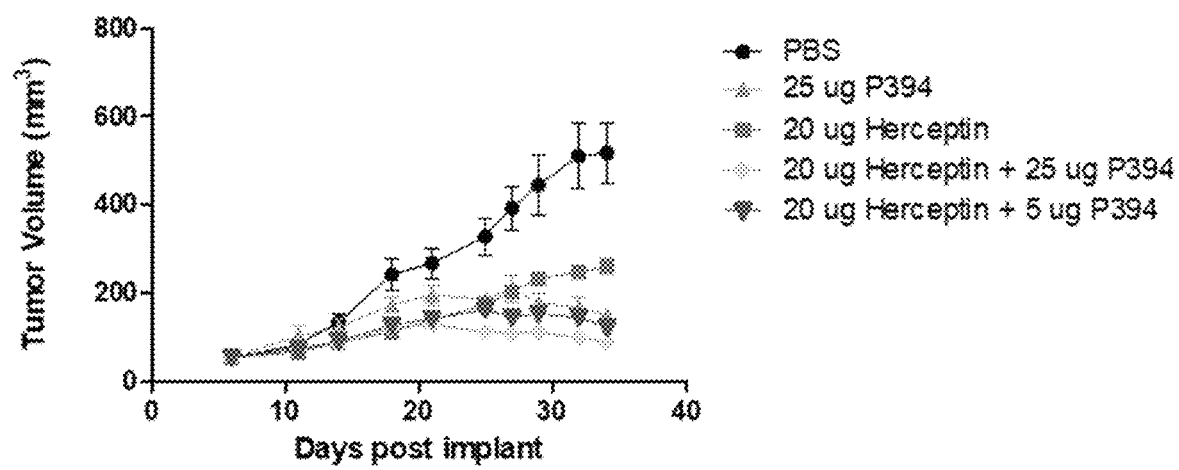
FIG. 23 depicts change of tumor volume in animal model of NSG mice with N87 tumors after treatment with a) 25 μg of P394, b) 20 μg of Herceptin, c) 20 μg of Herceptin and 25 μg of P394, or d) 20 μg of Herceptin and 5 μg of P394.

As shown in FIG. 23, Herceptin and 25 µg P394 monotherapy reduced tumor growth relative to PBS control. Combination of Herceptin and 25 µg P394 further reduces tumor growth compared to Herceptin or P394 monotherapy showing an additive anti-tumor effect.

Example 32: Anti-Mesothelin Antibodies and/or IL-21-Anti-HSA Fusion Proteins in Treating Cancer NCI-N87 cells were cultured and maintained in RPMI media supplemented with 10% FBS+glutamax+Pen/Strep. Cells were trypsinized, washed with media, and counted. Cells were then washed with PBS, and 3×10⁶ cells (in 100 ul PBS) were injected subcutaneously into anesthetized SCID mice (Taconic) using an 18-gauge needle. Stock study drug was diluted to the appropriate concentration in PBS on the day of dosing, and animals were dosed IP with 100 µg P303F (anti-mesothelin antibody) or P303F in combination with 25 µg P390 (mouse IL-21-anti-HSA), 5 µg P390, or 2.5 µg recombinant mouse IL-21 (equivalent molarity to the 5 µg P390 dose) in 100 ul PBS twice per week for a total of 5 doses. Tumor measurements (length (L) and width (W)) were collected twice per week using digital calipers, and the tumor volume was calculated (L×W×W)/2.

Figure 24:
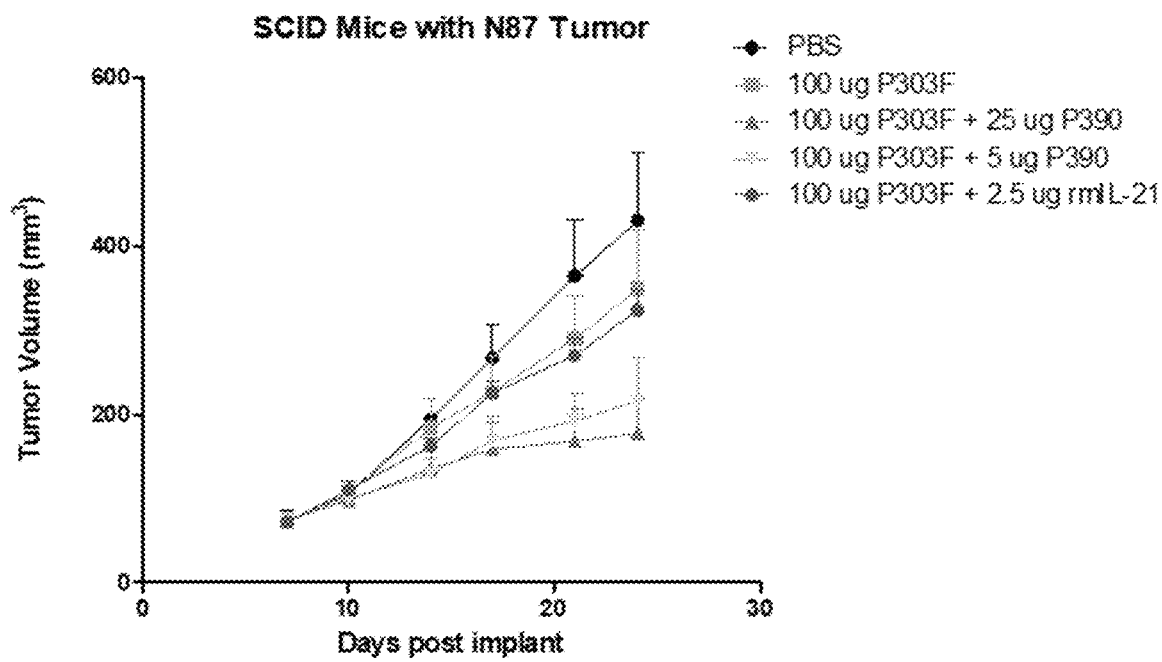
FIG. 24 depicts change of tumor volume in animal model of SCID mice with N87 tumors after treatment with 100 μg of P303F alone or in combination with a) 25 μg of P390 b) 5 μg of P390, or c) 2.5 μg of rmIL-21.

As shown in FIG. 24, the combination of P303F and 25 µg or 5 µg P390 resulted in significantly reduced tumor growth compared to PBS control, P303F monotherapy and P303F combined with rmIL-21. P303F with 2.5 µg rmIL-21 showed similar tumor growth as P303F suggesting that recombinant IL-21 is not efficacious at this dose. The combination of P303F with 5 µg P390 shows significantly reduced tumor growth compared to P303F with 2.5 µg rmIL-21, highlighting the improved efficacy of half-life extended IL-21 compared to the recombinant cytokine.

Example 33: IL-21-Anti-HSA Fusion Protein in Treating Cancer

MC38 murine colon cancer cells ($1\times10^6$ cells) were implanted subcutaneously into the flanks of C57BL/6 mice on day 0. Mice were treated with either PBS, 25 µg P390 (mouse IL-21-anti-HSA) or recombinant mouse IL-21 twice per week for 2 weeks (4 total doses). Tumor measurements (length (L) and width (W)) were collected three times per week using digital calipers, and the tumor volume was calculated (L×W×W)/2.

Figure 25:
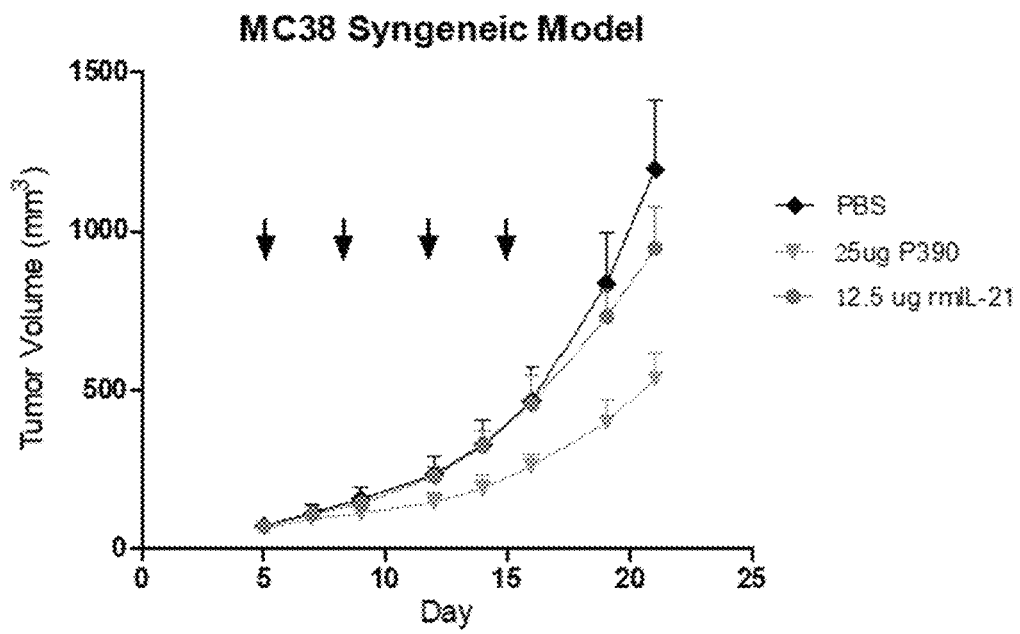
FIG. 25 depicts change of tumor volume in animal model of MC38 syngeneic model after treatment of 25 μg of P390 or 12.5 μg of rmIL-21.

As shown in FIG. 25, P390 (mouse IL-21-anti-HSA) reduces tumor growth in MC38 tumors compared to PBS control, but 12.5 µg recombinant mouse IL-21, a molar equivalent, has minimal effect on tumor growth relative to PBS control. IL-21-anti-HSA (P390) has superior anti-tumor efficacy relative to recombinant IL-21 in a syngeneic mouse colon cancer model.

Example 34: IL-21-Anti-HSA Fusion Protein in Combination with Anti-PD-1 Antibody for Treating Cancer CT26 mouse cells transfected with human mesothelin (CT26/MSLN) were cultured and maintained in RPMI media supplemented with 10% FBS+glutamax+Pen/Strep. Cells were trypsinized, washed with media, and counted. Cells were then washed with PBS, and $1\times10^6$ cells (in 100 ul PBS) were injected subcutaneously into anesthetized BALB/c mice using a 23-gauge needle. Stock study drug was diluted to the appropriate concentration in PBS on the day of dosing, and animals were dosed IP with 5 mg/kg anti-PD-1 antibody. 1.25 mg/kg P390 (mouse IL-21-anti-HSA) or a combination of anti-PD-1 with P390 twice per week for a total of 4 doses. Tumor measurements (length (L) and width (W)) were collected twice per week using digital calipers, and the tumor volume was calculated (L×W×W)/2.

Figure 26:
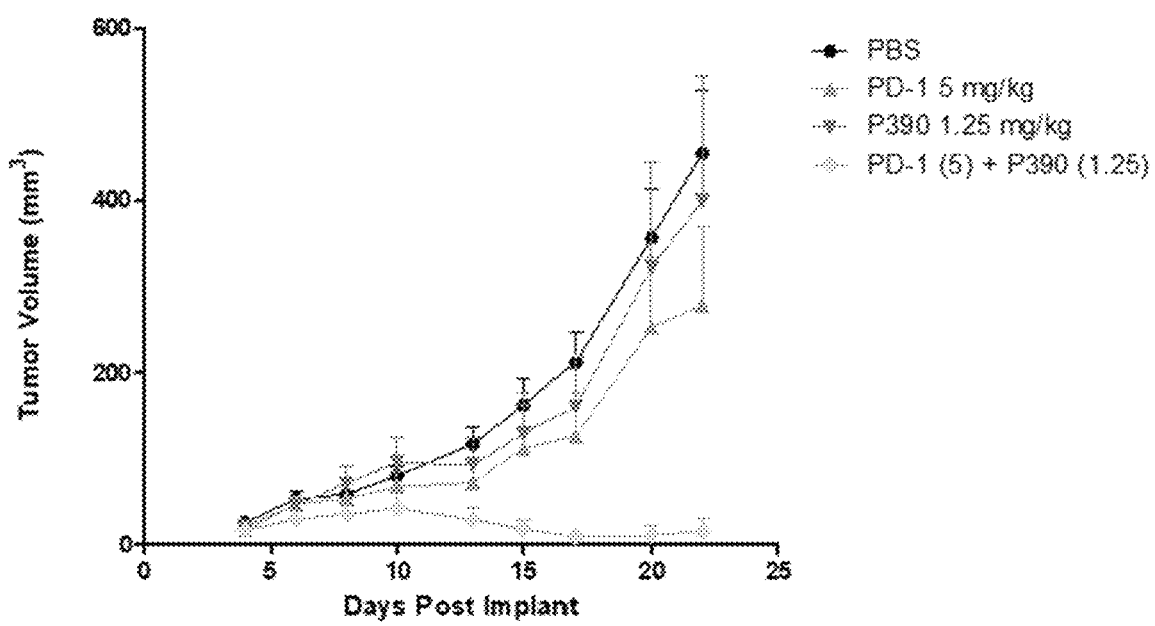
FIG. 26 depicts change of tumor volume in animal model of CT-26/MSLN after treatment of anti-PD-1 antibody alone, P390 alone, or a combination of anti-PD-1 antibody and P390.

As shown in FIG. 26, anti-PD-1 and P390 monotherapy have minimal effect on tumor growth relative to PBS control. The combination of anti-PD-1 and P390 results in a synergistic reduction in tumor growth with 4/5 mice having no measurable tumor by day 22.

Example 35: IL-21-Anti-HSA Fusion Protein in Combination with Anti-PD-1 Antibody for Treating Cancer MC38 cells were cultured and maintained in DMEM media supplemented with 10% FBS+glutamax+NEAA+sodium pyruvate+Pen/Strep. Cells were trypsinized, washed with media, and counted. Cells were then washed with PBS, and $0.5\times10^6$ cells (in 50 ul PBS) were injected subcutaneously into anesthetized C57BL/6 mice (Taconic) using an 18-gauge needle. Stock study drug was diluted to the appropriate concentration in PBS on the day of dosing, and animals were dosed IP with PBS, 100 µg anti-PD-1 antibody, 25 µg P394 (human IL-21-anti-HSA) or 100 µg anti-PD-1 in combination with 25 µg P394 in 100 ul PBS twice per week for a total of 5 doses. Tumor measurements (length (L) and width (W)) were collected twice per week using digital calipers, and the tumor volume was calculated (L×W×W)/2.

Figure 27:
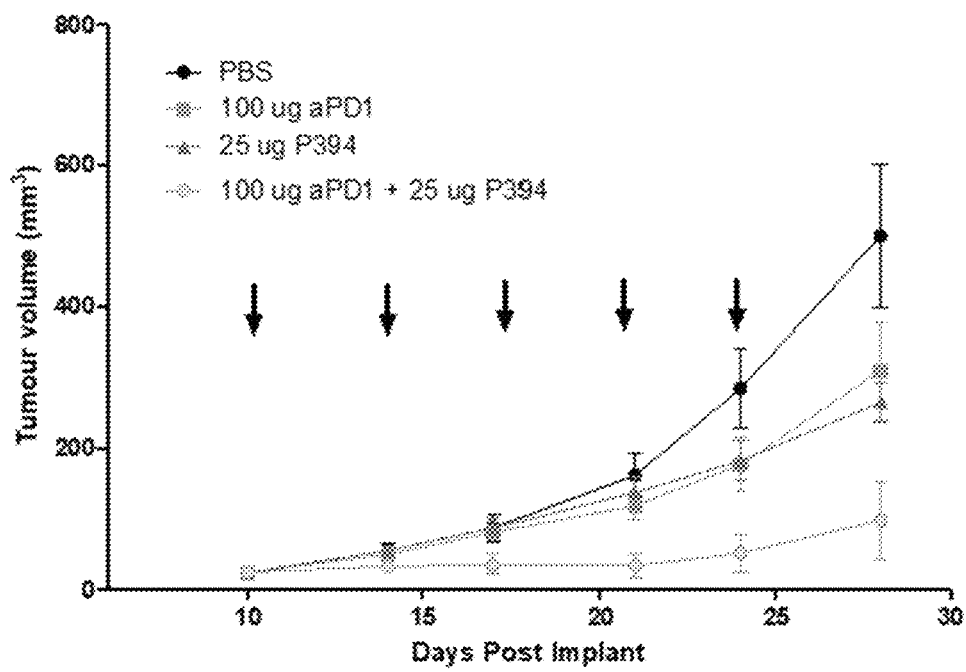
FIG. 27 depicts change of tumor volume in animal model of MC38 syngeneic model after treatment of anti-PD-1 antibody alone, P394 alone, or a combination of anti-PD-1 antibody and P394.

As shown in FIG. 27, combination of IL-21-anti-HSA (P394) with anti-PD-1 antibody reduces tumor growth better than either monotherapy in a syngeneic mouse colon cancer model.

Example 36: Pharmacokinetic Evaluation of IL-21-Anti-HSA Fusion Proteins

MC38 murine colon cancer cells ($1\times10^6$ cells) were implanted subcutaneously into the flanks of C57BL/6 mice on day 0. Mice were treated with either PBS or 25 µg P380 (anti-HSA-human IL-33) for 2 weeks (4 total doses). Tumor measurements (length (L) and width (W)) were collected three times per week using digital calipers, and the tumor volume was calculated (L×W×W)/2.

Figure 28:
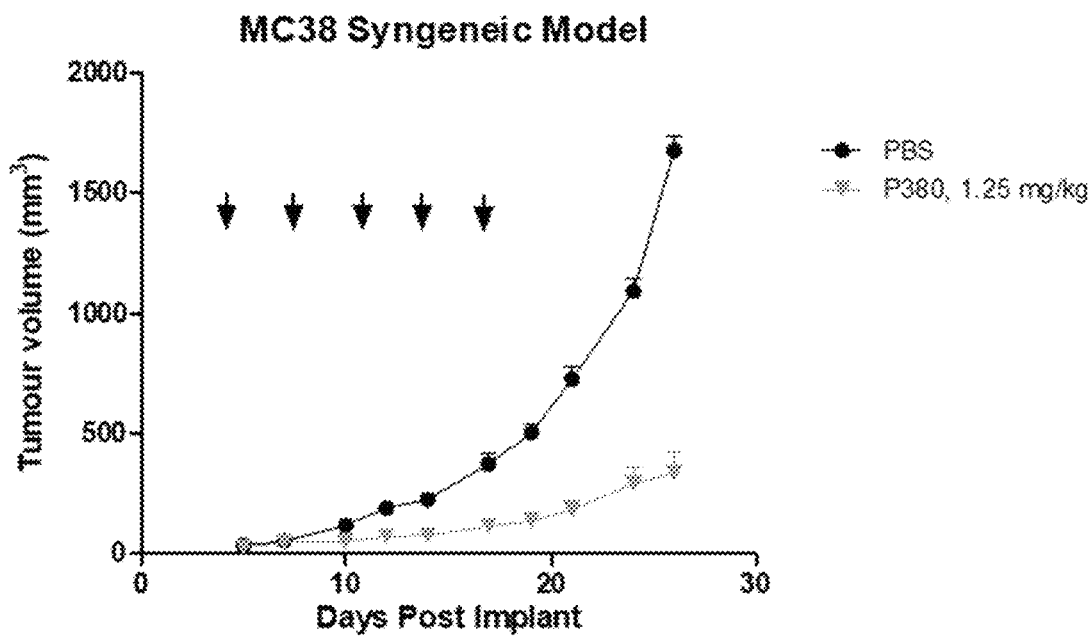
FIG. 28 depicts change in tumor volume in mouse MC38 syngeneic tumor model after treatment with anti-HSA-IL-33 fusion protein (P380).

As shown in FIG. 28, treatment with extended half-life IL-33 reduced tumor growth relative to PBS control.

Example 37: Impact of IL-21-Anti-HSA Fusion Protein on Granzyme B Positive NK Cells and CD8 T Cells MC38 murine colon cancer cells ($1\times10^6$ cells) were implanted subcutaneously into the flanks of C57BL/6 mice on day 0. Mice were treated with either PBS, 100 µg anti-PD-1, 25 µg P390 (mouse IL-21-anti-HSA) or 100 µg anti-PD-1+25 µg P390 twice per week starting on day 5 for a total of 5 doses. On day 24, mice were sacrificed and tumors were excised. Tumors were homogenized to release the cells, and the cells were stained for CD45, CD8, NK1.1 and granzyme B. The percentage of granzyme B positive cells among CD8 T cells and NK cells is plotted.

Figure 29A:
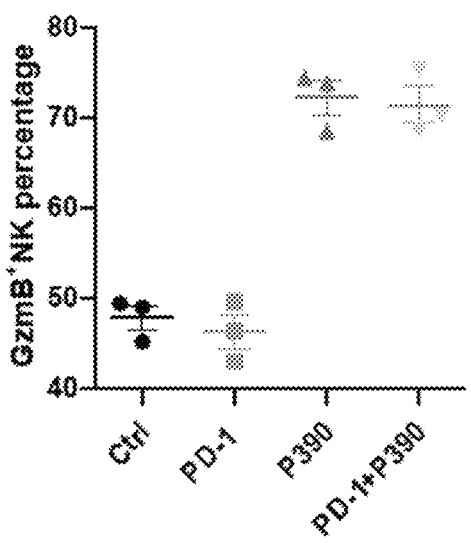
FIGS. 29A-29B depicts percentage change of granzyme B positive NK cells (FIG. 29A) and CD8 T cells (FIG. 29B) after treatment with P390.
Figure 29B:
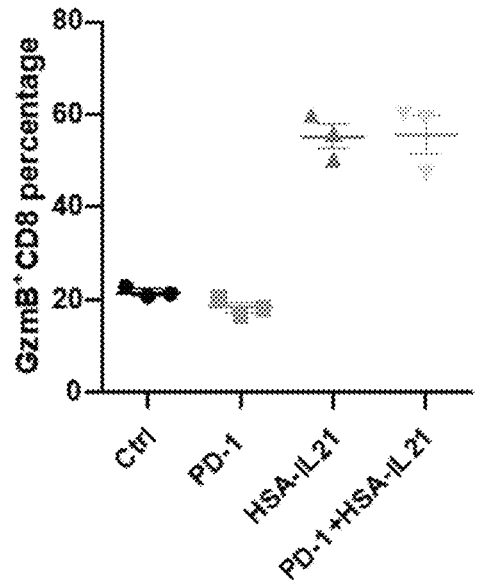

As shown in FIGS. 29A-29B, P390 treatment increases the percentage of granzyme B positive CD8 T cells and NK cells.

Example 38: Impact of a Combined Use of IL-21-Anti-HSA Fusion Protein and Anti-PD-1 Antibody on the Expression of IL-21 Receptor MC38 murine colon cancer cells ($1\times10^6$ cells) were implanted subcutaneously into the flanks of C57BL/6 mice on day 0. Mice were treated with either PBS, 100 µg anti-PD-1, 25 µg P390 (mouse IL-21-anti-HSA) or 100 µg anti-PD-1+25 µg P390 twice per week starting on day 5 for a total of 5 doses. On day 24, mice were sacrificed, and tumors were excised. Tumors were homogenized to release the cells, and the cells were stained for CD45, CD8, CD4, NK1.1 and IL-21R. The percentage of IL-21R positive cells among CD4 T cells, CD8 T cells and NK cells is plotted.

Figure 30A:
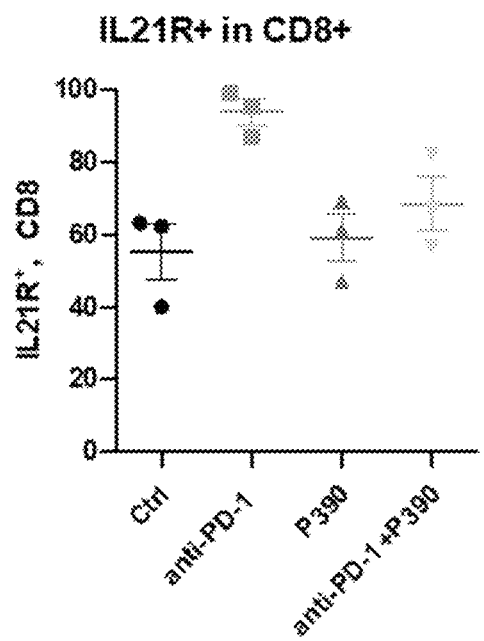
FIGS. 30A-30C depicts change of expression levels of IL-21 receptor in CD8 T cells (FIG. 32A), CD4 T cell (FIG. 32B) and NK cells (FIG. 32C) after treatment with anti-PD-1 antibody alone or anti-PD-1 antibody in combination with P390.
Figure 30B:
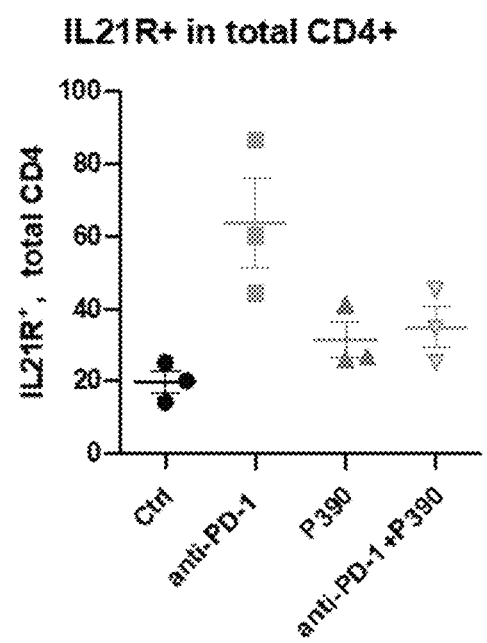
Figure 30C:
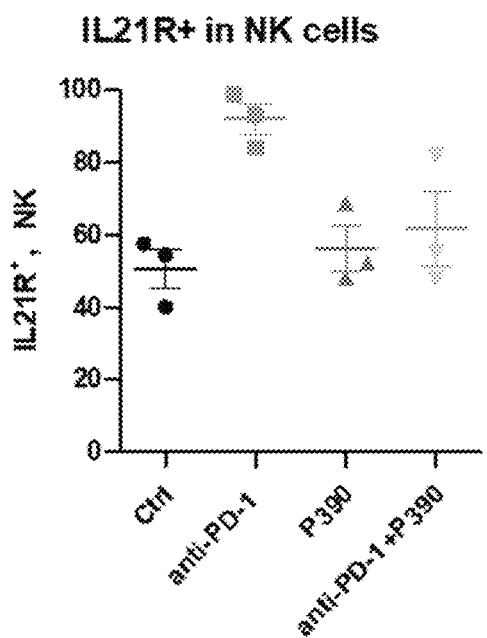

As shown in FIGS. 30A-30C, treatment with anti-PD-1 antibody increases expression of IL-21 receptor in CD4 T cells, CD8 T cells and NK cells, and treatment with P390 (mouse IL-21-anti-HSA) in combination with anti-PD-1 reduces IL-21 receptor expression.

Example 39: Impact of IL-21-Anti-HSA Fusion Protein on IFN-Gamma Secreting Immune Cells MC38 murine colon cancer cells ($1\times10^6$ cells) were implanted subcutaneously into the flanks of C57BL/6 mice on day 0). Mice were treated with either PBS, 100 µg anti-PD-1, 25 µg P390 (mouse IL-21-anti-HSA) or 100 µg anti-PD-1+25 µg P390 twice per week starting on day 5 for a total of 5 doses. On day 24, mice were sacrificed, and mouse spleens were removed. Spleens were homogenized to release the splenocytes, and the splenocytes were placed in an IFN-γ ELISpot assay with fresh MC38 cells. The ELISpot assay was run according to manufacturer's instructions, and the number of IFN-g spots, representing the number of MC38 responsive immune cells, were counted.

Figure 31:
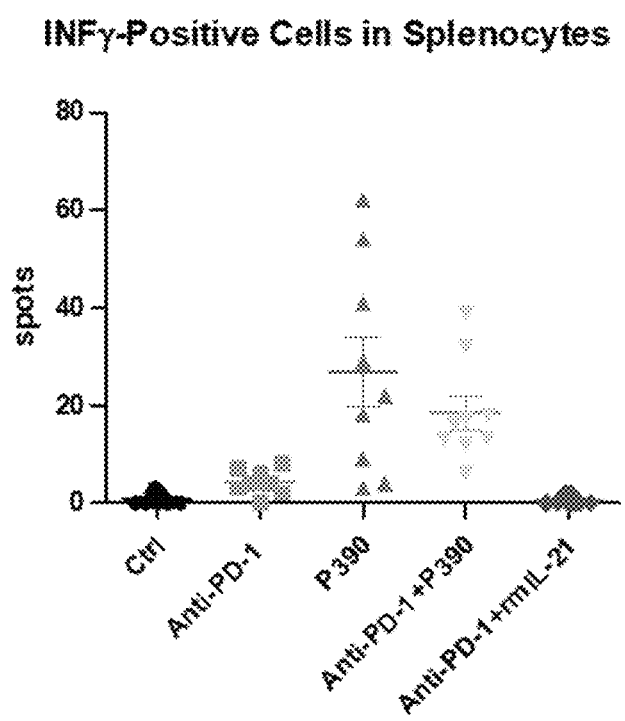
FIG. 31 depicts cell number of IFN-gamma secreting immune cells in spleen after treatment with anti-PD-1 antibody alone, P390 alone, a combination of anti-PD-1 antibody and P390, or a combination of anti-PD-1 antibody and rmIL-21.

As shown in FIG. 31, treatment with extended half life IL-21 results in increased number of tumor reactive, IFN-γ secreting immune cells in the spleen.

Example 40: Fusion of Extended Half-Life IL-21 with Anti-MSLN Antibody

CT26 mouse cells transfected with human mesothelin (CT26/MSLN) were cultured and maintained in RPMI media supplemented with 10% FBS+glutamax+Pen/Strep. Cells were trypsinized, washed with media, and counted. Cells were then washed with PBS, and 1×10$^6$ cells (in 100 ul PBS) were injected subcutaneously into anesthetized BALB/c mice using a 23-gauge needle. Stock study drug was diluted to the appropriate concentration in PBS on the day of dosing, and animals were dosed with 1.25 mg/kg (100 ul) P375 (IL-21-anti-albumin-anti-MSLN) IP twice per week for a total of 5 doses. Tumor measurements (length (L) and width (W)) were collected twice per week using digital calipers, and the tumor volume was calculated (L×W×W)/2.

Figure 32:
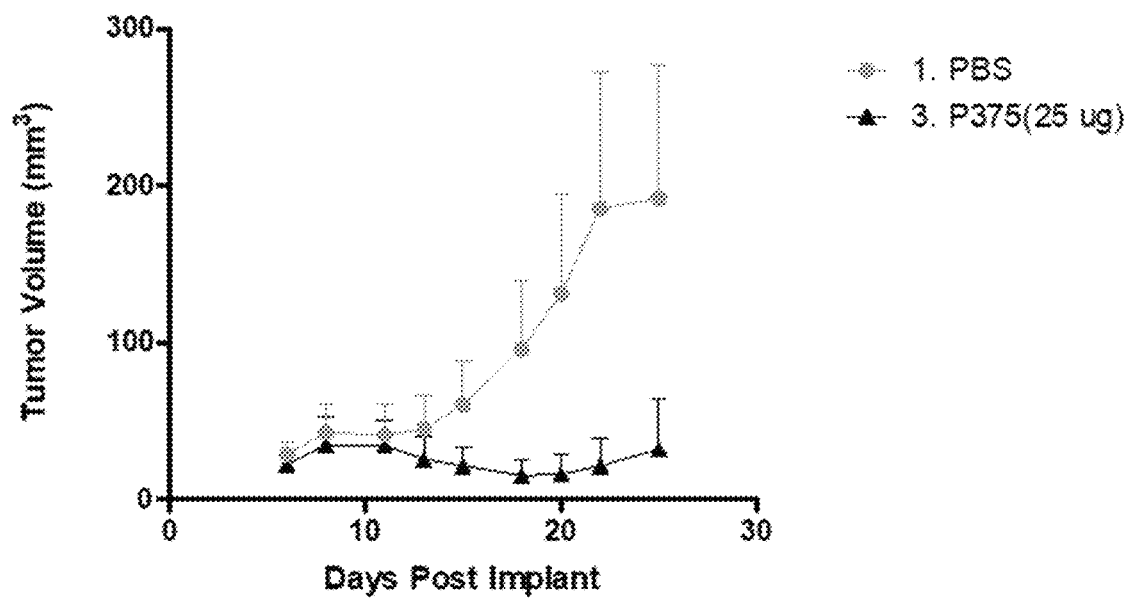
FIG. 32 depicts change in tumor volume in mouse syngeneic CT26/MSLN tumor model using IL-21-anti-HSA-anti-MSLN fusion protein (P375).

As shown in FIG. 32, the IL-21-anti-albumin-anti-MSLN fusion protein (P375) was able to reduce tumor growth relative to PBS control.

Example 41: Fusion of Extended Half-Life IL-15Ra/IL-15 with Anti-MSLN Antibody NCI-N87 cells were cultured and maintained in RPMI media supplemented with 10% FBS+glutamax+Pen/Strep. Cells were trypsinized, washed with media, and counted. Cells were then washed with PBS, and 3×10$^6$ cells (in 100 ul PBS) were injected subcutaneously into anesthetized NSG mice (Jackson) using a 23-gauge needle. After 6 days, 10×10$^6$ human PBMCs were injected into the tail vein in 100 ul PBS per mouse. Stock study drug P197 was diluted to the appropriate concentration in PBS on the day of dosing, and animals were dosed with 0.25 mg/kg (100 ul) P669 (anti-MSLN-anti-albumin-IL-15Ra-IL-15) IP twice per week for a total of 5 doses. Tumor measurements (length (L) and width (W)) were collected twice per week using digital calipers, and the tumor volume was calculated (L×W×W)/2.

Figure 33:
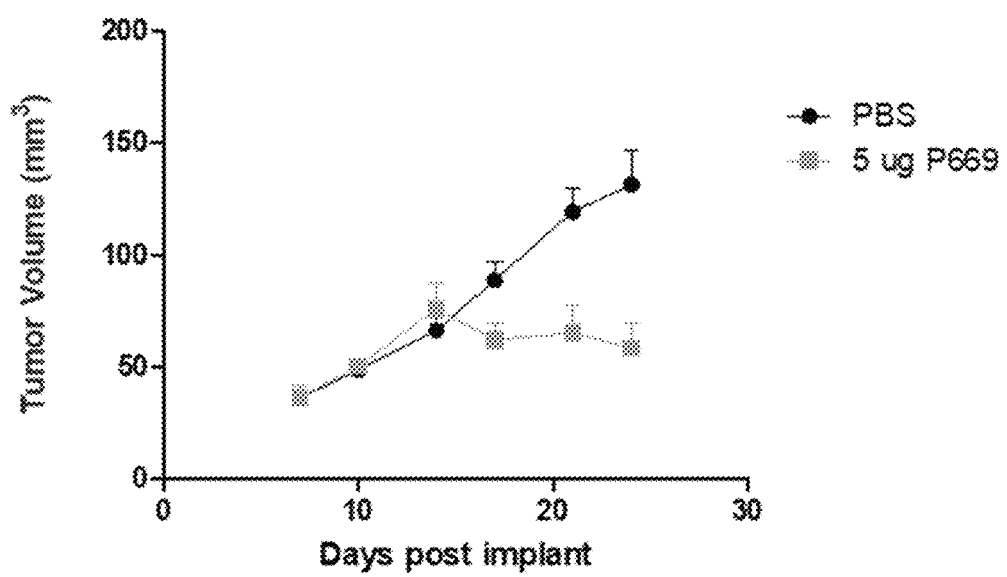
FIG. 33 depicts change of tumor volume in animal model of NSG mice with N87 tumors after treatment with anti-MSLN-anti-HSA-IL-15Rα/IL15 fusion protein (P669).

As shown in FIG. 33, the anti-MSLN-anti-albumin-IL-15Ra-IL-15 fusion protein (P669) was able to reduce tumor growth relative to PBS control.

Example 42

Pfeiffer cells were maintained in RPMI-1640 containing 10% fetal bovine serum and penicillin/streptomycin. 100,000 Pfeiffer cells were treated with the indicated concentration of recombinant human P394 (IL-21-(GSG) 4 (SEQ ID NO: 12)-HSA), P593 (IL21-A (EAAAK) 4A (SEQ ID NO: 24)-HAS), P795 (IL21 [1-122]-(GSG) 4 (SEQ ID NO: 12)-HSA), P796 (IL21|1-122|-(G4S) 3 (SEQ ID NO: 14)-HSA), P797 (IL21 [1-122]-HSA), P799 (IL21 [1-122]-VLLC (SEQ ID NO: 17)-HSA), P800 (IL21 [1-122]-VHCHI (SEQ ID NO: 158)-HSA), P750 (IL21-(GSG) 4 (SEQ ID NO: 12)-HSA), P751 (IL21-A (EAAAK) 4A (SEQ ID NO: 24)-HSA), or P744 (IL21 [1-122]-A (EAAAK) 4A (SEQ ID NO: 24)-HSA) for 30 minutes at 37 C, 5% $CO_2$ in Hanks Balanced Salt Solution containing 10 mM HEPES. Phospho-STAT3 was measured using a phospho-STAT3 (Tyr705) homogeneous time resolved fluorescence (HTRF) assay (Cisbio) according to the manufacturer's instructions. The signal ratio of 665 nm/620 nm was multiplied by 1000, plotted and fit using a dose response curve (Graphpad Prism) to calculate the EC50.

Figure 34:
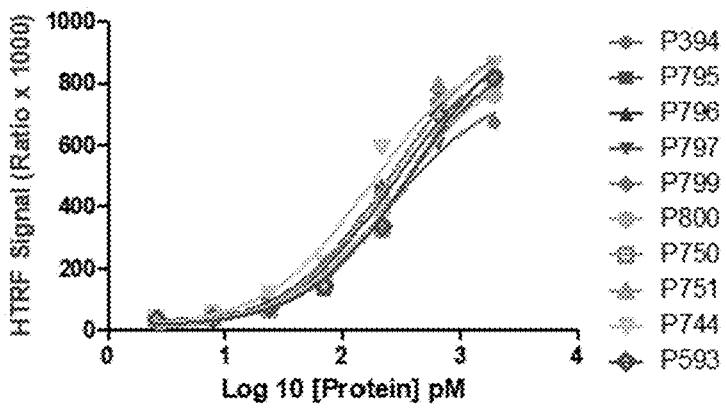
FIG. 34 depicts various IL-21 fusion proteins have similar signaling potency.

As shown in FIG. 34, all IL-21 fusion proteins tested have similar ADCC activity.

Example 43

NCI-N87 cancer cell lines were maintained in RPMI-1640 containing 10% fetal bovine serum and penicillin/streptomycin. On day 0, 10,000 NCI-N87 cells/well were plated in culture medium in a 96-well flat bottom plate. On day 1, NK cells were isolated from human buffy coat using RosetteSep NK Isolation kit (Stemcell Technologies), and 100,000 NK cells/well were added to the cancer cells together with the indicated treatment. Plates were incubated for 48 hrs at 37 C, 5% $CO_2$, and cells were then fixed with 4% paraformaldehyde and nuclei stained with Sytox Orange. The number of remaining cancer cells was calculated by counting the number of cancer cell nuclei remaining in each well using the Cytation 1™ (Biotek). Lower cell counts indicated better NK mediated cell killing. (P593 (IL21-A (EAAAK) 4A (SEQ ID NO: 24)-HAS), P795 (IL21[1-122]-(GSG) 4 (SEQ ID NO: 12)-HSA), P796 (IL21 [1-122]-(G4S) 3 (SEQ ID NO: 14)-HSA), P797 (IL21[1-122]-HSA), P799 (IL21[1-122]-VLLC (SEQ ID NO: 17)-HSA), P800 (IL21[1-122]-VHCH1 (SEQ ID NO: 158)-HSA), P750 (IL21-(GSG) 4 (SEQ ID NO: 12)-HSA), P751 (IL21-A (EAAAK) 4A (SEQ ID NO: 24)-HSA), or P744 (IL21[1-122]-A (EAAAK) 4A (SEQ ID NO: 24)-HSA)).

Figure 35:
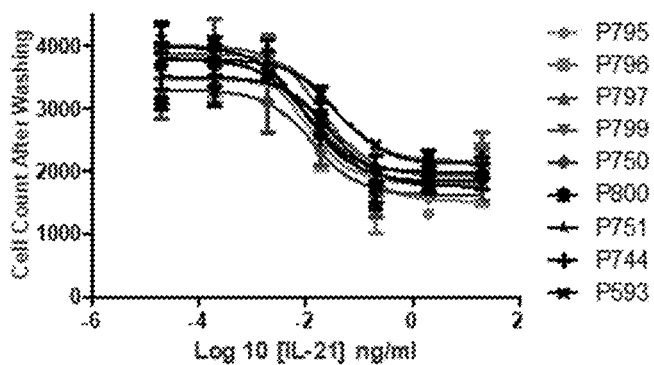
FIG. 35 depicts various IL-21 fusion proteins have similar ADCC activity.

As shown in FIG. 35, all IL-21 fusion proteins tested have similar ADCC activity.

SEQUENCE TABLE

| SEQ ID NO | Description | Amino acid sequence (CDR sequences are underlined and bold) |
|---|---|---|
| 1. | Human IL21 full length | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHLSSRTHGSE DS |
| 2. | Human IL21 truncated (1-123) | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHL |
| 3. | G148-ABD-wt | LAEAKVLANRELDKYGVSDYYKNLINNAKTVEGVKALIDEILA ALP |

-continued

SEQUENCE TABLE

| SEQ ID NO | Description | Amino acid sequence (CDR sequences are underlined and bold) |
|---|---|---|
| 4. | LI-ABD-1 | LAEAKVLANRELDKYGVSDFAKRLINKAKTVEGVEALKDEILAALP |
| 5. | LI-ABD-2 | LAEAKVLANRELDKYGVSDFAKRAINKAKTVEGVEALKDEILAALP |
| 6. | LI-ABD-3 | LAEAKVLANRELDKYGVSDFAKRAINKAKTVEGAEALKDEILAALP |
| 7. | ABD-035 | LAEAKVLANRELDKYGVSDFYKRLINKAKTVEGVEALKHILAALP |
| 8. | ABD$_{Y21A}$ | LAEAKVLANRELDKYGVSDYAKNLINNAKTVEGVKALIDEILAALP |
| 9. | ABD$_{S18Y20K22A}$ | LAEAKVLANRELDKYGVADAYANLINNAKTVEGVKALIDEILAALP |
| 10. | ABDcon | LKEAKEKAIEELKKAGITSDYYFDLINKAKTVEGVNALKDEILKA |
| 11. | ABDcon12 | TIDEWLLKEAKEKAIEELKKAGITSDYYFDLINKAKTVEGVNALKDEILKA |
| 12. | GSG linker, n = 2-6 | (GSG)n |
| 13. | G3S linker, n = 1-6 | (G3S)n |
| 14. | G4S linker, n = 1-6 | (G4S)n |
| 15. | EAAAK linker, n = 1-6 | (EAAAK)n |
| 16. | PAPAP linker, n = 1-6 | (PAPAP)n |
| 17. | VLVH. Linker | IKRTVAAP |
| 18. | SIRPα linker | RAKPS |
| 19. | GSGS Linker, | (GSGS)n (n = 1-4) |
| 20. | GGSG Linker | (GGSG)n (n = 1-4) |
| 21. | PAPA Linker | (PAPA)n (n = 1-3) |
| 22. | PQPQ Linker | (PQPQ)n (n = 1-3) |
| 23. | VL-CL Native Linker | IKRADAAP |
| 24. | Helix-forming Linker | A(EAAAK)nA (n = 1-6) |
| 25. | Dromedary IgG3 hinge | GTNEVCKCPKCP |
| 26. | Dromedary IgG2a hinge | EPKIPQPQPKPQPQPQPKPQPKPEPECTCPKCP |
| 27. | F2A (cleavable) | RRKRAPVKQTLNFDLLKLAGDVESNPGP |
| 28. | UPA linker (cleavable) | SGRSA |
| 29. | MMP linker (cleavable) | PVGLIG |
| 30. | Cleavable linker | Lys-Gly-Pro-Gln-Gly-Ile-Ala-Gly-Gln |

-continued

SEQUENCE TABLE

| SEQ ID NO | Description | Amino acid sequence (CDR sequences are underlined and bold) |
|---|---|---|
| 31. | Cleavable linker | Phe-Gly-Pro-Gln-Gly-Leu-Ala-Gly-Gln |
| 32. | Cleavable linker | Arg-Gly-Pro-Gln-Gly-Ile-Phe-Gly-Gln |
| 33. | Cleavable linker | Ile-Gly-Pro-Gln-Gly-Ile-Trp-Gly-Gln |
| 34. | Cleavable linker | Met-Gly-Pro-Gln-Gly-Ile-Leu-Gly-Gln |
| 35. | Cleavable linker | Lys-Gly-Pro-Gln-Ser-Ile-Ala-Gly-Gln |
| 36. | Cleavable linker | Phe-Gly-Pro-Gln-Ser-Leu-Ala-Gly-Gln |
| 37. | Cleavable linker | Arg-Gly-Pro-Gln-Ser-Ile-Phe-Gly-Gln |
| 38. | Cleavable linker | Ile-Gly-Pro-Gln-Ser-Ile-Trp-Gly-Gln |
| 39. | Cleavable linker | Met-Gly-Pro-Gln-Ser-Ile-Leu-Gly-Gln |
| 40. | Cleavable linker | Lys-Gly-Pro-Gln-Thr-Ile-Ala-Gly-Gln |
| 41. | Cleavable linker | Phe-Gly-Pro-Gln-Thr-Leu-Ala-Gly-Gln |
| 42. | Cleavable linker | Arg-Gly-Pro-Gln-Thr-Ile-Phe-Gly-Gln |
| 43. | Cleavable linker | Ile-Gly-Pro-Gln-Thr-Ile-Trp-Gly-Gln |
| 44. | Cleavable linker | Phe-Arg-Pro-Arg-Ser-Ile-Thr-Gly-Gln |
| 45. | Cleavable linker | Met-Gly-Pro-Gln-Thr-Ile-Leu-Gly-Gln |
| 46. | P197/R2G12 CDR1 (IMGT) | GITFPVNA |
| 47. | P197/R2G12 CDR2 (IMGT) | ISAGGTT |
| 48. | P197/R2G12 CDR3 (IMGT) | QRRIGMLRDY |
| 49. | R3C7/P303 CDR1 (IMGT) | GRTLESYV |
| 50. | R3C7/P303 CDR2 (IMGT) | INWSSGRL |
| 51. | MSLN antigen 2 | VQKLLGPHVEGLKAEERHRPVRDWILRQRQDDLDTLGLGLQGGIPNG YLV |
| 52. | HSA isoform 1 | MKWVTFISLLFLFSSAYSRGVFRRDAHKSEVAHRFKDLGEENF KALVLIAFAQYLQQCPFEDHVKLVNEVTEFAKTCVADESAENC DKSLHTLFGDKLCTVATLRETYGEMADCCAKQEPERNECFLQH KDDNPNLPRLVRPEVDVMCTAFHDNEETFLKKYLYEIARRHPY FYAPELLFFAKRYKAAFTECCQAADKAACLLPKLDELRDEGKA SSAKQRLKCASLQKFGERAFKAWAVARLSQRFPKAEFAEVSKL VTDLTKVHTECCHGDLLECADDRADLAKYICENQDSISSKLKE CCEKPLLEKSHCIAEVENDEMPADLPSLAADFVESKDVCKNYA EAKDVFLGMFLYEYARRHPDYSVVLLLRLAKTYETTLEKCCA AADPHECYAKVFDEFKPLVEEPQNLIKQNCELFEQLGEYKFQN ALLVRYTKKVPQVSTPTLVEVSRNLGKVGSKCCKHPEAKRMP CAEDYLSVVLNQLCVLHEKTPVSDRVTKCCTESLVNRRPCFSA LEVDETYVPKEFNAETFTFHADICTLSEKERQIKKQTALVELVK HKPKATKEQLKAVMDDFAAFVEKCCKADDKETCFAEEGKKLV AASQAALGL |
| 53. | HSA isoform 2 | MKWVTFISLLFLFSSAYSRGVFRRDAHKSEVAHRFKDLGEENF KAWAVARLSQRFPKAEFAEVSKLVTDLTKVHTECCHGDLLEC ADDRADLAKYICENQDSISSKLKECCEKPLLEKSHCIAEVENDE MPADLPSLAADFVESKDVCKNYAEAKDVFLGMFLYEYARRHP DYSVVLLLRLAKTYETTLEKCCAAADPHECYAKVFDEFKPLVE EPQNLIKQNCELFEQLGEYKFQNALLVRYTKKVPQVSTPTLVE VSRNLGKVGSKCCKHPEAKRMPCAEDYLSVVLNQLCVLHEKT PVSDRVTKCCTESLVNRRPCFSALEVDETYVPKEFNAETFTFHA DICTLSEKERQIKKQTALVELVKHKPKATKEQLKAVMDDFAAF VEKCCKADDKETCFAEEGKKLVAASQAALGL |

SEQUENCE TABLE

| SEQ ID NO | Description | Amino acid sequence (CDR sequences are underlined and bold) |
|---|---|---|
| 54. | HSA isoform 3 | MKWVTFISLLFLFSSAYSRGVFRRDAHKSEVAHRFKDLGEENF KALVLIAFAQYLQQCPFEDHVKLVNEVTEFAKTCVADESAENC DKSLHTLFGDKLCTVATLRETYGEMADCCAKQEPERNECFLQH KDDNPNLPRLVRPEVDVMCTAFHDNEETFLKKYLYETTLEKCC AAADPHECYAKVFDEFKPLVEEPQNLIKQNCELFEQLGEYKFQ NALLVRYTKKVPQVSTPTLVEVSRNLGKVGSKCCKHPEAKRM PCAEDYLSVVLNQLCVLHEKTPVSDRVTKCCTESLVNRRPCFS ALEVDETYVPKEFNAETFTFHADICTLSEKERQIKKQTALVELV KHKPKATKEQLKAVMDDFAAFVEKCCKADDKETCFAEEGKKL VAASQAALGL |
| 55. | Mature HSA | DAHKSEVAHRFKDLGEENFKALVLIAFAQYLQQCPFEDHVKLV NEVTEFAKTCVADESAENCDKSLHTLFGDKLCTVATLRETYGE MADCCAKQEPERNECFLQHKDDNPNLPRLVRPEVDVMCTAFH DNEETFLKKYLYEIARRHPYFYAPELLFFAKRYKAAFTECCQA ADKAACLLPKLDELRDEGKASSAKQGLKCASLQKFGERAFKA WAVARLSQRFPKAEFAEVSKLVTDLTKVHTECCHGDLLECAD DRADLAKYICENQDSISSKLKECCEKPLLEKSHCIAEVENDEMP ADLPSLAADFVGSKDVCKNYAEAKDVFLGMFLYEYARRHPDY SVVLLLRLAKTYETTLEKCCAAADPHECYAKVFDEFKPLVEEP QNLIKQNCELFEQLGEYKFQNALLVRYTKKVPQVSTPTLVEVS RNLGKVGSKCCKHPEAKRMPCAEDCLSVFLNQLCVLHEKTPVS DRVTKCCTESLVNGRPCFSALEVDETYVPKEFNAETFTFHADIC TLSEKERQIKKQTALVELVKHKPKATKEQLKAVMDDFAAFVE KCCKADDKETCFAEEGKKLVAASQAALGL |
| 56. | Mesothelin isoform1 | MALPTARPLLGSCGTPALGSLLFLLFSLGWVQPSRTLAGETGQE AAPLDGVLANPPNISSLSPRQLLGFPCAEVSGLSTERVRELAVA LAQKNVKLSTEQLRCLAHRLSEPPEDLDALPLDLLLFLNPDAFS GPQACTRFFSRITKANVDLLPRGAPERQRLLPAALACWGVRGS LLSEADVRALGGLACDLPGRFVAESAEVLLPRLVSCPGPLDQD QQEAARAALQGGGPPYGPPSTWSVSTMDALRGLLPVLGQPIIRS IPQGIVAAWRQRSSRDPSWRQPERTILRPRFRREVEKTACPSGK KAREIDESLIFYKKWELEACVDAALLATQMDRVNAIPFTYEQL DVLKHKLDELYPQGYPESVIQHLGYLFLKMSPEDIRKWNVTSL ETLKALLEVNKGHEMSPQAPRRPLPQVATLIDRFVKGRGQLDK DTLDTLTAFYPGYLCSLSPEELSSVPPSSIWAVRPQDLDTCDPRQ LDVLYPKARLAFQNMNGSEYFVKIQSFLGGAPTEDLKALSQQN VSMDLATFMKLRTDAVLPLTVAEVQKLLGPHVEGLKAEERHR PVRDWILRQRQDDLDTLGLGLQGGIPNGYLVLDLSMQEALSGT PCLLGPGPVLTVLALLLASTLA |
| 57. | Mesothelin isoform 2 (major form) | MALPTARPLLGSCGTPALGSLLFLLFSLGWVQPSRTLAGETGQE AAPLDGVLANPPNISSLSPRQLLGFPCAEVSGLSTERVRELAVA LAQKNVKLSTEQLRCLAHRLSEPPEDLDALPLDLLLFLNPDAFS GPQACTRFFSRITKANVDLLPRGAPERQRLLPAALACWGVRGS LLSEADVRALGGLACDLPGRFVAESAEVLLPRLVSCPGPLDQD QQEAARAALQGGGPPYGPPSTWSVSTMDALRGLLPVLGQPIIRS IPQGIVAAWRQRSSRDPSWRQPERTILRPRFRREVEKTACPSGK KAREIDESLIFYKKWELEACVDAALLATQMDRVNAIPFTYEQL DVLKHKLDELYPQGYPESVIQHLGYLFLKMSPEDIRKWNVTSL ETLKALLEVNKGHEMSPQVATLIDRFVKGRGQLDKDTLDTLTA FYPGYLCSLSPEELSSVPPSSIWAVRPQDLDTCDPRQLDVLYPK ARLAFQNMNGSEYFVKIQSFLGGAPTEDLKALSQQNVSMDLAT FMKLRTDAVLPLTVAEVQKLLGPHVEGLKAEERHRPVRDWILR QRQDDLDTLGLGLQGGIPNGYLVLDLSMQEALSGTPCLLGPGP VLTVLALLLASTLA |
| 58. | Mesothelin isoform 3 | MALPTARPLLGSCGTPALGSLLFLLFSLGWVQPSRTLAGETGQE AAPLDGVLANPPNISSLSPRQLLGFPCAEVSGLSTERVRELAVA LAQKNVKLSTEQLRCLAHRLSEPPEDLDALPLDLLLFLNPDAFS GPQACTRFFSRITKANVDLLPRGAPERQRLLPAALACWGVRGS LLSEADVRALGGLACDLPGRFVAESAEVLLPRLVSCPGPLDQD QQEAARAALQGGGPPYGPPSTWSVSTMDALRGLLPVLGQPIIRS IPQGIVAAWRQRSSRDPSWRQPERTILRPRFRREVEKTACPSGK KAREIDESLIFYKKWELEACVDAALLATQMDRVNAIPFTYEQL DVLKHKLDELYPQGYPESVIQHLGYLFLKMSPEDIRKWNVTSL ETLKALLEVNKGHEMSPQVATLIDRFVKGRGQLDKDTLDTLTA FYPGYLCSLSPEELSSVPPSSIWAVRPQDLDTCDPRQLDVLYPK ARLAFQNMNGSEYFVKIQSFLGGAPTEDLKALSQQNVSMDLAT FMKLRTDAVLPLTVAEVQKLLGPHVEGLKAEERHRPVRDWILR |

SEQUENCE TABLE

| SEQ ID NO | Description | Amino acid sequence (CDR sequences are underlined and bold) |
|---|---|---|
|  |  | QRQDDLDTLGLGLQGGIPNGYLVLDLSVQGGRGGQARAGGRA GGVEVGALSHPSLCRGPLGDALPPRTWTCSHRPGTAPSLHPGL RAPLPC |
| 59. | Mesothelin isoform 4 | MALPTARPLLGSCGTPALGSLLFLLFSLGWVQPSRTLAGETGQA APLDGVLANPPNISSLSPRQLLGFPCAEVSGLSTERVRELAVAL AQKNVKLSTEQLRCLAHRLSEPPEDLDALPLDLLLFLNPDAFSG PQACTRFFSRITKANVDLLPRGAPERQRLLPAALACWGVRGSL LSEADVRALGGLACDLPGRFVAESAEVLLPRLVSCPGPLDQDQ QEAARAALQGGGPPYGPPSTWSVSTMDALRGLLPVLGQPIIRSI PQGIVAAWRQRSSRDPSWRQPERTILRPRFRREVEKTACPSGKK AREIDESLIFYKKWELEACVDAALLATQMDRVNAIPFTYEQLD VLKHKLDELYPQGYPESVIQHLGYLFLKMSPEDIRKWNVTSLE TLKALLEVNKGHEMSPQVATLIDRFVKGRGQLDKDTLDTLTAF YPGYLCSLSPEELSSVPPSSIWAVRPQDLDTCDPRQLDVLYPKA RLAFQNMNGSEYFVKIQSFLGGAPTEDLKALSQQNVSMDLATF MKLRTDAVLPLTVAEVQKLLGPHVEGLKAEEERHRPVRDWILR QRQDDLDTLGLGLQGGIPNGYLVLDLSMQEALSGTPCLLGPGP VLTVLALLLASTLA |
| 60. | P275 | QVQLVESGGGLVQPGGSLRLSCAASGRIFSTYAMGWFRQPPGK EREFVASINRSGDSTYYADSVKGRFTISRDNAKNTGYLQMSSLK PEDTAVYYCAADSDGIGWFNSFEYDYWGRGTQVTVSS |
| 61. | P276 | QVQLVESGGGLVQAGGSLRLSCAASGRSVSLYHVGWFRHTPG KEREFVAATAWHDGSTSYADSVKGRFTISRNNAKNTVYLQMN SLQPEDTAVYYCAGEAKLGGIYSRWRDYEYWGQGTQVTVSS |
| 62. | P278 | QVQLVESGGGLVQAGGSLRLSCAASGRTFSIYDMGWFRQAPG KEREFVAATNLRGVSTRYADSVKGRFTISGDNAKNTVSLQMNS LIPEDTAVYYCAAAVSNWLAKDPSAYSYWGQGTQVTVSS |
| 63. | P357 | QVQLVESGGGLVQPGGSLRLSCAASGRIFSTYAMGWFRQPPGK EREFVASINRSGDSTYYADSVKGRFTISRDDAKNMGYLQMSSL KPEDTAVYYCAADSDGIGWFNSFEYDYWGRGTQVTVSS |
| 64. | P358 | QVQLVESGGGLVQPGGSLRLSCAASGPIFSTYAMGWFRQPPGK EREFVASINRSGDSTYYADSVKGRFTISRDNAKNTGYLQMSSLK PEDTAVYYCAADSDGIGWFNSFEYDYWGRGTQVTVSS |
| 65. | P362 | QVQLVESGGGLVQAGGSLRLSCAASGRSVSLYHVGWFRHTPG KEREFVAATAWHDGSTSYADSVKGRFTISRNNAKNTVYLQMN SLQPEDTAVYYCAGEAKLGGIYSRWRDYEYWGQGTQVTVSS |
| 66. | P364 | QVQLVESGGGLVQAGGSLRLSCAASGRSVSLYHVGWFRHTPG KEREFVAATAWHDGSTSYADSVKGRFTISRDSAKNTVFLQMSS LQPEDTAVYYCAADPGGSSWSQPWYDYWGQGTQVTVSS |
| 67. | P367 | QVQLVESGGGLVQPGGSLRLSCAASGSTWSINTLAWYRQAPG KQRDLVARISSGGSTHYADSVKGRFTVSRDNAENTLVLQMNSL KPEDTAVYYCYAQSTWYPPSWGQGTQVTVSS |
| 68. | P371 | QVQLVESGGGLVQAGGSLRLSCAASGRTFSNDAMGWFRQAPG KERVFVATISWKSSTYYADSVKGRFTISRDHAKNTVYLQMNNL KPEDTAVYYCVADPYGLGFNPSDYDYWGQGTQVTVSS |
| 69. | P275 CDR1 (IMGT) | GRIFSTYA |
| 70. | P275 CDR2 (IMGT) | INRSGDST |
| 71. | P275 CDR3 (IMGT) | AADSDGIGWFNSFEYDY |
| 72. | P276 CDR1 (IMGT) | GRSVSLYH |
| 73. | P276 CDR2 (IMGT) | TAWHDGST |
| 74. | P276 CDR3 (IMGT) | AGEAKLGGIYSRWRDYEY |

-continued

SEQUENCE TABLE

| SEQ ID NO | Description | Amino acid sequence (CDR sequences are underlined and bold) |
|---|---|---|
| 75. | P278 CDR1 (IMGT) | GRTFSIYD |
| 76. | P278 CDR2 (IMGT) | TNLRGVST |
| 77. | P278 CDR3 (IMGT) | AAAVSNWLAKDPSAYS |
| 78. | P357 CDR1 (IMGT) | GRIFSTYA |
| 79. | P357 CDR2 (IMGT) | INRSGDST |
| 80. | P357 CDR3 (IMGT) | AADSDGIGWFNSFEYDY |
| 81. | P358 CDR1 (IMGT) | GPIFSTYA |
| 82. | P358 CDR2 (IMGT) | INRSGDST |
| 83. | P358 CDR3 (IMGT) | AADSDGIGWFNSFEYDY |
| 84. | P362 CDR1 (IMGT) | GRSVSLYH |
| 85. | P362 CDR2 (IMGT) | TAWHDGST |
| 86. | P362 CDR3 (IMGT) | AGEAKLGGIYSRWRDYE |
| 87. | P364 CDR1 (IMGT) | GRSVSLYH |
| 88. | P364 CDR2 (IMGT) | TAWHDGST |
| 89. | P364 CDR3 (IMGT) | AADPGGSSWSQPWYD |
| 90. | P367 CDR1 (IMGT) | GSTWSINT |
| 91. | P367 CDR2 (IMGT) | ISSGGST |
| 92. | P367 CDR3 (IMGT) | YAQSTWYPPS |
| 93. | P371 CDR1 (IMGT) | GRTFSNDA |
| 94. | P371 CDR2 (IMGT) | ISWKSST |
| 95. | P371 CDR3 (IMGT) | VADPYGLGFNPSDYD |
| 96. | Human IL-7 | DCDIEGKDGKQYESVLMVSIDQLLDSMKEIGSNCLNNEFNFFK RHICDANKEGMFLFRAARKLRQFLKMNSTGDFDLHLLKVSEGT TILLNCTGQVKGRKPAALGEAQPTKSLEENKSLKEQKKLNDLC FLKRLLQEIKTCWNKILMGTKEH |
| 97. | Human IL-7 (isoform 1) | MFHVSFRYIFGLPPLILVLLPVASSDCDIEGKDGKQYESVLMVSI DQLLDSMKEIGSNCLNNEFNFFKRHICDANKEGMFLFRAARKL RQFLKMNSTGDFDLHLLKVSEGTTILLNCTGQVKGRKPAALGE AQPTKSLEENKSLKEQKKLNDLCFLKRLLQEIKTCWNKILMGT KEH |

-continued

SEQUENCE TABLE

| SEQ ID NO | Description | Amino acid sequence (CDR sequences are underlined and bold) |
|---|---|---|
| 98. | Human IL-7 (isoform 1- without signal sequence) | DCDIEGKDGKQYESVLMVSIDQLLDSMKEIGSNCLNNEFNFFK RHICDANKEGMFLFRAARKLRQFLKMNSTGDFDLHLLKVSEGT TILLNCTGQVKGRKPAALGEAQPTKSLEENKSLKEQKKLNDLC FLKRLLQEIKTCWNKILMGTKEH |
| 99. | Human IL-15 | NWVNVISDLKKIEDLIQSMHIDATLYTESDVHPSCKVTAMKCFL LELQVISHESGDTDIHDTVENLIILANNILSSNGNITESGCKECEE LEEKNIKEFLQSFVHIVQMFINTS |
| 100. | Human IL-15 (isoform IL15-S48AA) | MRISKPHLRSISIQCYLCLLLNSHFLTEAGIHVFILGCFSAGLPKT EANWVNVISDLKKIEDLIQSMHIDATLYTESDVHPSCKVTAMK CFLLELQVISLESGDASIHDTVENLIILANNSLSSNGNVTESGCKE CEELEEKNIKEFLQSFVHIVQMFINTS |
| 101. | Human IL-15Rα (isoform 1) | MAPRRARGCRTLGLPALLLLLLLRPPATRGITCPPPMSVEHADI WVKSYSLYSRERYICNSGFKRKAGTSSLTECVLNKATNVAHWT TPSLKCIRDPALVHQRPAPPSTVTTAGVTPQPESLSPSGKEPAAS SPSSNNTAATTAAIVPGSQLMPSKSPSTGTTEISSHESSHGTPSQT TAKNWELTASASHQPPGVYPQGHSDTTVAISTSTVLLCGLSAVS LLACYLKSRQTPPLASVEMEAMEALPVTWGTSSRDEDLENCSH HL |
| 102. | Human IL-15Rα (isoform 1 - without signal sequence) | ITCPPPMSVEHADIWVKSYSLYSRERYICNSGFKRKAGTSSLTEC VLNKATNVAHWTTPSLKCIRDPALVHQRPAPPSTVTTAGVTPQ PESLSPSGKEPAASSPSSNNTAATTAAIVPGSQLMPSKSPSTGTT EISSHESSHGTPSQTTAKNWELTASASHQPPGVYPQGHSDTTVA ISTSTVLLCGLSAVSLLACYLKSRQTPPLASVEMEAMEALPVTW GTSSRDEDLENCSHHL |
| 103. | Human IL-15Rα (isoform 1 - without signal sequence) variant 1 | ITCPPPMSVEHADIWVKSYSLYSRERYICNSGFKRKAGTSSLTEC VLNKATNVAHWTTPSLKCIR |
| 104. | Human IL-15Rα (isoform 1 - without signal sequence) variant 2 | ITCPPPMSVEHADIWVKSYSLYSRERYICNSGFKRKAGTSSLTEC VLNKATNVAHWTTPSLKCIRDPALVHQRPAPP |
| 105. | Human IL-15Rα (isoform 2) | MAPRRARGCRTLGLPALLLLLLLRPPATRGITCPPPMSVEHADI WVKSYSLYSRERYICNSGFKRKAGTSSLTECVLNKATNVAHWT TPSLKCIKPAASSPSSNNTAATTAAIVPGSQLMPSKSPSTGTTEIS SHESSHGTPSQTTAKNWELTASASHQPPGVYPQGHSDTTVAIST STVLLCGLSAVSLLACYLKSRQTPPLASVEMEAMEALPVTWGT SSRDEDLENCSHHL |
| 106. | Human IL-15Rα (isoform 3) | MAPRRARGCRTLGLPALLLLLLLRPPATRGITCPPPMSVEHADI WVKSYSLYSRERYICNSGFKRKAGTSSLTECVLNKATNVAHWT TPSLKCIRDPALVHQRPAPPSTVTTAGVTPQPESLSPSGKEPAAS SPSSNNTAATTAAIVPGSQLMPSKSPSTGTTEISSHESSHGTPSQT TAKNWELTASASHQPPGVYPQGHSDTTVAISTSTVLLCGLSAVS LLACYLKSRASVCSCHPRSAGHTCSVGSVC |
| 107. | Human IL-15Rα (isoform 4) | MAPRRARGCRTLGLPALLLLLLLRPPATRGITCPPPMSVEHADI WVKSYSLYSRERYICNSGFKRKAGTSSLTECVLNKATNVAHWT TPSLKCIKPAASSPSSNNTAATTAAIVPGSQLMPSKSPSTGTTEIS SHESSHGTPSQTTAKNWELTASASHQPPGVYPQGHSDTTVAIST STVLLCGLSAVSLLACYLKSRASVCSCHPRSAGHTCSVGSVC |
| 108. | Human IL-15Rα (isoform 9) | MSVEHADIWVKSYSLYSRERYICNSGFKRKAGTSSLTECVLNK ATNVAHWTTPSLKCIRDPALVHQRPAPPSTVTTAGVTPQPESLS PSGKEPAASSPSSNNTAATTAAIVPGSQLMPSKSPSTGTTEISSHE SSHGTPSQTTAKNWELTASASHQPPGVYPQGHSDTTVAISTSTV LLCGLSAVSLLACYLKSRQTPPLASVEMEAMEALPVTWGTSSR DEDLENCSHHL |
| 109. | Human IL-33 | MKPKMKYSTNKISTAKWKNTASKALCFKLGKSQQKAKEVCP MYFMKLRSGLMIKKEACYFRRETTKRPSLKTGRKHKRHLVLA ACQQQSTVECFAFGISGVQKYTRALHDSSITGISPITEYLASLST YNDQSITFALEDESYEIYVEDLKKDEKKDKVLLSYYESQHPSNE |

SEQUENCE TABLE

| SEQ ID NO | Description | Amino acid sequence (CDR sequences are underlined and bold) |
|---|---|---|
| | | SGDGVDGKMLMVTLSPTKDFWLHANNKEHSVELHKCEKPLPD QAFFVLHNMHSNCVSFECKTDPGVFIGVKDNHLALIKVDSSEN LCTENILFKLSET |
| 110. | Human IL-22 | MAALQKSVSSFLMGTLATSCLLLLALLVQGGAAAPISSHCRLD KSNFQQPYITNRTFMLAKEASLADNNTDVRLIGEKLFHGVSMS ERCYLMKQVLNFTLEEVLFPQSDRFQPYMQEVVPFLARLSNRL STCHIEGDDLHIQRNVQKLKDTVKKLGESGEIKAIGELDLLFMS LRNACI |
| 111. | Human IL-22 (without signal sequence) | APISSHCRLDKSNFQQPYITNRTFMLAKEASLADNNTDVRLIGE KLFHGVSMSERCYLMKQVLNFTLEEVLFPQSDRFQPYMQEVVP FLARLSNRLSTCHIEGDDLHIQRNVQKLKDTVKKLGESGEIKAI GELDLLFMSLRNACI |
| 112. | P275/P357/P358/P371 FR1 (matched human gem line: IGHV3-23*04) | EVQLVESGGGLVQPGGSLRLSCAASG |
| 113. | P276/P278/P362/P364 FR1 (matched human gem line: IGHV3-64*04) | QVQLVESGGGLVQPGGSLRLSCSAS |
| 114. | P367 FR1 (matched human gem line: IGHV3-66*01) | EVQLVESGGGLVQPGGSLRLSCAAS |
| 115. | P275/P357/P358/P371 FR2 (matched human gem line: IGHV3-23*04) | MSWVRQAPGKGLEWVSA |
| 116. | P276/P278/P362/P364 FR2 (matched human gem line: IGHV3-64*04) | MHWVRQAPGKGLEYVSA |
| 117. | P367 FR2 (matched human gem line: IGHV3-66*01) | MSWVRQAPGKGLEWVSV |
| 118. | P275/P276/P278/P357/P358/P362/P364/P371 FR3 (matched human gem line: IGHV3-23*04 or IGHV3-64*04) | YYADSVKGRFTISRDNSKNTLYLQMNSLRAEDTAVYYCA |
| 119. | P367 FR3 (matched human gem line: IGHV3-66*01) | YYADSVKGRFTISRDNSKNTLYLQMNSLRAEDT |
| 120. | P390 Mouse IL-21-(GSG)4-anti- | QGPDRLLIRLRHLIDIVEQLKIYENDLDPELLSAPQDVKGHCEH AAFACFQKAKLKPSNPGNNKTFIIDLVAQLRRRLPARRGGKKQ KHIAKCPSCDSYEKRTPKEFLERLKWLLQKMIHQHLSGSGGSG |

| SEQ ID NO | Description | Amino acid sequence (CDR sequences are underlined and bold) |
|---|---|---|
| | albumin VHH | GSGGSGQVQLVESGGGLVQPGGSLRLSCAASGSTWSINTLAWY RQAPGKQRDLVARISSGGSTHYADSVKGRFTVSRDNAENTLVL QMNSLKPEDTAVYYCYAQSTWYPPSWGQGTQVTVSS |
| 121. | P394 human IL21-(GSG)4 - anti-albumin VHH | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHLSSRTHGSE DSGSGGSGGSGGSGQVQLVESGGGLVQPGGSLRLSCAASGSTW SINTLAWYRQAPGKQRDLVARISSGGSTHYADSVKGRFTVSRD NAENTLVLQMNSLKPEDTAVYYCYAQSTWYPPSWGQGTQVT VSS |
| 122. | P480 anti-albumin VHH-(GGGGS)4-human IL15R sushi-cleavable linker-human IL15 | QVQLVESGGGLVQPGGSLRLSCAASGSTWSINTLAWYRQAPG KQRDLVARISSGGSTHYADSVKGRFTVSRDNAENTLVLQMNSL KPEDTAVYYCYAQSTWYPPSWGQGTQVTVSSGGGGSGGGGSG GGGSGGGGSITCPPPMSVEHADIWVKSYSLYSRERYICNSGFKR KAGTSSLTECVLNKATNVAHWTTPSLKCIRDPALVHQRPAPPR RKRAPVKQTLNFDLLKLAGDVESNPGPNWVNVISDLKKIEDLI QSMHIDATLYTESDVHPSCKVTAMKCFLLELQVISLESGDASIH DTVENLIILANNSLSSNGNVTESGCKECEELEEKNIKEFLQSFVH IVQMFINTS |
| 123. | P461 (IL-15) | NWVNVISDLKKIEDLIQSMHIDATLYTESDVHPSCKVTAMKCFL LELQVISLESGDASIHDTVENLIILANNSLSSNGNVTESGCKECE ELEEKNIKEFLQSFVHIVQMFINTS |
| 124. | P462 Anti-albumin VHH-(GGGGS)4-IL-15R sushi 1 | QVQLVESGGGLVQPGGSLRLSCAASGSTWSINTLAWYRQAPG KQRDLVARISSGGSTHYADSVKGRFTVSRDNAENTLVLQMNSL KPEDTAVYYCYAQSTWYPPSWGQGTQVTVSSGGGGSGGGGSG GGGSGGGGSITCPPPMSVEHADIWVKSYSLYSRERYICNSGFKR KAGTSSLTECVLNKATNVAHWTTPSLKCIR |
| 125. | P463 Anti-albumin VHH-(GGGGS)4-IL-15R sushi 2 | QVQLVESGGGLVQPGGSLRLSCAASGSTWSINTLAWYRQAPG KQRDLVARISSGGSTHYADSVKGRFTVSRDNAENTLVLQMNSL KPEDTAVYYCYAQSTWYPPSWGQGTQVTVSSGGGGSGGGGSG GGGSGGGGSITCPPPMSVEHADIWVKSYSLYSRERYICNSGFKR KAGTSSLTECVLNKATNVAHWTTPSLKCIRDPALVHQRPAPP |
| 126 | Human IL21 truncated (11aa) (1-122) | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQH |
| 127. | IL-15 R sushi 1 | ITCPPPMSVEHADIWVKSYSLYSRERYICNSGFKRKAGTSSLTEC VLNKATNVAHWTTPSLKCIR |
| 128. | IL-15 R sushi 2 | ITCPPPMSVEHADIWVKSYSLYSRERYICNSGFKRKAGTSSLTEC VLNKATNVAHWTTPSLKCIRDPALVHQRPAPP |
| 129. | P593 IL21(1-122)]-A(EAAAK)4A-[HSA_P367] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHAEAAAKEA AAKEAAAKEAAAKAQVQLVESGGGLVQPGGSLRLSCAASGST WSINTLAWYRQAPGKQRDLVARISSGGSTHYADSVKGRFTVSR DNAENTLVLQMNSLKPEDTAVYYCYAQSTWYPPSWGQGTQV TVSS |
| 130. | P636 IL21(1-119)]-GSG4-[HSA_P367] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIGSGGSGGSGGSG QVQLVESGGGLVQPGGSLRLSCAASGSTWSINTLAWYRQAPG KQRDLVARISSGGSTHYADSVKGRFTVSRDNAENTLVLQMNSL KPEDTAVYYCYAQSTWYPPSWGQGTQVTVSS |
| 131. | P637 [IL-21(1-120)] GSG4-[HSA_P367] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHGSGGSGGSGGS GQVQLVESGGGLVQPGGSLRLSCAASGSTWSINTLAWYRQAP GKQRDLVARISSGGSTHYADSVKGRFTVSRDNAENTLVLQMNS LKPEDTAVYYCYAQSTWYPPSWGQGTQVTVSS |
| 132. | P744 [IL21(1-122)]-A(EAAAK)4A-[HSA_P494] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHAEAAAKEA AAKEAAAKEAAAKAEVQLVESGGGLVQPGGSLRLSCAASGST |

SEQUENCE TABLE

| SEQ ID NO | Description | Amino acid sequence (CDR sequences are underlined and bold) |
|---|---|---|
| | | WSINTLAWYRQAPGKQRDLVARISSGGSTYYADSVKGRFTISR DNSKNTLYLQMNSLRAEDTAVYYCYAQSTWYPPSWGQGTLV TVSS |
| 133. | P748 [HSA-610]-A(EAAAK)4A-[IL21(1-122)] | QVQLVESGGGVVQPGGSLRLSCAASGFAFRGFGMSWVRQAPG KGLEWVSSINNGGSDTYYADSVKGRFTISRDNSKNTLYLQMNS LRAEDTAVYYCAIGGPGASPSGQGTQVTVSSAEAAAKEAAAKE AAAKEAAAKAQGQDRHMIRMRQLIDIVDQLKNYVNDLVPEFL PAPEDVETNCEWSAFSCFQKAQLKSANTGNNERIINVSIKKLKR KPPSTNAGRRQKHRLTCPSCDSYEKKPPKEFLERFKSLLQKMIH QH |
| 134. | P750 [IL21]-GSG4-[HSA_P494] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHLSSRTHGSE DSGSGGSGGSGGSGEVQLVESGGGLVQPGGSLRLSCAASGSTW SINTLAWYRQAPGKQRDLVARISSGGSTYYADSVKGRFTISRDN SKNTLYLQMNSLRAEDTAVYYCYAQSTWYPPSWGQGTLVTVS S |
| 135. | P751 [IL21]-A(EAAAK)4A-[HSA_P494] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHLSSRTHGSE DSAEAAAKEAAAKEAAAKEAAAKAEVQLVESGGGLVQPGGSL RLSCAASGSTWSINTLAWYRQAPGKQRDLVARISSGGSTYYAD SVKGRFTISRDNSKNTLYLQMNSLRAEDTAVYYCYAQSTWYPP SWGQGTLVTVSS |
| 136. | P783 [IL21(1-122)]-A(EAAAK)4A-[HSA-609] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHAEAAAKEA AAKEAAAKEAAAKAQVQLVESGGGVVQPGGSLRLSCAASGFA FRGFGMSWVRQAPGKGFEWVSSINNGGSDTYYADSVKGRFTIS RDNSKNTLYLQMNSLRAEDTAVYYCAIGGPGASPSGQGTQVT VSS |
| 137. | P795 [IL21(1-122)]-GSG4-[HSA P494] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHGSGGSGGSG GSGEVQLVESGGGLVQPGGSLRLSCAASGSTWSINTLAWYRQA PGKQRDLVARISSGGSTYYADSVKGRFTISRDNSKNTLYLQMN SLRAEDTAVYYCYAQSTWYPPSWGQGTLVTVSS |
| 138. | P796 [IL21(1-122)]-G4S3-[HSA P494] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHGGGGSGGG GSGGGGSEVQLVESGGGLVQPGGSLRLSCAASGSTWSINTLAW YRQAPGKQRDLVARISSGGSTYYADSVKGRFTISRDNSKNTLY LQMNSLRAEDTAVYYCYAQSTWYPPSWGQGTLVTVSS |
| 139. | P797 [IL21(1-122)]-[HSA P494] (no linker) | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHEVQLVESGG GLVQPGGSLRLSCAASGSTWSINTLAWYRQAPGKQRDLVARIS SGGSTYYADSVKGRFTISRDNSKNTLYLQMNSLRAEDTAVYYC YAQSTWYPPSWGQGTLVTVSS |
| 140. | P798 [IL21]-[HSA P494] (no linker) | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHLSSRTHGSE DSEVQLVESGGGLVQPGGSLRLSCAASGSTWSINTLAWYRQAP GKQRDLVARISSGGSTYYADSVKGRFTISRDNSKNTLYLQMNS LRAEDTAVYYCYAQSTWYPPSWGQGTLVTVSS |
| 141. | P799 [IL21(1-122)]-VLLC-[HSA P494] | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHIKRTVAAPE VQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSS |
| 142 | P800 [IL21(1-122)]-VHCH1-[HSA | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIHQHASTKGPSVE |

| SEQ ID NO | Description | Amino acid sequence (CDR sequences are underlined and bold) |
|---|---|---|
| | P494] | VQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSS |
| 143. | P806 [HSA P494]-A(EAAAK)4A-[IL21] | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSAEAAAKEAAAK EAAAKEAAAKAQGQDRHMIRMRQLIDIVDQLKNYVNDLVPEF LPAPEDVETNCEWSAFSCFQKAQLKSANTGNNERIINVSIKKLK RKPPSTNAGRRQKHRLTCPSCDSYEKKPPKEFLERFKSLLQKMI HQHLSSRTHGSEDS |
| 144 | P807 [HSA P494]-G4S3-[IL21] | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSGGGGSGGGGSG GGGSQGQDRHMIRMRQLIDIVDQLKNYVNDLVPEFLPAPEDVE TNCEWSAFSCFQKAQLKSANTGNNERIINVSIKKLKRKPPSTNA GRRQKHRLTCPSCDSYEKKPPKEFLERFKSLLQKMIHQHLSSRT HGSEDS |
| 145. | P808 [HSA P494]-[IL21] (no linker) | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSQGQDRHMIRMR QLIDIVDQLKNYVNDLVPEFLPAPEDVETNCEWSAFSCFQKAQL KSANTGNNERIINVSIKKLKRKPPSTNAGRRQKHRLTCPSCDSY EKKPPKEFLERFKSLLQKMIHQHLSSRTHGSEDS |
| 146. | P809 [HSA P494]-A(EAAAK)4A-[IL21(1-122)] | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSAEAAAKEAAAK EAAAKEAAAKAQGQDRHMIRMRQLIDIVDQLKNYVNDLVPEF LPAPEDVETNCEWSAFSCFQKAQLKSANTGNNERIINVSIKKLK RKPPSTNAGRRQKHRLTCPSCDSYEKKPPKEFLERFKSLLQKMI HQH |
| 147. | P810 [HSA P494]-G4S3-[IL21(1-122)] | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSGGGGSGGGGSG GGGSQGQDRHMIRMRQLIDIVDQLKNYVNDLVPEFLPAPEDVE TNCEWSAFSCFQKAQLKSANTGNNERIINVSIKKLKRKPPSTNA GRRQKHRLTCPSCDSYEKKPPKEFLERFKSLLQKMIHQH |
| 148. | P811 [HSA P494]-[IL21(1-122)] (no linker) | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSQGQDRHMIRMR QLIDIVDQLKNYVNDLVPEFLPAPEDVETNCEWSAFSCFQKAQL KSANTGNNERIINVSIKKLKRKPPSTNAGRRQKHRLTCPSCDSY EKKPPKEFLERFKSLLQKMIHQH |
| 149. | P817 [HSA P494]-VHCH1-[IL21] | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSASTKGPQGQDRH MIRMRQLIDIVDQLKNYVNDLVPEFLPAPEDVETNCEWSAFSCF QKAQLKSANTGNNERIINVSIKKLKRKPPSTNAGRRQKHRLTCP SCDSYEKKPPKEFLERFKSLLQKMIHQHLSSRTHGSEDS |
| 150. | P818 [HSA P494]-VHCH1-[IL21(1-122)] | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSSASTKGPQGQDRH MIRMRQLIDIVDQLKNYVNDLVPEFLPAPEDVETNCEWSAFSCF QKAQLKSANTGNNERIINVSIKKLKRKPPSTNAGRRQKHRLTCP SCDSYEKKPPKEFLERFKSLLQKMIHQH |
| 151. | P380 [HSA-P367]-G3S4-[IL33 C4S (95-270aa)] | QVQLVESGGGLVQPGGSLRLSCAASGSTWSINTLAWYRQAPG KQRDLVARISSGGSTHYADSVKGRFTVSRDNAENTLVLQMNSL KPEDTAVYYCYAQSTWYPPSWGQGTQVTVSSGGGSGGGSGGG SGGGSAFGISGVQKYTRALHDSSITGISPITEYLASLSTYNDQSIT FALEDESYEIYVEDLKKDEKKDKVLLSYYESQHPSNESGDGVD GKMLMVTLSPTKDFWLHANNKEHSVELHKSEKPLPDQAFFVL HNMHSNSVSFESKTDPGVFIGVKDNHLALIKVDSSENLSTENILF KLSET |
| 152. | P803 [HSA-P494]- | EVQLVESGGGLVQPGGSLRLSCAASGSTWSINTLAWYRQAPGK QRDLVARISSGGSTYYADSVKGRFTISRDNSKNTLYLQMNSLR |

SEQUENCE TABLE

| SEQ ID NO | Description | Amino acid sequence (CDR sequences are underlined and bold) |
|---|---|---|
|  | G3S4-[IL33 C4S (112-270aa)] | AEDTAVYYCYAQSTWYPPSWGQGTLVTVSSGGGSGGGSGGGS GGGSSITGISPITEYLASLSTYNDQSITFALEDESYEIYVEDLKKD EKKDKVLLSYYESQHPSNESGDGVDGKMLMVTLSPTKDFWLH ANNKEHSVELHKSEKPLPDQAFFVLHNMHSNSVSFESKTDPGV FIGVKDNHLALIKVDSSENLSTENILFKLSET |
| 153. | P821 [HSA-P494]- [IL33 C4S (95- 270aa, no linker)] | EVQLVESGGGLVQPGGSLRLCAASGSTWSINTLAWYRQAPGK QRDLVARISSGGSTYYADSVKGRFTISRDNSKNTLYLQMNSLR AEDTAVYYCYAQSTWYPPSWGQGTLVTVSSAFGISGVQKYTR ALHDSSITGISPITEYLASLSTYNDQSITFALEDESYEIYVEDLKK DEKKDKVLLSYYESQHPSNESGDGVDGKMLMVTLSPTKDFWL HANNKEHSVELHKSEKPLPDQAFFVLHNMHSNSVSFESKTDPG VFIGVKDNHLALIKVDSSENLSTENILFKLSET |
| 154. | P822 [HSA-P494]- G3S4-[IL33 C4S (117- 270aa)] | EVQLVESGGGLVQPGGSLRLCAASGSTWSINTLAWYRQAPGK QRDLVARISSGGSTYYADSVKGRFTISRDNSKNTLYLQMNSLR AEDTAVYYCYAQSTWYPPSWGQGTLVTVSSGGGSGGGSGGGS GGGSSPITEYLASLSTYNDQSITFALEDESYEIYVEDLKKDEKKD KVLLSYYESQHPSNESGDGVDGKMLMVTLSPTKDFWLHANNK EHSVELHKSEKPLPDQAFFVLHNMHSNSVSFESKTDPGVFIGVK DNHLALIKVDSSENLSTENILFKLSET |
| 155. | IL33 C4S mutant, 95- 270aa | AFGISGVQKYTRALHDSSITGISPITEYLASLSTYNDQSITFALED ESYEIYVEDLKKDEKKDKVLLSYYESQHPSNESGDGVDGKML MVTLSPTKDFWLHANNKEHSVELHKSEKPLPDQAFFVLHNMH SNSVSFESKTDPGVFIGVKDNHLALIKVDSSENLSTENILFKLSE T |
| 156. | IL33 C4S mutant, 112- 270aa | SITGISPITEYLASLSTYNDQSITFALEDESYEIYVEDLKKDEKKD KVLLSYYESQHPSNESGDGVDGKMLMVTLSPTKDFWLHANNK EHSVELHKSEKPLPDQAFFVLHNMHSNSVSFESKTDPGVFIGVK DNHLALIKVDSSENLSTENILFKLSET |
| 157. | IL33 C4S mutant, 117- 270aa | SPITEYLASLSTYNDQSITFALEDESYEIYVEDLKKDEKKDKVLL SYYESQHPSNESGDGVDGKMLMVTLSPTKDFWLHANNKEHSV ELHKSEKPLPDQAFFVLHNMHSNSVSFESKTDPGVFIGVKDNHL ALIKVDSSENLSTENILFKLSET |
| 158. | VHCH1 linker | ASTKGPSV |
| 159. | VHCH1 linker | ASTKGP |
| 160. | P479 HSA-P367- IL15RA Sushi- F2A-IL15 | QVQLVESGGGLVQPGGSLRLCAASGSTWSINTLAWYRQAPG KQRDLVARISSGGSTHYADSVKGRFTVSRDNAENTLVLQMNSL KPEDTAVYYCYAQSTWYPPSWGQGTQVTVSSGGGGSGGGGSG GGGSGGGGSITCPPPMSVEHADIWVKSYSLYSRERYICNSGFKR KAGTSSLTECVLNKATNVAHWTTPSLKCIRRRKRAPVKQTLNF DLLKLAGDVESNPGPNWVNVISDLKKIEDLIQSMHIDATLYTES DVHPSCKVTAMKCFLLELQVISLESGDASIHDTVENLIILANNSL SSNGNVTESGCKECEELEEKNIKEFLQSFVHIVQMFINTS |
| 161. | P597 [HSA-P367]- [IL15RA Sushi Plus-(G4S)3.5- IL15] | QVQLVESGGGLVQPGGSLRLCAASGSTWSINTLAWYRQAPG KQRDLVARISSGGSTHYADSVKGRFTVSRDNAENTLVLQMNSL KPEDTAVYYCYAQSTWYPPSWGQGTQVTVSSGGGGSGGGGSG GGGSGGGGSITCPPPMSVEHADIWVKSYSLYSRERYICNSGFKR KAGTSSLTECVLNKATNVAHWTTPSLKCIRDPALVHQRPAPGG GSGGGGSGGGSGGGGSLQNWVNVISDLKKIEDLIQSMHIDATL YTESDVHPSCKVTAMKCFLLELQVISLESGDASIHDTVENLIILA NNSLSSNGNVTESGCKECEELEEKNIKEFLQSFVHIVQMFINTS |
| 162. | P669 [R2G12v1.1]- [HSA-P367]- [IL15RA Sushi Plus-(G4S)3.5- IL15] | QVQLVESGGGLVQPGGSLRLCAASGITFPVNAYGWYRQAPG KQRDLVAIISAGGTTNYADSVKGRFTISRDNSKNTLYLQMNSLR AEDTAVYYCYLQRRIGMLRDYWGQGTQVTVSSGGGSGGGSG GGSGGGGSQVQLVESGGGLVQPGGSLRLCAASGSTWSINTLAW YRQAPGKQRDLVARISSGGSTHYADSVKGRFTVSRDNAENTLV LQMNSLKPEDTAVYYCYAQSTWYPPSWGQGTQVTVSSGGGGS GGGGSGGGGSGGGGSITCPPPMSVEHADIWVKSYSLYSRERYIC NSGFKRKAGTSSLTECVLNKATNVAHWTTPSLKCIRDPALVHQ RPAPPGGSGGGGSGGGSGGGGSLQNWVNVISDLKKIEDLIQSM HIDATLYTESDVHPSCKVTAMKCFLLELQVISLESGDASIHDTV ENLIILANNSLSSNGNVTESGCKECEELEEKNIKEFLQSFVHIVQ MFINTS |

SEQUENCE TABLE

| SEQ ID NO | Description | Amino acid sequence (CDR sequences are underlined and bold) |
|---|---|---|
| 163. | P375 IL21-GSG4-HSA-P367-G3S4-R3C7 v1.5 | QGQDRHMIRMRQLIDIVDQLKNYVNDLVPEFLPAPEDVETNCE WSAFSCFQKAQLKSANTGNNERIIINVSIKKLKRKPPSTNAGRRQ KHRLTCPSCDSYEKKPPKEFLERFKSLLQKMIHQHLSSRTHGSE DSGSGGSGGSGGSGQVQLVESGGGLVQPGGSLRLSCAASGSTW SINTLAWYRQAPGKQRDLVARISSGGSTHYADSVKGRFTVSRD NAENTLVLQMNSLKPEDTAVYYCYAQSTWYPPSWGQGTQVT VSSGGGSGGGSGGGSGGGSQVQLVESGGGLVQPGGSLRLSCA ASGRTLESYVMAWFRQAPGKEREAVASINWSSGRLIYADSVKG RFTISRDNSKNTLYLQMNSLRAEDTAVYYCAAGRYWGQGTQV TVSS |
| 164. | P431 hIL21-HSA-P367-SGRSA-R3C7 v1.5-hIgG1 (KIH v.11 "Knob") | QGQDRHMIRMRQLIDIVDQLKNYVNDLVPEFLPAPEDVETNCE WSAFSCFQKAQLKSANTGNNERIIINVSIKKLKRKPPSTNAGRRQ KHRLTCPSCDSYEKKPPKEFLERFKSLLQKMIHQHLSSRTHGSE DSGSGGSGGSGGSGQVQLVESGGGLVQPGGSLRLSCAASGSTW SINTLAWYRQAPGKQRDLVARISSGGSTHYADSVKGRFTVSRD NAENTLVLQMNSLKPEDTAVYYCYAQSTWYPPSWGQGTQVT VSSGGGSGGGSGGGSGGGSGRSAGGGSQVQLVESGG GLVQPGGSLRLSCAASGRTLESYVMAWFRQAPGKEREAVASIN WSSGRLIYADSVKGRFTISRDNSKNTLYLQMNSLRAEDTAVYY CAAGRYWGQGTQVTVSSDKTHTCPPCPAPELLGGPSVFLFPPPK PKDTLMISRTPEVTCVVVDVSHEDPEVKFNWYVDGVEVHNAK TKPREEQYNSTYRVVSVLTVLHQDWLNGKEYKCKVSNKALPA PIEKTISKAKGQPREPQVYTLPPCREEMTKNQVSLWCLVKGFYP SDIAVEWESNGQPENNYKTTPPVLDSDGSFFLYSKLTVDKSRW QQGNVFSCSVMHEALHNHYTQKSLSLSPGK |
| 165. | P435 R3C7 v1.5-hIgG1 (KIH v.11 "Hole") | QVQLVESGGGLVQPGGSLRLSCAASGRTLESYVMAWFRQAPG KEREAVASINWSSGRLIYADSVKGRFTISRDNSKNTLYLQMNSL RAEDTAVYYCAAGRYWGQGTQVTVSSDKTHTCPPCPAPELLG GPSVFLFPPKPKDTLMISRTPEVTCVVVDVSHEDPEVKFNWYV DGVEVHNAKTKPREEQYNSTYRVVSVLTVLHQDWLNGKEYK CKVSNKALPAPIEKTISKAKGQPREPQVCTLPPSREEMTKNQVS LSCAVKGFYPSDIAVEWESNGQPENNYKTTPPVLDSDGSFFLVS KLTVDKSRWQQGNVFSCSVMHEALHNHYTQKSLSLSPGK |
| 166. | P286 hIL21-R3C7-hIgG1 KIH v.11 (S354C, T366W, "Knob") | QGQDRHMIRMRQLIDIVDQLKNYVNDLVPEFLPAPEDVETNCE WSAFSCFQKAQLKSANTGNNERIIINVSIKKLKRKPPSTNAGRRQ KHRLTCPSCDSYEKKPPKEFLERFKSLLQKMIHQHLSSRTHGSE DSGSGGSGGSGGSGQVQLVESGGGLVEAGDSLRLSCVVSGRTL ESYVMAWFRQAPGKEREAVASINWSSGRLIYADFVKGRFTISR DYEKNTIYLSMNNLKPEDTAVYYCAAGRYWGQGTQVTVSSDK THTCPPCPAPELLGGPSVFLFPPKPKDTLMISRTPEVTCVVVDVS HEDPEVKFNWYVDGVEVHNAKTKPREEQYNSTYRVVSVLTVL HQDWLNGKEYKCKVSNKALPAPIEKTISKAKGQPREPQVYTLP PCREEMTKNQVSLWCLVKGFYPSDIAVEWESNGQPENNYKTTP PVLDSDGSFFLYSKLTVDKSRWQQGNVFSCSVMHEALHNHYT QKSLSLSPGK |
| 167. | P288 R2G12-hFR3-hIgG1 KIH v.11 (Y349C, T366S, L368A, Y407V, "Hole") | QVQLVESGGGLVQAGGSLRLSCAASGITFPVNAYGWYRQAPG KQRDLVAIISAGGTTNYADSVKGRFTISRDNSKNTLYLQMNSLR AEDTAVYYCYLQRRIGMLRDYWGQGTQVTVSSDKTHTCPPCP APELLGGPSVFLFPPKPKDTLMISRTPEVTCVVVDVSHEDPEVK FNWYVDGVEVHNAKTKPREEQYNSTYRVVSVLTVLHQDWLN GKEYKCKVSNKALPAPIEKTISKAKGQPREPQVCTLPPSREEMT KNQVSLSCAVKGFYPSDIAVEWESNGQPENNYKTTPPVLDSDG SFFLVSKLTVDKSRWQQGNVFSCSVMHEALHNHYTQKSLSLSP GK |
| 168. | P494 Anti-HSA antibody | EVQLVESGGGLVQPGGSLRLSCAASGSTWSINTLAWYRQAPGK QRDLVARISSGGSTYYADSVKGRFTISRDNSKNTLYLQMNSLR AEDTAVYYCYAQSTWYPPSWGQGTLVTVSS |
| 169. | P610 Anti-HSA antibody | QVQLVESGGGVVQPGGSLRLSCAASGFAFRGFGMSWVRQAPG KGLEWVSSINNGGSDTYYADSVKGRFTISRDNSKNTLYLQMNS LRAEDTAVYYCAIGGPGASPSGQGTQVTVSS |
| 170. | P609 Anti-HSA antibody | QVQLVESGGGVVQPGGSLRLSCAASGFAFRGFGMSWVRQAPG KGFEWVSSINNGGSDTYYADSVKGRFTISRDNSKNTLYLQMNS LRAEDTAVYYCAIGGPGASPSGQGTQVTVSS |

SEQUENCE TABLE

| SEQ ID NO | Description | Amino acid sequence (CDR sequences are underlined and bold) |
|---|---|---|
| 171. | IL-21 truncated (1-119) | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMI |
| 172. | IL-21 truncated (1-120) | QGQDRHMIRMRQLIDIVDQLKNYVNDLVPEFLPAPEDVETNCE WSAFSCFQKAQLKSANTGNNERIINVSIKKLKRKPPSTNAGRRQ KHRLTCPSCDSYEKKPPKEFLERFKSLLQKMIH |
| 173. | Anti-MSLN-3 R3-B08(D5) or R3D5 | QVQLVESGGGLVQAGGSLRLSCAASGSISSIRHMRWYRQAPGK QRELVATVSNDGSAYYLGSVKGRFTISRTNAKNTLLYLQMNSL KPEDSALYICNADTWGWPGADYWGQGTQVTVSS |
| 174. | Anti-MSLN-6 R3-E08(C7) or R3C7 | QVQLVESGGGLVEAGDSLRLSCVVSGRTLESYVMAWFRQAPG KEREAVASINWSSGRLIYADFVKGRFTISRDYEKNTIYLSMNNL KPEDTAVYYCAAGRYWGQGTQVTVSS |
| 175. | Anti-MSLN-9 R2-G06(G12) or R2G12 | QVQLVESGGGLVQAGGSLRLSCAASGITFPVNAYGWYRQAPG KQRDLVAIISAGGTTNYADSVKGRFAISKDNVNNTVYLQMNSL TSEDTGVYYCYLQRRIGMLRDYWGQGTQVTVSS |
| 176. | Anti-MSLN-35 (humanized) R2G12 v1.1 | QVQLVESGGGLVQPGGSLRLSCAASGITFPVNAYGWYRQAPG KQRDLVAIISAGGTTNYADSVKGRFTISRDNSKNTLYLQMNSLR AEDTAVYYCYLQRRIGMLRDYWGQGTQVTVSS |
| 177. | Anti-MSLN-36 (humanized) R2G12 v1.2 | QVQLVESGGGLVQAGGSLRLSCAASGITFPVNAYGWYRQAPG KGLELVAIISAGGTTNYADSVKGRFAISKDNVNNTVYLQMNSL TSEDTGVYYCYLQRRIGMLRDYWGQGTQVTVSS |
| 178. | Anti-MSLN-37 (humanized) R2G12 v1.3 | QVQLVESGGGLVQPGGSLRLSCAASGITFPVNAYGWYRQAPG KGLELVAIISAGGTTNYADSVKGRFAISKDNVNNTVYLQMNSL TSEDTGVYYCYLQRRIGMLRDYWGQGTQVTVSS |
| 179. | Anti-MSLN-38 (humanized) R3D5 v1.1 | QVQLVESGGGLVQPGGSLRLSCAASGSISSIRHMRWYRQAPGK QRELVATVSNDGSAYYAGSVKGRFTISRDNSKNTLLYLQMNSL RAEDTAVYICNADTWGWPGADYWGQGTQVTVSS |
| 180. | Anti-MSLN-39 (humanized) R3D5 v1.2 | QVQLVESGGGLVQAGGSLRLSCAASGSISSIRHMRWYRQAPGK GLELVATVSNDGSAYYLGSVKGRFTISRTNAKNTLLYLQMNSL KPEDSALYICNADTWGWPGADYWGQGTQVTVSS |
| 181. | Anti-MSLN-40 (humanized) R3D5 v1.3 | QVQLVESGGGLVQPGGSLRLSCAASGSISSIRHMRWYRQAPGK GLELVATVSNDGSAYYLGSVKGRFTISRTNAKNTLLYLQMNSL KPEDSALYICNADTWGWPGADYWGQGTQVTVSS |
| 182. | Anti-MSLN-41 (humanized) R3C7 v1.1 | QVQLVESGGGLVQPGGSLRLSCVVSGRTLESYVMAWFRQAPG KEREAVASINWSSGRLIYADFVKGRFTISRDNSKNTLYLQMNSL RPEDTAVYYCAAGRYWGQGTQVTVSS |
| 183. | Anti-MSLN-42 (humanized) R3C7 v1.2 | QVQLVESGGGLVQPGGSLRLSCVVSGRTLESYVMAWFRQAPG KGLEAVASINWSSGRLIYADFVKGRFTISRDNSKNTLYLQMNSL RPEDTAVYYCAAGRYWGQGTQVTVSS |
| 184. | Anti-MSLN-43 (humanized) R3C7 v1.3 | QVQLVESGGGLVQPGGSLRLSCAASGRTLESYVMAWFRQAPG KGLEAVASINWSSGRLIYADFVKGRFTISRDNSKNTLYLQMNSL RPEDTAVYYCAAGRYWGQGTQVTVSS |
| 185. | Anti-MSLN-44 (humanized) R3C7 v1.4 | QVQLVESGGGLVQPGGSLRLSCAASGRTLESYVMAWFRQAPG KGLEAVASINWSSGRLIYADSVKGRFTISRDNSKNTLYLQMNSL RAEDTAVYYCAAGRYWGQGTQVTVSS |
| 186. | Anti-MSLN-45 (humanized) R3C7 v1.5 | QVQLVESGGGLVQPGGSLRLSCAASGRTLESYVMAWFRQAPG KEREAVASINWSSGRLIYADSVKGRFTISRDNSKNTLYLQMNSL RAEDTAVYYCAAGRYWGQGTQVTVSS |
| 187. | Anti-MSLN-3 CDR1 | GSISSIRH |
| 188. | Anti-MSLN-3 CDR2 | VSNDGSA |
| 189. | Anti-MSLN-3 CDR3 | NADTWGWPGADY |

SEQUENCE TABLE

| SEQ ID NO | Description | Amino acid sequence (CDR sequences are underlined and bold) |
|---|---|---|
| 190. | Anti-MSLN-6 CDR1 | GRTLESYV |
| 191. | Anti-MSLN-6 CDR2 | INWSSGRL |
| 192. | Anti-MSLN-6 CDR3 | AAGRY |
| 193. | Anti-MSLN-9 CDR1 | GITFPVNA |
| 194. | Anti-MSLN-9 CDR2 | ISAGGTT |
| 195. | Anti-MSLN-9 CDR3 | YLQRRIGMLRDY |
| 196. | MSLN antigen 1 | EVEKTACPSGKKAREIDESLIFYKKWELEACVDAALLATQMDR VNAIPFTYEQLDVLKHKLDELYPQGYPESVIQHLGYLFLKMSPE DIRKWNVTSLETLKALLEVNKGHEMSPQAPRRPLPQVATLIDRF VKGRGQLDKDTLDTLTAFYPGYLCSLSPEELSSVPPSSIWAVRP QDLDTCDPRQLDVLYPKARLAFQNMNGSEYFVKIQSFLGGAPT EDLKALSQQNVSMDLATFMKLRTDAVLPLTVAEVQKLLGPHV EGLKAEERHRPVRDWILRQRQDDLDTLGLGLQGGIPNGYLVLD LSMQEALS |

The invention claimed is:

1. A fusion protein comprising: a) an IL-21 and b) an albumin binding moiety that is a single domain antibody (sdAb) comprising:
 (1) a CDR1 comprising the amino acid sequence of SEQ ID NO: 69;
  a CDR2 comprising the amino acid sequence of SEQ ID NO: 70; and
  a CDR3 comprising the amino acid sequence of SEQ ID NO: 71;
 (2) a CDR1 comprising the amino acid sequence of SEQ ID NO: 72;
  a CDR2 comprising the amino acid sequence of SEQ ID NO: 73; and
  a CDR3 comprising the amino acid sequence of SEQ ID NO: 74;
 (3) a CDR1 comprising the amino acid sequence of SEQ ID NO: 75;
  a CDR2 comprising the amino acid sequence of SEQ ID NO: 76; and
  a CDR3 comprising the amino acid sequence of SEQ ID NO: 77;
 (4) a CDR1 comprising the amino acid sequence of SEQ ID NO: 78;
  a CDR2 comprising the amino acid sequence of SEQ ID NO: 79; and
  a CDR3 comprising the amino acid sequence of SEQ ID NO: 80;
 (5) a CDR1 comprising the amino acid sequence of SEQ ID NO: 81;
  a CDR2 comprising the amino acid sequence of SEQ ID NO: 82; and
  a CDR3 comprising the amino acid sequence of SEQ ID NO: 83;
 (6) a CDR1 comprising the amino acid sequence of SEQ ID NO: 84;
  a CDR2 comprising the amino acid sequence of SEQ ID NO: 85; and
  a CDR3 comprising the amino acid sequence of SEQ ID NO: 86;
 (7) a CDR1 comprising the amino acid sequence of SEQ ID NO: 87;
  a CDR2 comprising the amino acid sequence of SEQ ID NO: 88; and
  a CDR3 comprising the amino acid sequence of SEQ ID NO: 89;
 (8) a CDR1 comprising the amino acid sequence of SEQ ID NO: 90;
  a CDR2 comprising the amino acid sequence of SEQ ID NO: 91; and
  a CDR3 comprising the amino acid sequence of SEQ ID NO: 92; or
 (9) a CDR1 comprising the amino acid sequence of SEQ ID NO: 93;
  a CDR2 comprising the amino acid sequence of SEQ ID NO: 94; and
  a CDR3 comprising the amino acid sequence of SEQ ID NO: 95.

2. The fusion protein of claim 1, wherein the IL-21 comprises the amino acid sequence of SEQ ID NO: 1, 2, 126, 171, or 172.

3. The fusion protein of claim 1, wherein the IL-21 is truncated IL-21 comprising the amino acid sequence of SEQ ID NO: 126, 171, or 172.

4. The fusion protein of claim 1, wherein the fusion protein comprises the amino acid sequence of any one of SEQ ID NOs: 120, 121, 129-150, 163, and 164.

5. A pharmaceutical composition comprising the fusion protein of claim 1 and a pharmaceutically acceptable carrier.

6. The fusion protein of claim 1, wherein the single domain antibody (sdAb) comprises a CDR1 comprising the amino acid sequence of SEQ ID NO: 78; a CDR2 comprising the amino acid sequence of SEQ ID NO: 79; and a CDR3 comprising the amino acid sequence of SEQ ID NO: 80.

7. The fusion protein of claim 1, wherein the single domain antibody (sdAb) comprises a CDR1 comprising the amino acid sequence of SEQ ID NO: 81; a CDR2 comprising the amino acid sequence of SEQ ID NO: 82; and a CDR3 comprising the amino acid sequence of SEQ ID NO: 83.

8. The fusion protein of claim 1, wherein the single domain antibody (sdAb) comprises a CDR1 comprising the amino acid sequence of SEQ ID NO: 84; a CDR2 comprising the amino acid sequence of SEQ ID NO: 85; and a CDR3 comprising the amino acid sequence of SEQ ID NO: 86.

9. The fusion protein of claim 1, wherein the single domain antibody (sdAb) comprises a CDR1 comprising the amino acid sequence of SEQ ID NO: 87; a CDR2 comprising the amino acid sequence of SEQ ID NO: 88; and a CDR3 comprising the amino acid sequence of SEQ ID NO: 89.

10. The fusion protein of claim 1, wherein the single domain antibody (sdAb) comprises a CDR1 comprising the amino acid sequence of SEQ ID NO: 90; a CDR2 comprising the amino acid sequence of SEQ ID NO: 91; and a CDR3 comprising the amino acid sequence of SEQ ID NO: 92.

11. The fusion protein of claim 1, wherein the single domain antibody (sdAb) comprises a CDR1 comprising the amino acid sequence of SEQ ID NO: 93; a CDR2 comprising the amino acid sequence of SEQ ID NO: 94; and a CDR3 comprising the amino acid sequence of SEQ ID NO: 95.

12. The fusion protein of claim 1, wherein the single domain antibody (sdAb) comprises the amino acid sequence of any one of SEQ ID NOs: 60 to 68 and 168.

13. The fusion protein of claim 1, wherein the single domain antibody (sdAb) comprises the amino acid sequence of SEQ ID NO: 168.

14. The fusion protein of claim 1, wherein the fusion protein comprises the amino acid sequence of SEQ ID NO: 139.

15. The fusion protein of claim 1, wherein the fusion protein comprises the amino acid sequence of SEQ ID NO: 140.

16. The fusion protein of claim 1, wherein the fusion protein comprises the amino acid sequence of SEQ ID NO: 145.

17. The fusion protein of claim 1, wherein the fusion protein comprises the amino acid sequence of SEQ ID NO: 148.

18. The fusion protein of claim 1, wherein the IL-21 comprises the amino acid sequence of SEQ ID NO: 1.

* * * * *